US008748570B2

(12) United States Patent
Robinson et al.

(10) Patent No.: US 8,748,570 B2
(45) Date of Patent: Jun. 10, 2014

(54) INSULIN ANALOGUES

(75) Inventors: Andrea Robinson, St. Kilda (AU);
Bianca Van Lierop, Chum Creek (AU)

(73) Assignee: Syngene Limited, Toorak (AU)

( * ) Notice: Subject to any disclaimer, the term of this patent is extended or adjusted under 35 U.S.C. 154(b) by 0 days.

(21) Appl. No.: 13/502,085

(22) PCT Filed: May 25, 2011

(86) PCT No.: PCT/AU2011/000614
§ 371 (c)(1),
(2), (4) Date: Apr. 13, 2012

(87) PCT Pub. No.: WO2011/146973
PCT Pub. Date: Dec. 1, 2011

(65) Prior Publication Data
US 2012/0225811 A1    Sep. 6, 2012

Related U.S. Application Data

(60) Provisional application No. 61/348,085, filed on May 25, 2010, provisional application No. 61/348,045, filed on May 25, 2010, provisional application No. 61/348,065, filed on May 25, 2010.

(51) Int. Cl.
*C07K 14/62* (2006.01)
(52) U.S. Cl.
USPC .......................... 530/303; 530/317; 556/136
(58) Field of Classification Search
USPC .................................. 530/303, 317; 556/136
IPC ............. C07K 14/62; A61K 38/12; C07F 17/00
See application file for complete search history.

(56) References Cited

U.S. PATENT DOCUMENTS

| 3,907,763 | A | * | 9/1975 | Brandenburg et al. ....... 530/303 |
| 5,811,515 | A | | 9/1998 | Grubbs et al. |
| 5,856,525 | A | | 1/1999 | Li et al. |
| 6,559,126 | B2 | | 5/2003 | Tournaire et al. |
| 2007/0197429 | A1 | | 8/2007 | Robinson et al. |

FOREIGN PATENT DOCUMENTS

| WO | WO-2005/012347 A2 | 2/2005 |
| WO | WO-2007/093014 A1 | 8/2007 |
| WO | WO-2008/098280 A1 | 8/2008 |

OTHER PUBLICATIONS

Videnov et al., Towards the synthesis of an A7-B7-dicarba insulin analoge, *Peptides*, 21: 232-3 (1990).
Videnov et al., Studies on the total synthesis of an A7, B7-Dicarbainsul III. Assembly of segments and generation of biological activity, Biological Chemistry Hopp-Seyler, 371(1): 1057-66 (1990).
International Search Report and Written Opinion of the International Searching Authority for PCT/AU2011/000614, Australian Patent Office, date of mailing Jun. 22, 2011.
Aguilera et al., Synthesis of diaminousberic acid derivatives via ring-closing alkyne metathesis. *J. Org. Chem.*, 66(10): 3584-9 (2001).
Berezowska et al., Cyclic dermorphin tetrapeptide analogues obtained via ring-closing metathesis. *Acta Biochimica Polonica*,53(1): 73-6 (2006).
Berezowska et al., Cyclic opioid peptide agonists and antagonists obtained via ring-closing metathesis. *Chem. Bio. Drug Des.*, 74(4): 329-34 (2009).
Berezowska et al., Dicarba analogues of the cyclic enkephalin peptides H-Tyr-c[D-Cys-Gly-Phe-D(or L)-Cys]NH2 retain high opioid activity. *J. Med. Chem.*, 50: 1414-7 (2007).
Diver et al., Enyne metathesis (Enyne bond reorganization). *Chem. Rev.* 104(3): 1317-82 (2004).
Elaridi et al., Controlled synthesis of (S,S)-2,7-diaminosuberic acid: A method for regioselective constructions of dicarba analogues of multicystine-containing peptides.*J. Org. Chem.*,71: 7538-45 (2006).
Fürstner et al., A chemo- and stereoclective reduction of cycloaclkynes to (E)-cycloalkaenes. *Chem. Commun.*, 2182-3 (2002).
Fürstner et al., Alkyne metathesis. *Chem. Commun.*, 2307-20 (2005).
Ghalit et al., Ring-closing alkyne metathesis approach toward the synthesis of alkyne mimics of thioeyther A-, B-, C- and DE-ring systems of the lantibiotic nisin *Z. Org. Lett.*, 7(14): 2961-4 (2005).
Ghalit et al., Synthesis of bicyclic alkene/alkane-bridged nisin mimics by ring-closing metathesis and their biochemical evaluation as lipid II binders: toward the design of potential novel antibiotics, Chembiochem, 2007, 8, 1540-1554.
Grela et al., An improved catalyst for ring-closing alkyne metathesis based on molybdenum hexacarbonyl/2-fluorophenol. *Org. Lett.*, 4(21): 3747 (1992).
Grubbs et al., Ruthenium-based heterocyclic carbine-coordinated olefin metathesis catalysts. *Chem Rev.*, 110: 1746-87 (2010).
Hossain et al., Solid phase synthesis and structural analysis of noval A-chain dicarba analogs of human relaxin-3 (INSL7) that exhibit full biological activity. *Org. Biomol. Chem.*, 7: 1547-53 (2009).
Ijsselstijn et al., Ring-closing alkyne metathesis mediated synthesis of cyclic β-turn mimetics. *Tetrahedron Lett.*, 45: 4379-82 (2004).
Ijsselstijn et al., Synthesis of novel acetylene-containing amino acids. *Amino Acids*, 24: 263-6 (2003).
Illesinghe et al., Metathesis assisted synthesis of cylic peptides. *Chem. Commun.*, 295-7 (2009).
Kaiser et al., Synthetic applications of aliphatic unsaturated α-H-α-amino acids. *Org. Biomol. Chem.*, 3: 3453-67 (2005).

(Continued)

*Primary Examiner* — David Lukton
(74) *Attorney, Agent, or Firm* — Marshall, Gerstein & Borun LLP

(57)    ABSTRACT

A dicarba analogue of insulin comprising an A-chain and a B-chain or fragments, salts, solvates, derivatives, isomers or tautomers of the A-chain, the B-chain or both, provided that the dicarba analogue is not [A7,B7-(2,7-diaminosuberoyl]-des-(B26-B30)-insulin B25-amide.

38 Claims, 6 Drawing Sheets

(56) References Cited

OTHER PUBLICATIONS

Kluwer et al., Homogeneous Hydrogenation of Alkynes and Dienes, *The Handbook of Homogeneous Hydrogenation*, Ch 14:, pp. 375-411, Wiley-VCH (2007).

Lacombe et al., (E)-cycloalkenes and (E,E)-cycloakadienes by ring closing diyne- or enyne-yne metathesis/semi-reduction. *Tetrahedron*, 60: 7315-24 (2004).

MacRaild et al., Structure and activity of (2,8)-dicarba-(3,12)-cystino alpha-lml, an alpha-conotoxin containing a nonreducible cystine analogue. *J. Med. Chem.*, 52: 755-62 (2009).

March, Advanced Organic Chemistry: Reactions, Mechanisms and Structure, pp. 771-780 (1992).

Mortreux et al., Alkyne metathesis catalysts: Scope an future. *Mol. Catal. A: Chem.*, 254: 96-104 (2006).

Ojima, I. Catalytic Asymmetric Synthesis; Wiley-VCH: New York, 2000; Second Edition, Chapter 1, 1-110.*

Pattabiraman et al., Multiple on-resin olefin metathesis to form ring-expanded analogues of the lantibiotic peptide, Lacticin 3147 A2, *Org. Lett.*, 9(4): 699-702 (2007).

Robinson et al., Microwave-assisted RCM for the synthesis of carbocyclic peptides. *J. Peptide Sci.*, 13: 280-5 (2007).

Robinson et al., Regioselective formation of interlocked dicarba bridges in naturally occurring cyclic peptide toxins using olefin metathesis. *Chem. Commun.*, 4293-5 (2009).

Robinson et. al., A one pot, metathesis-hydrogenation sequence for the selective formation of carbon-carbon bonds. *Chem. Commun.*, 5544-5 (2005).

Samojilowicz et al., Ruthenium-based olefin metathesis catalysts bearing N-heterocyclic carbine ligands. *Chem. Rev.*, 109: 3708-42 (2009).

Santini et al., A measure of solvent effects on swelling of resins for solid phase organic synthesis. *Tetrahedron Lett.*, 39: 8951-4 (1998).

Schrock, High Odidation state alkylidene and alkylidyne complexes. *Chem. Commun.*, 2773-7 (2005).

Scott et al., Characterization of novel splice variants of LGR7 and LGR8 reveals that receptor signaling is mediated by their unique low density lipoprotein class A modules. *J. Biol. Chem.*, 281: 34942-54 (2006).

Stymiest et al., Synthesis of biologically active dicarba analogues of the peptide hormone oxytocins using ring-closing metathesis. *Org. Lett.*, 5(1): 47-9 (2003).

Tiede et al., Highly active chiral ruthenium-based metathesis catalysts through a monosubstitution in the N-heterocyclic carbine. *Angew. Chem. Int. Ed.*, 49: 3849 (2010).

van Lierop et al., 5,5-dimethylproline didpeptides: An acid-stable class of pseudoproline. *Tetrahedron*, 66: 5357-66 (2010).

van Lierop et al., Methods for enhancing ring closing metathesis yield in peptides: Synthesis of a dicarba human growth hormone fragment. *Int. J. Pept. Res. Ther.*, 16: 133-44 (2010).

Whelan et. al., A tandem metathesis-hydrogenation route to dicarba analoguesof cystine-containing cyclic peptides. *Tetrahedron Lett.*, 45: 9545-7 (2004).

Whelan et. al., Metal-catalysed tandem metathesis-hydrogenation reactions for the synthesis of carba analogues of cyclic peptides. *Can. J. Chem.*, 83(6-7): 875-81 (2005).

Zhang et al., Alkyne Metathesis: Catalysts and synthetic Applications. *Adv. Synth. Catal.*, 349: 93-120 (2007).

Zhang et al., Role of the intra-A-chain disulfide bond of insulin-like peptide 3 in binding and activation of its receptor, RXFP2. *Peptides*, 31(9):1730-6 (2010).

* cited by examiner

FIGURE 1

- Insulin
- Dicarba 13(I)$_A$
- Dicarba 13(I)$_B$
- Dicarba 13(II)$_A$
- Dicarba 13(II)$_B$

```
                         SEQUENCE LISTING

<160> NUMBER OF SEQ ID NOS: 112

<210> SEQ ID NO 1
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is Allylglycine (Agl)
<220> FEATURE:
<221> NAME/KEY: MISC_FEATURE
<222> LOCATION: (7)..(7)
<223> OTHER INFORMATION: Bound to thiol protecting group
<220> FEATURE:
<221> NAME/KEY: MOD_RES
<222> LOCATION: (11)..(11)
<223> OTHER INFORMATION: Xaa is Allylglycine (Agl)
<220> FEATURE:
<221> NAME/KEY: MISC_FEATURE
<222> LOCATION: (20)..(20)
<223> OTHER INFORMATION: Bound to thiol protecting group

<400> SEQUENCE: 1

Gly Ile Val Glu Gln Xaa Cys Thr Ser Ile Xaa Ser Leu Tyr Gln Leu
1               5                   10                  15

Glu Asn Tyr Cys Asn
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via double bond
<220> FEATURE:
<221> NAME/KEY: MISC_FEATURE
<222> LOCATION: (7)..(7)
<223> OTHER INFORMATION: Bound to thiol protecting group
<220> FEATURE:
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: MISC_FEATURE
<222> LOCATION: (20)..(20)
<223> OTHER INFORMATION: Bound to thiol protecting group

<400> SEQUENCE: 2

Gly Ile Val Glu Gln Xaa Cys Thr Ser Ile Xaa Ser Leu Tyr Gln Leu
1               5                   10                  15

Glu Asn Tyr Cys Asn
            20

<210> SEQ ID NO 3
<211> LENGTH: 30
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (19)..(19)
<223> OTHER INFORMATION: Bound to thiol protecting group

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via double bond
<220> FEATURE:
<221> NAME/KEY: DISULFID
<222> LOCATION: (7)..(7)
<223> OTHER INFORMATION: Bound to Cys at position 7 of SEQ ID NO: 3 via
      disulfide bond to form dimer
<220> FEATURE:
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: MISC_FEATURE
<222> LOCATION: (20)..(20)
<223> OTHER INFORMATION: Bound to thiol protecting group

<400> SEQUENCE: 4

Gly Ile Val Glu Gln Xaa Cys Thr Ser Ile Xaa Ser Leu Tyr Gln Leu
1               5                   10                  15

Glu Asn Tyr Cys Asn
            20

<210> SEQ ID NO 5
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via double bond
<220> FEATURE:
<221> NAME/KEY: DISULFID
<222> LOCATION: (7)..(7)
<223> OTHER INFORMATION: Bound to Cys at position 7 of SEQ ID NO: 112
      via disulfide bond to form dimer
<220> FEATURE:
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: DISULFID
```

```
<222> LOCATION: (20)..(20)
<223> OTHER INFORMATION: Bound to Cys at position 19 of SEQ ID NO: 112
      via disulfide bond to form dimer

<400> SEQUENCE: 5

Gly Ile Val Glu Gln Xaa Cys Thr Ser Ile Xaa Ser Leu Tyr Gln Leu
1               5                   10                  15

Glu Asn Tyr Cys Asn
            20

<210> SEQ ID NO 6
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is Allylglycine (Agl)
<220> FEATURE:
<221> NAME/KEY: MISC_FEATURE
<222> LOCATION: (6)..(7)
<223> OTHER INFORMATION: Alg-Pseudoproline-Cys
<220> FEATURE:
<221> NAME/KEY: MOD_RES
<222> LOCATION: (11)..(11)
<223> OTHER INFORMATION: Xaa is Allylglycine (Agl)

<400> SEQUENCE: 6

Gly Ile Val Glu Gln Xaa Cys Thr Ser Ile Xaa Ser Leu Tyr Gln Leu
1               5                   10                  15

Glu Asn Tyr Cys Asn
            20

<210> SEQ ID NO 7
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is Allylglycine (Agl)
<220> FEATURE:
<221> NAME/KEY: MISC_FEATURE
<222> LOCATION: (7)..(8)
<223> OTHER INFORMATION: Cys-pseudoproline-Thr
<220> FEATURE:
<221> NAME/KEY: MOD_RES
<222> LOCATION: (11)..(11)
<223> OTHER INFORMATION: Xaa is Allylglycine (Agl)

<400> SEQUENCE: 7

Gly Ile Val Glu Gln Xaa Cys Thr Ser Ile Xaa Ser Leu Tyr Gln Leu
1               5                   10                  15

Glu Asn Tyr Cys Asn
            20

<210> SEQ ID NO 8
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is Allylglycine (Agl)
<220> FEATURE:
```

```
<221> NAME/KEY: MISC_FEATURE
<222> LOCATION: (8)..(9)
<223> OTHER INFORMATION: Thr-pseudoproline-Ser
<220> FEATURE:
<221> NAME/KEY: MOD_RES
<222> LOCATION: (11)..(11)
<223> OTHER INFORMATION: Xaa is Allylglycine (Agl)

<400> SEQUENCE: 8

Gly Ile Val Glu Gln Xaa Cys Thr Ser Ile Xaa Ser Leu Tyr Gln Leu
1               5                   10                  15

Glu Asn Tyr Cys Asn
            20

<210> SEQ ID NO 9
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via double bond
<220> FEATURE:
<221> NAME/KEY: MISC_FEATURE
<222> LOCATION: (7)..(7)
<223> OTHER INFORMATION: Bound to thiol protecting group
<220> FEATURE:
<221> NAME/KEY: MISC_FEATURE
<222> LOCATION: (8)..(9)
<223> OTHER INFORMATION: Thr-pseudoproline-Ser
<220> FEATURE:
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: MISC_FEATURE
<222> LOCATION: (20)..(20)
<223> OTHER INFORMATION: Bound to thiol protecting group

<400> SEQUENCE: 9

Gly Ile Val Glu Gln Xaa Cys Thr Ser Ile Xaa Ser Leu Tyr Gln Leu
1               5                   10                  15

Glu Asn Tyr Cys Asn
            20

<210> SEQ ID NO 10
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is Allylglycine (Agl)
<220> FEATURE:
<221> NAME/KEY: MISC_FEATURE
<222> LOCATION: (2)..(2)
<223> OTHER INFORMATION: Bound to thiol protecting group
<220> FEATURE:
<221> NAME/KEY: MOD_RES
<222> LOCATION: (6)..(6)
<223> OTHER INFORMATION: Xaa is Allylglycine (Agl)
<220> FEATURE:
<221> NAME/KEY: MISC_FEATURE
<222> LOCATION: (15)..(15)
<223> OTHER INFORMATION: Bound to thiol protecting group
```

```
<400> SEQUENCE: 10

Xaa Cys Thr Ser Ile Xaa Ser Leu Tyr Gln Leu Glu Asn Tyr Cys Asn
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is Allylglycine (Agl)
<220> FEATURE:
<221> NAME/KEY: MOD_RES
<222> LOCATION: (2)..(2)
<223> OTHER INFORMATION: Xaa is Prenylglycine (Pre)
<220> FEATURE:
<221> NAME/KEY: MOD_RES
<222> LOCATION: (6)..(6)
<223> OTHER INFORMATION: Xaa is Allylglycine (Agl)
<220> FEATURE:
<221> NAME/KEY: MISC_FEATURE
<222> LOCATION: (15)..(15)
<223> OTHER INFORMATION: Bound to thiol protecting group

<400> SEQUENCE: 11

Xaa Xaa Thr Ser Ile Xaa Ser Leu Tyr Gln Leu Glu Asn Tyr Cys Asn
1               5                   10                  15

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide

<400> SEQUENCE: 12

Gly Ile Val Glu Gln
1               5

<210> SEQ ID NO 13
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is delta-4 diaminosuberic acid (Das)
<220> FEATURE:
<221> NAME/KEY: MISC_FEATURE
<222> LOCATION: (1)..(6)
<223> OTHER INFORMATION: Linked via double bond
<220> FEATURE:
<221> NAME/KEY: MISC_FEATURE
<222> LOCATION: (2)..(2)
<223> OTHER INFORMATION: Bound to thiol protecting group
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (15)..(15)
<223> OTHER INFORMATION: Bound to thiol protecting group

<400> SEQUENCE: 13

Xaa Cys Thr Ser Ile Xaa Ser Leu Tyr Gln Leu Glu Asn Tyr Cys Asn
1               5                   10                  15
```

```
<210> SEQ ID NO 14
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is delta-4 diaminosuberic acid (Das)
<220> FEATURE:
<221> NAME/KEY: MISC_FEATURE
<222> LOCATION: (1)..(6)
<223> OTHER INFORMATION: Linked via double bond
<220> FEATURE:
<221> NAME/KEY: MOD_RES
<222> LOCATION: (2)..(2)
<223> OTHER INFORMATION: Xaa is Prenylglycine (Pre)
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (15)..(15)
<223> OTHER INFORMATION: Bound to thiol protecting group

<400> SEQUENCE: 14

Xaa Xaa Thr Ser Ile Xaa Ser Leu Tyr Gln Leu Glu Asn Tyr Cys Asn
 1               5                  10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is diaminosuberic acid (Das)
<220> FEATURE:
<221> NAME/KEY: MISC_FEATURE
<222> LOCATION: (1)..(6)
<223> OTHER INFORMATION: Linked via single bond
<220> FEATURE:
<221> NAME/KEY: MISC_FEATURE
<222> LOCATION: (2)..(2)
<223> OTHER INFORMATION: Bound to thiol protecting group
<220> FEATURE:
<221> NAME/KEY: MOD_RES
<222> LOCATION: (6)..(6)
<223> OTHER INFORMATION: Xaa is diaminosuberic acid (Das)
<220> FEATURE:
<221> NAME/KEY: MISC_FEATURE
<222> LOCATION: (15)..(15)
<223> OTHER INFORMATION: Bound to thiol protecting group

<400> SEQUENCE: 15

Xaa Cys Thr Ser Ile Xaa Ser Leu Tyr Gln Leu Glu Asn Tyr Cys Asn
 1               5                  10                  15

<210> SEQ ID NO 16
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is diaminosuberic acid (Das)
<220> FEATURE:
<221> NAME/KEY: MISC_FEATURE
<222> LOCATION: (6)..(11)
```

```
<223> OTHER INFORMATION: Linked via single bond
<220> FEATURE:
<221> NAME/KEY: MISC_FEATURE
<222> LOCATION: (7)..(7)
<223> OTHER INFORMATION: Bound to thiol protecting group
<220> FEATURE:
<221> NAME/KEY: MOD_RES
<222> LOCATION: (11)..(11)
<223> OTHER INFORMATION: Xaa is diaminosuberic acid (Das)
<220> FEATURE:
<221> NAME/KEY: MISC_FEATURE
<222> LOCATION: (20)..(20)
<223> OTHER INFORMATION: Bound to thiol protecting group

<400> SEQUENCE: 16

Gly Ile Val Glu Gln Xaa Cys Thr Ser Ile Xaa Ser Leu Tyr Gln Leu
1               5                   10                  15

Glu Asn Tyr Cys Asn
            20

<210> SEQ ID NO 17
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is diaminosuberic acid (Das)
<220> FEATURE:
<221> NAME/KEY: MISC_FEATURE
<222> LOCATION: (1)..(6)
<223> OTHER INFORMATION: Linked via single bond
<220> FEATURE:
<221> NAME/KEY: MOD_RES
<222> LOCATION: (2)..(2)
<223> OTHER INFORMATION: Xaa is Crotylglycine (Crt)
<220> FEATURE:
<221> NAME/KEY: MOD_RES
<222> LOCATION: (6)..(6)
<223> OTHER INFORMATION: Xaa is diaminosuberic acid (Das)
<220> FEATURE:
<221> NAME/KEY: MISC_FEATURE
<222> LOCATION: (15)..(15)
<223> OTHER INFORMATION: Bound to thiol protecting group

<400> SEQUENCE: 17

Xaa Xaa Thr Ser Ile Xaa Ser Leu Tyr Gly Leu Glu Asn Tyr Cys Asn
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is diaminosuberic acid (Das)
<220> FEATURE:
<221> NAME/KEY: MOD_RES
<222> LOCATION: (2)..(2)
<223> OTHER INFORMATION: Xaa is delta-4 diaminosuberic acid (Das)
<220> FEATURE:
<221> NAME/KEY: MISC_FEATURE
<222> LOCATION: (2)..(2)
<223> OTHER INFORMATION: Linked to delta-4 diaminosuberic acid (Das) via
      double bond
<220> FEATURE:
<221> NAME/KEY: MOD_RES
<222> LOCATION: (6)..(6)
<223> OTHER INFORMATION: Xaa is diaminosuberic acid (Das)
<220> FEATURE:
```

```
<221> NAME/KEY: MISC_FEATURE
<222> LOCATION: (15)..(15)
<223> OTHER INFORMATION: Bound to thiol protecting group

<400> SEQUENCE: 18

Xaa Xaa Thr Ser Ile Xaa Ser Leu Tyr Gly Leu Glu Asn Tyr Cys Asn
1               5                   10                  15

<210> SEQ ID NO 19
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is diaminosuberic acid (Das)
<220> FEATURE:
<221> NAME/KEY: MOD_RES
<222> LOCATION: (7)..(7)
<223> OTHER INFORMATION: Xaa is delta-4 diaminosuberic acid (Das)
<220> FEATURE:
<221> NAME/KEY: MISC_FEATURE
<222> LOCATION: (7)..(7)
<223> OTHER INFORMATION: Linked to delta-4 diaminosuberic acid (Das) via
      double bond
<220> FEATURE:
<221> NAME/KEY: MOD_RES
<222> LOCATION: (11)..(11)
<223> OTHER INFORMATION: Xaa is diaminosuberic acid (Das)
<220> FEATURE:
<221> NAME/KEY: MISC_FEATURE
<222> LOCATION: (20)..(20)
<223> OTHER INFORMATION: Bound to thiol protecting group

<400> SEQUENCE: 19

Gly Ile Val Glu Gln Xaa Xaa Thr Ser Ile Xaa Ser Leu Tyr Gly Leu
1               5                   10                  15

Glu Asn Tyr Cys Asn
            20

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is N-acetyl-2-(but-2-ynyl)glycine (Bgl)
<220> FEATURE:
<221> NAME/KEY: MISC_FEATURE
<222> LOCATION: (2)..(2)
<223> OTHER INFORMATION: Bound to thiol protecting group
<220> FEATURE:
<221> NAME/KEY: MOD_RES
<222> LOCATION: (6)..(6)
<223> OTHER INFORMATION: Xaa is N-acetyl-2-(but-2-ynyl)glycine (Bgl)

<400> SEQUENCE: 20

Xaa Cys Thr Ser Ile Xaa Ser Leu
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
```

```
<222> LOCATION: (1)..(1)
<223> OTHER INFORMATION: Xaa is N-acetyl-2-(but-2-ynyl)glycine (Bgl)
<220> FEATURE:
<221> NAME/KEY: MISC_FEATURE
<222> LOCATION: (2)..(2)
<223> OTHER INFORMATION: Bound to thiol protecting group
<220> FEATURE:
<221> NAME/KEY: MOD_RES
<222> LOCATION: (6)..(6)
<223> OTHER INFORMATION: Xaa is N-acetyl-2-(but-2-ynyl)glycine (Bgl)

<400> SEQUENCE: 21

Xaa Cys Pro Ser Ile Xaa Ser Leu
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is delta-4 diaminosuberic acid (Das)
<220> FEATURE:
<221> NAME/KEY: MISC_FEATURE
<222> LOCATION: (1)..(6)
<223> OTHER INFORMATION: Linked via triple bond
<220> FEATURE:
<221> NAME/KEY: MISC_FEATURE
<222> LOCATION: (2)..(2)
<223> OTHER INFORMATION: Bound to thiol protecting group
<220> FEATURE:
<221> NAME/KEY: MOD_RES
<222> LOCATION: (6)..(6)
<223> OTHER INFORMATION: Xaa is delta-4 diaminosuberic acid (Das)

<400> SEQUENCE: 22

Xaa Cys Thr Ser Ile Xaa Ser Leu
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is delta-4 diaminosuberic acid (Das)
<220> FEATURE:
<221> NAME/KEY: MISC_FEATURE
<222> LOCATION: (1)..(6)
<223> OTHER INFORMATION: Linked via triple bond
<220> FEATURE:
<221> NAME/KEY: MISC_FEATURE
<222> LOCATION: (2)..(2)
<223> OTHER INFORMATION: Bound to thiol protecting group
<220> FEATURE:
<221> NAME/KEY: MOD_RES
<222> LOCATION: (6)..(6)
<223> OTHER INFORMATION: Xaa is delta-4 diaminosuberic acid (Das)

<400> SEQUENCE: 23

Xaa Cys Pro Ser Ile Xaa Ser Leu
1               5

<210> SEQ ID NO 24
<211> LENGTH: 13
<212> TYPE: PRT
<213> ORGANISM: Artificial Sequence
<220> FEATURE:
```

-continued

```
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via triple bond
<220> FEATURE:
<221> NAME/KEY: MOD_RES
<222> LOCATION: (11)..(11)
<223> OTHER INFORMATION: Xaa is delta-4 diaminosuberic acid (Das)

<400> SEQUENCE: 24

Gly Ile Val Glu Gln Xaa Cys Pro Ser Ile Xaa Ser Leu
1               5                   10

<210> SEQ ID NO 25
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: Xaa is Allylglycine (Agl)
<220> FEATURE:
<221> NAME/KEY: MOD_RES
<222> LOCATION: (16)..(16)
<223> OTHER INFORMATION: Xaa is Allylglycine (Agl)

<400> SEQUENCE: 25

Phe Val Asn Gln His Leu Xaa Gly Pro Gly Ile Val Glu Gln Cys Xaa
1               5                   10                  15

Thr

<210> SEQ ID NO 26
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: Xaa is delta-4 diaminosuberic acid (Das)
<220> FEATURE:
<221> NAME/KEY: MISC_FEATURE
<222> LOCATION: (7)..(16)
<223> OTHER INFORMATION: Linked via double bond
<220> FEATURE:
<221> NAME/KEY: MOD_RES
<222> LOCATION: (16)..(16)
<223> OTHER INFORMATION: Xaa is delta-4 diaminosuberic acid (Das)

<400> SEQUENCE: 26

Phe Val Asn Gln His Leu Xaa Gly Pro Gly Ile Val Glu Gln Cys Xaa
1               5                   10                  15

Thr

<210> SEQ ID NO 27
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is Allylglycine (Agl)
```

```
<220> FEATURE:
<221> NAME/KEY: MOD_RES
<222> LOCATION: (10)..(10)
<223> OTHER INFORMATION: Xaa is Allylglycine (Agl)

<400> SEQUENCE: 27

Xaa Gly Pro Gly Ile Val Glu Gln Cys Xaa Thr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is delta-4 diaminosuberic acid (Das)
<220> FEATURE:
<221> NAME/KEY: MISC_FEATURE
<222> LOCATION: (1)..(10)
<223> OTHER INFORMATION: Linked via double bond
<220> FEATURE:
<221> NAME/KEY: MOD_RES
<222> LOCATION: (10)..(10)
<223> OTHER INFORMATION: Xaa is delta-4 diaminosuberic acid (Das)

<400> SEQUENCE: 28

Xaa Gly Pro Gly Ile Val Glu Gln Cys Xaa Thr
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: Xaa is Allylglycine (Agl)

<400> SEQUENCE: 29

Gly Ile Val Glu Gln Cys Xaa Thr Ser
1               5

<210> SEQ ID NO 30
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is hydroxy-6-nitrobenzaldehyde (HnB)
<220> FEATURE:
<221> NAME/KEY: MOD_RES
<222> LOCATION: (9)..(9)
<223> OTHER INFORMATION: Xaa is Allylglycine (Agl)

<400> SEQUENCE: 30

Gly Xaa Gly Ile Val Glu Gln Cys Xaa Thr Ser
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MOD_RES
<222> LOCATION: (1)..(1)
<223> OTHER INFORMATION: Xaa is Allylglycine (Agl)
<220> FEATURE:
<221> NAME/KEY: MOD_RES
<222> LOCATION: (3)..(3)
<223> OTHER INFORMATION: Xaa is hydroxy-6-nitrobenzaldehyde (HnB)
<220> FEATURE:
<221> NAME/KEY: MOD_RES
<222> LOCATION: (10)..(10)
<223> OTHER INFORMATION: Xaa is Allylgylcine (Alg)

<400> SEQUENCE: 31

Xaa Gly Xaa Gly Ile Val Glu Gln Cys Xaa Thr Ser
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is delta-4 diaminosuberic acid (Das)
<220> FEATURE:
<221> NAME/KEY: MISC_FEATURE
<222> LOCATION: (1)..(10)
<223> OTHER INFORMATION: Linked via double bond
<220> FEATURE:
<221> NAME/KEY: MOD_RES
<222> LOCATION: (3)..(3)
<223> OTHER INFORMATION: Xaa is hydroxy-6-nitrobenzaldehyde (HnB)
<220> FEATURE:
<221> NAME/KEY: MOD_RES
<222> LOCATION: (10)..(10)
<223> OTHER INFORMATION: Xaa is delta-4 diaminosuberic acid (Das)

<400> SEQUENCE: 32

Xaa Gly Xaa Gly Ile Val Glu Gln Cys Xaa Thr Ser
1               5                   10

<210> SEQ ID NO 33
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is Allylglycine (Agl)
<220> FEATURE:
<221> NAME/KEY: MISC_FEATURE
<222> LOCATION: (2)..(2)
<223> OTHER INFORMATION: Bound to thiol protecting group
<220> FEATURE:
<221> NAME/KEY: MOD_RES
<222> LOCATION: (6)..(6)
<223> OTHER INFORMATION: Xaa is Allylglycine (Agl)
<220> FEATURE:
<221> NAME/KEY: MISC_FEATURE
<222> LOCATION: (15)..(15)
<223> OTHER INFORMATION: Bound to thiol protecting group

<400> SEQUENCE: 33

Xaa Cys Thr Ser Ile Xaa Ser Leu Tyr Gln Leu Glu Asn Tyr Cys Gly
1               5                   10                  15

<210> SEQ ID NO 34
<211> LENGTH: 16
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is delta-4 diaminosuberic acid (Das)
<220> FEATURE:
<221> NAME/KEY: MISC_FEATURE
<222> LOCATION: (1)..(6)
<223> OTHER INFORMATION: Linked via double bond
<220> FEATURE:
<221> NAME/KEY: MISC_FEATURE
<222> LOCATION: (2)..(2)
<223> OTHER INFORMATION: Bound to thiol protecting group
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (15)..(15)
<223> OTHER INFORMATION: Bound to thiol protecting group

<400> SEQUENCE: 34

Xaa Cys Thr Ser Ile Xaa Ser Leu Tyr Gly Leu Glu Asn Tyr Cys Gly
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is diaminosuberic acid (Das)
<220> FEATURE:
<221> NAME/KEY: MISC_FEATURE
<222> LOCATION: (1)..(6)
<223> OTHER INFORMATION: Linked via single bond
<220> FEATURE:
<221> NAME/KEY: MISC_FEATURE
<222> LOCATION: (2)..(2)
<223> OTHER INFORMATION: Bound to thiol protecting group
<220> FEATURE:
<221> NAME/KEY: MOD_RES
<222> LOCATION: (6)..(6)
<223> OTHER INFORMATION: Xaa is diaminosuberic acid (Das)
<220> FEATURE:
<221> NAME/KEY: MISC_FEATURE
<222> LOCATION: (15)..(15)
<223> OTHER INFORMATION: Bound to thiol protecting group

<400> SEQUENCE: 35

Xaa Cys Thr Ser Ile Xaa Ser Leu Tyr Gly Leu Glu Asn Tyr Cys Gly
1               5                   10                  15

<210> SEQ ID NO 36
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via double bond
<220> FEATURE:
<221> NAME/KEY: MISC_FEATURE
<222> LOCATION: (7)..(7)
```

<223> OTHER INFORMATION: Bound to thiol protecting group
<220> FEATURE:
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: MISC_FEATURE
<222> LOCATION: (20)..(20)
<223> OTHER INFORMATION: Bound to thiol protecting group

<400> SEQUENCE: 36

Gly Ile Val Glu Gln Xaa Cys Thr Ser Ile Xaa Ser Leu Tyr Gln Leu
1               5                   10                  15

Glu Asn Tyr Cys Gly
            20

<210> SEQ ID NO 37
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is diaminosuberic acid (Das)
<220> FEATURE:
<221> NAME/KEY: MISC_FEATURE
<222> LOCATION: (6)..(11)
<223> OTHER INFORMATION: Linked via single bond
<220> FEATURE:
<221> NAME/KEY: MISC_FEATURE
<222> LOCATION: (7)..(7)
<223> OTHER INFORMATION: Bound to thiol protecting group
<220> FEATURE:
<221> NAME/KEY: MOD_RES
<222> LOCATION: (11)..(11)
<223> OTHER INFORMATION: Xaa is diaminosuberic acid (Das)
<220> FEATURE:
<221> NAME/KEY: MISC_FEATURE
<222> LOCATION: (20)..(20)
<223> OTHER INFORMATION: Bound to thiol protecting group

<400> SEQUENCE: 37

Gly Ile Val Glu Gln Xaa Cys Thr Ser Ile Xaa Ser Leu Tyr Gln Leu
1               5                   10                  15

Glu Asn Tyr Cys Gly
            20

<210> SEQ ID NO 38
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (19)..(19)
<223> OTHER INFORMATION: Bound to thiol protecting group

<400> SEQUENCE: 38

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 39
<211> LENGTH: 21
<212> TYPE: PRT
<213> ORGANISM: Artificial Sequence
<220> FEATURE:

```
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via double bond
<220> FEATURE:
<221> NAME/KEY: DISULFID
<222> LOCATION: (7)..(7)
<223> OTHER INFORMATION: Bound to Cys at position 7 of SEQ ID NO: 38 via
      disulfide bond to form dimer
<220> FEATURE:
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: MISC_FEATURE
<222> LOCATION: (20)..(20)
<223> OTHER INFORMATION: Bound to thiol protecting group

<400> SEQUENCE: 39

Gly Ile Val Glu Gln Xaa Cys Thr Ser Ile Xaa Ser Leu Tyr Gln Leu
1               5                   10                  15

Glu Asn Tyr Cys Gly
            20

<210> SEQ ID NO 40
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is diaminosuberic acid (Das)
<220> FEATURE:
<221> NAME/KEY: MISC_FEATURE
<222> LOCATION: (6)..(11)
<223> OTHER INFORMATION: Linked via single bond
<220> FEATURE:
<221> NAME/KEY: DISULFID
<222> LOCATION: (7)..(7)
<223> OTHER INFORMATION: Bound to Cys at position 7 of SEQ ID NO: 38 via
      disulfide bond to form dimer
<220> FEATURE:
<221> NAME/KEY: MOD_RES
<222> LOCATION: (11)..(11)
<223> OTHER INFORMATION: Xaa is diaminosuberic acid (Das)
<220> FEATURE:
<221> NAME/KEY: MISC_FEATURE
<222> LOCATION: (20)..(20)
<223> OTHER INFORMATION: Bound to thiol protecting group

<400> SEQUENCE: 40

Gly Ile Val Glu Gln Xaa Cys Thr Ser Ile Xaa Ser Leu Tyr Gln Leu
1               5                   10                  15

Glu Asn Tyr Cys Gly
            20

<210> SEQ ID NO 41
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
```

```
<221> NAME/KEY: MISC_FEATURE
<222> LOCATION: (6)..(11)
<223> OTHER INFORMATION: Linked via double bond
<220> FEATURE:
<221> NAME/KEY: DISULFID
<222> LOCATION: (7)..(7)
<223> OTHER INFORMATION: Bound to Cys at position 7 of SEQ ID NO: 103
      via disulfide bond to form dimer
<220> FEATURE:
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: DISULFID
<222> LOCATION: (20)..(20)
<223> OTHER INFORMATION: Bound to Cys at position 20 of SEQ ID NO: 103
      via disulfide bond to form dimer

<400> SEQUENCE: 41

Gly Ile Val Glu Gln Xaa Cys Thr Ser Ile Xaa Ser Leu Tyr Gln Leu
1               5                   10                  15

Glu Asn Tyr Cys Gly
            20

<210> SEQ ID NO 42
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is diaminosuberic acid (Das)
<220> FEATURE:
<221> NAME/KEY: MISC_FEATURE
<222> LOCATION: (6)..(11)
<223> OTHER INFORMATION: Linked via single bond
<220> FEATURE:
<221> NAME/KEY: DISULFID
<222> LOCATION: (7)..(7)
<223> OTHER INFORMATION: Bound to Cys at position 7 of SEQ ID NO: 90
      via disulfide bond to form dimer
<220> FEATURE:
<221> NAME/KEY: MOD_RES
<222> LOCATION: (11)..(11)
<223> OTHER INFORMATION: Xaa is diaminosuberic acid (Das)
<220> FEATURE:
<221> NAME/KEY: DISULFID
<222> LOCATION: (20)..(20)
<223> OTHER INFORMATION: Bound to Cys at position 19 of SEQ ID NO: 90
      via disulfide bond to form dimer

<400> SEQUENCE: 42

Gly Ile Val Glu Gln Xaa Cys Thr Ser Ile Xaa Ser Leu Tyr Gln Leu
1               5                   10                  15

Glu Asn Tyr Cys Gly
            20

<210> SEQ ID NO 43
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is diaminosuberic acid (Das)
<220> FEATURE:
<221> NAME/KEY: MISC_FEATURE
<222> LOCATION: (6)..(11)
<223> OTHER INFORMATION: Linked via single bond
<220> FEATURE:
```

```
<221> NAME/KEY: DISULFID
<222> LOCATION: (7)..(7)
<223> OTHER INFORMATION: Bound to Cys at position 7 of SEQ ID NO: 82 via
      disulfide bond to form dimer
<220> FEATURE:
<221> NAME/KEY: MOD_RES
<222> LOCATION: (11)..(11)
<223> OTHER INFORMATION: Xaa is diaminosuberic acid (Das)
<220> FEATURE:
<221> NAME/KEY: DISULFID
<222> LOCATION: (20)..(20)
<223> OTHER INFORMATION: Bound to Cys at position 19 of SEQ ID NO: 82
      via disulfide bond to form dimer

<400> SEQUENCE: 43

Gly Ile Val Glu Gln Xaa Cys Thr Ser Ile Xaa Ser Leu Tyr Gln Leu
1               5                   10                  15

Glu Asn Tyr Cys Asn
            20

<210> SEQ ID NO 44
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via double bond
<220> FEATURE:
<221> NAME/KEY: DISULFID
<222> LOCATION: (7)..(7)
<223> OTHER INFORMATION: Bound to Cys at position 7 of SEQ ID NO: 3 via
      disulfide bond to form dimer
<220> FEATURE:
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: MISC_FEATURE
<222> LOCATION: (20)..(20)
<223> OTHER INFORMATION: Bound to thiol protecting group

<400> SEQUENCE: 44

Gly Ile Val Glu Gln Xaa Cys Thr Ser Ile Xaa Ser Leu Tyr Gln Leu
1               5                   10                  15

Glu Asn Tyr Cys Gly
            20

<210> SEQ ID NO 45
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via double bond
<220> FEATURE:
<221> NAME/KEY: DISULFID
<222> LOCATION: (7)..(7)
<223> OTHER INFORMATION: Bound to Cys at position 7 of SEQ ID NO: 112
      via disulfide bond to form dimer
<220> FEATURE:
```

```
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: DISULFID
<222> LOCATION: (20)..(20)
<223> OTHER INFORMATION: Bound to Cys at position 19 of SEQ ID NO: 112
      via disulfide bond to form dimer

<400> SEQUENCE: 45

Gly Ile Val Glu Gln Xaa Cys Thr Ser Ile Xaa Ser Leu Tyr Gln Leu
1               5                   10                  15

Glu Asn Tyr Cys Gly
            20

<210> SEQ ID NO 46
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is Allylglycine (Agl)
<220> FEATURE:
<221> NAME/KEY: MISC_FEATURE
<222> LOCATION: (2)..(2)
<223> OTHER INFORMATION: Bound to thiol protecting group
<220> FEATURE:
<221> NAME/KEY: MOD_RES
<222> LOCATION: (6)..(6)
<223> OTHER INFORMATION: Xaa is Allylglycine (Agl)
<220> FEATURE:
<221> NAME/KEY: MISC_FEATURE
<222> LOCATION: (15)..(15)
<223> OTHER INFORMATION: Bound to thiol protecting group

<400> SEQUENCE: 46

Xaa Cys Thr Ser Ile Xaa Ser Leu Tyr Gln Leu Glu Asn Tyr Cys Asp
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is delta-4 diaminosuberic acid (Das)
<220> FEATURE:
<221> NAME/KEY: MISC_FEATURE
<222> LOCATION: (1)..(6)
<223> OTHER INFORMATION: Linked via double bond
<220> FEATURE:
<221> NAME/KEY: MISC_FEATURE
<222> LOCATION: (2)..(2)
<223> OTHER INFORMATION: Bound to thiol protecting group
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (15)..(15)
<223> OTHER INFORMATION: Bound to thiol protecting group

<400> SEQUENCE: 47

Xaa Cys Thr Ser Ile Xaa Ser Leu Tyr Gly Leu Glu Asn Tyr Cys Asp
1               5                   10                  15
```

```
<210> SEQ ID NO 48
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via double bond
<220> FEATURE:
<221> NAME/KEY: MISC_FEATURE
<222> LOCATION: (7)..(7)
<223> OTHER INFORMATION: Bound to thiol protecting group
<220> FEATURE:
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: MISC_FEATURE
<222> LOCATION: (20)..(20)
<223> OTHER INFORMATION: Bound to thiol protecting group

<400> SEQUENCE: 48

Gly Ile Val Glu Gln Xaa Cys Thr Ser Ile Xaa Ser Leu Tyr Gln Leu
1               5                   10                  15

Glu Asn Tyr Cys Asp
            20

<210> SEQ ID NO 49
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via double bond
<220> FEATURE:
<221> NAME/KEY: DISULFID
<222> LOCATION: (7)..(7)
<223> OTHER INFORMATION: Bound to Cys at position 7 of SEQ ID NO: 103
      via disulfide bond to form dimer
<220> FEATURE:
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: MISC_FEATURE
<222> LOCATION: (20)..(20)
<223> OTHER INFORMATION: Bound to thiol protecting group

<400> SEQUENCE: 49

Gly Ile Val Glu Gln Xaa Cys Thr Ser Ile Xaa Ser Leu Tyr Gln Leu
1               5                   10                  15

Glu Asn Tyr Cys Asp
            20

<210> SEQ ID NO 50
<211> LENGTH: 21
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via double bond
<220> FEATURE:
<221> NAME/KEY: DISULFID
<222> LOCATION: (7)..(7)
<223> OTHER INFORMATION: Bound to Cys at position 7 of SEQ ID NO: 82 via
      disulfide bond to form dimer
<220> FEATURE:
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: DISULFID
<222> LOCATION: (20)..(20)
<223> OTHER INFORMATION: Bound to Cys at position 19 of SEQ ID NO: 82
      via disulfide bond to form dimer

<400> SEQUENCE: 50

Gly Ile Val Glu Gln Xaa Cys Thr Ser Ile Xaa Ser Leu Tyr Gln Leu
1               5                   10                  15

Glu Asn Tyr Cys Asp
            20

<210> SEQ ID NO 51
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is diaminosuberic acid (Das)
<220> FEATURE:
<221> NAME/KEY: MISC_FEATURE
<222> LOCATION: (1)..(6)
<223> OTHER INFORMATION: Linked via single bond
<220> FEATURE:
<221> NAME/KEY: MOD_RES
<222> LOCATION: (2)..(2)
<223> OTHER INFORMATION: Xaa is Prenylglycine (Pre)
<220> FEATURE:
<221> NAME/KEY: MOD_RES
<222> LOCATION: (6)..(6)
<223> OTHER INFORMATION: Xaa is diaminosuberic acid (Das)
<220> FEATURE:
<221> NAME/KEY: MISC_FEATURE
<222> LOCATION: (15)..(15)
<223> OTHER INFORMATION: Bound to thiol protecting group

<400> SEQUENCE: 51

Xaa Xaa Thr Ser Ile Xaa Ser Leu Tyr Gly Leu Glu Asn Tyr Cys Asn
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is diaminosuberic acid (Das)
<220> FEATURE:
<221> NAME/KEY: MISC_FEATURE
<222> LOCATION: (1)..(6)
<223> OTHER INFORMATION: Linked via single bond
<220> FEATURE:
<221> NAME/KEY: MOD_RES
```

```
<222> LOCATION: (2)..(2)
<223> OTHER INFORMATION: Xaa is Homoleucine (Hle)
<220> FEATURE:
<221> NAME/KEY: MOD_RES
<222> LOCATION: (6)..(6)
<223> OTHER INFORMATION: Xaa is diaminosuberic acid (Das)
<220> FEATURE:
<221> NAME/KEY: MISC_FEATURE
<222> LOCATION: (15)..(15)
<223> OTHER INFORMATION: Bound to thiol protecting group

<400> SEQUENCE: 52

Xaa Xaa Thr Ser Ile Xaa Ser Leu Tyr Gly Leu Glu Asn Tyr Cys Asn
1               5                   10                  15

<210> SEQ ID NO 53
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Bound to thiol protecting group
<220> FEATURE:
<221> NAME/KEY: MOD_RES
<222> LOCATION: (3)..(3)
<223> OTHER INFORMATION: Xaa is Allylglycine (Agl)

<400> SEQUENCE: 53

Gln Cys Xaa Thr
1

<210> SEQ ID NO 54
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Bound to thiol protecting group

<400> SEQUENCE: 54

Ser Ser Ile Cys
1

<210> SEQ ID NO 55
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Bound to thiol protecting group
<220> FEATURE:
<221> NAME/KEY: MOD_RES
<222> LOCATION: (3)..(3)
<223> OTHER INFORMATION: Xaa is Allylglycine (Agl)
<220> FEATURE:
<221> NAME/KEY: MISC_FEATURE
<222> LOCATION: (4)..(4)
<223> OTHER INFORMATION: Bond to 5' of SEQ ID NO: 54 to form ester

<400> SEQUENCE: 55

Gln Cys Xaa Thr
1
```

```
<210> SEQ ID NO 56
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Bound to thiol protecting group
<220> FEATURE:
<221> NAME/KEY: MOD_RES
<222> LOCATION: (3)..(3)
<223> OTHER INFORMATION: Xaa is Crotylglycine (Crt)
<220> FEATURE:
<221> NAME/KEY: MISC_FEATURE
<222> LOCATION: (4)..(4)
<223> OTHER INFORMATION: Bound to thiol protecting group

<400> SEQUENCE: 56

Gln Cys Xaa Thr
1

<210> SEQ ID NO 57
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Bound to thiol protecting group
<220> FEATURE:
<221> NAME/KEY: MOD_RES
<222> LOCATION: (3)..(3)
<223> OTHER INFORMATION: Xaa is Crotylglycine (Crt)
<220> FEATURE:
<221> NAME/KEY: MISC_FEATURE
<222> LOCATION: (4)..(4)
<223> OTHER INFORMATION: Bound to thiol protecting group
<220> FEATURE:
<221> NAME/KEY: MISC_FEATURE
<222> LOCATION: (4)..(4)
<223> OTHER INFORMATION: Bond to 5' of SEQ ID NO: 54 to form ester

<400> SEQUENCE: 57

Gln Cys Xaa Thr
1

<210> SEQ ID NO 58
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Bound to a thiol protecting group
<220> FEATURE:
<221> NAME/KEY: MOD_RES
<222> LOCATION: (3)..(3)
<223> OTHER INFORMATION: Xaa is Allylglycine (Agl)
<220> FEATURE:
<221> NAME/KEY: MISC_FEATURE
<222> LOCATION: (7)..(7)
<223> OTHER INFORMATION: Bound to a thiol protecting group

<400> SEQUENCE: 58

Gln Cys Xaa Thr Ser Ile Cys
1               5

<210> SEQ ID NO 59
```

```
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Bound to thiol protecting group
<220> FEATURE:
<221> NAME/KEY: MOD_RES
<222> LOCATION: (3)..(3)
<223> OTHER INFORMATION: Xaa is delta-4 diaminosuberic acid (Das)
<220> FEATURE:
<221> NAME/KEY: MISC_FEATURE
<222> LOCATION: (3)..(3)
<223> OTHER INFORMATION: Linked to delta-4 diaminosuberic acid (Das) via
      double bond
<220> FEATURE:
<221> NAME/KEY: MISC_FEATURE
<222> LOCATION: (7)..(7)
<223> OTHER INFORMATION: Bound to thiol protecting group

<400> SEQUENCE: 59

Gln Cys Xaa Thr Ser Ile Cys
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Xaa is Allylglycine (Agl)

<400> SEQUENCE: 60

Gln Ala Xaa Thr Ser
1               5

<210> SEQ ID NO 61
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Xaa is delta-4 diaminosuberic acid (Das)
<220> FEATURE:
<221> NAME/KEY: MISC_FEATURE
<222> LOCATION: (3)..(3)
<223> OTHER INFORMATION: Linked to delta-4 diaminosuberic acid (Das) via
      double bond

<400> SEQUENCE: 61

Gln Ala Xaa Thr Ser
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Protecting group
<220> FEATURE:
<221> NAME/KEY: MOD_RES
```

```
<222> LOCATION: (4)..(4)
<223> OTHER INFORMATION: Xaa is Allylglycine (Agl)
<220> FEATURE:
<221> NAME/KEY: MISC_FEATURE
<222> LOCATION: (6)..(6)
<223> OTHER INFORMATION: Protecting group
<220> FEATURE:
<221> NAME/KEY: MISC_FEATURE
<222> LOCATION: (7)..(7)
<223> OTHER INFORMATION: Protecting group

<400> SEQUENCE: 62

Tyr Leu Val Xaa Gly Glu Arg
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: Xaa is delta-4 diaminosuberic acid (Das)
<220> FEATURE:
<221> NAME/KEY: MISC_FEATURE
<222> LOCATION: (4)..(4)
<223> OTHER INFORMATION: Linked to delta-4 diaminosuberic acid (Das) via
      double bond

<400> SEQUENCE: 63

Tyr Leu Val Xaa Gly Glu Arg
1               5

<210> SEQ ID NO 64
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: Xaa is Allylglycine (Agl)
<220> FEATURE:
<221> NAME/KEY: MOD_RES
<222> LOCATION: (16)..(16)
<223> OTHER INFORMATION: Xaa is Allylglycine (Agl)

<400> SEQUENCE: 64

Phe Val Asn Gln His Leu Xaa Gly Pro Gly Ile Val Glu Gln Cys Xaa
1               5                   10                  15

Thr

<210> SEQ ID NO 65
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: Xaa is delta-4 diaminosuberic acid (Das)
<220> FEATURE:
<221> NAME/KEY: MISC_FEATURE
<222> LOCATION: (7)..(16)
<223> OTHER INFORMATION: Linked via double bond
<220> FEATURE:
<221> NAME/KEY: MOD_RES
<222> LOCATION: (16)..(16)
<223> OTHER INFORMATION: Xaa is delta-4 diaminosuberic acid (Das)
```

```
<400> SEQUENCE: 65

Phe Val Asn Gln His Leu Xaa Gly Pro Gly Ile Val Glu Gln Cys Xaa
1               5                   10                  15

Thr

<210> SEQ ID NO 66
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is Allylglycine (Agl)
<220> FEATURE:
<221> NAME/KEY: MOD_RES
<222> LOCATION: (10)..(10)
<223> OTHER INFORMATION: Xaa is Allylglycine (Agl)

<400> SEQUENCE: 66

Xaa Gly Pro Gly Ile Val Glu Gln Cys Xaa Thr
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is delta-4 diaminosuberic acid (Das)
<220> FEATURE:
<221> NAME/KEY: MISC_FEATURE
<222> LOCATION: (1)..(10)
<223> OTHER INFORMATION: Linked via double bond
<220> FEATURE:
<221> NAME/KEY: MOD_RES
<222> LOCATION: (10)..(10)
<223> OTHER INFORMATION: Xaa is delta-4 diaminosuberic acid (Das)

<400> SEQUENCE: 67

Xaa Gly Pro Gly Ile Val Glu Gln Cys Xaa Thr
1               5                   10

<210> SEQ ID NO 68
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: Xaa is Allylglycine (Agl)

<400> SEQUENCE: 68

Gly Ile Val Glu Gln Cys Xaa Thr Ser
1               5

<210> SEQ ID NO 69
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
```

```
<222> LOCATION: (6)..(6)
<223> OTHER INFORMATION: Xaa is Allylglycine (Agl)
<220> FEATURE:
<221> NAME/KEY: MOD_RES
<222> LOCATION: (7)..(7)
<223> OTHER INFORMATION: Xaa is Prenylglycine (Pre)
<220> FEATURE:
<221> NAME/KEY: MOD_RES
<222> LOCATION: (11)..(11)
<223> OTHER INFORMATION: Xaa is Allylglycine (Agl)

<400> SEQUENCE: 69

Gly Ile Val Glu Gln Xaa Xaa Thr Ser Ile Xaa Ser Leu Tyr Gly Leu
1               5                   10                  15

Glu Asn Tyr Cys Asn
            20

<210> SEQ ID NO 70
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via double bond
<220> FEATURE:
<221> NAME/KEY: MOD_RES
<222> LOCATION: (7)..(7)
<223> OTHER INFORMATION: Xaa is Prenylglycine (Pre)
<220> FEATURE:
<221> NAME/KEY: MISC_FEATURE
<222> LOCATION: (8)..(9)
<223> OTHER INFORMATION: Thr-pseudoproline-Ser
<220> FEATURE:
<221> NAME/KEY: MOD_RES
<222> LOCATION: (11)..(11)
<223> OTHER INFORMATION: Xaa is delta-4 diaminosuberic acid (Das)

<400> SEQUENCE: 70

Gly Ile Val Glu Gln Xaa Xaa Thr Ser Ile Xaa Ser Leu Tyr Gln Leu
1               5                   10                  15

Glu Asn Tyr Cys Asn
            20

<210> SEQ ID NO 71
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is diaminosuberic acid (Das)
<220> FEATURE:
<221> NAME/KEY: MISC_FEATURE
<222> LOCATION: (6)..(11)
<223> OTHER INFORMATION: Linked via single bond
<220> FEATURE:
<221> NAME/KEY: MOD_RES
<222> LOCATION: (7)..(7)
<223> OTHER INFORMATION: Xaa is Prenylglycine (Pre)
<220> FEATURE:
<221> NAME/KEY: MISC_FEATURE
<222> LOCATION: (8)..(9)
<223> OTHER INFORMATION: Thr-pseudoproline-Ser
<220> FEATURE:
<221> NAME/KEY: MOD_RES
```

```
<222> LOCATION: (11)..(11)
<223> OTHER INFORMATION: Xaa is diaminosuberic acid (Das)

<400> SEQUENCE: 71

Gly Ile Val Glu Gln Xaa Xaa Thr Ser Ile Xaa Ser Leu Tyr Gln Leu
1               5                   10                  15

Glu Asn Tyr Cys Asn
            20

<210> SEQ ID NO 72
<211> LENGTH: 21
<212> TYPE: PRT
<213> ORGANISM: Homo sapiens

<400> SEQUENCE: 72

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 73
<211> LENGTH: 21
<212> TYPE: PRT
<213> ORGANISM: Bos taurus

<400> SEQUENCE: 73

Gly Ile Val Glu Gln Cys Cys Ala Ser Val Cys Ser Leu Tyr Gln Leu
1               5                   10                  15

Glu Asn Tyr Cys Asn
            20

<210> SEQ ID NO 74
<211> LENGTH: 21
<212> TYPE: PRT
<213> ORGANISM: Sus scrofa

<400> SEQUENCE: 74

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 75
<211> LENGTH: 21
<212> TYPE: PRT
<213> ORGANISM: Erethizon dorsatum

<400> SEQUENCE: 75

Gly Ile Val Asp Gln Cys Cys Thr Gly Val Cys Ser Leu Tyr Gln Leu
1               5                   10                  15

Gln Asn Tyr Cys Asn
            20

<210> SEQ ID NO 76
<211> LENGTH: 30
<212> TYPE: PRT
<213> ORGANISM: Homo sapiens

<400> SEQUENCE: 76

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

```
<210> SEQ ID NO 77
<211> LENGTH: 30
<212> TYPE: PRT
<213> ORGANISM: Bos taurus

<400> SEQUENCE: 77

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala
            20                  25                  30

<210> SEQ ID NO 78
<211> LENGTH: 30
<212> TYPE: PRT
<213> ORGANISM: Sus scrofa

<400> SEQUENCE: 78

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala
            20                  25                  30

<210> SEQ ID NO 79
<211> LENGTH: 30
<212> TYPE: PRT
<213> ORGANISM: Erethizon dorsatum

<400> SEQUENCE: 79

Phe Val Asn Gln His Leu Cys Gly Ser His Leu Val Glu Ala Leu Tyr
1               5                   10                  15

Asn Asp Cys Gly Asn Asp Gly Phe Phe Tyr Arg Pro Lys Thr
            20                  25                  30

<210> SEQ ID NO 80
<211> LENGTH: 21
<212> TYPE: PRT
<213> ORGANISM: Homo sapiens
<220> FEATURE:
<221> NAME/KEY: DISULFID
<222> LOCATION: (6)..(11)
<223> OTHER INFORMATION: Linked via disulfide bond

<400> SEQUENCE: 80

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 81
<211> LENGTH: 30
<212> TYPE: PRT
<213> ORGANISM: Homo sapiens

<400> SEQUENCE: 81

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 82
<211> LENGTH: 30
<212> TYPE: PRT
<213> ORGANISM: Artificial Sequence
```

```
<220> FEATURE:
<223> OTHER INFORMATION: Synthetic polypeptide

<400> SEQUENCE: 82

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 83
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 83

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30

<210> SEQ ID NO 84
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 84

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Glu Thr
            20                  25                  30

<210> SEQ ID NO 85
<211> LENGTH: 21
<212> TYPE: PRT
<213> ORGANISM: Homo sapiens
<220> FEATURE:
<221> NAME/KEY: DISULFID
<222> LOCATION: (6)..(6)
<223> OTHER INFORMATION: Linked via disulfide bond
<220> FEATURE:
<221> NAME/KEY: DISULFID
<222> LOCATION: (7)..(7)
<223> OTHER INFORMATION: Bound to Cys at position 7 of SEQ ID NO: 81 via
      disulfide bond to form dimer
<220> FEATURE:
<221> NAME/KEY: DISULFID
<222> LOCATION: (20)..(20)
<223> OTHER INFORMATION: Bound to Cys at position 19 of SEQ ID NO: 81
      via disulfide bond to form dimer

<400> SEQUENCE: 85

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 86
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: DISULFID
```

```
<222> LOCATION: (6)..(6)
<223> OTHER INFORMATION: Linked via disulfide bond
<220> FEATURE:
<221> NAME/KEY: DISULFID
<222> LOCATION: (7)..(7)
<223> OTHER INFORMATION: Bound to Cys at position 7 of SEQ ID NO: 82 via
      disulfide bond to form dimer
<220> FEATURE:
<221> NAME/KEY: DISULFID
<222> LOCATION: (20)..(20)
<223> OTHER INFORMATION: Bound to Cys at position 19 of SEQ ID NO: 82
      via disulfide bond to form dimer

<400> SEQUENCE: 86

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 87
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: DISULFID
<222> LOCATION: (6)..(6)
<223> OTHER INFORMATION: Linked via disulfide bond
<220> FEATURE:
<221> NAME/KEY: DISULFID
<222> LOCATION: (7)..(7)
<223> OTHER INFORMATION: Bound to Cys at position 7 of SEQ ID NO: 83 via
      disulfide bond to form dimer
<220> FEATURE:
<221> NAME/KEY: DISULFID
<222> LOCATION: (20)..(20)
<223> OTHER INFORMATION: Bound to Cys at position 19 of SEQ ID NO: 83
      via disulfide bond to form dimer

<400> SEQUENCE: 87

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 88
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: DISULFID
<222> LOCATION: (6)..(6)
<223> OTHER INFORMATION: Linked via disulfide bond
<220> FEATURE:
<221> NAME/KEY: DISULFID
<222> LOCATION: (7)..(7)
<223> OTHER INFORMATION: Bound to Cys at position 7 of SEQ ID NO: 84 via
      disulfide bond to form dimer
<220> FEATURE:
<221> NAME/KEY: DISULFID
<222> LOCATION: (20)..(20)
<223> OTHER INFORMATION: Bound to Cys at position 19 of SEQ ID NO: 84
      via disulfide bond to form dimer

<400> SEQUENCE: 88

Gly Ile Val Glu Gln Cys Cys Thr Ser Ile Cys Ser Leu Tyr Gln Leu
1               5                   10                  15

Glu Asn Tyr Cys Asn
            20
```

```
<210> SEQ ID NO 89
<211> LENGTH: 21
<212> TYPE: PRT
<213> ORGANISM: Homo sapiens
<220> FEATURE:
<221> NAME/KEY: DISULFID
<222> LOCATION: (6)..(11)
<223> OTHER INFORMATION: Linked via disulfide bond

<400> SEQUENCE: 89

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 90
<211> LENGTH: 32
<212> TYPE: PRT
<213> ORGANISM: Homo sapiens

<400> SEQUENCE: 90

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 91
<211> LENGTH: 21
<212> TYPE: PRT
<213> ORGANISM: Homo sapiens
<220> FEATURE:
<221> NAME/KEY: DISULFID
<222> LOCATION: (6)..(6)
<223> OTHER INFORMATION: Linked via disulfide bond
<220> FEATURE:
<221> NAME/KEY: DISULFID
<222> LOCATION: (7)..(7)
<223> OTHER INFORMATION: Bound to Cys at position 7 of SEQ ID NO: 90 via
      disulfide bond to form dimer
<220> FEATURE:
<221> NAME/KEY: DISULFID
<222> LOCATION: (20)..(20)
<223> OTHER INFORMATION: Bound to Cys at position 19 of SEQ ID NO: 90
      via disulfide bond to form dimer

<400> SEQUENCE: 91

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 92
<211> LENGTH: 30
<212> TYPE: PRT
<213> ORGANISM: Homo sapiens
<220> FEATURE:
<221> NAME/KEY: MOD_RES
<222> LOCATION: (29)..(29)
<223> OTHER INFORMATION: Lys acylated with C14 fatty acid

<400> SEQUENCE: 92

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

```
<210> SEQ ID NO 93
<211> LENGTH: 21
<212> TYPE: PRT
<213> ORGANISM: Homo sapiens
<220> FEATURE:
<221> NAME/KEY: DISULFID
<222> LOCATION: (6)..(6)
<223> OTHER INFORMATION: Linked via disulfide bond
<220> FEATURE:
<221> NAME/KEY: DISULFID
<222> LOCATION: (7)..(7)
<223> OTHER INFORMATION: Bound to Cys at position 7 of SEQ ID NO: 92 via
      disulfide bond to form dimer
<220> FEATURE:
<221> NAME/KEY: DISULFID
<222> LOCATION: (20)..(20)
<223> OTHER INFORMATION: Bound to Cys at position 19 of SEQ ID NO:92 via
      disulfide bond to form dimer

<400> SEQUENCE: 93

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 94
<211> LENGTH: 30
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Xaa is Allylglycine (Agl)
<220> FEATURE:
<221> NAME/KEY: MISC_FEATURE
<222> LOCATION: (9)..(9)
<223> OTHER INFORMATION: Xaa is Pro or hydroxy-6-nitrobenzaldehyde (HnB)
<220> FEATURE:
<221> NAME/KEY: MOD_RES
<222> LOCATION: (16)..(16)
<223> OTHER INFORMATION: Xaa is Allylglycine (Agl)

<400> SEQUENCE: 94

Phe Val Asn Gln His Leu Xaa Gly Xaa Gly Ile Val Glu Gln Cys Xaa
1               5                   10                  15

Thr Ser Ile Cys Ser Leu Tyr Gln Leu Glu Asn Tyr Cys Asn
            20                  25                  30

<210> SEQ ID NO 95
<211> LENGTH: 30
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Xaa is delta-4 diaminosuberic acid (Das)
<220> FEATURE:
<221> NAME/KEY: MISC_FEATURE
<222> LOCATION: (7)..(16)
<223> OTHER INFORMATION: Linked via double bond
<220> FEATURE:
<221> NAME/KEY: MOD_RES
<222> LOCATION: (16)..(16)
<223> OTHER INFORMATION: Xaa is delta-4 diaminosuberic acid (Das)

<400> SEQUENCE: 95

Phe Val Asn Gln His Leu Xaa Gly Xaa Gly Ile Val Glu Gln Cys Xaa
1               5                   10                  15

Thr Ser Ile Cys Ser Leu Tyr Gln Leu Glu Asn Tyr Cys Asn
            20                  25                  30
```

```
<210> SEQ ID NO 96
<211> LENGTH: 21
<212> TYPE: PRT
<213> ORGANISM: Homo sapiens

<400> SEQUENCE: 96

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 97
<211> LENGTH: 8
<212> TYPE: PRT
<213> ORGANISM: Homo sapiens

<400> SEQUENCE: 97

Phe Val Asn Gln His Leu Cys Gly
1               5

<210> SEQ ID NO 98
<211> LENGTH: 21
<212> TYPE: PRT
<213> ORGANISM: Homo sapiens
<220> FEATURE:
<221> NAME/KEY: DISULFID
<222> LOCATION: (7)..(7)
<223> OTHER INFORMATION: Bound to Cys at position 7 of SEQ ID NO: 97 via
      disulfide bond to form dimer

<400> SEQUENCE: 98

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 99
<211> LENGTH: 30
<212> TYPE: PRT
<213> ORGANISM: Artificial Sequence
<220> FEATURE:
<223> OTHER INFORMATION: Synthetic peptide

<400> SEQUENCE: 99

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 100
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via double bond
<220> FEATURE:
<221> NAME/KEY: DISULFID
<222> LOCATION: (7)..(7)
<223> OTHER INFORMATION: Bound to Cys at position 7 of SEQ ID NO: 99 via
      disulfide bond to form dimer
<220> FEATURE:
```

```
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: DISULFID
<222> LOCATION: (20)..(20)
<223> OTHER INFORMATION: Bound to Cys at position 19 of SEQ ID NO: 99
      via disulfide bond to form dimer

<400> SEQUENCE: 100

Gly Ile Val Glu Gln Xaa Cys Thr Ser Ile Xaa Ser Leu Tyr Gln Leu
1               5                   10                  15

Glu Asn Tyr Cys Asn
            20

<210> SEQ ID NO 101
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (19)..(19)
<223> OTHER INFORMATION: Bound to thiol protecting group

<400> SEQUENCE: 101

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 102
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via double bond
<220> FEATURE:
<221> NAME/KEY: DISULFID
<222> LOCATION: (7)..(7)
<223> OTHER INFORMATION: Bound to Cys at position 7 of SEQ ID NO: 101
      via disulfide bond to form dimer
<220> FEATURE:
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: MISC_FEATURE
<222> LOCATION: (20)..(20)
<223> OTHER INFORMATION: Bound to thiol protecting group

<400> SEQUENCE: 102

Gly Ile Val Glu Gln Xaa Cys Thr Ser Ile Xaa Ser Leu Tyr Gln Leu
1               5                   10                  15

Glu Asn Tyr Cys Asn
            20

<210> SEQ ID NO 103
<211> LENGTH: 32
<212> TYPE: PRT
<213> ORGANISM: Artificial Sequence
<220> FEATURE:
```

-continued

<223> OTHER INFORMATION: Synthetic peptide

<400> SEQUENCE: 103

Phe Val Asn Gln His Leu Cys Gly Ser Asp Leu Val Glu Ala Leu Tyr
1               5                   10                  15
Leu Val Cys Gly Glu Arg Gly Phe Phe Tyr Thr Pro Lys Thr Arg Arg
            20                  25                  30

<210> SEQ ID NO 104
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (19)..(19)
<223> OTHER INFORMATION: Bound to thiol protecting group

<400> SEQUENCE: 104

Phe Val Asn Gln His Leu Cys Gly Ser His Leu Val Glu Ala Leu Tyr
1               5                   10                  15
Leu Val Cys Gly Glu Arg Gly Phe Phe Tyr Thr Lys Pro Thr
            20                  25                  30

<210> SEQ ID NO 105
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via double bond
<220> FEATURE:
<221> NAME/KEY: DISULFID
<222> LOCATION: (7)..(7)
<223> OTHER INFORMATION: Bound to Cys at position 7 of SEQ ID NO: 104
      via disulfide bond to form dimer
<220> FEATURE:
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: MISC_FEATURE
<222> LOCATION: (20)..(20)
<223> OTHER INFORMATION: Bound to thiol protecting group

<400> SEQUENCE: 105

Gly Ile Val Glu Gln Xaa Cys Thr Ser Ile Xaa Ser Leu Tyr Gln Leu
1               5                   10                  15
Glu Asn Tyr Cys Asn
            20

<210> SEQ ID NO 106
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE

```
<222> LOCATION: (6)..(11)
<223> OTHER INFORMATION: Linked via double bond
<220> FEATURE:
<221> NAME/KEY: DISULFID
<222> LOCATION: (7)..(7)
<223> OTHER INFORMATION: Bound to Cys at position 7 of SEQ ID NO: 110
      via disulfide bond to form dimer
<220> FEATURE:
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: DISULFID
<222> LOCATION: (20)..(20)
<223> OTHER INFORMATION: Bound to Cys at position 20 of SEQ ID NO: 110
      via disulfide bond to form dimer

<400> SEQUENCE: 106

Gly Ile Val Glu Gln Xaa Cys Thr Ser Ile Xaa Ser Leu Tyr Gln Leu
1               5                   10                  15

Glu Asn Tyr Cys Gly
            20

<210> SEQ ID NO 107
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via double bond
<220> FEATURE:
<221> NAME/KEY: DISULFID
<222> LOCATION: (7)..(7)
<223> OTHER INFORMATION: Bound to Cys at position 7 of SEQ ID NO: 82 via
      disulfide bond to form dimer
<220> FEATURE:
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: DISULFID
<222> LOCATION: (20)..(20)
<223> OTHER INFORMATION: Bound to Cys at position 19 of SEQ ID NO: 82
      via disulfide bond to form dimer

<400> SEQUENCE: 107

Gly Ile Val Glu Gln Xaa Cys Thr Ser Ile Xaa Ser Leu Tyr Gln Leu
1               5                   10                  15

Glu Asn Tyr Cys Asn
            20

<210> SEQ ID NO 108
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via double bond
<220> FEATURE:
<221> NAME/KEY: DISULFID
```

```
<222> LOCATION: (7)..(7)
<223> OTHER INFORMATION: Bound to Cys at position 7 of SEQ ID NO: 3 via
      disulfide bond to form dimer
<220> FEATURE:
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: MISC_FEATURE
<222> LOCATION: (20)..(20)
<223> OTHER INFORMATION: Bound to thiol protecting group

<400> SEQUENCE: 108

Gly Ile Val Glu Gln Xaa Cys Thr Ser Ile Xaa Ser Leu Tyr Gln Leu
1               5                   10                  15

Glu Asn Tyr Cys Asp
            20

<210> SEQ ID NO 109
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via double bond
<220> FEATURE:
<221> NAME/KEY: DISULFID
<222> LOCATION: (7)..(7)
<223> OTHER INFORMATION: Bound to Cys at position 7 of SEQ ID NO: 112
      via disulfide bond to form dimer
<220> FEATURE:
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: DISULFID
<222> LOCATION: (20)..(20)
<223> OTHER INFORMATION: Bound to Cys at position 19 of SEQ ID NO: 112
      via disulfide bond to form dimer

<400> SEQUENCE: 109

Gly Ile Val Glu Gln Xaa Cys Thr Ser Ile Xaa Ser Leu Tyr Gln Leu
1               5                   10                  15

Glu Asn Tyr Cys Asp
            20

<210> SEQ ID NO 110
<211> LENGTH: 32
<212> TYPE: PRT
<213> ORGANISM: Artificial Sequence
<220> FEATURE:
<223> OTHER INFORMATION: Synthetic peptide

<400> SEQUENCE: 110

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 111
<211> LENGTH: 21
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MOD_RES
<222> LOCATION: (6)..(6)
<223> OTHER INFORMATION: Xaa is delta-4 diaminosuberic acid (Das)
<220> FEATURE:
<221> NAME/KEY: MISC_FEATURE
<222> LOCATION: (6)..(11)
<223> OTHER INFORMATION: Linked via double bond
<220> FEATURE:
<221> NAME/KEY: DISULFID
<222> LOCATION: (7)..(7)
<223> OTHER INFORMATION: Bound to Cys at position 7 of SEQ ID NO: 110
      via disulfide bond to form dimer
<220> FEATURE:
<221> NAME/KEY: MOD_RES
<222> LOCATION: (11)..(11)
<223> OTHER INFORMATION: Xaa is delta-4 diaminosuberic acid (Das)
<220> FEATURE:
<221> NAME/KEY: DISULFID
<222> LOCATION: (20)..(20)
<223> OTHER INFORMATION: Bound to Cys at position 20 of SEQ ID NO: 110
      via disulfide bond to form dimer

<400> SEQUENCE: 111

Gly Ile Val Glu Gln Xaa Cys Thr Ser Ile Xaa Ser Leu Tyr Gln Leu
1               5                   10                  15

Glu Asn Tyr Cys Gly
            20

<210> SEQ ID NO 112
<211> LENGTH: 30
<212> TYPE: PRT
<213> ORGANISM: Artificial Sequence
<220> FEATURE:
<223> OTHER INFORMATION: Synthetic peptide

<400> SEQUENCE: 112

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

INSULIN ANALOGUES

CROSS REFERENCE TO RELATED APPLICATION

This application is the U.S. national phase of International Application No. PCT/AU2011/000614, filed 25 May 2011, incorporated herein by reference, which claims priority benefit of U.S. Provisional Application Nos. 61/348,085, 61/348,065, and 61/348,045, all filed 25 May 2010.

FIELD OF THE INVENTION

The present application broadly relates to insulin analogues, and methods for the synthesis of these analogues, including dicarba-disulfide bridge-containing insulin analogues.

BACKGROUND TO THE INVENTION

Diabetes is a chronic disease characterised by the onset of hyperglycaemia. This metabolic disorder arises either upon failure of the pancreas to secrete effective concentrations of insulin in the case of type 1 diabetes, or as a result of a build up of resistance by cells towards any bio-available insulin (type 2). Insulin is a peptidic hormone required by the body to transport glucose from the bloodstream to cells for energy. Failure of its production or effective use results in impaired glucose metabolism, and thus allows abnormally high quantities of this sugar to accumulate in the blood. In 2003, international surveys showed 194 million people have diabetes, and it is widely considered to be the world's fastest growing disease. Over one million Australians suffer from this disorder and it is Australia's sixth leading cause of death. These figures are cause for concern and unfortunately at present there is no cure. Diabetes is however manageable, but treatments such as insulin injections must be carried out everyday over a patient's lifetime after diagnosis, to allow a healthy and fulfilling life.

Discovery and isolation of the insulin molecule by Fredrick Banting and Charles Best in 1921 provided a significant breakthrough for those suffering diabetes, whose treatments until this time included only starvation diets. Medical benefits aside, scientists found insulin to be a fascinating molecule. It was the first protein to have its primary structure elucidated, and was the focal point of many Nobel Prize winning research projects. Knowledge of the key molecular determinants of insulin function is important not only for examining the downstream pathways leading to its physiological effects but also the development of new clinical compounds and biochemical/pharmacological probes. Despite the fact that nearly 85 years have passed since insulin was first isolated and 35 years since its structure was determined by X-ray crystallography, a high resolution, three dimensional structure of the insulin-receptor complex is still unavailable. Consequently, several key aspects of insulin's biochemistry remain to be discovered and understood. Recent studies using synthetic insulin analogues support the concept that insulin binds asymmetrically to two discrete sites within the receptor dimer, however, the biologically active conformation of the insulin molecule, complete structural features that constitute the receptor-binding domain, and the mechanism of insulin receptor activation, remain unknown.

The insulin receptor is a tetrameric integral membrane glycoprotein consisting of two 735 amino acid α-chains and two 620 amino acid β-chains. The α-chain resides on the extracellular side of the plasma membrane and contains the cysteine-rich insulin binding domain. Covalent insulin-receptor complexes have been isolated, however, the exact nature of this molecular interaction has yet to be fully elucidated. Insulin is firstly synthesised as a pre-prohormone precursor containing signal peptide-B-C-A domains. Mature insulin, however, consists of a 51 residue A-B heterodimer that is covalently linked by two interchain disulfide bonds. An intrachain disulfide bridge is also located within the insulin A-chain. The circulating and biologically active form of insulin is monomeric and its primary structure has been determined for at least 100 vertebrate species (FIG. 1). Of these, only six cysteine residues and ten other amino acids are fully conserved during evolution. The primary structure of insulin from several species is shown in FIG. 1. Invariance of these residues may be indicative of their key roles in receptor binding and/or maintaining a biologically active conformation.

Disulfide bonds serve structural and functional roles in peptides. In some peptides, the disulfide is involved in disulfide exchange chemistry at the receptor resulting in activation of receptors and downstream signaling. Yet in other peptides, the S—S motif serves only to preserve and/or create a bioactive conformation of the peptide. In such cases, chemistry can be used to replace the native disulfide with other bridging amino acid residues. Structural alteration will be well tolerated if key receptor interactions can be preserved and this will depend on the surrogate motif's ability to replicate native peptide tertiary and secondary structure. The role of each of insulin's disulfide bridges is currently unknown but it is highly likely that they play a key role in regulating insulin's function at its cell surface tyrosine kinase receptors. Invariance of the cysteine residues across the species highlights the importance of the S—S bridges to insulin's structure and function. The cystine framework found in insulin is also found in other so called 'insulin superfamily' molecules, e.g. relaxin. Despite their framework similarity to insulin, however, the relaxins bind and activate a different receptor, the G-protein coupled receptor, and are responsible for remarkably distinctive biological roles. Hence, nature has capitalized on a generic disulfide template to perform diverse neuroendocrine through to homeostasis roles.

Problems with insulin as a drug still exist and improved analogues are continually being sought. For example, insulin can only be taken by injection, as oral delivery results in protein cleavage by digestive enzymes before it can be absorbed into the bloodstream. In addition, insulin is generally refrigerated before use so that it does not degrade before it is injected. There is therefore a need for insulin analogues which display enhanced stability to proteolyic enzymes and those which can be stored at room temperature to facilitate transport and simplify storage.

Several studies have been conducted to determine the role of disulfide bonds in insulin and all have concluded that each cystine bridge, to varying degrees, is required to maintain biological function. In previous studies, however, cysteine residues have been replaced by non-bridging amino acids such as alanine and serine via site-directed mutagenesis. Previous research is difficult to analyse, since loss of biological activity cannot be unambiguously attributed to either unfolded protein structure and hence loss of a binding domain, or loss of a reactive disulfide motif. There is therefore a need to further investigate the role of the disulfide bonds in insulin.

Although insulin therapy provides a better quality of life for those afflicted with diabetes, it also remains a difficult drug to use. A narrow therapeutic index, inconsistent magnitude of effect, poor oral availability, weight gain, poor stability and limited potency are just of some of insulin's many limitations. Each of these make it very difficult for a diabetic patient to treat their disease and maintain the tightly regulated glucose concentrations of a healthy individual. The achievement of a "normal" 24 hour physiological insulin profile is nearly impossible to mimic. The nature of meals, exercise regimes, sleeping patterns, development of infections and endogenous production of glucose of the liver, are just some of the many causes of fluctuation in blood glucose levels. It is essential that basal insulin levels are maintained in the body 24 hours a day, but additionally extra supplies (bolus) are needed for the management of glucose ingested at meal times. Unfortunately, however, the ideal therapeutic window for insulin dosing is very narrow (4-6 mmol), and one of the major drawbacks of intensive insulin treatments is the potential for hyperglycaemic events (low blood sugar levels). The advent of recombinant access to insulin in the early 1980s, led to the development of analogues that are specifically engineered to accomplish slower, faster and more predictable activity profiles that help with timing, dosing and the maintenance of more stable physiological insulin levels (FIGS. 2A and 2B). Existing insulin analogues still, however, suffer from storage and stability problems.

Although there are a number of commerically available analogues of insulin, there is still a considerable desire to improve basal insulin treatments. This is partly because some of these existing analgoues have significant drawbacks. For example, some show enhanced IGF-1 (insulin-like growth factor 1) receptor binding activity which can result in enhanced mitogenic potency. Other analogues possess reduced potency in vivo. Accordingly, there is a need for insulin analogues with superior therapeutic profiles, as well as analogues which are able to retain all of the beneficial properties of the unmodified native insulin sequence while addressing the inherent physicochemical instability.

SUMMARY OF THE INVENTION

This application relates to a range of new insulin derivatives and methods for the synthesis of these analogues, including dicarba-disulfide bridge-containing insulin analogues.

The dicarba insulin analogues described herein display unrivalled biological activity and formulation stability. Several of the analogues show equipotent binding in competitive insulin binding studies at the insulin receptor (e.g. FIG. 4A) and excellent activity in phosphorylation studies at the insulin receptor (e.g. FIG. 4B). The analogues are also equipotent in stimulating glucose uptake in differentiated L6 GLUT4-myc cells (FIG. 7) and are also active in in vivo glucose uptake tests where some dicarba analogues lowered blood glucose levels over a 2 hour time period with a profile equivalent to Actrapid (FIG. 8). Significantly however, many of the dicarba analogues showed significantly less binding affinity for the IGF receptor compared to IGF and insulin (FIG. 5A). A study evaluating DNA stimulation by the dicarba analogues (FIG. 5B), a measure of mitogenic activity, showed significantly reduced activity as compared to insulin itself. It has been suggested that insulin analogues causing excess stimulation of the IGF-1 receptor (e.g. glargine) have the potential for promoting mitogenic effects and hence may increase the risk of cancer in insulin users. More significantly, the dicarba insulin analogues also display remarkable stability at room temperature. Cystine replacement with a dicarba bridge provides molecules which do not need to be refrigerated to preserve biological activity and potency. Thermally stable insulins are in great demand for the effective management of diabetic patients in remote and third world countries.

According to one embodiment, there is provided a dicarba analogue of insulin comprising an A-chain and a B-chain or fragments, salts, solvates, derivatives, isomers or tautomers of the A-chain, the B-chain or both, provided that the dicarba analogue is not A7, B7-(2,7-diaminosuberoyl]-des-(B26-B30)-insulin B25-amide.

Preferably, the dicarba analogue of insulin includes an intrachain or an interchain dicarba bridge. It is also preferred that the dicarba bridge is unsaturated.

The only previous study in relation to a dicarba analogues of insulin attempted to replace the A7-B7-disulfide bridge with a dicarba isostere, (S,S)-2,7-diaminosuberic acid, by solution phase convergent synthesis of four separate peptide fragments: A1-6, A8-21, B9-25 and a B1-8 fragment containing a preformed, orthogonally protected, 2,7-diaminosuberic acid unit at the B7 position. This study produced a truncated insulin molecule (46 residues, native insulin has 51 residues) as an unresolvable product which was cited to contain the target analogue 'in only a small amount'. Although the analogue mixture exhibited some biological activity, it was not possible to predict the intrinsic activity of this dicarba insulin. The fraction containing the postulated truncated and saturated dicarba-A7-B7-insulin molecule was subjected to receptor binding on cultured human lymphocytes. Relative binding affinity was determined to be 0.1% of human insulin. The crude, truncated and saturated dicarba-A7-B7-insulin preparation was also tested for insulin activity via lipogenesis in isolated rat adipocytes where it was found to possess an $ED_{50}$ of $4.8 \times 10^{-9}$M: The relative potency was quoted as 0.66% on a molar, and 0.72% on a weight basis, compared to human insulin.

A "dicarba analogue" refers to a peptide which contains an amino acid sequence corresponding to a naturally occurring, native or synthetic insulin, but containing at least one dicarba bridge either as an addition to the peptide, or as a substitution for one or more of the bridged cystine-amino acid residue pairs.

"Dicarba-substituted" analogues, which are analogues of naturally-occurring, native or synthetic insulins, but with one or more of the disulfide bridge forming cystine amino acid residue pairs, are a subclass of particular interest. A notable subclass of the dicarba analogues are the mono-dicarba analogues (which retain one or more of the disulfide bridges), and the bis- and higher dicarba analogues of insulin.

The present invention also relates to methods for the synthesis of these dicarba insulin analogues.

According to one embodiment, there is provided a method for the synthesis of a dicarba analogue of insulin comprising an A-chain and a B-chain or fragments, salts, solvates, derivatives, isomers or tautomers of the A-chain, the B-chain or both, the method comprising:

(i) providing the A-chain having at least one pair of complementary metathesisable groups;

(ii) subjecting the A-chain to metathesis to form at least one dicarba bridge between the pair of complementary metathesisable groups; and (iii) adding the B-chain.

The phrase "adding the B-chain" is taken to refer to any means by which the B-chain of insulin or a fragment, salt, solvate, derivative, isomer or tautomer thereof may be combined with the A-chain.

According to another embodiment, there is provided a method for the synthesis of a dicarba analogue of insulin comprising an A-chain and a B-chain or fragments, salts, solvates, derivatives, isomers or tautomers of the A-chain, the B-chain or both, the method comprising:

(i) providing part of the A-chain having at least two complementary metathesisable groups;

(ii) subjecting the A-chain to metathesis to form at least one dicarba bridge; and (iii) adding one or more further amino acids to one or both ends of the A-chain; and (iv) adding the B-chain.

According to a further embodiment, there is provided a method for the synthesis of a dicarba analogue of insulin comprising an A-chain and a B-chain or fragments, salts, solvates, derivatives, isomers or tautomers of the A-chain, the B-chain or both, the method comprising:

(i) providing a part of the A-chain and/or a part of the B-chain having at least two complementary metathesisable groups between them;

(ii) subjecting the A-chain and the B-chain to metathesis to form at least one dicarba bridge; and (iii) adding one or more further amino acids to one or both ends of the A-chain and/or B-chain.

According to yet a further embodiment, there is provided a method for the synthesis of a dicarba analogue of insulin comprising an A-chain and a B-chain or fragments, salts, solvates, derivatives, isomers or tautomers of the A-chain, the B-chain or both, the method comprising:

(i) providing a reactable peptide comprising a removable tether between the A-chain and the B-chain, the A-chain and the B-chain each having at least one complementary metathesisable group;

(ii) subjecting the reactable peptide to metathesis to form at least one dicarba bridge between the complementary metathesisable groups; and (iii) removing the removeable tether to produce a dicarba bridge linking the A-chain and the B-chain of insulin.

The method may also be used to include a second dicarba bridge. This may be achieved by any of the methods described above, wherein further complementary metathesisable groups are provided in the A-chain and/or the B-chain, and the method comprises subjecting the peptide to a further metathesis step to form a further dicarba bridge between the complementary metathesisable groups.

The present invention further provides an anti-hyperglycemic agent comprising a dicarba analogue of insulin or a fragment, salt, solvate, derivative, isomer or tautomer thereof, as defined above.

The dicarba analogue of insulin may be provided as a pharmaceutical composition together with a pharmaceutically acceptable carrier.

The dicarba analogue of insulin may also be used to reduce hypoglycemia, or for the treatment of diabetes mellitus or metabolic syndrome.

BRIEF DESCRIPTION OF THE FIGURES

FIG. 1 is a schematic diagram showing the primary structure of insulin A chain (Human (SEQ ID NO: 72), Bovine (SEQ ID NO: 73), Porcine (SEQ ID NO: 74) and Porcupine (SEQ ID NO: 75)) and B chain (Human (SEQ ID NO: 76), Bovine (SEQ ID NO: 77), Porcine (SEQ ID NO: 78) and Porcupine (SEQ ID NO: 79)) from several species. Invariant residues are shaded grey with the cysteine residues coloured dark grey.

DETAILED DESCRIPTION OF THE INVENTION

Figure 2A:
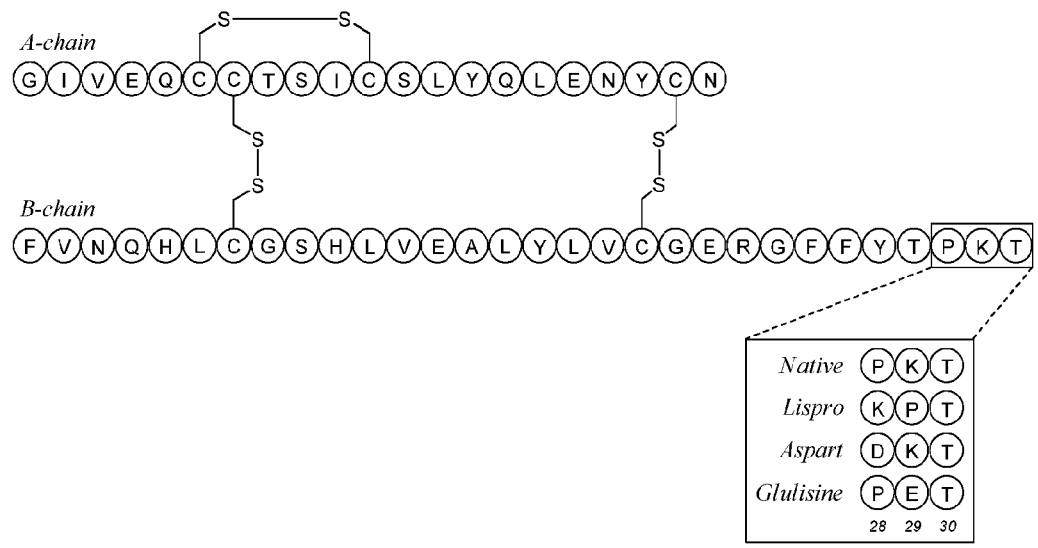
FIG. 2A is a schematic diagram showing the A-chain and the B-chain of human insulin (SEQ ID NO: 85) and the disulfide bridges present in human insulin compared to rapid acting insulin analogues, lispro (SEQ ID NO: 86), apart (SEQ ID NO: 87), and glulisine (SEQ ID NO: 88).

As described above, this application relates to insulin analogues, and methods for the synthesis of these analogues, including dicarba-disulfide bridge-containing peptides.

Insulin and Dicarba Analogues of Insulin

The term "insulin" as used herein is used in it broadest sense, and encompasses: (i) the peptide or peptide fragments that are produced in the islets of Langerhans in the pancreas, (ii) peptide or peptide fragments that are produced in the islets of Langerhans in the pancreas or analogues thereof which can be used in the treatment of diabetes mellitus, (iii) naturally-occurring or native human insulin, (iv) naturally-occurring or native insulin derived from non-human organisms, such as for example bovine or porcine insulin, (v) any insulin that is homologous to human, bovine or porcine insulin, (vi) insulin extracted from bovine and/or porcine sources, (vii) synthetically produced insulin, (viii) recombinantly produced insulin, and mixtures of any of these insulin products. The term insulin is also intended to encompass a fragment thereof, which may be one of the A-chain or the B-chain, both the A-chain and the B-chain or any truncation of the A-chain and/or the B-chain. The term insulin also includes an insulin which may include additional amino acid residues on the N- or C-terminus of either the A-chain or the B-chain. The term insulin is also intended to encompass the polypeptide normally used in the treatment of diabetes in a substantially purified form but encompasses the use of the polypeptide in its commercially available pharmaceutical form, which includes additional excipients. The term insulin also includes insulin analogues or derivatives of insulin. Examples of insulin analogues include rapid-acting and slow-acting insulins.

The term "dicarba analogue of insulin" or "dicarba insulin" or "dicarba insulin analogue" as used herein is intended to encompass any form of "insulin" as defined above, which shares a common functional activity with insulin itself and typically shares common structural features as well and which contains a dicarba bridge either as an addition to the peptide or as a substitution for one or more of the bridged cystine-amino acid residue pairs. The "dicarba analogue of insulin" encompasses any form of "insulin" as defined above, in which two or more amino acids are replaced by residues which form a dicarba bridge. Preferably, the dicarba bridge or bridges replace structural features present in the native insilun peptide. "Dicarba-substituted" analogues of insulin are analogues of insulin in which with one or more of the disulfide bridge forming cystine amino acid residue pairs are replaced by a dicarba bridge. Such analogues are a subclass of particular interest.

The dicarba bridge may replace one or more of the disulfide bridges located on the A- and/or B-chain of insulin or salt bridges or non-covalent interactions which contribute to the structure of native insulin. The dicarba bridge may be an intrachain dicarba bridge located in the A-chain of insulin and/or an interchain dicarba bridge linking the A-chain and the B-chain of insulin. A notable subclass of the dicarba analogues are the mono-dicarba analogues, and the bis- and higher dicarba analogues.

The Molecular Nature of Insulin

Without synthetic modifications, the insulin monomer exists as a small globular protein comprising two separate chains, the A and the B chain. In humans, these polypeptides are composed of 21 and 30 amino acids, respectively. The main structural features of this molecule include three α-helices over residues A2-A8, A13-A19 and B9-B19, a hydrophobic core and a primarily polar outer surface with two hydrophobic faces. At micromolar concentrations insulin dimerises, and further associates into hexamers in the presence of zinc ions, to bury the hydrophobic faces. Studies have shown that these hydrophobic chain portions are essential for receptor binding, hence monomeric insulin is the circulating and biologically active form of the molecule.

Figure 1:
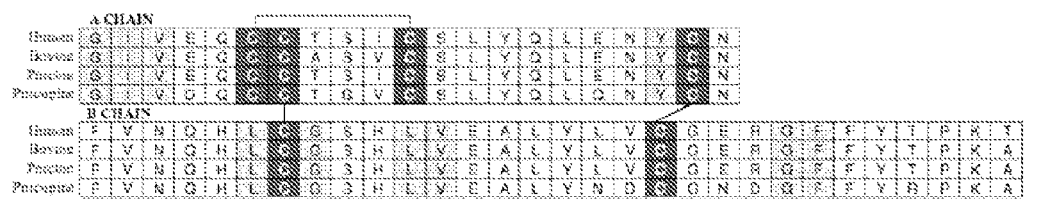
Figure 2B:
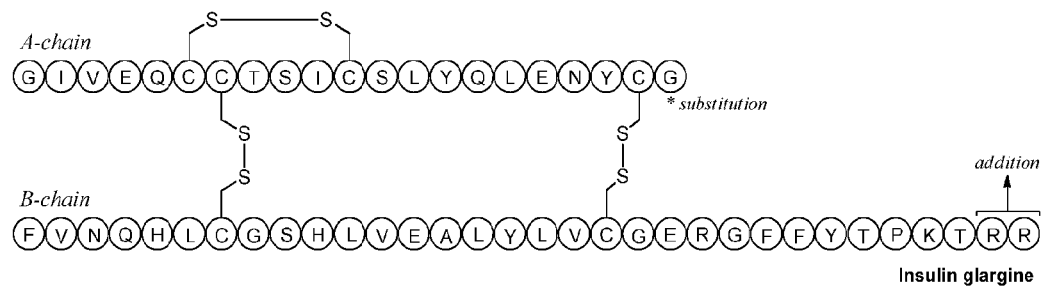
FIG. 2B is a schematic diagram showing the A-chain and the B-chain of human insulin and the disulfide bridges present in human insulin compared to long acting insulin analogues, glargine (SEQ ID NO: 91) and detemir (SEQ ID NO: 93).
Figure 2B:
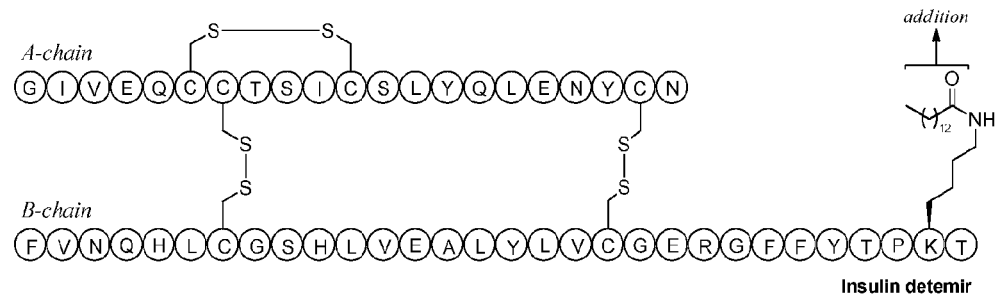

Additional key features of the insulin molecule include its three disulfide (or cystine) bridges (These are shown in the schematic diagram of the insulin A and B chains shown in FIGS. 1, 2A and 2B). Two of the three disulfide bridges are interchain bridges joining the A and B polypeptides together at the A7-B7 and A20-B19 positions, and one intrachain link creating a monocycle between the A6 and A11 residues (as shown in FIGS. 1, 2A and 2B). Disulfide bridges form upon oxidation of thiol side chains between cysteine residues within a peptide, and help to stabilise the secondary and tertiary structure of a protein. Although they do exist under physiological conditions, these bridges can be both chemically and metabolically labile, showing a tendency to undergo facile decomposition to reactive thiol groups under reducing, nucleophilic and basic conditions.

Rapid and Long Acting Insulins

The dicarba analogues of insulin of the present invention may be rapid or long acting insulins. The activity of the insulin may be modulated by mutating the native amino sequence to disrupt the self association between monomers of insulin, or by modification of one or more amino acids of the native insulin sequence. The activity of the insulin may be modulated by mutating the native amino sequence or by modification of one or more amino acids of the native insulin sequence to disrupt the solubility of the insulin. These modifications are encompassed by the dicarba analogues of insulin of the present invention.

Rapid-acting insulins, as the name suggests, have an almost immediate onset of action. At a molecular level, the primary sequence of these analogues have been modified to prevent the formation of dimers and hexamers through self-association, which limit the rate that monomers are absorbed into the blood stream. Through disruption of 13-sheet interactions in the B-chain by charge repulsion, or via alterations in the hydrophobic interactions responsible for self-association, three commercially available rapid-acting insulin formulations have been developed: Insulin lispro (Humalog®, Eli Lilly), insulin aspart (NovoRapid®, Novo Nordisk) and insulin glulisine (Apidra®, Sanofi Aventis). The structures of these rapid-acting insulin analogues, lispro, aspart and glulisine, compared with native human insulin are shown in FIG. 2A. These modifications to the native insulin sequence, and the corresponding dicarba analogues of insulin are encompassed by the present invention.

Insulin lispro utilises the latter strategy to disrupt the self-association surfaces of the insulin dimer through a simple $Pro_{B28} \rightarrow Lys_{B29}$ inversion. This sequence change leads to an analogue with more rapid pharmokinetic properties; it possesses an enhanced speed of in vivo action and clearance after subcutaneous injection. Insulin aspart and glulisine, on the other hand, both utilise charge repulsion strategies to disrupt association via a single amino acid substitution of aspartic acid for $Pro_{B28}$ in the case of aspart, and glutamic acid for $Lys_{629}$ in glulisine. Both of these analogues possess similar pharmacokinetic and pharmacodynamic properties to insulin lispro. In their storage vials, insulin lispro and aspart exist as stabilised Zn(II) hexamers that dissociate into monomeric forms more readily than native insulin formulations. Glulisine, however, is not administered as a Zn(II) hexamer and has overcome inherent storage-stability issues via formulation with detergent. These modifications to the native insulin sequence, and the corresponding dicarba analogues of insulin are encompassed by the present invention.

In direct contrast, intermediate- and long-acting insulin preparations display slower onsets of action and can often last up to 24 hours. Initial preparations involved altering the solubility profile of native insulin via complexation with zinc, or using additives such as protamine or phenol-like derivatives. This produced the original isophane insulin suspensions (NPH), Humulin N/L and Novolin N/L, which are absorbed slowly from the subcutaneous injection site. Unfortunately, use of these intermediate-acting insulin suspensions produces highly variable results, leading to inconsistent onset and duration of effect. More recently, however, sequence modification has been used to extend the duration of insulin action in a safe and reproducible manner. Two analogues, insulin glargine and detemir, are now available for commercial application (FIG. 2B). Insulin glargine exploits the reduced solubility of insulin at physiological pH to control release. Addition of two arginine residues to the C-terminus of the B-chain, in addition to a glycine substitution at A21, increases the isoelectric point of the native molecule and increases formulation stability of the peptide in acidic media. These structural alterations generate an analogue that precipitates in the presence of zinc at the site of subcutaneous injection, and then slowly and reproducibly solubilises to produce a steady supply of insulin at target tissues. Insulin detemir on the other hand, exerts its activity through the presence of a long fatty acid chain joined to the ε-amino group of $Lys_{B29}$.

This allows reversible, non-covalent binding to albumin in serum, which produces a human insulin analogue that displays a flatter and significantly longer time-action profile when compared to the native molecule. Although many diabetic patients are now enjoying the convenience of these long-acting analogues, there is still a considerable desire to improve basal insulin treatments. Unfortunately, both insulin variants have significant draw-backs, with glargine showing enhanced IGF-I receptor binding affinity, and detemir possessing reduced in vivo potency. In addition, both these analogues fail to produce a 24 hour duration of action, and hyperglycemia is still a common occurrence with these basal treatments. These modifications to the native insulin sequence, and the corresponding dicarba analogues of insulin are encompassed by the present invention.

Dicarba analogues of rapid, medium and slow acting insulins are all potential synthetic targets. Replacement of the native cystine framework of insulin, either partially or completely, with dicarba bridges (either saturated or unsaturated) can be performed in conjunction with other sequence modifications (such as those described above) which moderate onset of action. Hence, generation of rapid, medium and slow acting dicarba analogues of existing therapeutic insulins, including insulin glargine, lispro, insulin apart, insulin glulisine, isophane insulin suspensions and detemir, would be desirable.

Other Terminology Used in the Context of the Compounds and Components of the Peptides The term "amino acid" as used herein is used in its broadest sense and refers to L- and D-amino acids including the 20 common amino acids such as alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine; and the less common amino acid derivatives such as homo-amino acids (e.g. β-amino acids), N-alkyl amino acids, dehydroamino acids, aromatic amino acids and α,α-disubstituted amino acids, for example, cystine, 5-hydroxylysine, 4-hydroxyproline, α-aminoadipic acid, α-amino-n-butyric acid, 3,4-dihydroxyphenylalanine, homoserine, α-methylserine, ornithine, pipecolic acid, ortho, meta or para-aminobenzoic acid, citrulline, canavanine, norleucine, δ-glutamic acid, aminobutyric acid, L-fluorenylalanine, L-3-benzothienylalanine and thyroxine; β-amino acids (as compared with the typical α-amino acids) and any amino acid having a molecular weight less than about 500. The term amino acid can also include non-natural amino acids such as those described in U.S. Pat. No. 6,559,126, which are incorporated herein by reference. The term also encompasses amino acids in which the side chain of the amino acid comprises a metathesisable group, as described herein. Further, the amino acid may be a pseudoproline residue (ψPro).

The term "side chain" as used herein is used in the usual sense and refers to the side chain on the amino acid, and the backbone to the $H_2N-(C)_x-CO_2H$ (where x=1, 2 or 3) component, in which the carbon in bold text bears the side chain (the side chain being possibly linked to the amino nitrogen, as in the case of proline).

The amino acids may be optionally protected. The term "optionally protected" is used herein in its broadest sense and refers to an introduced functionality which renders a particular functional group, such as a hydroxyl, amino, carbonyl or carboxyl group, unreactive under selected conditions and which may later be optionally removed to unmask the functional group. A protected amino acid is one in which the reactive substituents of the amino acid, the amino group, carboxyl group or side chain of the amino acid are protected.

Suitable protecting groups are known in the art and include those disclosed in Greene, T. W., "Protective Groups in Organic Synthesis" John Wiley & Sons, New York 1999 (the contents of which are incorporated herein by reference) as are methods for their installation and removal.

The amino group of the amino acid may be optionally protected. Preferably the N-protecting group is a carbamate such as, 9-fluorenylmethyl carbamate (Fmoc), 2,2,2-trichloroethyl carbamate (Troc), t-butyl carbamate (Boc), allyl carbamate (Alloc), 2-trimethylsilylethyl (Teoc) and benzyl carbamate (Cbz), more preferably Fmoc.

The carboxyl group of the amino acid may be optionally protected. The carboxyl protecting group is preferably an ester such as an alkyl ester, for example, methyl ester, ethyl ester, t-Bu ester or a benzyl ester.

The side chain of the amino acid may be optionally protected. For example, the carboxyl groups of aspartic acid, glutamic acid and α-aminoadipic acid may be esterified (for example as a $C_1$-$C_6$ alkyl ester), the amino groups of lysine, ornithine and 5-hydroxylysine, may be converted to carbamates (for example as a $C(=O)OC_1$-$C_6$ alkyl or $C(=O)OCH_2Ar$ aromatic carbamates) or imides such as pthalimide or succinimide, the hydroxyl groups of 5-hydroxylysine, 4-hydroxyproline, serine, threonine, tyrosine, 3,4-dihydroxyphenylalanine, homoserine, α-methylserine and thyroxine may be converted to ethers (for example a $C_1$-$C_6$ alkyl or a ($C_1$-$C_6$ alkyl)arylether) or esters (for example a $C(=O)C_1$-$C_6$ alkyl ester) and the thiol group of cysteine may be converted to thioethers (for example a $C_1$-$C_6$ alkyl thioether) or thioesters (for example a $C(=O)C_1$-$C_6$ alkyl thioester).

The term "peptide" as used herein refers to any sequence of two or more amino acids, regardless of length, post-translation modification, or function. "Polypeptide", "peptide" and "protein" are used interchangeably herein. The peptides or mimetics thereof of the invention are typically, though not universally, of any length and therefore includes all truncations of the complete amino acid sequence of insulin.

The term "polypeptide" as used herein refers to an oligopeptide, peptide or protein. Where "polypeptide" is recited herein to refer to an amino acid sequence of a naturally-occurring protein molecule, "polypeptide" and like terms are not intended to limit the amino acid sequence to the complete, native amino acid sequence associated with insulin, but instead is intended to also encompass biologically active variants or fragments, including polypeptides having substantial sequence similarity or sequence identity relative to the amino acid sequences provided herein.

The dicarba analogues of insulin can be described as peptidomimetics—that is, a peptide that has a series of amino acids that mimics identically or closely, a naturally occurring peptide, but with the inclusion of at least one dicarba bridge. For example, the dicarba bridge may replace a naturally occurring cystine disulfide bridge, a salt bridge or a non-covalent interaction (such as a hydrogen bond, an ionic bond, van der Waals forces or hydrophobic interactions), which may be involved in formation of the 3-dimensional structural features of insulin. The dicarba analogues of insulin may also optionally include one or more further differences, such as the removal of a cystine bridge, a change by up to 20% of the amino acids in the sequence, a modification to the amino acid sequence to remove a protease cleavage site, a modification to the amino acid sequence to disrupt the self-association between monomers of the dicarba insulin analogue, or a modification to the amino acid sequence to alter the solubility profile of the dicarba insulin analogue, as non-limiting examples. These may also be classified as pseudo-peptides. As noted above, of particular interest are dicarba analogues of insulin, in which one or more of the disulfide bonds are replaced with dicarba bridges.

The dicarba analogues of insulin may be in the form of the free peptides, or in the form of a salt, solvate, derivative, isomer or tautomer thereof.

The salts of the peptides are preferably pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicylic, sulphanilic, aspartic, glutamic, edetic, stearic, palmitic, oleic, lauric, pantothenic, tannic, ascorbic and valeric acids; or salts or complexes with pharmaceutically acceptable metal ions, including non-toxic alkali metal salts such as sodium and potassium salts, or non-toxic transition metal complexes such as zinc.

In addition, some of the peptides may form solvates with water or common organic solvents. Such solvates are encompassed within the scope of the invention.

The term "derivative" as used herein refers to any salt, hydrate, protected form, ester, amide, active metabolite, analogue, residue or any other compound which is not biologically or otherwise undesirable and induces the desired pharmacological and/or physiological effect. Preferably the derivative is pharmaceutically acceptable. The term derivative does not encompass the natural insulin.

The term "tautomer" as used herein is used in its broadest sense and includes dicarba analogues of insulin which are capable of existing in a state of equilibrium between two isomeric forms. Such compounds may differ in the bond connecting two atoms or groups and the position of these atoms or groups in the compound.

The term "isomer" as used herein is used in its broadest sense and includes structural isomers, geometric isomers and stereoisomers. As the dicarba analogues of insulin that may be synthesised may have one or more stereogenic centres, they are capable of existing in enantiomeric forms.

The dicarba analogue of insulin may be synthesised, used or both synthesised and used as a purified enantiomer, as an enriched enantiomer or diastereomer, or as a mixture of any ratio of stereoisomers. Where the dicarba bridge of the dicarba analogues of insulin is an alkene-containing dicarba bridge the alkene-containing group of the bridge may be present as a mixture of any ratio of geometric isomers (e.g. as an E- or Z-configured alkene), or as an enriched geometric isomer. It is however preferred that where the dicarba analogue of insulin is present as a mixture of stereoisomers, the mixture is enriched in the preferred isomer.

In its broadest sense "enriched" means that the mixture contains more of the preferred isomer than of the other isomer. Preferably, an enriched mixture comprises greater than 50% of the preferred isomer, where the preferred isomer gives the desired level of potency and selectivity. More preferably, an enriched mixture comprises at least 60%, 70%, 80%, 90%, 95%, 97.5% or 99% of the preferred isomer. The dicarba analogue of insulin which is enriched in the preferred isomer can either be obtained via a stereospecific reaction, stereoselective reaction, isomeric enrichment via separation processes, or a combination of all three approaches.

In this specification, including the claims, except where the context requires otherwise due to express language or necessary implication, the word "comprising" or variations such as "comprise" or "comprises" is used in the inclusive sense, to specify the presence of the stated features or steps but not to preclude the presence or addition of further features or steps.

It must be noted that, as used in the specification, the singular forms "a", "an" and "the" include plural aspects unless the context clearly dictates otherwise. Thus, for example, reference to "a dicarba analogue of insulin" or "a dicarba bridge" includes a single dicarba analogue of insulin or a single dicarba bridge, as well as two or more dicarba analogues of insulin or two or more dicarba bridges, respectively; and so forth.

Dicarba Bridges

Replacement of the disulfide bridge in insulin with biostable structural mimics may lead to enhanced chemical stability and a greater potential to treat diabetes. For this to be feasible, however, the role of each disulfide bond in the structure and activity of insulin must be determined. In some cystine containing peptides, the bridges have a functional purpose and represent segments of a binding domain or active site, which release chelating metal ions upon reduction or undergo disulfide exchange. In many other disulfide-containing peptides the role of the disulfide bridge is purely structural, being present to maintain secondary and tertiary structure.

The dicarba bridge may form a bridge between the two separate peptide chains of insulin (e.g. the A-chain and the B-chain of insulin), to form an interchain dicarba bridge, or it may form a bridge between two points in a single peptide chain (for example as found in insulin's A-chain, or a fragment thereof), so as to form an intrachain dicarba bridge, otherwise known as a ring. Preferably, the dicarba analogue of insulin at least contains an intrachain dicarba bridge.

In some instances it may be difficult to form intrachain dicarba bridges due to steric hindrance, aggregation and/or the need to bring the reactable (metathesisable) groups together. We have found that the use of one or more of (i) microwave radiation in the cross-metathesis step, (ii) turn-inducing groups, and/or (iii) alternating solid phase peptide synthesis (SPPS) and catalysis enables such dicarba bridges to be formed within insulin analogues, often in an efficient manner. This is discussed below.

In some instances it may be difficult to form interchain dicarba bridges due to the peptide sequence and the positioning of the reacting motifs. We have also found that the use of a removeable tether between two amino acids or peptides to be connected may enhance the metathesis. This is discussed below.

The term "dicarba bridge" as used herein is used broadly, unless the context indicates otherwise, to refer to a bridging group that includes at least one of the groups selected from —C—C—, —C═C— and —C≡C—. This means that the dicarba bridge could be wholly or partly composed of the groups —C—C—, —C═C— and —C≡C—, or could for example be one of the dicarba bridges shown in formula (I) to (VI) below. In a preferred embodiment, the atoms directly attached to the carbon atoms of the dicarba bridge are C or H. Further or alternative reactions may be performed to introduce substituents other than hydrogen onto the carbon atoms of the dicarba sequence of the dicarba bridge.

Preferably, the dicarba analogue of insulin contains at least one unsaturated dicarba bridge. The term "unsaturated dicarba bridge" as used herein refers to dicarba bridges which contain the group —C=C—(an alkene-containing dicarba bridge) or dicarba bridges which contain the group —C≡C—(an alkyne-containing dicarba bridge). The term "unsaturated hydrogen dicarba bridge" as used herein refers to dicarba bridges which contain the group —CH=CH—.

The term "alkyne-containing dicarba bridge" as used herein is used broadly, unless the context indicates otherwise, to refer to a bridging group that includes at least an alkyne group (—C≡C—). This means that the alkyne-containing dicarba bridge could be wholly or partly composed of the group —C≡C—, or could for example be one of the dicarba bridges shown in formula (I) or (II) below.

In addition to the alkyne group, the alkyne-containing dicarba bridge may include any other series of atoms, typically selected from C, N, O, S and P. The atoms directly attached to the carbon atoms of the alkyne-containing dicarba bridge are preferably carbon. However, any of the other atoms listed above may also be present, with the proviso that the nitrogen atoms present in the compound during metathesis are not free amines (protected amines, such as carbamates and salts, are acceptable). The alkyne-containing dicarba bridge encompasses the following possible bridges, as illustrative examples:

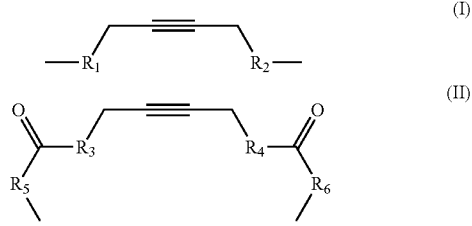

wherein $R_1$ to $R_6$ are each independently absent or selected from a divalent linking group. $R_1$ to $R_6$ may be the same (for example $R_1 \neq R_2$) or different (for example $R_1 \neq R_2$), or one or more or all of $R_1$ to $R_6$ may be absent. Such divalent linking groups should not be groups that poison the metathesis catalyst. Preferably, the divalent linking groups $R_1$ to $R_6$ are substituted or unsubstituted alkylene or substituted or unsubstituted alkoxyl groups.

The term "alkylene" as used herein refers to divalent alkyl groups including straight chain and branched alkylene groups having from 1 to about 20 carbon atoms. Typically, the alkylene groups have from 1 to 15 carbons or, in some embodiments, from 1 to 8, 1 to 6, or 1 to 4 carbon atoms. Examples of straight chain alkylene groups include methyl, ethyl, n-propyl, n-butyl, n-pentyl, n-hexyl, n-heptyl, and n-octyl groups. Examples of branched alkyl groups include, but are not limited to, iso-propyl, iso-butyl, sec-butyl, tert-butyl, neo-pentyl, iso-pentyl, and 2,2-dimethylpropyl groups. The alkylene groups may also be substituted and may include one or more substituents.

The term "alkoxyl" as used herein refers to the divalent group —OR— where R is an alkylene group as defined above. Examples of straight chain alkoxy groups include methoxyl, ethoxyl, propoxyl and longer chain variants. Examples of branched alkoxyl groups include, but are not limited to, α-methylmethoxyl and α-methylethoxyl groups. The alkoxyl groups may also be substituted and may include one or more substituents, which are as defined below.

A "substituted" alkylene or alkoxyl group has one or more of its hydrogen atoms replaced by non-hydrogen or non-carbon atoms. Substituted groups also include groups in which one or more bonds to a carbon(s) or hydrogen(s) atom are replaced by one or more bonds, including double or triple bonds which may optionally be blocked via an adjacent heteroatom. Thus, a substituted group will be substituted with one or more substituents, unless otherwise specified. In some embodiments, a substituted group is substituted (in protected or unprotected form) with 1, 2, 3, 4, 5, or 6 substituents. Examples of substituent groups include halogens (i.e., F, Cl, Br and I), hydroxyls, alkoxyl, alkenoxyl, alkynoxyl, aryloxyl, aralkyloxyl, heterocyclyloxyl, and heterocyclylalkoxyl groups; carbonyls (oxo); carboxyls; esters; ethers, urethanes; oximes; hydroxylamines; alkoxyamines; aralkoxyamines; thiols; sufides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitriles (i.e. CN); and the like. Such substituents should not be groups that poison the metathesis catalyst or affect its selectivity.

The term "alkene-containing dicarba bridge" as used herein is used broadly, unless the context indicates otherwise, to refer to a bridging group that includes at least an unsaturated alkene (—C=C—). This means that the dicarba bridge could be wholly or partly composed of the group —C=C—, or could for example be one of the dicarba bridges shown in formula (III) or (IV) below. The alkene-containing dicarba bridge (—C=C—) may possess cis- or trans-geometry.

In a preferred embodiment, the atoms directly attached to the carbon atoms of the alkene-containing dicarba bridge are typically H or C. Further or alternative reactions can be performed to introduce substituents other than hydrogen onto the carbon atoms of the dicarba sequence or at other positions on the dicarba bridge.

In addition to the —C=C— dicarba sequence, the dicarba bridge may include any other series of atoms, typically selected from C, N, O, S and P, although the atoms to either side of the dicarba sequence are preferably carbon, and with the proviso that the nitrogen atoms present in the compound during metathesis are not free amines protected amines, such as carbamates, and salts are acceptable). Thus, the dicarba bridge encompasses the following possible bridges, as illustrative examples:

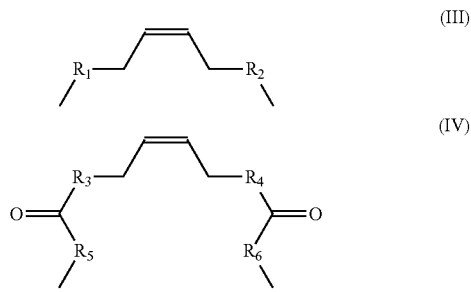

wherein $R_1$ to $R_6$ are each independently absent or selected from a divalent linking group. $R_1$ to $R_6$ may be the same (for example $R_1=R_2$) or different (for example $R_1 \neq R_2$), or one or more or all of $R_1$ to $R_6$ may be absent. Such divalent linking groups should not be groups that poison the metathesis catalyst. Preferably, the divalent linking groups $R_1$ and $R_2$ are substituted or unsubstituted alkylene or substituted or unsubstituted alkoxyl group, as defined above.

The term "saturated dicarba bridge" or "alkane-containing dicarba bridge" is used broadly, unless the context indicates otherwise, to refer to a bridging group that includes at least a saturated alkane containing dicarba bridge (—C—C—). This means that the dicarba bridge could be wholly or partly composed of the groups —C—C—, or could for example be one of the dicarba bridges shown in formula (V) or (VI) below.

The atoms directly attached to the carbon atoms of the saturated dicarba bridge are typically H or C, although further or alternative reactions can be performed to introduce substituents other than hydrogen onto the carbon atoms of the dicarba sequence of the dicarba bridge. The term "saturated hydrogen dicarba bridge" refers to the specific case where the dicarba bridge is —CH$_2$—CH$_2$—. Typically, saturated dicarba bridges are prepared by hydrogenation or other reduction of unsaturated dicarba bridges.

In addition to the dicarba sequence, the dicarba bridge may include any other series of atoms, typically selected from C, N, O, S and P, although the atoms to either side of the dicarba sequence are preferably carbon, and with the proviso that the nitrogen atoms present in the compound during metathesis are not free amines (protected amines, such as carbamates, and salts are acceptable). Thus, the dicarba bridge encompasses the following possible bridges, as illustrative examples:

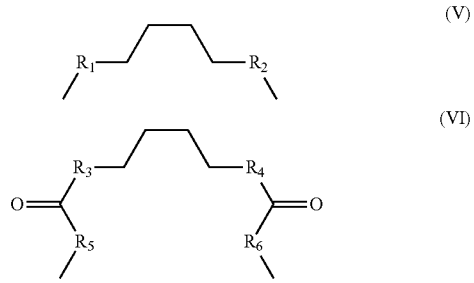

wherein R$_1$ to R$_6$ are each independently absent or selected from a divalent linking group. R$_1$ to R$_6$ may be the same (for example R$_1$=R$_2$) or different (for example R$_1$≠R$_2$) or one or more or all of R$_1$ to R$_6$ may be absent. Such divalent linking groups should not be groups that poison the metathesis catalyst. Preferably, the divalent linking groups R$_1$ and R$_2$ are substituted or unsubstituted alkylene or substituted or unsubstituted alkoxyl group, as defined above.

Where the terms "alkyne-containing", "alkene-containing" or "alkane-containing" or "saturated" are not specified, the term "dicarba bridge" is taken to refer to a bridging group that includes at least one of the groups selected from a saturated dicarba bridge (—C—C—), an unsaturated alkene-containing dicarba bridge (—C=C—) and an alkyne-containing dicarba bridge (—C≡C—) as described above. This means that the dicarba bridge could be wholly or partly composed of the groups —C—C—, —C=C— or —C≡C—, or could for example be any one of the dicarba bridges shown in formula (I) to (VI) above.

Methods for the Preparation of Dicarba Insulin Analogues
Metathesis

Metathesis is a powerful synthetic tool that enables the synthesis of carbon-carbon bonds via a transition metal-catalysed transformation of alkyl-unsaturated reactants. The construction of dicarba analogues of mufti-cystine containing peptides, however, presents more of a synthetic challenge.

The use of uniform metathesis substrates leads to a statistical product distribution and therefore metathesis selectivity is severely compromised. For example, homodimerisation of equivalent olefins A and B in the absence of selectivity results in a statistical mixture of three products (as shown below). The yield of desired products (A-A and B-B) is not more than 50% in the absence of selection. In order to exclusively form the target A-B product, selective metathesis strategies must be employed to avoid the formation of the A-A and B-B homodimers.

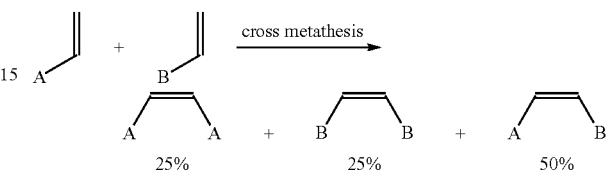

Cross-metathesis (CM) is a type of metathesis reaction involving the formation of a new bond across two unblocked, reactive metathesisable groups, to form a new bridge between the two reactive metathesisable groups. For example, cross-metathesis can be used to generate a dicarba analogue of insulin having an intermolecular bridge via formation of a dicarba bridge between two reactive metathesisable groups each located in different chains of insulin. Ring-closing metathesis (RCM) is a type of metathesis reaction where the two reactive metathesisable groups are located within one peptide chain so as to form an intramolecular bridge, or ring. For example, ring-closing metathesis involves the formation of a dicarba bridge between two reactable metathesisable groups located on a single chain of insulin to produce a dicarba analogue of insulin having an intrachain bridge.

The dicarba analogues of insulin or fragments, salts, solvates, derivatives, isomers or tautomers as described above, may be synthesised by a method comprising:
(i) providing the A-chain having at least one pair of complementary metathesisable groups;
(ii) subjecting the A-chain to metathesis to form at least one dicarba bridge between the pair of complementary metathesisable groups; and
(iii) adding the B-chain.

In some instances, the dicarba analogue of insulin may need to assume a particular conformation in order to serve as a suitable peptidomimetic of insulin. In particular, when the dicarba bridge replaces one or more of the disulfide bonds present in insulin, it may be advantageous for the dicarba bridge to adopt a particular geometry. The ability of the dicarba bridge to mimic the conformation of the disulfide bridge formed in the active form of insulin may effect the activity of the dicarba analogue of insulin compared to the activity of the native form of insulin.

The initial product of the metathesis reaction is a compound with an unsaturated dicarba bridge (—C≡C— or —C=C—). That is an alkyne-containing dicarba bridge formed by alkyne metathesis or an alkene-containing dicarba bridge formed by alkene metathesis.

If the target insulin analogue is to contain an alkene-containing dicarba bridge (—C=C—) or a saturated alkane-containing dicarba bridge (—C—C—), the process may further comprise the step of subjecting the unsaturated dicarba bridge to hydrogenation.

In the preparation of the dicarba analogues of insulin it is preferred that at least one chain of insulin is provided on a solid support. The types of solid supports that may be used are described below. Tethering a peptide sequence to a solid support can also promote RCM: A pseudo-dilution effect operates on resin to promote RCM over otherwise competing CM reaction. Hence high dilution is not required for the promotion of RCM conversion.

The preparation of the dicarba analogues of the present invention provides a number of advantages when at least one chain of insulin is provided on a solid support. The combination of SPPS and catalysis using a single solid support is highly efficient. Homogeneous catalysts, such as those used to affect metathesis and hydrogenation, can be exposed to a resin bound peptide and simply separated from the product peptide via filtration of the resin-peptide from the reaction solution. This eliminates and/or minimises metal-contamination of the product and aids the separation of the product peptide from solution phase by-products and/or impurities. Protecting groups for reactive sidechains which are commonly employed in SPPS protocols are also tolerated by organotransition metal catalysts and hence catalysis can conveniently be performed immediately after SPPS.

The dicarba analogues of insulin or fragments, salts, solvates, derivatives, isomers or tautomers as described above, may be synthesised by a method comprising:
(i) providing a part of the A-chain having at least two complementary metathesisable groups;
(ii) subjecting the A-chain to metathesis to form at least one dicarba bridge; and
(iii) adding one or more further amino acids to one or both ends of the A-chain; and
(iv) adding the B-chain.

The dicarba analogues of insulin or fragments, salts, solvates, derivatives, isomers or tautomers as described above, may also be synthesised by a method comprising:
(i) providing a part of the A-chain and/or a part of the B-chain having at least two complementary metathesisable groups between them;
(ii) subjecting the A-chain and B-chain to metathesis to form at least one dicarba bridge; and
(iii) adding one or more further amino acids to one or both ends of the A-chain and/or B-chain.

Additionally, alternating SPPS-Catalysis-SPPS methods can be used to introduce metathesisable groups into a sequence, stepwise. Such a technique removes and/or eliminates the need for orthogonal protecting group strategies. The technique also assists the catalysis of 'difficult' sequences (e.g. residues which promote deleterious aggregation, unfavourable conformations, and poor peptide solubility and reagent penetration) by allowing troublesome sections of the sequence to be omitted until after the scheduled catalysis has been performed. The omitted residues are added to the truncated sequence via SPPS.

The dicarba analogues of insulin or fragments, salts, solvates, derivatives, isomers or tautomers as described above, may be synthesised by a method comprising:
(i) providing or synthesising a reactable peptide comprising a removable tether between the A-chain and the B-chain, the A-chain and the B-chain each having at least one complementary metathesisable group; and
(ii) subjecting the reactable peptide to metathesis to form at least one dicarba bridge between the complementary metathesisable groups; and
(ii) removing the removeable tether to produce a dicarba bridge linking the A-chain and the B-chain of insulin.

This approach enhances metathesis to form interchain dicarba bridges, which may be difficult due to the nature of the peptide sequence and the positioning of the reacting motifs. This approach provides an alternative to performing direct cross metathesis, and can assist in formation of an interchain dicarba bridge. The approach forms an intramolecular dicarba bridge between two amino acids or peptides to be joined, which are provided in a contiguous sequence, connected by a removeable tether. Once the dicarba bridge has been formed, the removeable tether is removed to produce the interchain dicarba bridge.

During the step of metathesis may be performed with the peptide attached to a resin. Preferably, when the peptide substrate is attached to a resin, the metathesis step uses a homogeneous catalyst.

Alkyne Metathesis

Alkyne metathesis can be used to install one or more alkyne-containing dicarba bridge to form a dicarba analogue of insulin. The alkyne containing dicarba bridges may be intramolecular or intermolecular.

Alkyne metathesis involves the formation of a new alkyne bond from two unblocked or reactive alkynes. The new alkynyl bridge covalently joins the two reactive starting alkynes. As shown below, the alkyne-containing dicarba bridge may be formed between two reactable metathesisable groups provided within the scaffold of insulin. The two reactable metathesisable groups may each be residues of separate peptides, to form an intermolecular bridge (a cross metathesis reaction). Cross-metathesis occurs when the alkyne-containing dicarba bridge is formed between two or more peptides having between them a pair of complementary alkyne-containing metathesisable groups. In this case, the alkyne-containing dicarba bridge is an intermolecular dicarba bridge (shown as (A) below). Alternatively, ring closing metathesis occurs when the alkyne-containing dicarba bridge is formed between two amino acids within a single reactable peptide. In this case, the alkyne-containing dicarba bridge is an intramolecular dicarba bridge (shown as B below).

(A) Alkyne Cross Metathesis (CAM)

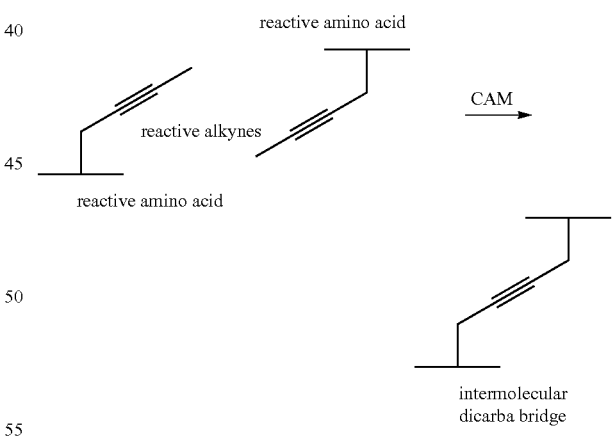

(B) Ring Closing Alkyne Metathesis (RCAM)

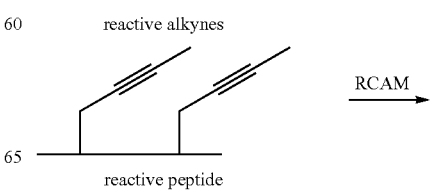

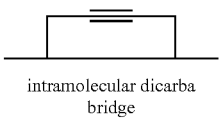

intramolecular dicarba bridge

In some sequences, it can be difficult to form intramolecular bridges due to aggregation and deleterious hydrogen bonding, and the need to bring the reactable (metathesisable) groups together. We have found that the use of microwave radiation, turn-inducing groups in the metathesis step and/or alternating solid phase peptide synthesis and catalysis strategies (as discussed below), facilitates the metathesis reaction to occur, or occur more efficiently.

In one embodiment of the present invention, the dicarba analogue contains an alkyne-containing dicarba bridge. This alkyne-containing dicarba bridge may subsequently be subjected to stereoselective reduction to preferentially generate either the cis- or the trans isomer of the alkene-containing dicarba bridge. This approach produces a dicarba analogue of insulin which is enriched in one of the geometric isomers of the alkene-containing dicarba bridge. In this manner, the most/only active isomer may be targeted. Advantageously, the need for time-consuming chromatographic separation of the unwanted geometric isomer can be avoided using this approach.

Alkyne metathesis is facilitated by a catalyst. Some metal-complexes are highly active alkyne metathesis catalysts and some are capable of highly selective alkyne metathesis in the presence of other potentially reactable groups, e.g. alkenes.

Catalysts which may be used to perform alkyne metathesis in the method of the present invention are those catalysts which are selective for alkyne-containing metathesisable groups, while not interfering with the functional groups present in the amino acids and peptides between which the alkyne-containing dicarba bridge is formed. Examples of suitable catalysts include those described in Fürstner, A.; Davies, P. W. Chem. Commun. 2005, 2307-2320; Zhang, W.; Moore, Jeffrey S. Adv. Synth. Catal. 2007, 349, 93-120; Grela, K., Ignatowska, J., Organic Letters, 1992, 4(21), 3747; and Mortreux, A.; Coutelier, O. J. Mol. Catal. A: Chem. 2006, 254, 96-104, incorporated herein by reference. There are many catalysts available to achieve this transformation, which vary in their ability to catalyse the metathesis reaction, in their ability to tolerate other functional groups, and their stability towards water and other functional groups. Preferably the catalyst used for alkyne metathesis is a homogenous catalyst. More preferably, the catalyst is a tungsten containing catalyst, or a molybdenum-containing catalyst such as those based on W(IV) and Mo(CO)6/phenol systems. Still more preferably, the catalyst is a tungsten-containing catalyst. An example of a suitable tungsten-containing catalysts is tris(tert-butoxy)(2,2-dimethylpropylidyne)tungsten.

A preferred tungsten-containing alkyne-metathesis catalyst is a tungsten-alkylidyne complex commonly known as Schrock's catalyst, tris(tert-butoxy)(2,2-dimethylpropylidyne) tungsten(VI), which is shown below. This catalyst is a highly air and moisture sensitive molecule which necessitates the rigorous use of inert and anhydrous reaction atmosphere and solvents respectively. It is however, highly tolerant of a wide range of functionality which is often found in peptide sequences.

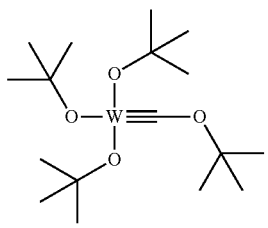

Schrock's catalyst

Schrock's catalyst

The formation of an alkyne-containing dicarba bridge involves the use of complementary pairs of alkyne-containing metathesisable groups which may be connected to an amino acid in a peptide of insulin. A metathesisable group is a functional group that can undergo metathesis when unblocked or in an activated state. The alkyne containing metathesisable group may be connected to an amino acid via the amino acid side chain or via the amino group of the amino acid. As an example, a side chain of the amino acid may include at least an alkyne-containing metathesisable group, and the side chain may be wholly or partly composed of the group —C≡C—.

The term "alkyne-containing metathesisable group" as used herein is used broadly, unless the context indicates otherwise, to refer to a group that includes at least an alkyne moiety. The alkyne-containing metathesisable group could for example be an alkyne-containing metathesisable group of the general formula drawn below:

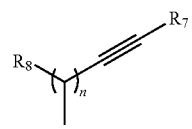

The integer n may be 0, 1, 2, 3, 4, 5, 6, 7, 8, 9 or 10. The $R_7$ and $R_8$ groups should not be a group that poisons the metathesis catalyst. Preferably, the $R_7$ group is substituted or unsubstituted alkyl. The $R_8$ group is either H or substituted or unsubstituted alkyl. Preferably, the $R_8$ group either H or methyl.

The term "alkyl" as used herein refers to a monovalent alkyl group including straight chain and branched alkyl groups having from 1 to about 20 carbon atoms. Typically, the alkyl group has from 1 to 15 carbons or, in some embodiments, from 1 to 8, 1 to 6, or 1 to 4 carbon atoms. Examples of straight chain alkyl groups include methyl, ethyl, n-propyl, n-butyl, n-pentyl, n-hexyl, n-heptyl, and n-octyl groups. Examples of branched alkyl groups include, but are not limited to, iso-propyl, iso-butyl, sec-butyl, tert-butyl, neo-pentyl, iso-pentyl, and 2,2-dimethylpropyl groups. The alkyl group may also be substituted and may include one or more substituents. The term "substituted" is as defined above in relation to alkylene groups.

The alkyne-containing metathesisable group may be connected to an amino acid of insulin. The metathesisable group is preferably located on the amino group or on the side chain of the amino acid.

During the metathesis reaction, a by-product is produced, which comprises an alkyne bond which is substituted with the $R_7$ group. Preferably, the $R_7$ groups are such that the resulting by-product is gaseous, and is eliminated from the reaction mixture. For example, when $R_7$ is methyl, the by-product is 2-butyne, which evaporates from the reaction mixture to leave the reaction product. Other alkyne by-products, such as 2-pentyne and 3-hexyne (having boiling points of 56° C. and 81° C. respectively), could also be generated from the combination of butynylglycine and pentynylglycine residues. These low boiling point liquids are readily removed from the metathesis reaction mixture. It will however be appreciated that techniques for the separation of a non-gaseous by-product from the reaction mixture would also be known by a person skilled in the art.

It is noted that a pair of complementary alkyne-containing metathesisable groups need not be identical. For example, an alkyne-containing metathesisable group in which $R_7$ is methyl can react with an alkyne-containing metathesisable group in which $R_7$ is ethyl to form an alkyne-containing dicarba bridge. The term "complementary" is used to indicate that the pair of unblocked alkyne-containing metathesisable groups are not necessarily identical, but are merely complementary in the sense that metathesis can take place between the two alkyne-containing groups.

Alkene Metathesis

Alkene metathesis provides a versatile method for the cleavage and formation of C=C bonds, and involves a mutual intermolecular exchange of alkylidene fragments between two alkene groups.

In alkene metathesis reactions, the redistribution can result in three main outcomes shown below: (A) ring-opening metathesis (ROM) which is sometimes followed by polymerization of the diene (ROMP); (B) ring-closing metathesis (RCM); and (C) cross metathesis. Of particular interest to the present invention are the latter two. ADMET, acyclic diene metathesis, is also an important process.

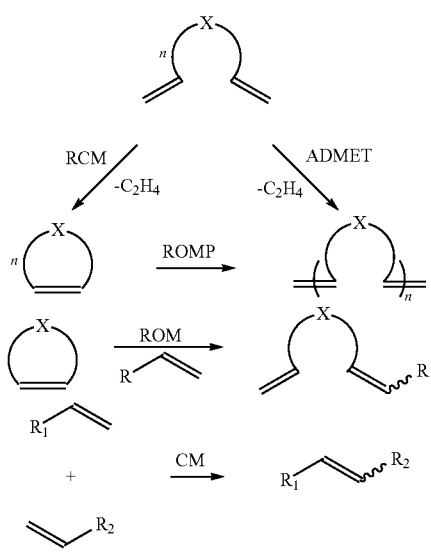

In the synthesis of a peptide having an alkyne-containing dicarba bridge and at least one additional alkene-containing dicarba bridge, the formation of each bridge may occur in any order. For example, alkyne metathesis to form the alkyne-containing dicarba bridge may occur before or after formation of any alkene-containing dicarba bridges.

When a pair of alkene-containing metathesisable groups are incorporated into the primary sequence of a single peptide and subjected to metathesis conditions, an intramolecular reaction will result in the formation of a cyclic peptide (RCM). If however, the pair of alkene-containing metathesisable groups are present within two separate peptide chains, an intermolecular CM reaction will result in the formation of a link between the two peptides. This is shown below.

(A) Alkene Cross Metathesis (CM)

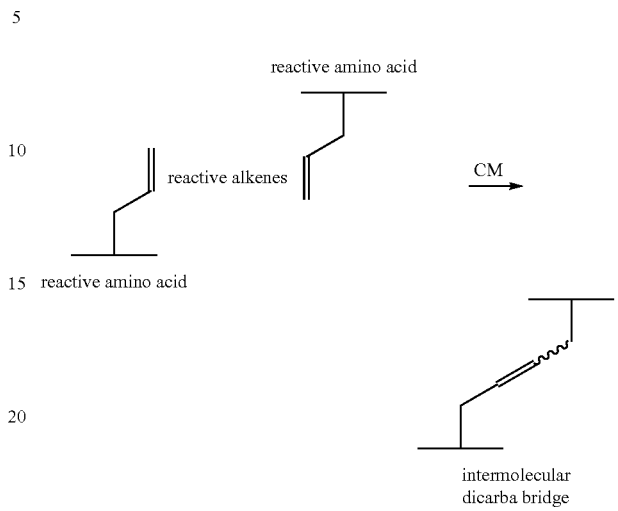

(B) Ring Closing Alkene Metathesis (RCM)

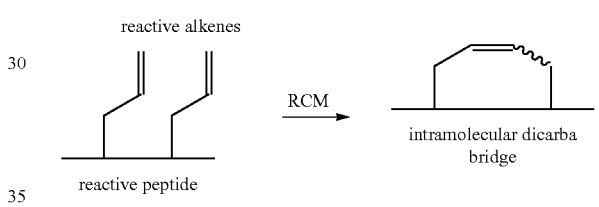

In some peptide sequences, such as insulin, it may be difficult to form intramolecular bridges, due to aggregation and deleterious hydrogen bonding, and the need to bring the reactable (metathesisable) groups together. The use of microwave radiation, turn-inducing groups and/or an alternating SPPS-catalysis strategy to promote metathesis conversion (as discussed below) facilitates dicarba bridge formation.

In some peptide sequences, such as insulin, it may be difficult to form interchain dicarba bridges due to the nature of the peptide sequence and the positioning of the reacting motifs. The use of a removeable tether between two amino acids or peptides to be connected may enhance the metathesis. This is discussed below.

In one embodiment of the present invention, the alkene-containing dicarba bridge that is formed can subsequently be subjected to reduction to generate the corresponding saturated alkane-containing dicarba bridge.

Alkene metathesis is also facilitated by a catalyst. Catalysts which may be used to perform alkene metathesis in the method of the present invention are those catalysts which are selective for the alkene-containing metathesisable groups, while not interfering with the functional groups present in the amino acids and peptides between which the alkene-containing dicarba bridge is formed. Examples of suitable catalysts include those described in Grubbs, R. H., Vougioukalakis, G. C. *Chem. Rev.*, 2010, 110, 1746-1787, Tiede, S., Berger, A., Schlesiger, D., Rost, D., Lühl, A., Blechert S., *Angew. Chem. Int. Ed.*, 2010, 49, 1-5, and Samojlowicz, C., Bieniek, M., Grela, K. *Chem. Rev.*, 2009, 109, 3708-3742. Preferably, the catalyst used for alkene metathesis is a homogeneous catalyst, such as a ruthenium-based alkylidene catalyst.

Many alkene metathesis catalysts are now commercially available or easily synthesised in the laboratory. While early catalysts were poorly defined, lacked functional group tolerance and were highly moisture and oxygen sensitive, later generation catalysts have largely overcome these initial problems. Currently used Ru-based catalysts, for example Grubbs' first and second generation catalysts, and the Hoveyda-Grubbs analogues, are robust, display high functional group tolerance and have tuneable reactivity under mild experimental conditions. Despite their differing substitution around the core Ru centre, all of the catalysts cycle through an active ruthenium alkylidene species. The variation around the reactive core however, plays an important role in mediating initiation, propagation and substrate specificity.

Where a dicarba analogue of insulin is to contain an alkene-containing dicarba bridge and an alkyne-containing dicarba bridge, it is useful to tailor the catalyst used in the metathesis reaction to the substrate in order to achieve regioselective dicarba bridge formation. For example, on exposure to second generation Grubbs' catalyst (a ruthenium alkylidene catalyst bearing phosphine, N-heterocyclic carbene and chloride ligands), a peptide sequence possessing an alkyne and alkene functional group will undergo en-yne metathesis. The same peptide however, exposed to first generation Grubbs' catalyst (a ruthenium alkylidene catalyst bearing only phosphine and chloride ligands), will only undergo alkene cross metathesis.

Preferably, the catalyst is a metal carbene complex such as those shown below. More preferably, where a peptide is to contain at least one alkene-containing dicarba bridge and at least one alkyne-containing dicarba bridge the catalyst used for alkene metathesis is a first generation catalyst.

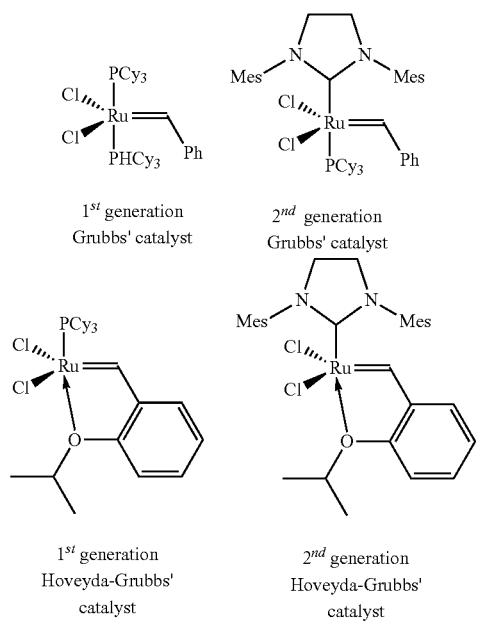

Cy = cyclohexyl
Mes = mesitylene

The formation of an alkene-containing dicarba bridge involves the use of complementary pairs of alkene-containing metathesisable groups connected to an amino acid or connected to an amino acid in a peptide of insulin. A metathesisable group is a functional group that can undergo metathesis when unblocked or in an activated state. The alkene-containing metathesisable group may be connected to an amino acid via the amino acid side chain or via the amino group of the amino acid. As an example, a side chain of the amino acid may include at least an alkene-containing metathesisable group, and the side chain may be wholly or partly composed of the group —C═C—.

The term "alkene-containing metathesisable group" as used herein is used broadly, unless the context indicates otherwise, to refer to a group that includes at least an alkene moiety. The alkene-containing metathesisable group could, for example, be an alkene containing metathesisable group of the general formula drawn below:

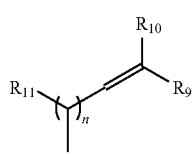

The integer n may be 0, 1, 2, 3, 4, 5, 6, 7, 8, 9 or 10. The R9, R10 and R11 groups should not be a group which poisons the metathesis catalyst. Preferably the R9 and R10 groups are each independently H or a substituted or unsubstituted alkyl as defined above. The R11 group is either H or a substituted or unsubstituted alkyl. Preferably the R11 group is either H or methyl.

The alkene-containing metathesisable group may be connected to an amino acid of insulin. The alkene-containing metathesisable group is preferably located on the amino group or on the side chain of the amino acid.

The alkene-containing metathesisable group could for example include the alkene-containing metathesisable groups:—allylglycine (A), crotylglycine (B), prenylglycine (C) and the extended acrylate (D) (as drawn below).

The reactivity of alkenes towards homodimerisation during metathesis, has been categorised into four classes—Type I through IV. Type I alkenes are the most reactive, and are characterised by sterically unhindered and electron-rich olefins such as allyl—(A) and crotyl-glycine (B). Increasing steric hindrance and decreasing electron density about the olefin, results in slow to non-existent homodimerisation, and sees these alkenes categorised in Types II through IV. These include residues such as prenylglycine (C) and the extended acrylate (D). These glycine derivatives are shown below.

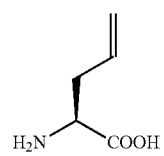

A

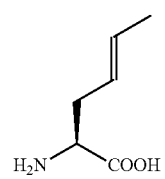

B

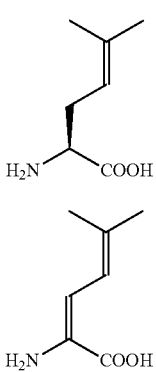

During the metathesis reaction, a by-product is produced. Preferably, the by-product is gaseous, and evaporates from the reaction mixture. It will however be appreciated that techniques for the separation of non-gaseous by-products from the reaction mixture would also be known by a person skilled in the art.

It is noted that a pair of complementary alkene-containing metathesisable groups need not be identical. For example, an allylglycine residue can be metathesised with a crotylglycine residue to generate a new dicarba bridge. The term "complementary" is used to indicate that the pair of unblocked alkene-containing metathesisable groups are not necessarily identical, but are merely complementary in the sense that metathesis can take place between the two alkene-containing groups.

Microwave Reaction Conditions

It has been found that when the metathesis reaction is performed under microwave reaction conditions, the reaction may take place in situations where the reaction would not otherwise take place—for instance, when the metathesisable groups are unblocked, but the arrangement, length or spatial orientation of the reactable organic compound prevents the metathesisable groups from being close enough to one another to enable the reaction to proceed. An alternative strategy is described below (see the description of "Turn-inducing groups" below).

The microwave reaction conditions involve applying microwave radiation to the reactable peptide (preferably attached to a solid support) in the presence of the metathesis catalyst for at least part of the reaction, usually for the duration of the reaction. The microwave or microwave reactor may be of any type known in the art, operated at any suitable frequency. Typical frequencies in commercially available microwave reactors are 2.45 GHz, at a power of up to 500 W, usually of up to 300 W. The temperature of the reaction is preferably at elevated as a consequence of the microwave radiation. Preferably, the temperature of the reaction is at reflux, or around 100° C., as appropriate in each case. The reaction is preferably performed in a period of not more than 5 hours, suitably for up to about 2 hours.

Turn-Inducing Groups

Another strategy devised for improving the performance of a metathesis (particularly ring closing metathesis) reaction between two complementary metathesisable groups (alkenes or alkynes) is the use of turn-inducing groups. This strategy is particularly useful for ring-closing metathesis where the metathesisable groups are located within a single peptide. As described above, this strategy can also be used in combination with microwave irradiation.

According to this embodiment, there is provided a method for the synthesis of a dicarba analogue of insulin comprising an A-chain and a B-chain or fragments, salts, solvates, derivatives, isomers or tautomers of the A-chain, the B-chain or both, the method comprising:

(i) providing the A-chain, the B-chain or a peptide comprising both the A-chain and the B-chain, the A-chain, the B-chain or the peptide having a pair of unblocked complementary metathesisable groups, and a turn-inducing group located between the pair of complementary metathesisable groups, and (ii) subjecting the peptide to metathesis to form a dicarba analogue of insulin comprising a dicarba bridge.

This method can be used to facilitate the production of alkyne dicarba bridge formation and/or alkene dicarba bridge formation. Where the method is performed on a peptide comprising the A-chain or the B-chain, the method may also comprise the step of adding the other chain of insulin. Where the method is performed on a peptide comprising the A-chain and the B-chain of insulin, the peptide may further comprise a removeable tether and the method may further comprise the step of removing the removable tether from the peptide, to produce a dicarba insulin analogue containing an interchain dicarba bridge.

In order to facilitate the production of an alkyne dicarba bridge, the at least two complementary metathesisable groups in step (i) will be complementary alkyne-containing metathesisable groups. In order to facilitate the production of an alkene dicarba bridge, the at least two complementary metathesisable groups in step (i) will be complementary alkene-containing metathesisable groups.

The peptide backbone in α-peptides is generally linear as the component amino acids (especially when these are the 20 common amino acids, with the exception of proline) form trans-configured peptide bonds. Proline, a pyrrolidine analogue, can induce a turn in an otherwise linear peptide. This is a naturally-occurring turn-inducing group. This embodiment is particularly suited to those peptides that do not contain a naturally-occurring turn-inducing amino acid, such as proline. In this case, a synthetic (non-naturally occurring) turn-inducing group is located in the amino acid sequence of insulin.

The linear —C≡C— geometry of the alkyne metathesisable groups can disfavour productive metathesis. The new alkyne bond (—C≡C—) that is formed will be linear, and the alkyne-containing metathesisable groups need to be brought in close proximity in order to react. Particularly, in ring-closing alkyne metathesis (ROAM), this may require that the backbone of the peptide curve around to bring the two alkyne-containing metathesisable groups into such a conformation. In some instances this can be sterically disfavoured and therefore alkyne metathesis may be relatively low yielding or not occur. Accordingly, it may be preferable to include a turn-inducing group between a pair of complementary alkyne-containing metathesisable groups or in a position adjacent to an alkyne-containing metathesisable group so that the conformation of the peptide backbone can be 'unnaturally' altered to allow a pair of complementary alkyne-containing metathesisable groups to be brought into an improved conformation for alkyne metathesis.

Preferably the turn-inducing group is a turn-inducing amino acid, dipeptide or protein, and is preferably synthetic (non-naturally occurring). Examples of suitable synthetic turn-inducing amino acids are the pseudoprolines, including derivatives of serine, threonine and cysteine (shown below). The pseudoprolines have been derivatised to contain a cyclic group between the amino acid sidechain (via the —OH or —SH group), and the amino nitrogen atom. A typical derivatising agent is $CH_3$—$C(=O)$—$CH_3$, such that the turn-inducing amino acids are:

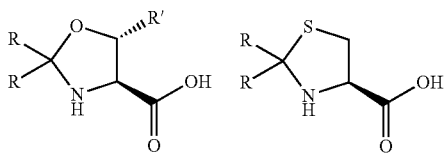

R = H, Me
R' = Me (threonine-derived)
R' = H (serine-derived)

These turn-inducing residues are often prepared as dipeptide units to aid incorporation into peptides. An example of a suitable turn-inducing residue is 5,5-dimethylproline which is stable and may stay in the peptide permanently. However, after metathesis, some pseudoproline(s) may be converted back to the underivatised amino acid (serine, threonine or cysteine) by removal of the derivatising agent usually on treatment with acid. The conditions for cleavage of the peptide from a solid support will usually achieve this.

If, for example, the turn-inducing amino acid is one of pseudo-serine, pseudo-threonine or pseudo-cysteine, then the method may further comprise the step of converting the pseudo-serine, pseudo-threonine or pseudo-cysteine to serine, threonine or cysteine, respectively.

The use of pseudoproline residues can be combined with the other preferred features described herein. As one example, pseudoproline residues can be used in combination with microwave conditions.

Alternating Solid Phase Peptide Synthesis and Metathesis

As described above, ring closing metathesis, whether driven via alkene or alkyne metathesis, can be difficult and low yielding with some sequences. Another strategy which may be used to improve the performance of ring closing metathesis between two complementary metathesisable groups (alkenes or alkynes) which are within the one peptide is by alternating peptide synthesis and catalysis steps. This approach may also be combined with the other preferred features described herein. For example, the peptide may be provided on a solid phase, and catalysis can be combined with the use of turn-inducing groups (e.g. pseudo-proline residues) and/or in combination with the use of microwave conditions.

According to this embodiment, there is provided a method for the synthesis of a dicarba analogue of insulin comprising an A-chain and a B-chain or fragments, salts, solvates, derivatives, isomers or tautomers of the A-chain, the B-chain or both, the method comprising:

(i) providing a part of the A-chain having at least two complementary metathesisable groups;
(ii) subjecting the A-chain to metathesis to form at least one dicarba bridge;
(iii) adding one or more further amino acids to one or both ends of the A-chain; and
(iv) adding the B-chain.

According to this embodiment, there is further provided a method for the synthesis of a dicarba analogue of insulin comprising an A-chain and a B-chain or fragments, salts, solvates, derivatives, isomers or tautomers of the A-chain, the B-chain or both, the method comprising:

(i) providing a part of the A-chain and/or a part of the B-chain having at least two complementary metathesisable groups between them;
(ii) subjecting the A-chain and B-chain to metathesis to form at least one dicarba bridge; and
(iii) adding one or more further amino acids to one or both ends of the A-chain and/or B-chain.

In this approach, the sequence is grown in a stepwise fashion until both metathesisable residues have been incorporated.

This method can be used to facilitate the production of alkyne dicarba bridge formation and/or alkene dicarba bridge formation. In order to facilitate the production of an alkyne dicarba bridge, the at least two complementary metathesisable groups in step (i) will be complementary alkyne-containing metathesisable groups. In order to facilitate the production of an alkene dicarba bridge, the at least two complementary metathesisable groups in step (i) will be complementary alkene-containing metathesisable groups.

One of the fragments of insulin may be provided on a solid support. Preferably, the second metathesisable group of the pair is located at or near the N-terminus of the peptide. The resin-supported, incomplete sequence is then exposed to the metathesis catalyst to form the dicarba bridge. Following the metathesis step, the resin can either be subjected to secondary catalysis (i.e. hydrogenation or metathesis), or followed immediately with solid phase peptide synthesis (SPPS) to add the one or more further amino acids. The one or more further amino acids may be added to complete the sequence of the A-chain or the B-chain of insulin or to add one or more further amino acid residues to the fragments of insulin. Amino acid residues may be added to either end of the A-chain or the B-chain of insulin. Preferably, amino acid residues are added to the N-terminus of the desired target peptide.

It will be appreciated that this process can be conducted iteratively in order to introduce more than one dicarba bridge. This interrupted approach, shown below, can be highly successful with sequences which are difficult to metathesise.

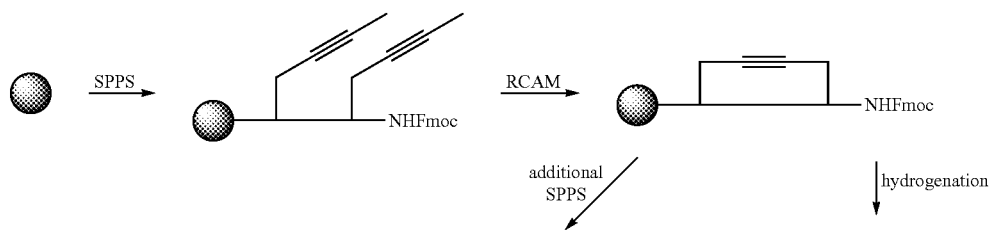

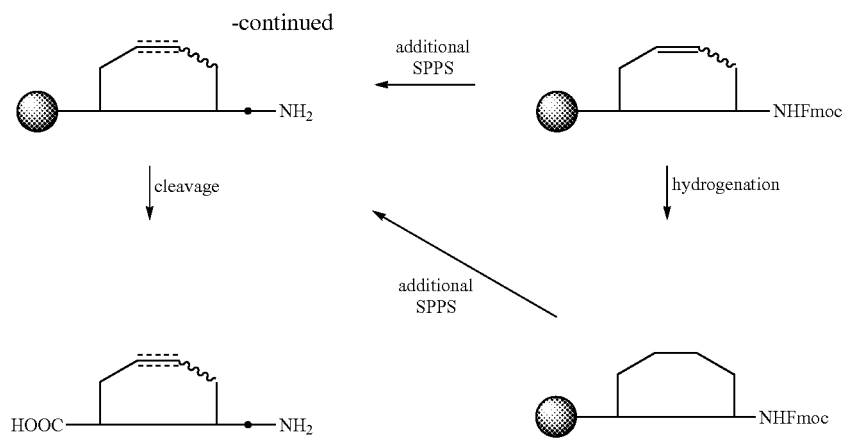

Tethers Between Peptide Sequences

In some instances, cross-metathesis between peptide sequences can be difficult and low yielding. Success is often sequence dependent and relies on favourable positioning of reacting motifs which can be hampered by peptide size, aggregation, deleterious hydrogen bonding/salt bridges and steric constraints imposed by the primary sequence.

One approach by which we can enhance the metathesis between two complementary metathesisable groups (alkenes or alkynes) is to utilise a contiguous peptide sequence, containing the two amino acids or peptides to be connected by a dicarba bridge, joined together via a removeable tether. Such an approach capitalises on the improved positioning of the reactive motifs imposed by the tether and hence exploits the enhanced reactivity via an intramolecular reaction (RCM) compared to an intermolecular reaction (CM) to produce superior ligation yields. Such an approach is illustrated below:

performed on the resin-bound peptide (RCM, RCAM and/or H) and the resultant cyclic peptide is then cleaved open at the tether to result in the target acyclic peptide. The final peptide is analogous to that produced via a direct CM reaction between two peptide sequences. The resin-appended sequence can then be further elaborated via SPPS in a number of positions as shown below.

Groups which may function as a removeable tether are structurally diverse. Any motif which can be chemoselectively incorporated and removed from the sequence, either chemically or enzymatically. The removeable tether may be a motif which can be added by reductive amination. The removeable tether may be a motif which can be removed by photolysis. Preferably, the removeable tether is a motif which also promotes a turn in the backbone of the primary sequence (similarly to the turn inducing residues described above). In this situation, the metathesis reaction may be enhanced by

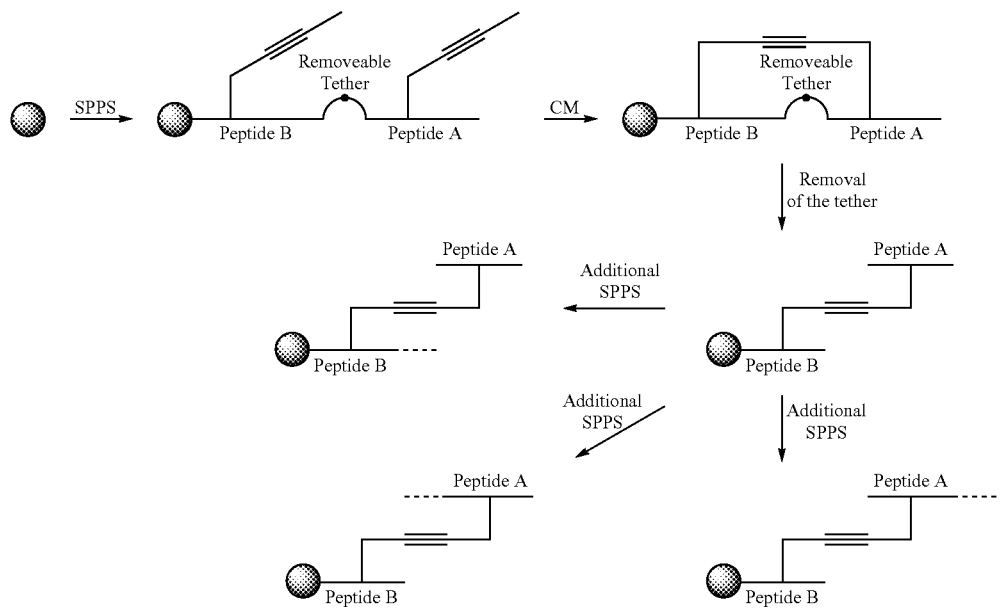

In this example, SPPS is used to generate a single peptide sequence where a transient/removeable tether is positioned between the two metathesisable groups. Catalysis is then suitable positioning of the reactive motifs could be used. As one example, the removeable tether may be hydroxy-6-nitrobenzaldehyde.

Solvents

The metathesis reaction may be performed in any suitable solvent which provides good catalytic turnover and good resin swell.

Particularly for reactions conducted with the reactable peptide or the first reactable peptide attached to a solid support such as a resin, metathesis is preferably performed in a solvent combination comprising a resin-swelling solvent with a co-ordinating solvent for the catalyst is preferably also used. In resin-supported reactions, swelling of the resin is required to avoid aggregation and to promote catalyst access to reactive functional groups. Some solvents which are suitable for swelling resins are not compatible with metathesis and/or hydrogenation catalysts, and hence careful selection must be made. For example, polystyrene-based resins show optimal swelling in chlorinated solvents such as dichloromethane, however these solvents are not compatible with hydrogenation catalysts. The solvents react with such catalysts to compromise catalyst function—which in turn reduces the catalytic cycle (or turn-over number—TON), resulting in incomplete conversion. It was found that the addition of a small amount of a co-ordinating solvent for the catalyst, such as an alcohol (e.g. methanol, isopropanol) which can co-ordinate into a vacant site of the catalyst to facilitate stability, overcame this problem. The co-ordinating solvent is suitably used in an amount of about 1-30%, for example constituting 10% of the solvent, by volume. The resin swelling agent may be any polar solvent known to swell the resin, such as dichloromethane. Other suitable solvents for a range of resins are as set out in Santini, R., Griffith, M. C. and Qi, M., *Tet. Lett.*, 1998, 39, 8951-8954, the entirety of which is incorporated herein by reference.

Solid Supports

The peptide or peptides used in the preparation of dicarba analogues of insulin are preferably attached to a solid support. The A-chain or B-chain of insulin may be attached to a solid support, or both the A-chain and the B-chain may be attached to a solid support.

A plethora of solid supports are known and available in the art, and include pins, crowns, lanterns and resins. Examples are polystyrene-based resins (sometimes referred to as solid supports), including cross-linked polystyrene resins (via ~1% divinylbenzene) functionalised with linkers (or handles) to provide reversible linkages between the reactable organic compound (which may be a peptide sequence containing side-chains with cross-metathesisable groups) and the resin. Examples of polystyrene-based resins include Wang resin, Rink amide resin, BHA-Gly-Gly-HMBA resin and 2-chlorotrityl chloride resin. Other forms of solid supports that may not necessarily be characterised as resins can also be used.

Under microwave reaction conditions it is possible to have a higher solid support loading than is conventionally used in peptide synthesis on solid supports. Typical solid support loadings are at the 0.1 mmol/g level, but microwave radiation (optionally combined with solvent choice, as described above) overcomes the aggregation problems at higher solid support loadings, so that solid support loading at around 0.9 mmol/g (nine times higher) is achievable. The solid support loadings may also be at around 0.2 mmol/g and above, such as 0.5 mmol/g and above.

Formation of One or More Disulfide Bridges to Prepare Dicarba Analogues of Insulin The following refers to the use of dicarba bridges in dicarba analogues to replace the disulfide bridges of insulin. It will be appreciated that the following decription could also be applied to the preparation of other dicarba analogues of insulin in which the dicarba bridges are used to replace other structural motifs, such as salt bridges, or other non-covalent interactions.

Insulin has three disulfide bonds: $Cys_{A6}$ and $Cys_{A11}$ oxidise to form the intramolecular disulfide bridge. $Cys_{A7}$ and $Cys_{B7}$ oxidise to form an intermolecular disulfide bridge and $Cys_{A20}$ and $Cys_{B19}$ oxidise to form the second intermolecular bridge. This connectivity needs to be preserved to maintain biological activity. Hence, disulfide formation, and hence chain combination, must be performed via a regioselective approach.

Significantly, undirected ligation of two or more peptide chains is usually only partially successful in native molecules. When sequence modifications are introduced however, unnatural folding can become more significant and exert a deleterious effect on chain combination. The resultant topoisomers contaminate the required product and lower the yield of native isomer. These challenges have been reported extensively in the literature, particularly in the unsuccessful syntheses of insulin analogues containing modified A- and B-chains.

The dicarba analogues of insulin may have one or more disulfide bonds as well as at least one dicarba bridge. The disulfide bonds may be introduced at any location, however, it is preferred that they are introduced into a peptide or peptides at locations where disulfide bonds are present in the native insulin.

Where more than one disulfide bridge is to be introduced into the peptide or peptides, disulfide formation, and hence chain combination, must be performed via a regioselective approach. One approach is to use orthogonally-protected cysteine residues to sequentially construct the disulfide bridges. An example of the regioselective bond forming strategy was used in the regioselective synthesis in Wade et al., *J. Biol. Chem.*, 2006, 281, 34942-34954, which is incorporated herein by reference. Preferably, a combination of complementary thiol protecting groups (e.g. Acm, $^t$Bu, Trt) is used to regioselectively install disulfide bridges.

Reduction of Unsaturated Dicarba Bridges in Dicarba Analogues of Insulin

In some instances, the dicarba bridge of the dicarba analogue of insulin may have improved activity where the dicarba bridge has a particular conformation in order to serve as a peptidominetic of insulin. It may therefore be advantageous for the dicarba bridge to adopt a particular geometry.

The product of alkyne or alkene metathesis is a dicarba analogue of insulin with a new unsaturated alkyne or alkene-containing dicarba bridge (—C≡C— or —C=C—). If the target compound is to contain an alkane-containing dicarba bridge (—CH$_2$—CH$_2$—), the preparation of the dicarba analogue may also involve subjecting the alkyne/alkene-containing dicarba bridge to complete reduction. If the target compound is to contain an alkene-containing dicarba bridge (—CH=CH—), the preparation may involve semi-reduction of the alkyne-containing dicarba bridge.

Hydrogenation of an Alkyne- or Alkene-Containing Dicarba Bridge

The product of the alkyne or alkene metathesis is a dicarba analogue of insulin with a new unsaturated alkyne- or alkene-containing dicarba bridge (—C≡C— or —C=C—). If the target compound is to contain an alkene-containing dicarba bridge (—C=C—) or an alkane-containing dicarba bridge (—C—C—) the process may further comprise the step of hydrogenating the alkyne or alkene bond.

The hydrogenation can be conducted at any temperature, such as room temperature or at an elevated temperature. The reaction is typically conducted at elevated pressure, although if slower reaction times can be tolerated, the reaction can be performed at atmospheric pressure. The hydrogenation reaction can be performed on substrates which are attached or unattached to a solid support.

Hydrogenation of the unsaturated dicarba bridge can be performed with any known hydrogenation catalyst. Examples of suitable catalysts include those described in March, *J. Advanced Organic Chemistry: Reactions, Mechanisms and Structure*. 1992, pages 771 to 780 and in Ojima, I. *Catalytic Asymmetric Synthesis*; Wiley-VCH: New York, 2000; Second Edition, Chapter 1, 1-110, incorporated herein by reference. Suitable hydrogenation catalysts are chemoselective for unblocked, non-conjugated carbon-carbon double or triple bonds.

Suitable hydrogenation catalysts may be either insoluble in the reaction medium (heterogeneous catalysts) or soluble in the reaction medium (homogeneous catalysts). Examples of suitable heterogeneous catalysts include Raney nickel, palladium-on-charcoal (Pd/C) and platinum oxide. Examples of suitable homogeneous catalysts include Wilkinson's catalyst, other Rh(I) phosphine complexes, and Ru(II) phosphine complexes.

The particular hydrogenation catalyst that is used will depend on the dicarba insulin analogue (the target compound) to be prepared. For example, if the target compound is to include a saturated alkane-containing dicarba bridge, a hydrogenation catalyst capable of reducing an alkyne bond (possibly via an alkene intermediate) or an alkene bond to an alkane bond will be selected ("complete hydrogenation"). As another example, if the target compound is to include an unsaturated alkene-containing dicarba bridge, a hydrogenation catalyst capable of reducing an alkyne bond to an alkene bond ("semi-hydrogenation") will be selected.

If the target compound is to include a saturated alkane-containing dicarba bridge, the hydrogenation is performed with a catalyst that is chemoselective for unblocked, non-conjugated carbon-carbon triple and carbon-carbon double bonds as distinct from other double bonds such as carbon-oxygen double bonds in carbonyl groups, carboxylic acids and blocked conjugated double bonds. The hydrogenation of an alkyne (—C≡C—) bridge to an alkane (—CH2—CH2—) bridge involves the initial step of producing an alkene (—C=C—) bridge. The alkene bridge then becomes a substrate for further reduction to finally produce the required —CH2—CH2— bridge.

Any catalyst which is chemoselective for unblocked, non-conjugated carbon-carbon triple and double bonds may be used. Examples of hydrogenation catalysts capable of reducing an alkyne bond to an alkane bond include palladium-on-charcoal (Pd/C), platinum oxide, and Raney nickel. Hydrogenation catalysts which are suitable for reducing an alkyne or alkene bond to an alkane bond also include asymmetric hydrogenation catalysts. Although the use of an asymmetric hydrogenation catalyst is not necessary for the hydrogenation of the alkyne- or alkene-containing dicarba bridges, asymmetric hydrogenation catalysts can nevertheless be used. Any asymmetric hydrogenation catalyst which is chemoselective for unblocked non-conjugated carbon-carbon double or triple bonds may be used. Catalysts in this class are described in U.S. Pat. No. 5,856,525 which is incorporated herein by reference. Such homogenous hydrogenation catalysts are tolerant of sulfide, and disulfide bonds, so that the presence of disulfide bonds and the like will not interfere with the synthetic strategy. Examples of suitable asymmetric hydrogenation catalysts are the chiral phosphine catalysts, including chiral phospholane Rh(I) catalysts.

Some hydrogenation catalysts are chemoselective for alkyne groups as distinct from alkene groups. Such catalysts are thus capable of hydrogenating an alkyne and stopping the reaction at an alkene. The hydrogenation of an alkyne-containing dicarba bridge (—C≡C—) to form an alkene containing dicarba bridge (—C=C—) is therefore performed with a catalyst that is chemoselective for unblocked non-conjugated carbon-carbon triple bonds as distinct from other double bonds such as carbon-carbon double bonds, carbon-oxygen double bonds in carbonyl groups, carboxylic acids and blocked conjugated double bonds. Any catalyst which is chemoselective for unblocked non-conjugated carbon-carbon triple bonds may be used.

Within the group of hydrogenation catalysts are catalysts that are chemoselective for alkyne groups as distinct from alkene groups. These catalysts are also able to stereoselectively reduce an alkyne-containing dicarba bridge to form an alkene-containing dicarba bridge that is enriched in either the cis- or the trans-isomer. This method allows biased generation of either the cis- or trans-isomer by selecting a catalyst which produces a product enriched in the desired isomer.

The controlled reduction of C=C and C≡C in organic compounds is an important synthetic transformation and many catalysts are available to achieve this end. Partial conversion of alkynes into alkenes provides a particularly useful route to geometrically well defined alkenes. A large number of well defined homogeneous transition metal complexes can be used to affect stereoselective semi-hydrogenation of the C≡C bond, and many of these catalysts are also tolerant of a wide range of organic functionality. Organochromium, iron, ruthenium, osmium, rhodium, iridium and palladiaum complexes, inter alia, have all been used in semi-hydrogenation reactions of alkynes. Reaction conditions (e.g. solvent, temperature) play a large role in influencing reaction selectivity. Towards this end, catalysts and reaction conditions can be coupled to selectivity and stereoselectivity perform C≡C→C=C transformations in the presence of existing C=C bonds without resulting in over-reduction. For example, zerovalent palladium catalysts bearing bidentate nitrogen ligands are able to homogeneously hydrogenate alkynes to Z-alkenes and do not reduce existing alkene functionality.

Any catalyst which is stereoselective and chemoselective for unblocked non-conjugated carbon-carbon triple bonds may be used. Catalysts in this class include those described in Kluwer, A. M., Elsevier, C. J. "The Handbook of Homogeneous Hydrogenation", 2007, Wiley-VCH (de Vries, J. G., Elsevier, C. J. (Editors)), Ch 14: Homogeneous Hydrogenation of Alkynes and Dienes, pp 375-411, incorporated herein by reference. Examples of suitable chemoselective hydrogenation catalysts include poisoned Lindlar's catalyst, Pd(0), Ru(II), ruthenium carbonyl clusters, Pt(0), P2-Ni, chromium tricarbonyl compounds of the generic formula [Cr(CO)3(arene)], Fe(II) catalyst presursors such as [(PR3)FeH(N2)]BPh4, [(PR3)FeH(H2)]BPh4 and (PR3=P(CH2CH2PPh2)3), osmium catalysts such as [OsH(Cl)(CO)(PR3)2] and rhodium catalysts such as the Schrock/Osborn cationic Rh-catalyst.

In one example of chemoselective and stereoselective hydrogenation, the alkyne-containing dicarba bridge is hydrogenated in the presence of Pd(0)-catalyst. The resulting dicarba analogue of insulin has an alkyne-containing dicarba bridge that is enriched in the cis-isomer. In another example performing the hydrogenation in the presence of a Ru(II)-catalyst results in a dicarba analogue of insulin having an alkene-containing dicarba bridge that is enriched in the trans-isomer. This is shown schematically below.

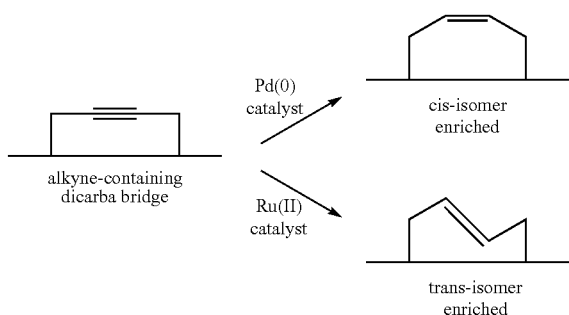

Where the dicarba bridge of the dicarba analogue of insulin is an alkene-containing dicarba bridge, the alkene containing group of the bridge may be present as a mixture of any ratio of geometric isomers (e.g. E- or Z-configured alkenes), or as an enriched geometric isomer. As defined above, "enriched" means that the mixture contains more of the preferred isomer than of the other isomer. Preferably, an enriched mixture comprises greater than 50% of the preferred isomer, where the preferred isomer gives the desired level of potency and selectivity. More preferably, an enriched mixture comprises at least 60%, 70%, 80%, 90%, 95%, 97.5% or 99% of the preferred isomer.

When the product produced by the method of the present invention is a peptide having an alkyne-containing dicarba bridge, the step of hydrogenating the alkyne-containing dicarba bridge can be performed with the peptide attached to a resin. Preferably, when the peptide substrate is attached to a resin, the hydrogenation step uses a homogeneous, hydrogenation catalyst.

Reduction of an Alkyne-Containing Dicarba Bridge

As described above, alkyne metathesis produces an alkyne-containing dicarba bridge formed between two amino acids. This alkyne-containing dicarba bridge may be converted to the corresponding alkene-containing or alkane-containing dicarba bridge by reduction methods other than hydrogenation of the alkyne-containing dicarba bridge.

Reduction of the alkyne-containing dicarba bridge may be stereo-selective to reduce an alkyne-containing dicarba bridge to an alkene-containing dicarba bridge that is enriched in either the cis- or the trans-isomer.

In one example, the alkyne-containing dicarba bridge may be stereo-selectively reduced via hydrosilylation and protodesilylation to produce an alkene-containing dicarba bridge. The alkene that results is enriched in the trans-isomer. This type of reduction is described in Fürstner, A., Radkowski, K. *Chem. Commun.* 2002, 2182 and Lacombe, F., Radkowski, K., Seidel, G. and Fürstner, A., *Tetrahedron*, 2004, 60, 7315, and incorporated herein by reference. In this approach, the alkyne-containing dicarba bridge can be selectively reduced to the trans-isomer by trans-selective hydrosilylation followed by protodesilylation. The two steps involved in this selective reduction are shown below.

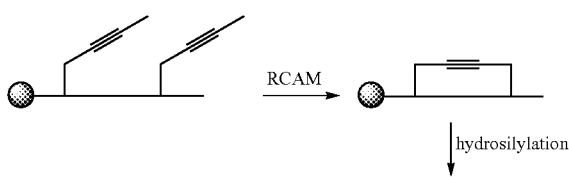

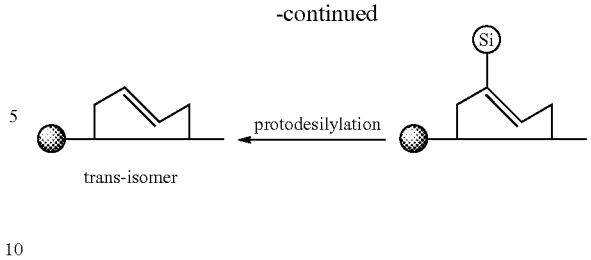

The hydrosilylation step may be performed using (EtO)$_3$SiH in the presence of the cationic ruthenium complex [Cp*Ru(MeCN)$_3$]PF$_6$. In this reaction the HSi(OEt)$_3$ reagent is added with cis-selectively across the alkyne bond of the alkyne-containing dicarba bridge. After protodesilylation, a product that is enriched in the trans-isomer across the alkene-containing dicarba bridge is produced.

When the product being produced is a peptide having an alkyne-containing dicarba bridge, the step of reducing the alkyne-containing dicarba bridge can be performed with the peptide attached to a resin.

Formation (Regioselectively) of Multiple Dicarba Bridges in the Peptide or Peptides The strategy for the formation of a dicarba bridge as described above is suitable to form dicarba analogues of insulin with multiple dicarba bridges, optionally with disulfide bridges, or to form dicarba analogues of insulin with at least one dicarba bridge and at least one disulfide bridge. The dicarba analogues of insulin may include more than one alkyne-containing dicarba bridge, more than one alkene-containing dicarba bridge or more than one alkane-containing dicarba bridge, or combinations thereof, with or without one or more disulfide bridges.

To form dicarba analogues of insulin having multiple dicarba bridges, it may be necessary to include at appropriate locations in the insulin peptides, pairs of complementary metathesisable groups which are blocked or deactivated for the times when different pairs of metathesisable groups are being linked together, and unblocked or "activated" to enable reaction to occur between those pairs. Accordingly, for each bridge-forming pair, there should to be an unblocking reaction available that will selectively unblock the required pairs.

The first pair of complementary metathesisable groups to be subjected to metathesis (alkene metathesis or alkyne metathesis) need not be blocked. The pair of unblocked complementary metathesisable groups is then subjected to the metathesis reaction, as described above, to form a dicarba bridge. Optionally, the newly formed unsaturated dicarba bridge may be subjected to reduction. The step of reduction may occur after the first dicarba bridge has been formed, or after the further dicarba bridges or disulfide bridges are formed.

When the dicarba analogue of insulin contains more than one dicarba bridge. The dicarba bridges may be selected from an alkyne-containing dicarba bridge, an alkene-containing dicarba bridge and an alkane-containing bridge. The two or more dicarba bridges may be the same or different.

As described above, metathesis is used to introduce dicarba bridges into the dicarba analogue of insulin.

Tandem Alkyne Metathesis

When the dicarba analogue of insulin is to contain two or more alkyne-containing dicarba bridges, it is important to avoid the formation of an intractable mixture of different products from random metathesis between pairs of alkyne-containing metathesisable groups or between an alkyne-containing metathesisable group or groups and a formed alkyne-containing dicarba bridge.

In one approach, a pair of complementary alkyne-containing metathesisable groups may be introduced during synthesis of a peptide and alkyne metathesis conducted to form a first alkyne-containing dicarba bridge before subsequent pairs of complementary alkyne-containing metathesisable groups are introduced into the peptide. This approach is the refered to as the Alternating-SPPS-catalysis approach and is as described above. In another approach, blocking groups may be used to allow regioselective formation of the particular alkyne containing dicarba bridges. It will be appreciated that any combination of these approaches may also be used to prepare the desired product.

An example of a typical route for the introduction of two alkyne-containing dicarba bridges into a dicarba analogue of insulin is shown below. In this example, alkyne-containing metathesisable groups are used to form dicarba analogues containing one intra-molecular dicarba bridge and one inter-molecular dicarba bridge, in which the peptides correspond to the A-chain or the B-chain of insulin or fragments, salts, solvates, derivatives, isomers or tautomers thereof.

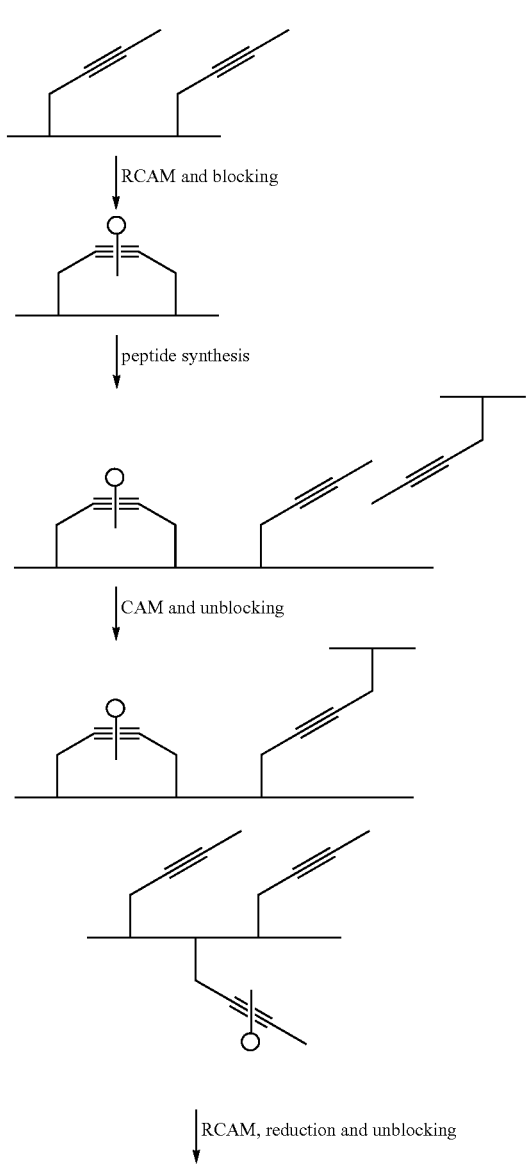

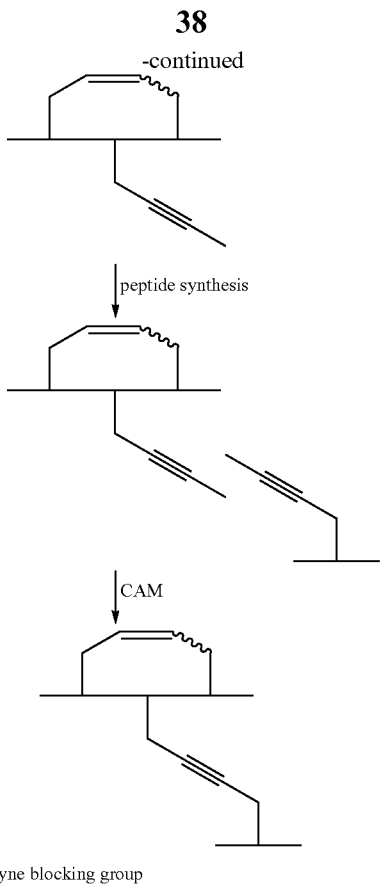

= alkyne blocking group

In example (A) above, two metathesisable groups in a single peptide are subjected to ring-closing alkyne-metathesis (RCAM) to produce an alkyne-containing dicarba bridge. Following this, the alkyne-containing dicarba bridge is blocked and peptide synthesis is conducted to introduce a further alkyne metathesisable group which is complementary to an alkyne-containing metathesisable group on a separate peptide. These two separate peptides represent the A-chain and/or the B-chain of insulin. The unblocked alkyne-containing metathesisable groups are then subjected to alkyne-metathesis (CAM) to produce a second alkyne-containing dicarba bridge. The blocked alkyne-containing dicarba bridge may then be unblocked to produce a peptide containing one intramolecular and one intermolecular alkyne-containing dicarba bridge.

In example (B) above, a peptide is synthesised having two unblocked metathesisable groups and a blocked metathesisable group between the two. The unblocked metathesisable groups are subjected to ring-closing alkyne-metathesis (ROAM) to produce an alkyne-containing dicarba bridge. Following this, the alkyne-containing dicarba bridge is reduced to an alkene-containing dicarba bridge and the blocked alkyne-containing metathesisable group is unblocked. A second peptide having an alkyne-containing metathesisable group is then introduced, and the two peptides are subjected to alkyne-metathesis (CAM) to produce a second alkyne-containing dicarba bridge.

Blocking and Activation for Alkyne Metathesis

For metathesis to occur between two alkynes, the alkynes must not be blocked or protected. A blocking group is any group that prevents metathesis from taking place in the presence of a metathesis catalyst. Preferably, a blocking group is used to prevent reaction of the alkyne metathesisable group during olefin metathesis, where the dicarba insulin analogue is to include both an alkyne-containing dicarba bridge and an alkene-containing dicarba bridge. Blocking groups may also be provided on a formed alkyne-containing bridge. In a preferred embodiment, the blocking group is provided on either the unreacted alkyne-containing metathesisable group or the alkyne-containing dicarba bridge, during olefin metathesis.

Examples of blocking groups for an alkyne include dicobalt hexacarbonyl groups. Removal of one or both of the blocking groups unblocks the alkyne-containing-metathesisable group to enable alkyne metathesis to take place or unblocks the alkyne-containing dicarba bridge. It is noted that for subsequent alkyne metathesis the pair of alkyne-containing metathesisable groups that remain after unblocking need not be identical. For example, after deblocking, but-4-ynylglycine and pent-4-ynylglycine may be metathesised to form a new alkyne bridge. The term "complementary" is used to indicate that the pair of unblocked alkyne-containing metathesisable groups are not necessarily identical, but are merely complementary in the sense that cross-metathesis can take place across the two alkyne groups.

As described above, using a combination of blocking and unblocking mechanisms allows regioselective synthesis of multiple dicarba bridges (intra- and/or interchain) in dicarba analogues of insulin.

Tandem Alkene Metathesis

When the dicarba analogue of insulin is to contain two or more alkene-containing dicarba bridges, it is also important to avoid random metathesis occurring between pairs of alkene-containing metathesisable groups or between an alkene-containing metathesisable group and a formed alkene-containing dicarba bridge.

For alkene metathesis, suitable groups for forming the first pair of complementary methathesisable groups which are not blocked are —CH=CH$_2$ and —CH=CH—CH$_3$. These groups may be included in insulin by peptide synthesis, and may be provided via an amino acid connected to —CH=CH$_2$ or having —CH=CH$_2$ in its side chain optionally with any divalent linking group linking the carbon at the "open" end (the —CH= carbon atom) to the amino acid backbone, such as an -alkylene-, -alkylene carbonyl-, and so forth. Examples of —CH=CH$_2$-containing amino acids and —CH=CH—CH$_3$-containing amino acids are allylglycine and crotylglycine, respectively. Each of these amino acids contains the divalent linking group —CH$_2$— between the alkylene and the amino acid (peptide) backbone.

At the completion of that reaction (and optionally after hydrogenation of the first dicarba bridge), the blocked second pair of complementary metathesisable groups, can be subjected to an unblocking reaction.

When the first pair of complementary metathesisable groups are olefins, suitable functional groups for forming the second pair of complementary metathesisable groups are di-blocked alkylenes, such as the group —CH=CR$_{12}$R$_{13}$, in which R$_{12}$ and R$_{13}$ are each independently selected from blocking groups, such as alkyl. R$_{12}$ and R$_{13}$ are preferably alkyl of C1 to C15. More preferably, R$_{12}$ and R$_{13}$ are small chain alkyls, for example methyl. Again, there may be a divalent linking group between the —CH= carbon atom, and the amino acid backbone, such as an alkylene group, for instance —CH$_2$—. An example of an amino acid containing this group is prenylglycine, or protected prenylglycine.

The unblocking reaction, or activation reaction, to convert the pair of di-blocked alkylenes into an unblocked alkylenes involves subjecting the blocked second pair of complementary metathesisable groups to cross-metathesis with a disposable olefin, to effect removal of the blocking groups (such as R$_{12}$ and R$_{13}$ in the example shown above).

It will be understood that in this case, cross-metathesis is used to replace the group =CR$_{12}$R$_{13}$ with another unblocked group =CH$_2$ or =CHR$_{14}$, (in which R$_{14}$ may be —H, a functionalised alkyl or alkyl for instance) which is then "activated" or "unblocked" and ready for being subjected to cross-metathesis for the formation of a dicarba bridge, using the same techniques described above.

The conditions for this activation-type of cross-metathesis are the same as described above for the dicarba bridge forming metathesis. It can be performed under microwave conditions, although it need not be, as the disposable olefin is a smaller molecule and less subject to the spatial constraints as larger reactable peptides and single reactable peptides in which intramolecular bridges are to be formed.

The "disposable olefin" is suitably a mono-substituted ethylene (such as monoalkylated ethylene—such as propene, which is mono-methylated ethylene), or a 1,2-disubstituted ethylene (such as high purity 2-butene, and optionally of cis or trans geometry, or a mixture thereof). Previously, commercial 2-butene has been attempted to be used as the disposable olefin in this unblocking reaction, and the reaction is thus sometimes referred to as "butenolysis". However, commercially available 2-butene (which is a mixture of cis- and trans-2-butene) can inhibit olefin metathesis due to low level butadiene contaminants.

The substituents on the substituted ethylene disposable olefin are substituents that do not participate in the reaction. Examples are alkyl or a functionalised (substituted) alkyl. The functional group of the functionalised alkyl is suitably a polar functional group, to assist with swelling of the solid support, and solubility. Examples are hydroxy, alkoxy, halo, nitrile and carboxylic acids/esters. One specific example is the di-ester functionalised disposable olefin 1,4-diacetoxy-2-butene.

Thus the disposable olefin is suitably a 1,3-butadiene-free disposable olefin, or a 1,3-butadiene-free mixture of disposable olefin and is preferably 1,3-butadiene-free olefin or olefin mixture of one or more of the following olefins:

wherein X and Y are each independently selected from the group consisting of —H, alkyl and alkyl substituted with one or more substituents selected from halo, hydroxy, alkoxy, nitrile, acid and ester.

Preferably, at least one of X and Y is not H.

Preferably, in the case of the alkyl substituents, the substituent is preferably on the carbon atom. Preferably the substituted alkyl is a substituted methyl. According to one embodiment, at least one of X and Y is a substituted alkyl, such as a substituted methyl. X and Y may be the same or different. The olefins may be cis or trans, or mixtures of both.

Blocking and Activation for Alkene Metathesis

For metathesis to occur between two alkene groups (olefins), the alkenes must not be blocked by any steric or electronic blocking groups. A steric blocking group is any bulky group that sterically prevents the metathesis from taking place in the presence of a cross-metathesis catalyst. An example of a steric blocking group on an olefin is an alkyl group. Prenylglycine is an example of an amino acid containing a dialkyl-blocked olefin side chain (specifically, dimethyl-blocked). Removal of one or both of the blocking groups unblocks the olefin, and enables the cross-metathesis to take place.

It is noted that the pair of metathesisable groups that remain after unblocking need not be identical—a mono-substituted olefin (such as a mono-methylated olefin, e.g. crotylglycine) and an unsubstituted olefin (being unsubstituted at the open olefinic end, e.g. allylglycine) can form a suitable pair of cross-metathesisable groups. The term "complementary" is used to indicate that the pair of unblocked metathesisable groups are not necessarily identical, but are merely complementary in the sense that cross-metathesis can take place across the two olefinic groups.

Electronic blocking refers to the presence of a group on the organic compound or reactable peptide that modifies the electronic nature of the olefin (alkene) group of the reactable peptide (which would otherwise undergo cross-metathesis), so as to prevent that olefin group from undergoing cross-metathesis. An example of an electronic blocking group is when the double bond is in conjugation with a C=O group— that is, a double bond adjacent to an α,β-unsaturated carbonyl containing group (e.g. C=C—C=C—C=O where the C=C portion is the otherwise reactable group). The α-β-unsaturation withdraws electrons away from the olefinic (C=O) cross-metathesisable group causing electronic blocking and prevention of cross-metathesis. By using a combination of blocking mechanisms, a series of pairs of metathesisable groups in the reactable peptide or peptides of insulin can be designed, with different reaction conditions to effect selective unblocking of particular pairs. In this way, it becomes possible to regioselectively synthesise multiple dicarba bridges (inter and/or intramolecular) in insulin.

containing complementary metathesisable groups or the dicarba bridge formed by alkyne metathesis is blocked during any alkene metathesis steps.

In the formation of a dicarba analogue of insulin having one alkyne-containing dicarba bridge and at least one alkene-containing dicarba bridge, it is possible to introduce a pair of complementary alkyne-containing or alkene-containing metathesisable groups during synthesis of a peptide and conduct metathesis to form the first dicarba bridge before subsequent pairs of complementary metathesisable groups are introduced into the peptide. It may also be necessary to use blocking groups to allow regioselective formation of the particular alkyne- or alkene-containing dicarba bridges.

Examples of synthetic routes for the introduction of one alkyne-containing dicarba bridge and one alkene dicarba bridge are shown below. These examples show the use of alkene-containing and alkyne-containing metathesisable groups to form dicarba analogues containing intrachain dicarba bridges in a peptide which may correspond to the A-chain, the B-chain or both of insulin.

In the catalytic pathways A and B, both combine alkyne and alkene metathesis for the regioselective formation of two dicarba bridges. Both routes involve alkene cross metathesis of a pair of alkene-containing metathesisable groups, alkyne cross metathesis of a pair of alkyne-containing metathesisable groups, and the optional reduction of the newly formed bridges to the corresponding alkanes. The difference between the two pathways is the order of the catalysis. In pathway A, alkyne metathesis (RCAM) preceeds alkene (RCM) metathesis, and in pathway B, alkene metathesis preceeds alkyne metathesis.

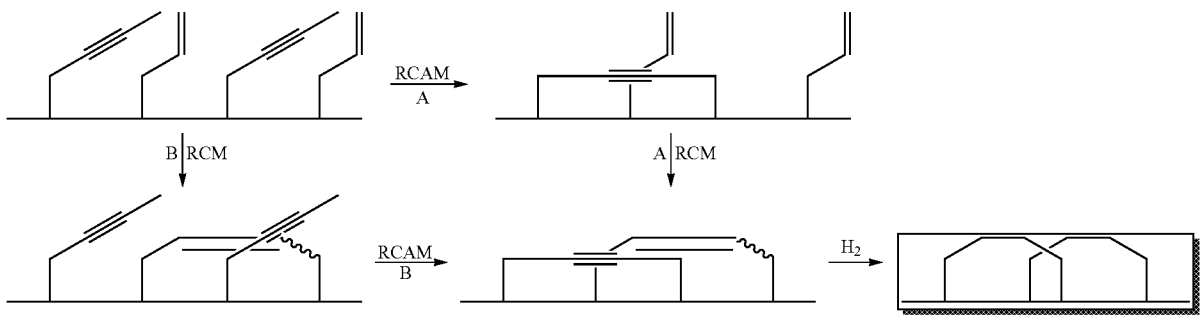

Tandem Alkene and Alkyne Metathesis

The use of tandem alkene and alkyne metathesis to facilitate regioselective synthesis of multiple dicarba bridges is a viable strategy for the synthesis of a peptide or peptides containing at least one alkyne containing dicarba bridge and at least one alkene-containing dicarba bridge. Modern metathesis catalysts are highly chemoselective and are readily tuned to unsaturated substrates to achieve maximum selectivity.

When the target peptide is to contain at least one alkyne-containing dicarba bridge and at least one alkene-containing dicarba bridge, it is important to avoid the formation of an intractable mixture of different products from random metathesis between pairs of metathesisable groups or between metathesisable groups and formed dicarba bridges.

It will be appreciated that the step of alkyne metathesis may occur before any number of steps involving alkene metathesis or at the conclusion of any number of steps involving alkene metathesis. However, it is preferred that either the alkyne Transition metal metathesis catalysts show varying degrees of chemo-specificity in their activity toward potential substrates. Transition metal alkylidene bearing catalysts, such as those employed in alkene metathesis, show an affinity for coordination and subsequent metathesis of reactable olefins. Some of these catalysts are able to coordinate alkynes and undergo enyne metathesis, the bond reorganisation of an alkyne to form a 1,3-diene (*Chem. Rev.,* 2004, 104(3), pp 1317-1382). These species may react with other alkenes to produce further products. Some alkene metathesis catalysts, such as the first generation Grubbs' catalyst, show limited propensity toward this side reaction in the presence of available alkynes. To avoid unwanted reaction of alkyne moieties the group may be blocked by an appropriate blocking group as described herein.

Transition metal alkylidyne bearing catalysts, such as Schrock's alkyne metathesis catalyst, show high activity toward alkyne metathesis but do not participate in olefin or enyne metathesis (R. R. Schrock, *Chem. Commun.*, 2005, 2773-2777). Hence, protection of olefins during alkyne metathesis is not necessary with catalysts of this kind. Preferably, alkyne metathesis in the presence of alkene-containing metathesisable groups or alkene-containing dicarba bridges is performed with Schrock's catalyst.

Blocking and activation of alkyne-containing metathesisable groups and alkene-containing metathesisable groups may be achieved as described herein when the dicarba analogue of insulin contains both an alkyne-containing dicarba bridge and an alkene-containing dicarba bridge.

Reduction of Peptides Having Additional Dicarba Bridges

The reduction of alkyne-containing dicarba bridges and alkene-containing dicarba bridges may be performed as described hereinabove. It will be appreciated by a person skilled in the art that when multiple dicarba bridges are to be present in a dicarba analogue of insulin, the step of reducing the initially installed alkyne- or alkene-containing dicarba bridge may take place before or after the metathesis reaction to additional dicarba bridges.

Peptide Synthesis

The method for the synthesis of a dicarba bridge in a peptide such as insulin is described above.

Generally, the peptide will be a protected peptide (such as Fmoc-protected), and will comprise a sequence corresponding to the A-chain or the B-chain or both of insulin or a fragment, salt, solvate, derivative, isomer or tautomer thereof. The amino acids which make up the sequence corresponding to insulin can be any of the amino acids described earlier, but it is convenient for the synthesis of peptidomimetics for the amino acids to be selected from the 20 naturally-occurring amino acids, γ- and β-amino acids and from any cross-metathesisable group-bearing analogues or alkyne metathesisable group bearing analogues thereof. An example of metathesisable group-bearing analogues are allylglycine and butynylglycine.

It will be appreciated that if a peptide sequence is added later through an intermolecular bridge, the corresponding metathesisable groups on that peptide need not be blocked— as they can be added to the reaction at the time of cross-metathesis, after the unblocking of the groups on the solid-supported peptide.

Uses Involving the Dicarba Insulin Analogues

In the field of insulin delivery, where multiple repeated administrations are required on a daily basis throughout the patient's life, it is desirable to create compositions of insulin that do not alter physiological clinical activity and that do not require injections. Oral delivery of insulin is a particularly desirable route of administration, for safety and convenience considerations. In addition to minimizing or eliminating the discomfort that often attends repeated hypodermic injections, it removes the needs for delivery devices (e.g. injecting devices) and allows the unit doses to be formulated into convenient forms (e.g. tablets) which are typically easier to handled, transport and stored. It has been a significant unmet goal in the art to imitate normal insulin levels in the portal and systemic circulation via oral administration of insulin.

Oral delivery of insulin may have advantages beyond convenience, acceptance and compliance issues. Insulin absorbed in the gastrointestinal tract is thought to mimic the physiologic route of insulin secreted by the pancreas because both are released into the portal vein and carried directly to the liver before being delivered into the peripheral circulation. Absorption into the portal vein maintains a peripheral-portal insulin gradient that regulates insulin secretion. In its first passage through the liver, roughly 60% of the insulin is retained and metabolized, thereby reducing the incidence of peripheral hyperinsulinemia, a factor linked to complications in diabetes.

Insulin exemplifies the problems confronted in the art in designing an effective oral drug delivery system for biological macromolecules. Insulin absorption in the gastrointestinal tract is presumably hindered by, amongst other things, its susceptibility for enzymatic degradation. The physicochemical properties of insulin and its susceptibility to enzymatic digestion have precluded the design of a commercially viable oral or alternate delivery system.

Insulin currently cannot be taken orally because it is broken down in the gastrointestinal tract to peptide fragments (even single amino acid components). This digestion of insulin results in a loss of activity.

The dicarba analogues of insulin have been found to be very stable upon storage over long periods of time, even in acidic conditions. It is envisaged that such insulin derivatives have the potential to be delivered orally whilst still providing a sustained profile of action. There are several ways to assess the stability of insulin. One way is an HPLC stability-indicating assay. This method determines the amount of intact insulin molecules present in a sample, but does not determine whether these molecules are in a bioactive conformation, which is necessary in order to have an effective product. Other methods are measurement of related substances (impurities) by HPLC and assessing the bioactivity of the product, which could be an in vivo assay or an in vitro predictor of in vivo performance. The biological activity of a dicarba insulin may be measured in an assay as known by a person skilled in the art as e.g. described in WO 2005/012347.

In one embodiment, a pharmaceutical composition comprising the therapeutic dicarba insulin is stable for more than 6 weeks of usage and for more than 3 years of storage. In another embodiment, the pharmaceutical composition comprising the therapeutic dicarba insulin is stable for more than 4 weeks of usage and for more than 3 years of storage. In another embodiment, the pharmaceutical composition comprising the therapeutic dicarba insulin is stable for more than 4 weeks of usage and for more than 2 years of storage. In another embodiment, the pharmaceutical composition comprising the therapeutic dicarba insulin is stable for more than 2 weeks of usage and for more than two years of storage. In another embodiment, the pharmaceutical composition comprising the therapeutic dicarba insulin is stable for more than 1 weeks of usage and for more than one year of storage.

In another embodiment, the pharmaceutical composition is in the form of a clear solution and is stable for more than 6 weeks of usage and for more than 3 years of storage. In another embodiment, the pharmaceutical composition is in the form of a clear solution and is stable for more than 4 weeks of usage and for more than 3 years of storage. In another embodiment, the pharmaceutical composition is in the form of a clear solution and is stable for more than 4 weeks of usage and for more than two years of storage. In another embodiment, the pharmaceutical composition is in the form of a clear solution and is stable for more than 2 weeks of usage and for more than two years of storage. In another embodiment, the pharmaceutical composition is in the form of a clear solution and is stable for more than 1 week of usage and for more than one year of storage.

In another embodiment, the pharmaceutical composition is in the form of a tablet and is stable for more than 3 years of storage. In another embodiment, the pharmaceutical composition is in the form of a tablet and is stable for more than two years of storage. In another embodiment, the pharmaceutical composition is in the form of a tablet and is stable for more than one year of storage.

Reference to "storage" above equates to "shelf-stability" or being "shelf-stable". Shelf-stability includes chemical stability as well as physical stability. Chemical instability involves degradation of covalent bonds, such as hydrolysis, racemization, oxidation or crosslinking. Chemical stability of the formulations is evaluated by means of reverse phase (RP-HPLC) and size exclusion chromatography SE-HPLC). In one aspect of the invention, the formation of peptide related impurities during shelf-life is less than 20% of the total peptide content. In a further aspect of the invention, the formation of peptide related during impurities during shelf-life is less than 10%. In a further aspect of the invention, the formation of peptide related during impurities during shelf-life is less than 5%. The RP-HPLC analysis is typically conducted in water-acetonitrile or water-ethanol mixtures. In one aspect, the solvent in the RP-HPLC step will comprise a salt such as Na2SO4, (NH4)2SO4, NaCl, KCl, and buffer systems such as phosphate, and citrate and maleic acid. The required concentration of salt in the solvent may be from about 0.1M to about 1M, preferable between 0.2 M to 0.5 M, most preferable between 0.3 to 0.4 M. Increase of the concentration of salt requires an increase in the concentration of organic solvent in order to achieve elution from the column within a suitable time. Physical instability involves conformational changes relative to the native structure, which includes loss of higher order structure, aggregation, fibrillation, precipitation or adsorption to surfaces. Peptides such as insulin peptides, GLP-1 compounds and amylin compounds are known to be prone to instability due to fibrillation. Physical stability of the formulations may be evaluated by conventional means of e.g. visual inspection and nephelometry after storage of the formulation at different temperatures for various time periods. Conformational stability may be evaluated by circular dichroism and NMR as described by e.g. Hudson and Andersen, Peptide Science, vol 76 (4), pp. 298-308 (2004).

A pharmaceutical composition of the present invention is preferably shelf-stable for at least the period which is required by regulatory agencies in connection with therapeutic proteins. Preferably, a shelf-stable pharmaceutical composition is stable for at least one year, more preferably at least two years, at 5° C. Preferably, a shelf-stable pharmaceutical composition is stable for at least one year, more preferably at least two years, at 25° C.

Methods of Treatment

The dicarba analogues of insulin of the present invention provide methods of treating subjects with the following diseases or conditions: hyperglycemia; impaired glucose tolerance; early stage diabetes; late stage diabetes; diabetes mellitus including diabetes type I and diabetes type II; and metabolic syndrome; or diseases or conditions that directly or indirectly result therefrom. For example, a hyperglycemia associated disease refers to a disorder or disorders that directly or indirectly result from elevated levels of glucose in the blood plasma.

The dicarba analogues of insulin of the present invention also provide methods of treating subjects in order to achieve glucose homeostasis or in order to reduce the incidence and/or severity of systemic hyperinsulinemia associated with chronic dosing of insulin. It is believed that the present invention also provides methods for reducing the incidence and/or severity of one or more disease states associated with chronic dosing of insulin; for prophylactically sparing β-cell function or for preventing β-cell death or dysfunction in a subject which has impaired glucose tolerance or early stage diabetes mellitus; and for long-term protection from developing overt or insulin dependent diabetes, or for delaying the onset of overt or insulin dependent diabetes, in a mammal which has impaired glucose tolerance or early stage diabetes.

The term "diabetes mellitus" refers to a group of metabolic diseases characterised by the onset of chronic hyperglycemia. Diabetes mellitus has been classified into three main groups:

1. Type I diabetes (previously referred to as insulin dependent or juvenile-onset diabetes) results from an absolute insulin deficiency arising from autoimmune destruction of insulin-secreting β-cells in the pancreas.

2. Type II diabetes is also known as non-insulin dependent diabetes, and manifests as a result of insulin resistance and a relative insulin deficiency. It is usually associated with obesity and onset is more common later in life. Although insulin therapy is not essential for those suffering type II diabetes in its initial stages, patients may eventually require treatment as their disease progresses.

3. Gestational diabetes is usually temporary, and is defined as any degree of glucose intolerance arising during pregnancy.

4. The term "metabolic syndrome" refers to a group of risk factors that raise your risk for heart disease and other health problems, such as diabetes and stroke. These risk factors include abdominal obesity, a high triglyceride level, a low HDL cholesterol level, high blood pressure and high fasting blood sugar.

Preferred diseases for which the dicarba insulin analogues are used include diabetes mellitus and metabolic syndrome.

The term "subject" refers to any animal having a disease which requires treatment with the dicarba analogues of insulin of the present invention. In a preferred embodiment, subjects are mammals, preferably humans. Examples of mammals which can be treated using the dicarba analogues of insulin, compositions and methods of the present invention include cows, sheep, goats, horses, dogs, cats, guinea pigs, rats or other bovine, ovine, equine, canine, feline, rodent or murine species. However, the invention can also be practiced in other species, such as avian species (e.g., chickens).

The term "therapeutically active dicarba analogue of insulin" or "therapeutic dicarba analogue of insulin" or "therapeutic dicarba insulin" as used herein refers to a dicarba analogue of insulin able to treat (including cure, alleviate or partially arrest) the clinical manifestations of diabetes and/or hyperglycemia and the complications therefrom.

The "treatment" or "treating" of a disease or condition as used herein means the management and care of a patient having developed the disease, condition or disorder. The purpose of treatment is to combat the disease, condition or disorder. Treatment includes the administration of a therapeutically active dicarba insulin to eliminate or control (e.g. inhibit or arrest development of) the disease, condition or disorder as well as to alleviate, relieve or ameliorate the symptoms, complications or effects associated with the disease, condition or disorder, and prevention of the disease, condition or disorder. The term "prevention of a disease" as used herein is defined as the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders.

The term "administering" should be understood to mean providing a therapeutic dicarba insulin of the invention to a subject in need of treatment.

Dose, Dose Regimes and Mode of Administration

The dicarba analogues of insulin of the invention may be administered by any suitable means. Examples of suitable routes of administration include parenterally, such as by subcutaneous, percutaneous, intravenous, intra-arterial, intramuscular, intra(trans)dermal, or intracisternal injection or infusion techniques (e.g., as sterile injectable aqueous or non-aqueous solutions or suspensions); nasally such as by inhalation spray or insufflation; topically, such as in the form of a cream or ointment ocularly in the form of a solution or suspension; and orally, in dosage unit formulations containing non-toxic, pharmaceutically acceptable vehicles or diluents. The compounds may, for example, be administered in a form suitable for immediate release or extended release. Immediate release or extended release may be achieved by the use of suitable pharmaceutical compositions comprising the certain dicarba analogues of insulin, or, by the use of devices such as subcutaneous implants or osmotic pumps.

In the treatment or prevention of conditions which require the administration of insulin, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. The dosage may be selected, for example to any dose within any of these ranges, for therapeutic efficacy and/or symptomatic adjustment of the dosage to the patient to be treated. The compounds will preferably be administered as necessary, and preferably on a regimen of 1 to 5 times per day, preferably once or twice per day.

Each unit dosage will suitably contain from 0.1 mg to 300 mg therapeutic dicarba insulin. In one embodiment each unit dosage contains from 0.5 mg to 100 mg of therapeutic dicarba insulin. In a further embodiment a unit dosage contains from 1 mg to 50 mg of dicarba insulin. In a further embodiment a unit dosage contains from 1.5 mg to 30 mg of dicarba insulin. Such unit dosage forms are suitable for administration 1-5 times daily depending upon the particular purpose of therapy.

It will be understood that the specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In one embodiment, the dicarba analogues of insulin are administered by subcutaneous injection. The pharmaceutical compositions containing the dicarba analogues of the present invention may be in a form suitable for any of the routes of administration described above, by inclusion of suitable pharmaceutically acceptable excipients.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable formulations.

For topical use, creams, ointments, jellies, solutions or suspensions, etc., containing the compounds of the present invention are employed. (For purposes of this application, topical application shall include mouthwashes and gargles.)

For application to the eye, the active compound may be in the form of a solution or suspension in a suitable sterile aqueous or non-aqueous vehicle. Additives, for instance buffers, preservatives including bactericidal and fungicidal agents, such as phenyl mercuric acetate or nitrate, benzalkonium chloride, or chlorohexidine and thickening agents such as hypromellose may also be included.

The dicarba insulin analogues of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolisable lipid capable of forming liposomes can be used. The present compositions in liposome form can contain, in addition to the dicarba insulin analogue of the present invention, stabilisers, preservatives, excipients and the like. The preferred lipids are the phospholipids and phosphatidyl cholines, both natural and synthetic. Methods to form liposomes are known in the art.

A particularly preferred mode of administration is oral administration.

The dicarba analogues of the present invention may also be presented for use in the form of veterinary compositions, which may be prepared, for example, by methods that are conventional in the art. Examples of such veterinary compositions include those adapted for:

parenteral administration for example by subcutaneous, intramuscular or intravenous injection, e.g. as a sterile solution or suspension; or (when appropriate) by intramammary injection where a suspension or solution is introduced in the udder via the teat;

topical applications, e.g. as a cream, ointment or spray applied to the skin.

oral

The term "therapeutically effective amount" refers to the amount of the dicarba insulin that will elicit the biological or medical response of a tissue, system, animal or human that is being sought by the researcher, veterinarian, medical doctor or other clinician.

In a preferred embodiment, administration of the pharmaceutical composition takes place multiple times daily, preferably at bedtime and preprandially during the day time, e.g., preprandially for breakfast, lunch and dinner. More preferably, administration of the pharmaceutical formulation is at or shortly prior to bedtime and concurrently with or shortly prior to ingestion of a meal, i.e., within about 15 minutes or less of ingestion of the meal.

In another preferred embodiment of the invention, the oral pharmaceutical composition formulation will be administered about once daily to about four times daily, preprandially and/or at bedtime, depending upon the extent of the patient's impaired glucose tolerance and need for exogenous glycemic control. If the patient has a need for fasting glycemic control, the oral pharmaceutical formulation will be administered only at or shortly prior to bedtime. If the subject has a need for post-prandial glycemic control, the oral pharmaceutical formulation will be administered preprandially for all meals. If the subject has a need for comprehensive glycemic control, the oral pharmaceutical formulation will be administered preprandially for all meals and at or shortly prior to bedtime.

Preferably, the dosage form of the present invention will be administered for at least one day, more preferably on a chronic basis, and can be administered for the life of the subject. Most preferably, the dosage form of the present invention will be administered on a chronic basis, e.g., for at least about two weeks.

Preferably, the therapeutic dicarba insulin treatment of the present invention will be administered to subjects having some form of impaired glucose tolerance. This can range from insulin resistance seen in pre-diabetics and early stage Type 2 diabetics to failure of insulin production by the pancreas seen in Type 1 diabetes and late stage Type 2 Diabetes. In certain embodiments, the resulting improved insulin utilization or insulin sensitivity of the subject's body is measured by HOMA (Homeostasis Model Assessment). In certain embodiments, the resulting improved insulin secretion capacity of the subject's body is measured by Stumvoll first-phase insulin secretion capacity index.

Further, the therapeutic dicarba insulin treatment of the present invention can be administered to a mammal with an $HbA_1c$ ranging from normal to elevated levels. More particularly, the treatment can be administered to anyone in the range of normal glycemic control to impaired glycemic control to late stage type 2 diabetes or type 1 diabetes. In certain embodiments, the resulting improved glycemic control in the subject's body is measured by a reduced serum fructosamine concentration. Preferably the average decline will be about 8.8% after at least two weeks of treatment with the present invention.

In preferred embodiments of the oral dosage forms of the invention described above, the oral dosage form is solid, and is preferably provided incorporated within a gelatin capsule or is contained in a tablet.

In certain preferred embodiments, the dose of the therapeutic dicarba insulin contained in one or more dosage forms is from about 50 Units to about 600 Units (from about 2 to about 23 mg), preferably from about 100 Units (3.8 mg) to about 450 Units (15.3 mg) insulin, more preferably from about 200 Units (7.66 mg) to about 350 Units (13.4 mg), and still more preferably about 300 Units (11.5 mg), based on the accepted conversion of factor of 26.11 Units per mg.

In certain preferred embodiments of the invention, the dosage forms begin delivering the dicarba insulin into the systemic circulation via the portal vein (via absorption through the mucosa of the gastrointestinal tract) to achieve peak levels within about 30 minutes or less.

In certain preferred embodiments, the dosage forms of the invention provide a $t_{max}$ for insulin at from about 5 minutes to about 30 minutes, and more preferably at from about 10 minutes to about 25 minutes after oral administration to diabetic subjects. In certain preferred embodiments of the invention, the dosage forms begin delivering the dicarba insulin into the systemic circulation to produce a peak plasma insulin concentration at about 10 to about 20 minutes post oral administration and in further preferred embodiments, a peak plasma insulin concentration at about 10 minutes to about 15 minutes post oral administration to subjects who ingested the dosage at about 0 or about 10 minutes prior to ingestion of a meal.

The invention is also directed in part to an oral dosage form comprising a dose of therapeutic analogue of insulin that achieves a therapeutically effective control of post prandial blood glucose after oral administration to human diabetic subjects in tablet form at or shortly before mealtime, the oral solid dosage form providing an insulin tmax at a time point from about 10 minutes to about 15 minutes after oral administration to said subjects, at least about 30% of the blood glucose concentration reduction caused by said dose of insulin occurring within about less than 1 hour after oral administration of said dosage form. In preferred embodiments of this invention, the oral dosage form is a tablet.

In certain preferred embodiments, the composition provides a tmax for maximum control of glucose excursion at about 0.25 to about 1.5 hours, more preferably at about 0.75 to about 1.25 hours, after oral administration. In certain preferred embodiments, the $t_{max}$ for post-prandial glucose control occurs preferably at less than about 120 minutes, more preferably at less than about 80 minutes, and still more preferably at about 45 minutes to about 60 minutes, after oral administration of the composition.

Because insulin entry into the bloodstream produces a decrease in blood glucose levels, oral absorption of the therapeutic dicarba insulin may be verified by observing the effect on a subject's blood glucose following oral administration of the composition. In a preferred embodiment of the invention, the oral dosage forms of the invention facilitate the oral delivery of therapeutic dicarba insulin, and after the therapeutic dicarba insulin is absorbed into the bloodstream, the composition produces a maximal decrease in blood glucose in treated type 2 diabetic subjects from about 5 to about 60 minutes after oral administration. In another embodiment of the present invention, the pharmaceutical composition produces a maximal decrease in blood glucose in treated type 2 diabetic subjects from about 10 to about 50 minutes post oral administration. More particularly, the pharmaceutical composition produces a maximal decrease in blood glucose in treated type 2 diabetic subjects within about 20 to about 40 minutes after oral administration.

The magnitude of the decrease in blood glucose produced by the therapeutic dicarba insulin absorbed into the bloodstream following entry into the gastrointestinal tract varies with the dose of therapeutic dicarba insulin. In certain embodiments of the invention, type 2 diabetic diabetic patients show a maximal decrease in blood glucose by at least 10% within one hour post oral administration. In another embodiment, type 2 diabetic diabetic patients show a maximal decrease in blood glucose by at least 20% within one hour post oral administration, alternatively, at least 30% within one hour post oral administration.

Normal levels of blood glucose vary throughout the day and in relation to the time since the last meal. One goal of the present invention is to provide oral compositions of therapeutic dicarba insulin that facilitate achieving close to normal levels of blood glucose throughout the 24-hour daily cycle. In a preferred embodiment of the invention, the pharmaceutical composition includes the therapeutic dicarba insulin as the active agent and optionally a delivery agent in an amount effective to achieve a fasting blood glucose concentration from about 90 to about 115 mg/dl. In another preferred embodiment of the invention, the pharmaceutical composition includes therapeutic dicarba insulin as the active agent and optionally a delivery agent in an amount effective to achieve a fasting blood glucose concentration from about 95 to about 110 mg/dl, more preferably, the subject manifests fasting blood glucose concentrations at about 100 mg/dl.

In the time after a meal is consumed, blood glucose concentration rises in response to digestion and absorption into the bloodstream of carbohydrates derived from the food eaten. The present invention provides oral compositions of therapeutic dicarba insulin that prevent or control very high levels of blood glucose from being reached and/or sustained. More particularly, the present invention provides compositions which facilitate achieving normal levels of blood glucose after a meal has been consumed, i.e., post-prandial. In a preferred embodiment of the invention, the pharmaceutical composition includes therapeutic dicarba insulin as the active agent and optionally a delivery agent in an amount effective to achieve a post-prandial blood glucose concentration from about 130 to about 190 mg/dl. In another preferred embodiment of the invention, the pharmaceutical composition includes therapeutic dicarba insulin as the active agent and optionally a delivery agent in an amount effective to achieve a post-prandial blood glucose concentration from about 150 to about 180 mg/dl, more preferably, the subject manifests fasting blood glucose concentrations at less than about 175 mg/dl.

The present invention provides pharmaceutical compositions for oral administration which includes therapeutic dicarba insulin as the active agent and optionally a delivery agent in an amount effective to achieve pre-prandial (before a meal is consumed) blood glucose concentration from about 90 to about 125 mg/dl. In a preferred embodiment, the present invention provides pharmaceutical compositions for oral administration which includes therapeutic dicarba insulin as the active agent and optionally a delivery agent in an amount effective to achieve pre-prandial blood glucose concentration from about 100 to about 115 mg/dl.

The present invention provides pharmaceutical compositions for oral administration which include therapeutic dicarba insulin as the active agent and optionally a delivery agent in an amount effective to achieve blood glucose concentrations within the normal range during the evening period from about 70 to about 120 mg/dl. In a preferred embodiment, the present invention provides pharmaceutical compositions for oral administration which include therapeutic dicarba insulin as the active agent and optionally a delivery agent in an amount effective to achieve blood glucose concentrations at about 4 hours after bed time from about 80 to about 120 mg/dl.

In general, the present invention provides a method of administering therapeutic dicarba insulin and pharmaceutical compositions useful for administering therapeutic dicarba insulin such that the therapeutic dicarba insulin is bioavailable and biopotent. The use of a delivery agent can be used to improve, enhance or facilitate the oral absorption of the therapeutic dicarba insulin through the mucosa of the stomach (either in the same dosage form, or simultaneously therewith), or sequentially (in either order, as long as both the delivery agent and therapeutic dicarba insulin are administered within a time period which provides both in the same location, e.g., the stomach, at the same time).

By virtue of the chronic administration of oral dosage forms of the present invention instead of equi-effective subcutaneous doses of insulin, it is anticipated that lower levels of hyperinsulinemia may be obtained. Therefore, the present invention provides a method for reducing the incidence and/or severity of systemic hyperinsulinemia associated with chronic dosing of insulin, and it is believed that the present invention also provides a method for reducing the incidence and/or severity of one or more disease states associated with chronic dosing of insulin.

By virtue of the chronic administration of oral dosage forms of the present invention, it is anticipated the patient may achieve improved glucose tolerance and glycemic control as compared with baseline levels prior to treatment, even without any statistically significant increase in weight, risk of hypoglycemia or risk of hyperinsulinemia over the treatment period. Further, by virtue of the chronic administration of oral dosage forms of the present invention, it is anticipated that the patient may achieve improved insulin utilization, insulin sensitivity insulin secretion capacity and HbA1c levels as compared with baseline levels prior to treatment.

It is also believed that the chronic administration of oral dosage forms of the present invention to replace the endogenous insulin production in a mammal with impaired glucose tolerance or early stage diabetes mellitus will result in prophylactically sparing the function of the mammal's β-cells or will prevent death or dysfunction of the mammal's β-cells, and will thereby provide long-term protection to the mammal from developing overt or insulin dependent diabetes, or will delay the onset of overt or insulin dependent diabetes in the mammal.

In certain preferred embodiments of the present invention, the oral therapeutic dicarba insulin compositions of the invention may be administered to a subject at meal time, and preferably slightly before (e.g., about 10-30 minutes before) ingestion of a meal, such that the peak plasma insulin concentrations are attained at or about the time of peak blood glucose concentrations resulting from the meal. As a further advantage in certain preferred embodiments, the administration of a relatively short-acting insulin (e.g., such as the insulin used to prepare the capsules administered in the clinical studies reported in the appended examples) will further result in plasma insulin levels returning to baseline levels within about 4 hours (and preferably within about 3 hours or less) after oral administration of the dicarba insulin compositions of the present invention.

The total amount of therapeutic dicarba insulin to be used can be determined by those skilled in the art. It is preferable that the oral dosage form comprise a therapeutically effective amount of therapeutic dicarba insulin, i.e., a pharmacologically or biologically effective amount, or an amount effective to accomplish the purpose of insulin. The dose of therapeutic dicarba insulin administered should preferably be in such an amount that, upon oral administration, it results in a measurable and statistically significant reduction in blood glucose levels in normal healthy human subjects.

However, the amount can be less than a pharmacologically or biologically effective amount when the composition is used in a dosage unit form, such as a tablet, because the dosage unit form may contain a multiplicity of delivery agent/biologically or chemically active agent compositions or may contain a divided pharmacologically or biologically effective amount. The total effective amounts can then be administered in cumulative units containing, in total, pharmacologically, biologically or chemically active amounts of biologically or pharmacologically active agent.

Preferred therapeutic dicarba insulin doses contained in one or more dosage forms, when dosed in combination with the delivery agents described herein, are about 50 to about 600 insulin Units USP (from about 2 to about 23 mg), preferably from about 100 Units (3.8 mg) to about 450 Units (15.3 mg), more preferably from about 200 Units (7.66 mg) to about 350 Units (13.4 mg), and still more preferably about 300 Units (11.5 mg), based on the accepted conversion of factor of 26.11 Units per mg.

Pharmaceutical Compositions

In the treatment or prevention of conditions which require the administration of insulin, it will be understood that determining an appropriate dosage may be achieved using routine experimentation, by constructing a matrix of values and testing different points in the matrix, which is all within the ordinary skills of a trained physician or veterinarian. The therapeutically active dicarba insulin may be present in an amount of from about 0.01% to about 40% by weight of the total pharmaceutical composition, preferably about 0.1% to about 20% by weight of the total pharmaceutical composition. In one embodiment, the therapeutically active dicarba insulin may be present in an amount from about 0.01% to about 30%, in another embodiment from about 0.01% to 20%, 0.1% to 30%, 1% to 20% or from about 1% to 10% by weight of the total composition. The choice of a particular level of dicarba insulin will be made in accordance with factors well-known in the pharmaceutical arts, including, for example, the solubility of the derivatized peptide, mode of administration and the size and condition of the patient. The present invention provides pharmaceutical compositions comprising at least one of the dicarba analogues of insulin or a fragment, salt, solvate, derivative, isomer or tautomer thereof and a pharmaceutically acceptable carrier. The carrier must be "pharmaceutically acceptable", which means that it is compatible with the other ingredients of the composition and is not deleterious to a subject. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavours, etc.) according to techniques such as those well known in the art of pharmaceutical formulation (See, for example, Remington: The Science and Practice of Pharmacy, 21st Ed., 2005, Lippincott Williams & Wilkins).

The pharmaceutical composition may comprise additional excipients commonly found in pharmaceutical compositions. Examples of such excipients include, but are not limited to, antioxidants, antimicrobial agents, enzyme inhibitors, stabilizers, preservatives, flavors, sweeteners and other components as described in Handbook of Pharmaceutical Excipients, Rowe et al., Eds., 4'h Edition, Pharmaceutical Press (2003), which is hereby incorporated by reference. These additional excipients may be in an amount from about 0.05-5% by weight of the total pharmaceutical composition. Antioxidants, anti-microbial agents, enzyme inhibitors, stabilizers or preservatives typically provide up to about 0.05-1 by weight of the total pharmaceutical composition. Sweetening or flavoring agents typically provide up to about 2.5% or 5% by weight of the total pharmaceutical composition. Examples of antioxidants include, but are not limited to, ascorbic acid and its derivatives, tocopherol and its derivatives, butyl hydroxyl anisole and butyl hydroxyl toluene.

In one embodiment, the composition comprises a buffer. The term "buffer" as used herein refers to a chemical compound in a pharmaceutical composition that reduces the tendency of pH of the composition to change over time as would otherwise occur due to chemical reactions. Buffers include chemicals such as sodium phosphate, TRIS, glycine and sodium citrate.

The term "preservative" as used herein refers to a chemical compound which is added to a pharmaceutical composition to prevent or delay microbial activity (growth and metabolism). Examples of pharmaceutically acceptable preservatives are phenol, m-cresol and a mixture of phenol and m-cresol.

The term "stabilizer" as used herein refers to chemicals added to peptide containing pharmaceutical compositions in order to stabilize the peptide, i.e. to increase the shelf life and/or in-use time of such compositions. Examples of stabilizers used in pharmaceutical formulations are L-glycine, L-histidine, arginine, glycylglycine, ethylenediamine, citrate, EDTA, zinc, sodium chloride, polyethylene glycol, carboxymethylcellulose, and surfactants and antioxidants like alfa-tocopherol and l-ascorbic acid.

The pharmaceutical composition and method of the present invention may further comprise other therapeutically active compounds as noted herein which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

When other therapeutic agents are employed in combination with the dicarba analogues of the present invention they may be used for example in amounts as noted in the Physician Desk Reference (PDR) or as otherwise determined by one of ordinary skill in the art.

In a preferred embodiment of the invention, the methods comprise orally administering a therapeutically effective dose of a pharmaceutical composition comprising a therapeutic dicarba insulin, optionally with a delivery agent that facilitates the absorption of the dicarba insulin from the gastrointestinal tract, to provide a therapeutically effective reduction in blood glucose and a plasma insulin concentration, to provide a therapeutically effective reduction and/or control in blood glucose concentration and a plasma insulin concentration that is reduced relative to the plasma insulin concentration provided by a therapeutically equivalent dose of subcutaneously injected insulin. The determination of insulin concentration obtained in subjects who have been administered subcutaneous insulin are well known to those skilled in the art.

The preferred pharmaceutical compositions of the invention comprise a combination of insulin and a delivery agent in a suitable pharmaceutical carrier or excipient as understood by practitioners in the art. The means of delivery of the pharmaceutical composition can be, for example, a capsule, compressed tablet, pill, solution, freeze-dried, powder ready for reconstitution or suspension suitable for administration to the subject.

Presently, different forms of typically subcutaneously-administered insulin preparations have been developed to provide different lengths of activity (activity profiles), often due to ingredients administered with insulin, ranging from short or rapid activity (e.g., solutions of regular, crystalline zinc insulin for injection; semilente insulin (prompt insulin zinc suspension); intermediate activity (e.g., NPH (isophane insulin suspension; lente (insulin zinc suspension; lente is a mixture of crystallized (ultralente) and amorphous (semilente) insulins in an acetate buffer); and slow activity (ultralente, which is extended insulin zinc suspension; protamine zinc). Short-acting insulin preparations that are commercially available in the U.S. include regular insulin and rapid-acting insulins. Regular insulin has an onset of action of 30-60 minutes, peak time of effect of 1.5 to 2 hours, and a duration of activity of 5 to 12 hours. Rapid acting insulins, such as aspart (Humalog®)/lispro (Novolog®), have an onset of action of 10-30 minutes, peak time of effect of 30-60 minutes, and a duration of activity of 3 to 5 hours. Intermediate-acting insulins, such as NPH (neutral protamine Hagedorn) and Lente insulins (insulin zinc suspension), have an onset of action of 1-2 hours, peak time of effect of 4 to 8 hours, and a duration of activity of 10 to 20 hours. In the case of long-acting insulins, Ultralente insulin has an onset of action of 2-4 hrs, peak time of effect of 8-20 hours, and a duration of activity of 16 to 24 hours, while Glargine insulin has an onset of action of 1 to 2 hours, a duration of action of 24 hours but no peak effect.

There are over 180 individual insulin preparations available world-wide. Approximately 25% of these are soluble insulin (unmodified form); about 35% are basal insulins (mixed with NPH or Lente insulins, increased pI, or isoelectric point (insulin glargine), or acylation (insulin detemir); these forms have reduced solubility, slow subcutaneous absorption and long duration of action relative to soluble insulins); about 2% are rapid-acting insulins (e.g., which are engineered by amino-acid change, and have reduced self-association and increased subcutaneous absorption); and about 38% pre-mixed insulins (e.g., NPH/soluble/rapid-acting insulins; these preparations have the benefit, e.g., of reduced number of daily injections). In many cases, regimens that use insulin in the management of diabetes combine long-acting and short-acting insulin. It is contemplated that the dicarba insulin analogues of the present invention, and in particular the oral formulations which include the dicarba insulin analogues preferably together with a pharmaceutically acceptable delivery agent that facilitates absorption of the dicarba insulin analogue from the gastrointestinal tract, may be utilized in combination therapy to include an insulin that has rapid action, intermediate action, and/or slow action, as described above, in order to provide effective basal insulin levels in the, for example, diabetic patient. It will be appreciated that the combination therapy may comprise one or more dicarba insulin and one or more non-dicarba insulin such as for example any one of the commercially available insulins disclosed above. The rate of action of the insulin may be caused by virtue of its solubility, and/or by virtue of its half-life, etc. Thus, in alternative embodiments, the oral formulations of the present invention may be designed to provide the intermediate activity which is found with, e.g., a subcutaneously administered NPH insulin, or a slow action which is found with protamine zinc insulin. In each case, the oral formulations of the invention, which preferably include a pharmaceutically acceptable delivery agent which facilitates absorption of the insulin (as described herein) provide effective control of blood glucose levels, albeit for different time periods and with different plasma glucose time curves. Intermediate-acting and long-acting insulin may be prepared using methodologies known to those skilled in the art to provide a continuous level of insulin, similar to the slow, steady (basal) secretion of insulin provided by the normal pancreas. For example, Lantus®, from Aventis Pharmaceuticals Inc., is a recombinant human insulin analog that is a long-acting, parenteral blood-glucose-lowering agent whose longer duration of action (up to 24 hours) is directly related to its slower rate of absorption. Lantus® is administered subcutaneously once a day, preferably at bedtime, and is said to provide a continuous level of insulin, similar to the slow, steady (basal) secretion of insulin provided by the normal pancreas. The activity of such a long-acting insulin results in a relatively constant concentration/time profile over 24 hours with no pronounced peak, thus allowing it to be administered once a day as a patient's basal insulin. Such long-acting insulin has a long-acting effect by virtue of its chemical composition, rather than by virtue of an addition to insulin when administered In a preferred embodiment, administration of a pharmaceutical composition comprising a long-acting form of insulin (e.g. a therapeutic dicarba analogue of a long-acting form of insulin) is once or twice a day. In a preferred embodiment, administration of a therapeutic dicarba insulin providing short-acting insulin effect can be once, twice, three times, four times or more than four times daily, and can be at nighttime, in the morning and/or preprandially. In a more preferred embodiment, administration of the dosage form is preferably at nighttime or morning and three times preprandially, and more preferably is at nighttime and preprandially for breakfast, lunch and dinner. Preferably, the therapeutic dicarba insulin compositions are administered to such human patients on a chronic basis, e.g., for at least about 2 weeks. In certain preferred embodiments of the invention, the oral formulations of the invention provide two forms of insulin having different activity rates in order to simulate the biphasic release of insulin in non-diabetic humans. For example, such oral formulations may include a rapid-acting dicarba analogue (e.g. a therapeutic dicarba analogue of a rapid-acting insulin) together with a slow-acting dicarba analogue (e.g. a therapeutic dicarba analogue of a slow-acting insulin) so as to provide a first peak of insulin which occurs rapidly and is short-lived, followed by a second peak of insulin which occurs at a later time, but which preferably has a longer duration. In further alternatively preferred embodiments of the invention, the oral formulations of the invention include a rapid-acting dicarba analogue together with a secretagogue that promotes the secretion of insulin from the beta-cells at a time and to an extent which mimics the second phase release of insulin in non-diabetic humans.

In alternatively preferred embodiments of the invention, the methods of administration of the invention provide two separate forms of dicarba insulin analogues having different activity rates in order for the regimen to simulate the biphasic release of insulin in non-diabetic humans. For example, the formulations (e.g. the oral formulations) may include a rapid-acting dicarba insulin so as to provide a first peak of insulin which occurs rapidly and is short-lived. Such fast-acting effect may be provided by a delivery agent that facilitates the absorption of insulin from the gastrointestinal tract. A slow-acting insulin (which may be a dicarba insulin) provides a second peak of insulin that occurs at a later time but that preferably has a longer duration. Such slower acting insulin may be provided by a separate dosage form, which may be administered orally or subcutaneously.

In further embodiments of the present invention, the pharmaceutical compositions, including the oral dosage formulations, described herein are administered as described herein in combination with an additional therapy to treat diabetes, impaired glucose tolerance, or to achieve glucose homeostasis, said additional therapy comprising, for example, an additional drug such as a sulfonylurea, a biguanide (such as Metformin), an alpha-glucosidase, insulin delivered via a different pathway (e.g., parenteral insulin), and/or an insulin sensitizer such as thiazolidinedione. The additional therapy may be administered via the same or different route of administration.

In further embodiments of the invention, the oral dosage forms described herein reduce the likelihood of hypoglycemic events. Hypoglycemia usually results from a mismatch between insulin levels and degree of glycemia, e.g., when the administration of insulin and the ingestion of the meal are not timed such that the insulin peak occurs at peak glycemia, and administration of insulin shortly before a meal is more practical for a patient and is also safer, because glucose is ingested soon thereafter. The risk of hypoglycemia is lowered mainly due to the portal-physiologic route of administration of oral insulin. One cannot hyperinsulinize the liver, because, even under hyperinsulinemic condition, the uptake of glucose by the liver will be unchanged. Unlike the peripheral tissue, the pancreas will not sequester additional glucose but rather will only cease producing endogenous insulin. Second, the brief peak of insulin that results from the oral composition described herein shows that, even if insulin were to reach high peripheral levels, the peak quickly drops precipitously.

In addition, further embodiments of the oral dosage forms described herein avoid the risk of hypoglycemic events that may occur in certain short acting insulin formulations, which may, between the time of administration of insulin and the time of ingestion of the meal, contribute to a lowering of blood glucose to a level that could range from undesirable to clinically hypoglycemic. In the oral dosage forms disclosed herein, dosing closer to a meal eliminated the dip in blood glucose levels, which was precarious by itself. The effect seems to have also translated to lowering of the subsequent glucose excursion.

In preferred embodiments of the dosage forms described herein, in the absence of a delivery agent, the dose of insulin is not sufficiently absorbed when orally administered to a human patient to provide a desirable therapeutic effect but said dose provides a desirable therapeutic effect when administered to the patient by another route of administration. As a result, effective oral drug delivery methods are provided to increase the oral bioavailability and absorption of insulin, which is currently administered parenterally.

The invention is thus directed to methods involving oral administration of a dosage form comprising a therapeutic dicarba insulin together with a pharmaceutically acceptable delivery agent that serves to render the insulin orally absorbable through the gastrointestinal mucosa, the delivery agent being present in an amount effective to facilitate the absorption of said insulin, such that a therapeutically effective amount of said dose of insulin is absorbed from the gastrointestinal tract of human diabetic patients. This allows the oral dosage form to be dosed much closed to a meal than was previously taught.

In preferred embodiments, the oral dosage forms of the present invention comprise a mixture of a dicarba insulin and a delivery agent, e.g., monosodium N-(4-chlorosalicyloyl)-4-aminobutyrate (4-CNAB), or separately containing insulin and the delivery agent.

The delivery agent may be used directly by mixing with the dicarba insulin prior to administration, either in dry powder form or wet granulated together. To this mixture, other pharmaceutically acceptable excipients may be added. The mixture may be then tableted or placed into gelatin capsules containing a unit dose of the active agent and the delivery agent. Alternatively, the delivery agent/insulin mixture may be prepared as an oral solution or suspension. The delivery agent and dicarba insulin do not need to be mixed together prior to administration, such that, in certain embodiments, the unit dose of insulin (with or without other pharmaceutically acceptable excipients) is orally administered without the delivery agents of this invention, and the delivery agent is separately orally administered (with or without other pharmaceutically acceptable excipients) before, after, or simultaneously with the insulin.

In certain preferred embodiments, the oral dosage forms of the present invention are solid. The dicarba insulin in dry powder form is stable, and in certain preferred embodiments is simply mixed with pharmaceutically acceptable excipients in a desirable ratio and tableted in accordance with standard tableting procedures known to those having ordinary skill in the art. In a preferred embodiment, the dicarba insulin is simply mixed with a delivery agent and other pharmaceutically acceptable excipients.

The dosage forms of the present invention may be produced by first dissolving the dicarba insulin and the pharmaceutically acceptable excipients, preferably including a delivery agent where the dosage form is an oral dosal form, into one solution or separate solutions. The solvent will preferably be an aqueous solution, but organic solvents or aqueous organic solvent mixtures may be used when necessary to solubilize certain components. If two solutions are used, the proportions of each necessary to provide the correct amount of dicarba insulin and, if present, delivery agent are combined and the resulting solution may be dried, by lyophilization or equivalent means. In one embodiment of the invention, the oral dosage form may be dried and rehydrated prior to oral administration.

The administration mixtures may be prepared, e.g., by mixing an aqueous solution of the delivery agent with an aqueous solution of dicarba insulin just prior to administration. Alternatively, the delivery agent and dicarba insulin can be admixed during the manufacturing process. The solutions may optionally contain additives such as phosphate buffer salts, citric acid, acetic acid, gelatin, and gum acacia.

In preferred embodiments of the oral dosage forms of the invention described above, the oral dosage form is solid, and is preferably provided incorporated within a gelatin capsule or is contained in a tablet.

Stabilizing additives may be incorporated into the delivery agent solution. With some drugs, the presence of such additives promotes the stability and dispersibility of the agent in solution. The stabilizing additives may be employed at a concentration ranging from about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. The preferred stabilizing additives are gum acacia, gelatin and methyl cellulose.

The oral dosage forms of the present invention, containing a mixture of the therapeutic dicarba insulin and optionally a delivery agent, may include additional materials known to those skilled in the art as pharmaceutical excipients. Any excipient or ingredient, including pharmaceutical ingredients or excipients. Such pharmaceutical excipients include, for example, the following: Acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Aerosol propellants (butane, dichlorodifluoro-methane, dichlorotetrafluoroethane, isobutane, propane, trichloromonofluoromethane); Air displacements (carbon dioxide, nitrogen); Alcohol denaturants (denatonium benzoate, methyl isobutyl ketone, sucrose octacetate); Alkalizing agents (strong ammonia solution, ammonium carbonate, diethanolamine, diisopropanolamine, potassium hydroxide, sodium bicarbonate, sodium borate, sodium carbonate, sodium hydroxide, trolamine); Anticaking agents (see glidant); Antifoaming agents (dimethicone, simethicone); Antimicrobial preservatives (benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, acorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Capsule lubricants (see tablet and capsule lubricant); Chelating agents (edetate disodium, ethylenediaminetetraacetic acid and salts, edetic acid); Coating agents (sodium carboxymethyl-cellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolmaide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oeyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, soritan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Glidants and/or anticaking agents (calcium silicate, magnesium silicate, colloidal silicon dioxide, talc); Humectants (glycerin, hexylene glycol, propylene glycol, sorbitol); Plasticizers (castor oil, diacetylated monoglycerides, diethyl phthalate, glycerin, mono- and di-acetylated monoglycerides, polyethylene glycol, propylene glycol, triacetin, triethyl citrate); Polymers (e.g., cellulose acetate, alkyl celloloses, hydroxyalkylcelloloses, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer 934p, carboxymethylcel-lulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methycellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner=s sugar); Tablet disintegrants (alginic acid, microcrystalline cellulose, croscarmellose sodium, corspovidone, polacrilin potassium, sodium starch glycolate, starch, pregelatinized starch); Tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, seame oil, soybean oil, squalane); Vehicle: solid carrier (sugar spheres); Vehicle: sterile (bacteriostatic water for injection, bacteriostatic sodium chloride injection); Viscosity-increasing (see suspending agent); Water repelling agent (cyclomethicone, dimethicone, simethicone); and Wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol). This list is not meant to be exclusive, but instead merely representative of the classes of excipients and the particular excipients which may be used in oral dosage forms of the present invention.

The stability of insulin has been well documented, and temperature, pH and moisture are some of the factors that affect the stability of insulin formulations. Likewise, the influence of pharmaceutical excipients on the stability of insulin has been well documented. In one embodiment, the present invention provides an oral pharmaceutical formulations in tablet form that is sufficiently stable to enable long term storage at room temperature (e.g. as demonstrated by a stability-indicating High Performance Liquid Chromatography (HPLC) assay methodology).

Following administration, the therapeutic dicarba insulin present in the dosage unit form is absorbed into the circulation. The circulating levels of the dicarba insulin itself can be measured directly. The bioavailability of the insulin is readily assessed by measuring a known pharmacological activity in blood, e.g., decreased blood glucose. Further physiologic effects of the insulin can be measured using tests, for example, measurement of plasma C-peptide concentration as a measure of endogenous insulin production.

In addition, a fructosamine assay can be performed to determine the measure of the diabetic patient's glycemic control over the previous period of two to three weeks. Fructosamine is formed by a non-enzymatic reaction between glucose and amino acid residues of proteins, and serum fructosamine levels are elevated in diabetic patients with elevated blood glucose concentration. Whereas blood glucose concentration is a short-term indicator of diabetes control, fructosamine is a short- to medium-term indicator of diabetes control that correlates well with both fasting and mean blood glucose over a 2-week period.

In the present invention, the methods for treating a mammal with impaired glucose tolerance or with early or late stage diabetes comprise orally administering to the mammal a pharmaceutical formulation that includes a therapeutically effective amount of dicarba insulin and optionally a delivery agent in an amount effective to facilitate the absorption of the insulin from the gastrointestinal tract. It is preferred that the administration be on a chronic basis, e.g., for at least two weeks, and be preprandially and at bedtime such that, after two weeks of treatment, the mammal achieves improved glucose tolerance and glycemic control, as well as improved insulin utilization, insulin sensitivity, insulin secretion capacity and HbA1c levels, as compared with baseline levels prior to treatment.

Improved glucose tolerance can be demonstrated by better endogenous capacity of the mammal to handle sugar load as measured by blood glucose concentration, following a sugar load, that is reduced by a statistically significant amount as compared with baseline blood glucose concentration, following a glucose load, prior to treatment. Preferably, the statistically significant reduction in blood glucose concentration is a mean of about 10-20%, preferably about 15%.

Improved glucose tolerance and better endogenous capacity of the mammal to handle sugar load can also be measured by an AUC of blood glucose excursion, following a glucose load, that is reduced by a statistically significant amount as compared with AUC of blood glucose excursion, following a glucose load, prior to treatment. Preferably, the statistically significant reduction in AUC of blood glucose excursion is a mean of about 10-30%, preferably about 20%.

Improved glycemic control can be demonstrated by decreased fasting blood glucose levels as measured by fasting blood glucose concentration that is reduced by a statistically significant amount as compared with baseline fasting blood glucose concentration prior to treatment. Preferably, the statistically significant reduction in fasting blood glucose concentration is a mean of about 10-30%, preferably about 19%.

Improved glycemic control can also be demonstrated by decreased serum fructosamine concentrations, as measured by serum fructosamine assay, that is reduced by a statistically significant amount as compared with baseline serum fructosamine concentrations prior to treatment. Preferably, the statistically significant reduction in serum fructosamine concentrations is a mean of about 5-20%, preferably about 9%.

Improved glycemic control can also be demonstrated by improved HbA1c levels after treatment compared with baseline levels prior to treatment. Preferably, the improved HbA1c levels are measured by a statistically significant decline in HbA1c levels. When treating a mammal with impaired glucose tolerance or with early or late stage diabetes, administration of the pharmaceutical formulation of the present invention can preferably be made to a mammal having an HbA1c level ranging from normal to elevated prior to treatment. In one embodiment, the mammal may have an HbA1c level preferably of less than about 8.0 prior to treatment.

Improved insulin utilization and insulin sensitivity of the patient's body can be measured by a statistically significant decline in HOMA (Homeostasis Model Assessment), and the improved insulin secretion capacity of the patient's body is measured by Stumvoll first-phase insulin secretion capacity index.

In preferred embodiments of the invention, by virtue of the chronic administration of oral dosage forms of the present invention, the subject achieves improved glucose tolerance and glycemic control as compared with baseline levels prior to treatment even without any statistically significant increase in weight, any statistically significant increase in risk of hypoglycemia or any statistically significant increase in risk of hyperinsulinemia in the mammal over the treatment period, and without the need for monitoring the mammal's blood glucose concentrations or HbA1c levels. Further, by virtue of the chronic administration of oral dosage forms of the present invention, the patient achieves improved insulin utilization, insulin sensitivity insulin secretion capacity and HbA1c levels as compared with baseline levels prior to treatment.

It is preferred that the administration of the oral pharmaceutical formulation will be about once daily to about four or more times daily, preprandially and/or at bedtime. In one embodiment of the invention, administration of the pharmaceutical formulation takes place once daily, either at bedtime or preprandially for one meal during the day time, e.g., for breakfast, lunch or dinner. In another embodiment, administration of the pharmaceutical formulation takes place multiple times daily, preferably at bedtime and preprandially for one meal during the day time, e.g., for breakfast, lunch or dinner. In a further embodiment, administration of the pharmaceutical formulation takes place multiple times daily, preferably at bedtime and preprandially for more than one meal during the day time. Administration of the pharmaceutical formulation can also be is at or shortly prior to bedtime and concurrently with or shortly prior to ingestion of each meal, i.e., within about 15 minutes or less of ingestion of each meal.

Preferably, the dicarba insulin formulations are administered to such human patients on a chronic basis, e.g., for at least about two weeks. The dosage form of the present invention can be administered for at least one day, for one week, for two weeks, for longer periods, for alternating on-off time periods, or for the life of the patient.

It is believed that the frequency of administration of the oral pharmaceutical formulation, on a daily basis (i.e., how often during one day-night period) and on a chronic basis (i.e., for how many days), will depend upon the patient's position along a "diabetes continuum", i.e., the extent of the patient's impaired glucose tolerance, the patient's stage of diabetes and the patient's need for exogenous glycemic control. This continuum ranges from normal glycemic control, to simple impaired glucose tolerance and insulin resistance seen in pre-diabetics or early stage type 2 diabetics, to failure of insulin production by the pancreas seen in type 1 diabetics and late stage type 2 diabetics. This can also be measured by the patient's HbA1c concentration, ranging from normal to elevated levels.

Although the remainder of the description refers to particular examples or embodiments of the invention, it is to be understood that modifications or improvements may be made thereto without departing from the scope of the invention.

Examples

Various embodiments/aspects of the present invention will now be described with reference to the following non-limiting examples.

Synthesis of Dicarba Analogues of Insulin

Regioselective unsaturated and saturated carbocyclic dicarba analogues of insulin have been constructed. These dicarba analogues of insulin incorporate tailor-made, non-proteinaceous olefinic, chiral amino acids into the insulin primary sequence. Summarised in Table 1 below is the strategy for using three different olefinic amino acids in alkene metathesis. Each residue possesses varying electronic and steric properties and displays different reactivity towards metathesis conditions.

TABLE 1

| | Regioselective dicarba bridge formation | | | | | | | | | |
|---|---|---|---|---|---|---|---|---|---|---|
| Substrates Side chain | | A Step 1: RCM 2nd gen. Grubbs' catalyst C=C | A Step 2: Wilkinson's hydrogenation C—C | A Step 3: CM 2nd gen. Grubbs catalyst Act | AB Step 4: CM 2nd gen. Grubbs catalyst C=C | AB Step 5: Wilkinson's hydrogenation C—C | A Step 6: RH(I) DuPHOS hydrogenation Act | A/B Step 7: CM 2nd gen. Grubbs catalyst Act | AB Step 8: RCM 2nd gen. Grubbs catalyst C=C | AB Step 9: Wilkinson's hydrogenation C—C | Products Summary |
| | | Reactivity | | | | | | | | | |
| (a) | | ✓ | ✓ | — | — | — | — | — | — | — | Terminal allylic olefin. No activation required. |
| (b) | | X | X | ✓ | ✓ | ✓ | — | — | — | — | Trisubstituted olefin. Activated via CM with 2-butene. |
| (c) | | X | X | X | X | X | ✓ | ✓ | ✓ | ✓ | Hindered extended acrylamide olefin. Activated via i) asymmetric hydrogenation and ii) CM with 2-butene. |

(✓ = Reactive olefin, X = unreactive olefin, — = unreactive dicarba bridge, Act = olefin activation step, RCM = ring closing metathesis, CM = cross metathesis)

Residue (a) is a Type I olefin, which will readily homodimerise under metathesis conditions to yield an unsaturated carbocycle via RCM. Amino acid (b) is sterically hindered (Type III) olefin, and thus will not homodimerise under the conditions of (a). It instead must undergo an activation step, such as CM with ethylene to produce Agl, before this olefin will be susceptible to RCM metathesis. Residue (c) is both electronic and sterically hindered, and thus must go through a double activation step to generate a receptive reactive Agl unit. This includes asymmetric hydrogenation to reduce the α-olefin, followed by CM with ethylene to produce a reactive Type I residue. It is important to note that both metathesis and hydrogenation catalysts are not poisoned by sulfur containing functionality, hence hybrid cystine-dicarba analogues are possible through the proposed catalytic approach. Scheme 1 illustrates a strategy to form a fully dicarba insulin molecule.

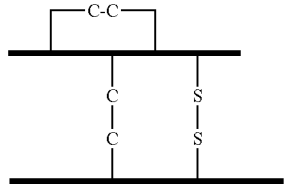
(II)

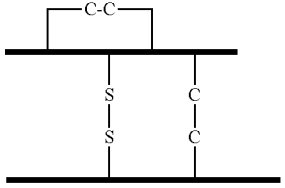
(III)

Scheme 1: A method for the synthesis of a fully dicarba analogue of insulin

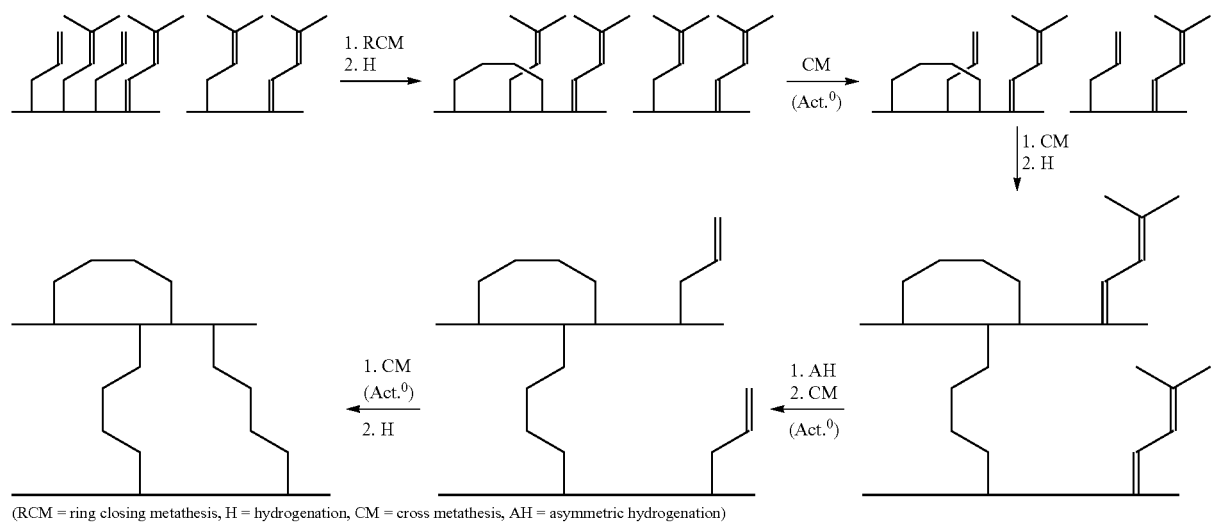

(RCM = ring closing metathesis, H = hydrogenation, CM = cross metathesis, AH = asymmetric hydrogenation)

Using both manual and automated solid phase peptide synthesis (SPPS) procedures and Fmoc-protected amino acids, the linear peptide chains can be constructed with strategic complementary pairing of alkene-containing metathesisable amino acid residues, where each has varying reactivity towards Ru- and Rh-catalysed metathesis and hydrogenation. The regioselective catalysis methodology will be utilised to create the target dicarba-insulins ranging from single through to triple cystine replacement (shown in Scheme 2):

Scheme 2: Target dicarba-insulin molecules

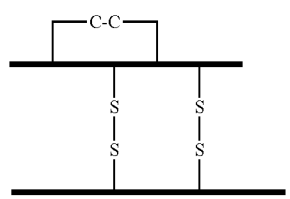
(I)

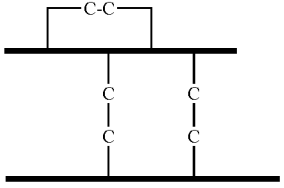
(IV)

Biological testing of the combinations of disulfide/dicarba links is used to identify which cystine bridges, if any, serve a functional purpose and which are purely structural. Mutation of the insulin sequence and inter-species variation suggests that the intrachain disulfide motif within the A segment is not essential for biological activity. This bridge may serve only a structural role in maintaining bioactive conformation. Investigations were conducted into the formation of the dicarba analogues of insulin having an intrachain dicarba bridge in the A-chain of insulin. By manual SPPS, A1-13 and A14-21 having Agl units in the A6 and A11 chain positions, as well as both cysteine and Agl or prenylglycine residues in the A7 and A20 positions can be prepared. Subjecting the alkene-containing metathesisable groups to RCM forms an A6-A11 carbocycle. In the event that improvement of the yield is desired, the implementation of serine or threonine derived pseudo-prolines are used to place the two reactive side chains in closer proximity, and thus increase cyclisation yield. Full A and B-chain sequences containing metathesisable residues can also be prepared and subjected to the same catalysis protocol.

The B-chain can be synthesised via automated SPPS procedures, to produce four analogues by varying the locations of cysteine, Agl and prenylglycine at B7 and B19. Using the tandem metathesis-hydrogenation steps outlined in Table 1 above, four full insulin targets, as shown in Table 2, can be synthesised upon linking the B and ligated A-chain combinations together.

Non-Peptide Model

Proof of principle for the methodology of three dicarba links has been provided by a non-peptidic model shown in Scheme 3. A nine step homogeneous catalytic reaction sequence was performed on an equimolar mixture of three olefins, including a protected allylglycine, prenylglycine and dehydroprenylglycine, and after quantitative conversions of each substrate following each reaction step, only three products were isolated in 81, 73 and 70% yields respectively; no cross-over was observed. This result demonstrates that regioselective multi dicarba bridge formation can be achieved in peptide substrates using amino acid residues bearing these metathesis-active sidechains.

TABLE 2

Dicarba strategies and targets

| Task | Investigation/Synthesis |
|---|---|
| A-chain A1 (1-13) + A2 (14-21) | A1: $A_6$-$A_{11}$ carbocycle formation |
| | A2: |
| B-chain | |
| Targets | |

Scheme 3: Reaction sequence for the construction of three dicarba bridges

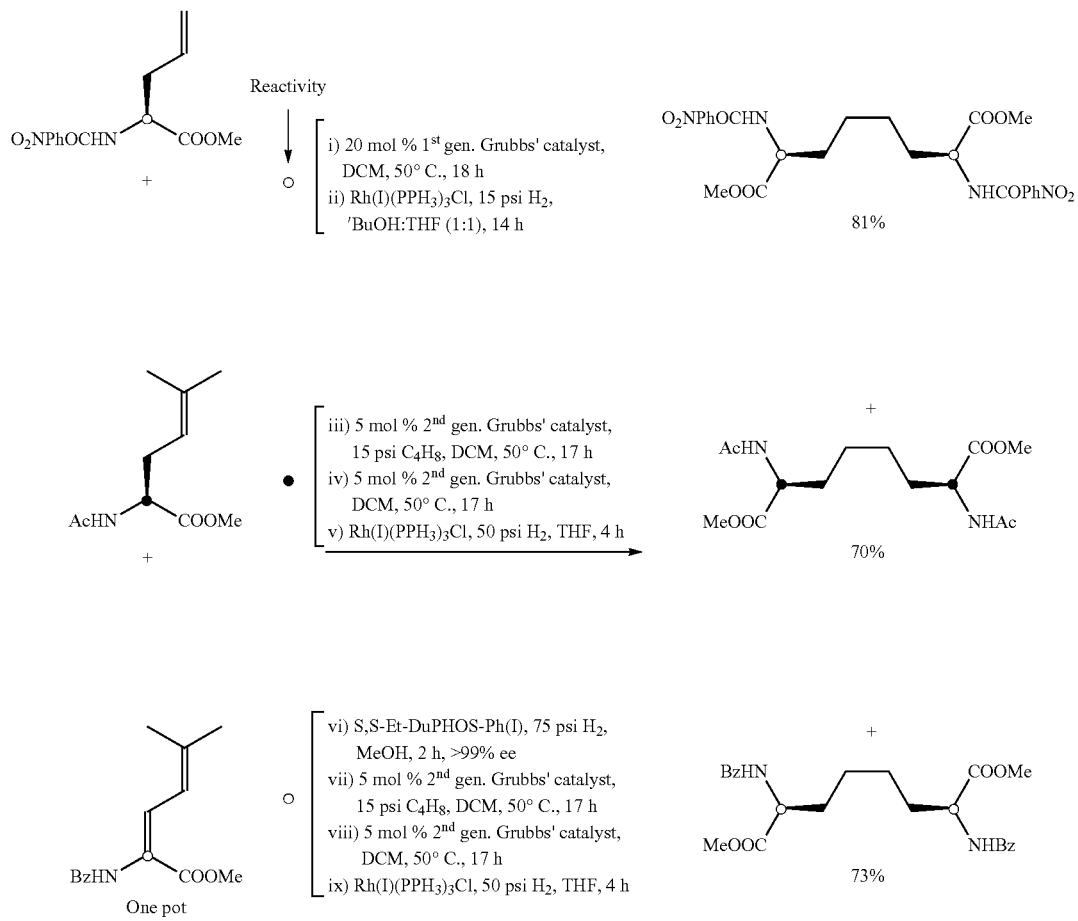

1. Preparation of Fmoc-Protected Non-Proteinaceous Chiral Amino Acids

The targeted replacement of insulin's disulfide links with non-reducible dicarba-bridging isosteres required strategic incorporation of Fmoc-protected, non-proteinaceous, olefinic, chiral amino acids into the primary sequence.

Both Fmoc-I-allylglycine 1 and Fmoc-I-prenylglycine 2 can be prepared via a multi-step synthesis, however, both are more readily obtained from commercially available I-allylglycine 3. These units were prepared prior to solid phase peptide synthesis of the insulin A- and B-chains.

The synthesis of Fmoc-L-Agl-OH 1 was achieved through a reaction of L-allylglycine 3 with Fmoc-OSu 4 in high yield (96%) (Scheme 4).

Scheme 4: Synthesis of Fmoc-L-Agl-OH 1

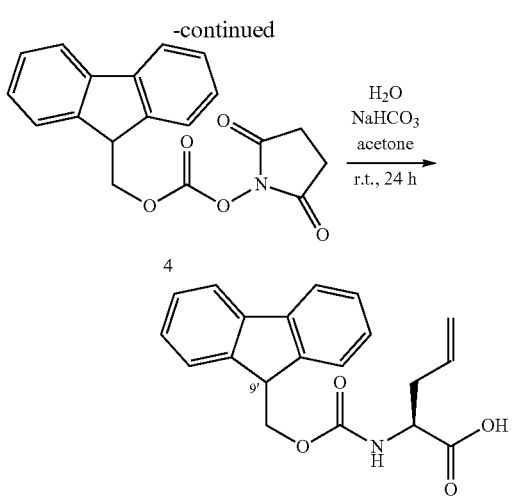

Formation of the desired Fmoc-protected amino acid 1 was supported by $^1$H n.m.r. spectroscopy, with the appearance of signals at δ 7.31, 7.38, 7.52-7.63 and 7.76, integrating for eight protons, a doublet at δ 4.42 representing two protons, and a triplet at δ 4.23 integrating for one proton. These resonances correspond to the aromatic protons, CH$_2$O and H9' portion of the attached Fmoc-protecting group, respectively. Melting point determination of the crude product (137-138° C.) was consistent with the value reported in the literature (134-136° C.). The crude product 1 was found to be of sufficient purity for use in solid phase peptide synthesis without further purification. Fmoc-L-Pre-OH 2 was prepared by cross metathesis of Fmoc-L-Agl-OH 1 and 2-methyl-2-butene in the presence of 5 mol % $2^{nd}$ generation Grubbs' catalyst (Scheme 5). The reaction proceeded with quantitative conversion to 2. The material could therefore be used without purification.

Scheme 5: Synthesis of Fmoc-L-Pre-OH 2

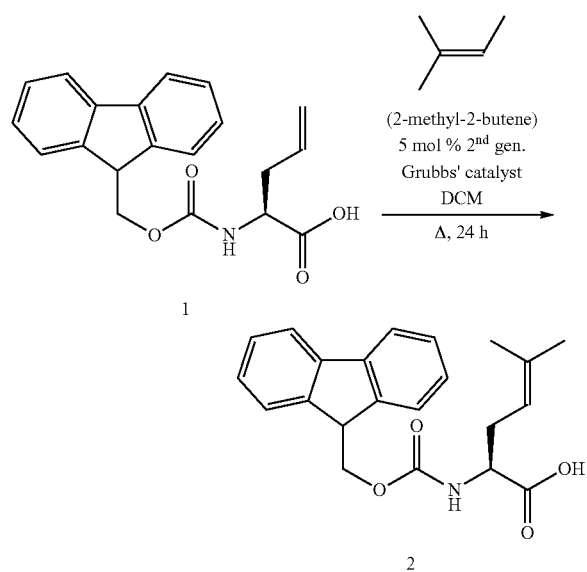

$^1$H n.m.r. spectroscopy confirmed the formation of the trisubstituted olefinic amino acid 2, with the disappearance of the multiplet at δ 5.18 integrating for two protons and appearance of two singlets at δ 1.62 and 1.73, each integrating for three protons. The appearance of two methyl carbon signals at δ 18.3 and 26.2 in the $^{13}$C n.m.r. spectrum further supported the formation of 2, with both spectra being consistent with the generation of a prenyl side chain.

Scheme 6: Synthesis of Fmoc-L-Bgl-OH 7

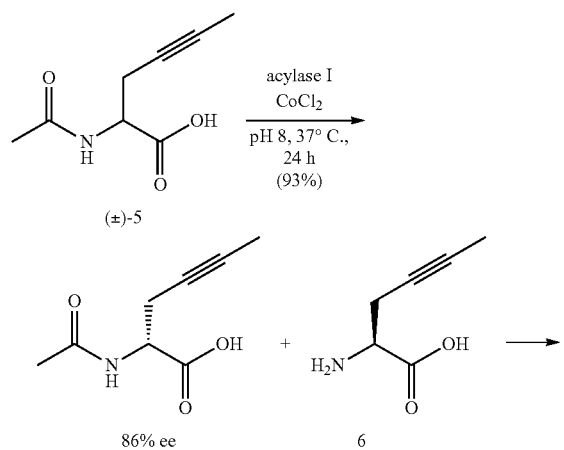

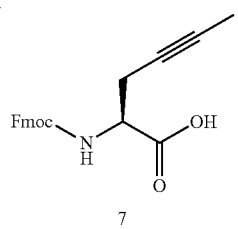

Exposure of a racemic mixture of N-acetyl 2-(but-2-ynyl) glycine 5 to acylase I, at pH 8 in the presence of $CoCl_2$, resulted in selective deacetylation of the L-isomer. The recovered (R)-N-acetyl 2-(but-2-ynyl)glycine was derivatised as its methyl ester and determined to be in 86% ee by chiral GC. The required (S)-2-(but-2-ynyl)glycine 6 was obtained in this manner and further enriched by standard methods. (S)-2-(But-2-ynyl)glycine 6 was readily protected to provide alkyne residues suitable for SPPS (e.g. Fmoc-L-Bgl-OH, 7) (Scheme 6).

2. Preparation of Human Dicarba Insulin Analogues c[$\Delta^4$A6,11]-Dicarba Human Insulin The native insulin A-chain is considered to be a "difficult sequence". Strongly hydrophobic patches and sequences, such as those found in transmembrane peptides and human insulin, are prone to significant β-sheet formation and aggregation which leads to poor coupling efficiencies and solvation. Although the A-chain of insulin consists of mainly polar residues, their side chains are reactive and must be protected with hydrophobic groups such as $^t$Bu and Trt during synthesis. In this sense, the A-chain is also considered highly hydrophobic and is therefore vulnerable to deleterious secondary structure formation. The use of microwave-accelerated SPPS has facilitated the production of linear insulin A-chain in high yield and purity.

Construction of the linear [$\Delta^4$A6,11]-Agl-[A7]-Cys($^t$Bu)-[20]-Cys(Acm) (SEQ ID NO: 1) analogue 8 of the human insulin A-chain was performed on preloaded Fmoc-Asn(Trt)-PEG-PS resin. This hybrid resin has a low substitution with a hydrophilic polyethylene glycol linker which helps to decrease deleterious crowding of the elongating peptide chains near the polystyrene solid support. It was thought that the use of this resin in combination with microwave-accelerated SPPS would decrease undesirable secondary structures and provide higher yielding sequence synthesis and possibly greater yields from catalysis (e.g. greater yields in CM/RCM/RCAM/H reactions).

(SEQ ID NO: 1)

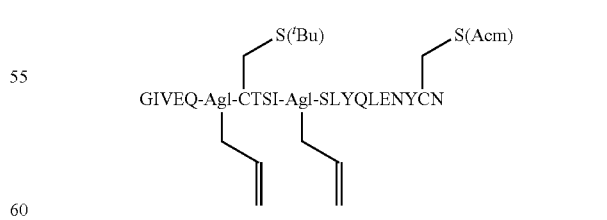

Microwave-accelerated SPPS using HATU-DIPEA activation and Fmoc-protected amino acids were used to construct the desired sequence 8, carrying through each intermediate without purification and characterisation until the 21 amino acid A-chain was constructed. Two strategically placed Agl residues were incorporated into the primary sequence to facilitate the formation of an intrachain dicarba bridge. In addition, cysteine residues with orthogonal protection were incorporated to allow regioselective disulfide oxidation between the A- and B-chains of insulin. After complete construction of the A-chain, a small aliquot of the resin-tethered peptide was subjected to Fmoc-deprotection and TFA-mediated cleavage. Mass spectral analysis of the resultant solid gave molecular ion peaks at m/z 1249.5 [M+2H]2+ and 833.5 [M+3H]3+, consistent with the formation of peptide 8.

Ring closing metathesis of the fully protected, resin-tethered linear peptide 8 was performed in the presence of 20 mol % 2nd generation Grubbs' catalyst in DCM. Lithium chloride (as a 0.4 M solution in DMF) was added to the reaction mixture to assist in the reduction of peptide aggregation and aid reagent penetration. Microwave irradiation of the peptide-resin at 100° C. for 2 h resulted in 30% conversion (by RP-HPLC) to the desired cyclic peptide 9. Mass spectral analysis of the Fmoc-deprotected and TFA-cleaved product mixture gave the required molecular ions with m/z 1235.7 [M+2H]2+ and 824.5 [M+3H]3+. The RP-HPLC trace showed the formation of two geometric isomers (9(I) and 9(II)) with two distinct retention times. Fmoc-deprotection and full TFA-cleavage of the resin-bound peptide 9 provided the target cyclic human insulin (hINS) A-chain (Scheme 7).

A-chain peptide and promotes formation of the required A-B heterodimer. Exposure of reaction mixture containing isomeric carbocycles 9(I) and 9(II) to an acidic cleavage containing trifluoromethane sulfonic acid (TfOH), TFA, anisol and 2,2'-dipyridyl disulfide for 1.5 h at 0° C. Not only would this reaction mixture cause rapid deprotection of the A7 cysteine residue with simultaneous reprotection of the exposed thiol group via disulfide exchange with the scavenging -2,2'-dipyridyl disulfide scavenging pyridyl group (Scheme 8). The latter becomes important during chain-combination as it prevents the formation of A-A and B-B homodimers and maximises conversion in favour of the target A-B heterodimer. Hence, simultaneous deprotection and reprotection of the A7 cysteine residue proceeded quantitatively and the crude peptide 10 was then purified by preparative RP-HPLC to remove traces of excess 2,2'-dipyridyl disulfide. The desired insulin A-chain analogue 10 was isolated upon lyophilization (Scheme 8) in low yield and >99% purity.

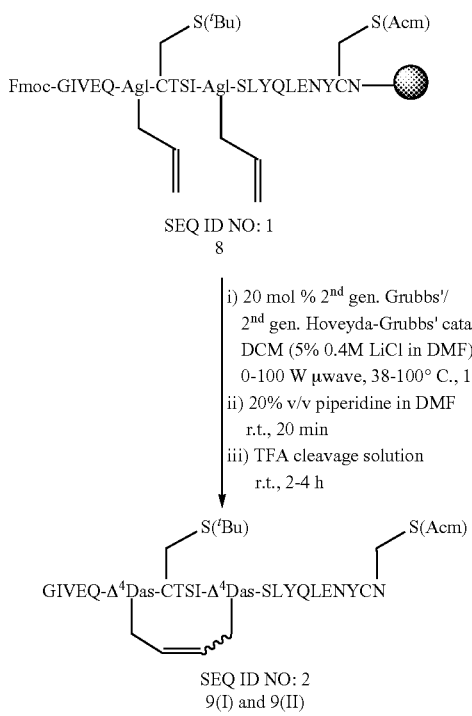

Scheme 7

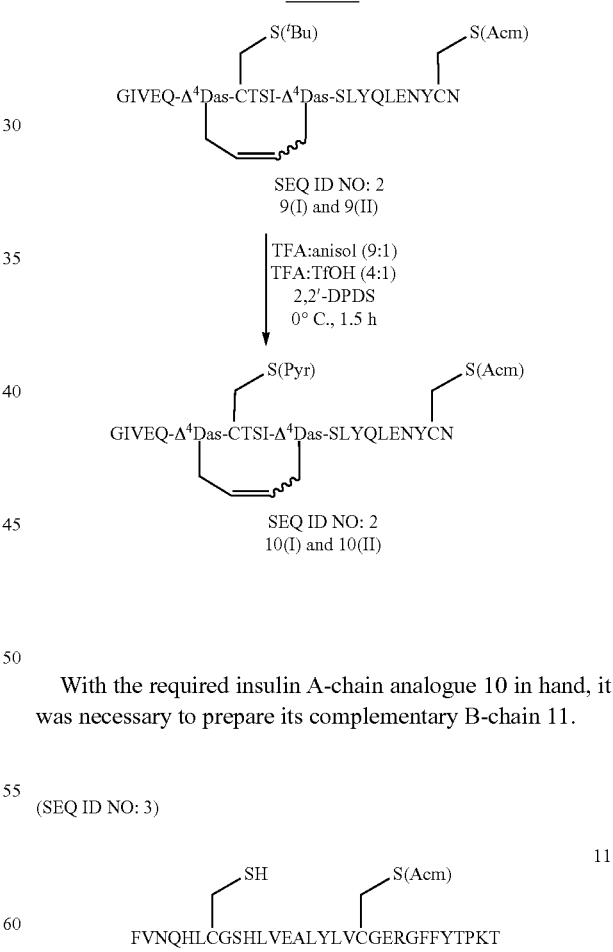

Scheme 8

Prior to the first regioselective disulfide bond oxidation between the insulin A- and B-chains, it was necessary to transprotect the $Cys_{A7}$ residue with a free thiol scavenging pyridinyl group. During initial chain combination, this new S-protecting group prevents homodimerisation of the With the required insulin A-chain analogue 10 in hand, it was necessary to prepare its complementary B-chain 11.

Microwave-accelerated SPPS using HBTU/HOBt-DIPEA activation and Fmoc-protected amino acids was used to construct the desired sequence on preloaded Fmoc-Thr(tBu)-PEG-PS resin. During chain elongation, orthogonally protected Cys(Trt) and Cys(Acm) residues were strategically incorporated into the primary sequence in the B7 and B19 positions respectively. Upon synthesis completion, a small aliquot of the resin-tethered peptide was subjected to TFA-mediated cleavage and mass spectral analysis of the resultant solid gave molecular ion peaks at m/z 1750.6 $[M+2H]^{2+}$, 1167.7 $[M+3H]^{3+}$, 876.0 $[M+4H]^{4+}$ and 701.0 $[M+5H]^{5+}$, consistent with the formation of linear target peptide 11. Preparative RP-HPLC then gave the required insulin B-chain 11 in 30% yield and 90% purity.

Following TFA-mediated cleavage of the remaining resin-bound peptide 11, preparative RP-HPLC was used to isolate the required insulin B-chain 11 in 31% yield and >90% purity. Two monocyclic A-B conjugates were next prepared by combination of the isomeric A-chains 10(I) and 10(II) with their corresponding B-chain 11 under basic conditions (Scheme 9).

The monocyclic A-B conjugate 12 was prepared on addition of A-chain 10 in 0.1% aqueous TFA to a stirred solution of B-chain 11 in 50 mM $NH_4HCO_3$ (Scheme 9). Dimerisation was complete within minutes, giving two geometric isomers of the required 51 amino acid peptide 12(I) and 12(II). Mass spectral analysis of the isolated solids supported formation of the A-B dimers showing the correct molecular ion peaks for $[M+3H]^{3+}$, $[M+4H]^{4+}$ and $[M+5H]^{5+}$. The conjugates were of high crude purity and could be subjected to the final iodine oxidation without purification.

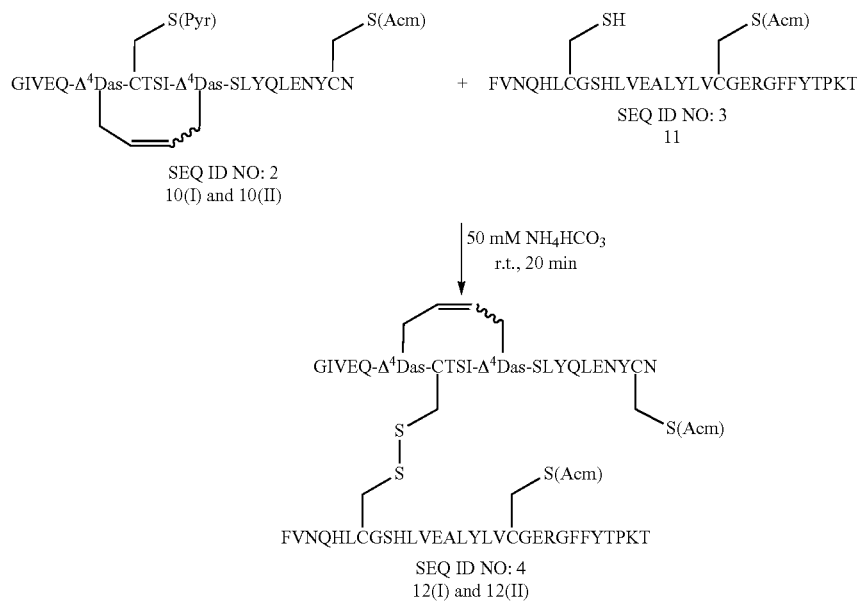

Scheme 9

The final disulfide bridge in c[$\Delta^4$A6,11]-unsaturated dicarba insulin 13, was formed on exposure of each of monocyclic A-B conjugates, 12(I) and 12(II) to iodine under acidic conditions (Scheme 10). Removal of the acetamidomethyl (Acm) protecting group at A19 and B20 resulted in spontaneous oxidation of the liberated free thiol groups to give the two target isomeric dicarba insulin peptides 13(I) and 13(II).

Scheme 10

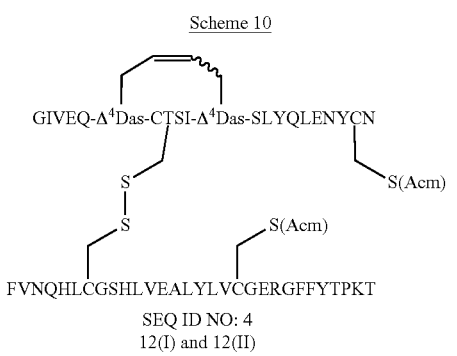

SEQ ID NO: 4
12(I) and 12(II)

i) glacial AcOH
   60 mM HCl
   20 mM I$_2$ in glacial AcOH
   r.t., 50 min
ii) 20 mM ascorbic acid

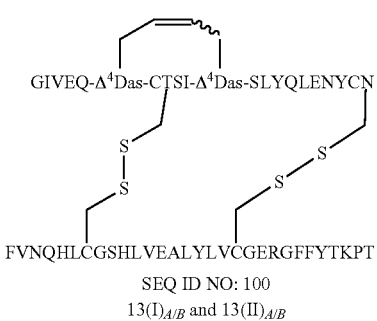

SEQ ID NO: 100
13(I)$_{A/B}$ and 13(II)$_{A/B}$

Chromatographic purification using acidic buffer systems showed broad peaks of identical and correct m/z value. Through the use of neutral RP-HPLC buffers (20 mM triethylammonium acetate), however, each broad peak resolved into two peaks of approximately equal intensity. Each of these peptides, 13(I)$_{A/B}$ and 13(II)$_{A/B}$, were found to have m/z values consistent with the target dicarba insulin. Using the latter RP-HPLC conditions and slow gradient elution, these compounds could be separated from each other. Following resolution and isolation, the four peaks were found to be stable, and did not re-equilibrate on subsequent chromatographic analysis. All four isomers were therefore independently subjected to biological testing as separate and purified analogues.

The above described metathesis on the resin-bound insulin A chain highlights the challenge of installing dicarba bridges into 'difficult sequences'. While experimental conditions (e.g. reaction time, temperature, choice of catalyst, % catalyst loading, pseudoproline insertion) can be modified to enhance conversion, incomplete conversion poses significant downstream problems particularly in regard to maintaining regioselectivity and purification of the peptide target.

3. Use of Pseudoproline Residues in Human Dicarba Insulin Analogues c[Δ$^4$A6,11]-Dicarba Human Insulin with Pseudoproline Retarded ring formation, in the case of insulin, is also likely to result from an inability to suitably localise reacting termini. The primary sequence of this peptide could therefore also benefit from the inclusion of a turn between the two residues undergoing metathesis. Fortunately, the residue precursors for pseudoproline formation, serine, threonine and cysteine, are all found in the intrachain loop of insulin (see Figure below). Although incorporation of C5-disubstituted proline analogues into linear sequences is straightforward, their subsequent acylation can be problematic due to steric crowding. Pseudoproline-derived oxa- and thiazolidine residues are therefore more readily incorporated into sequences as preformed dipeptides.

Figure: Pseudoproline dipeptides for the preparation of intrachain dicarba insulins

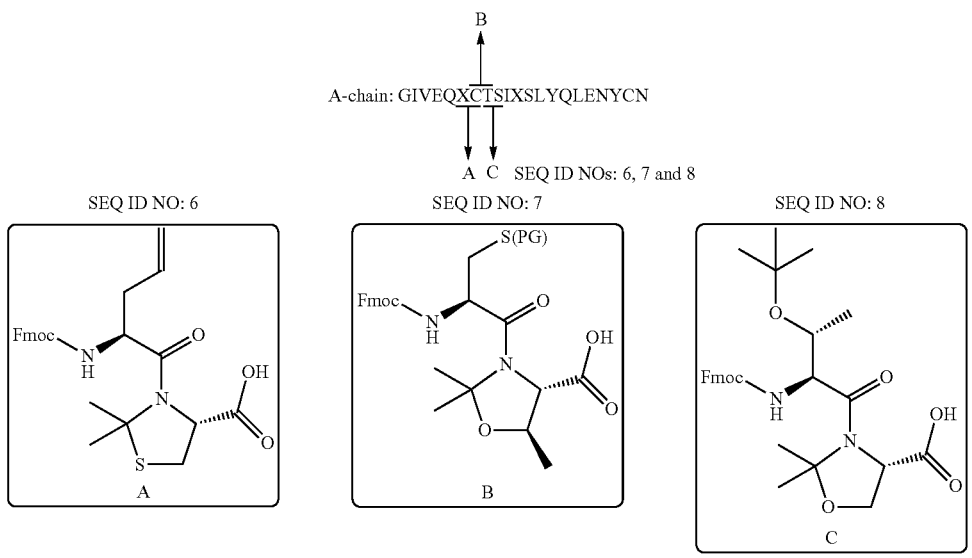

An oxazolidine-containing pseudoproline residue was incorporated into the complete insulin A-chain ψ8 via microwave-accelerated SPPS: Commercially available Fmoc-L-Asn(Trt)-PEG-PS resin, HATU-DIPEA activation and Fmoc-protected amino acids were employed as previously described. Since the oxazolidine motif is acid-labile, deprotection of the ring system during resin cleavage was expected to generate the parent threonine residue. Mass spectral analysis of an Fmoc-deprotected and TFA-cleaved aliquot of the product mixture therefore gave molecular ion peaks at m/z 1249.7 $[M+2H]^{2+}$ and 833.1 $[M+3H]^{3+}$ which were consistent with the formation of linear peptide ψ8.

Ring closing metathesis of the fully protected, resin-tethered peptide ψ8 was performed in the presence of 20 mol % second generation Grubbs' catalyst in DCM with 0.4 M w/v LiCl in DMF. Microwave irradiation of the peptidyl-resin at 100° C. for 2 h resulted in near quantitative conversion (98% by RP-HPLC) to the desired carbocycle ψ9 (Scheme 11). Interestingly, the RP-HPLC trace of the crude product mixture showed the presence of only one dicarba geometric isomer.

Mass spectral analysis of an aliquot of the Fmoc-deprotected and TFA-cleaved product mixture showed a single peak at m/z 1255.8. This is consistent with the molecular ion of the required peptide with its oxazolidine ring still intact ψ9. The stability of this pseudoproline building block was surprising since deprotection is usually complete within minutes of exposure to dilute TFA. This unusual lack of reactivity suggested that the metathesis-induced ring closure embeds central residues, resulting in limited reagent penetration.

Scheme 11

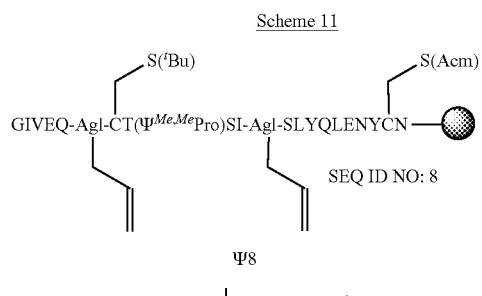

i) 20 mol % $2^{nd}$ gen. Grubbs' catalyst
DCM (5% 0.4M LiCl in DMF)
100 W μwave, 100° C., 2 h
ii) 20% v/v piperidine in DMF
r.t., 20 min
iii) TFA cleavage solution
r.t., 2-4 h

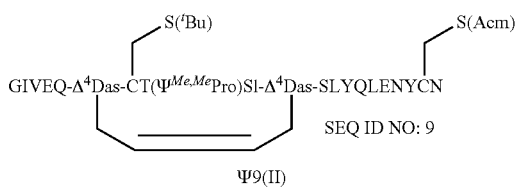

Using the isolated A-chain ψ9, the total synthesis of c[$\Delta^4$A6,11]-dicarba human insulin 13 was again initiated. Simultaneous tu deprotection and pyridinyl reprotection of $Cys_{A7}$ was carried out in the presence of trifluoromethanesulfonic acid (TfOH), TFA and 2,2'-DPDS to allow a chemically directed chain combination. Treatment with this acid cocktail also resulted in deprotection of the oxazolidine ring to give the required S-activated peptide 10 in 34% yield and >99% purity after preparative RP-HPLC purification. Comparison of the retention time of this product with the two geometric isomers isolated previously, again confirmed that the RCM of resin-bound, pseudoproline-containing sequence ψ8 had been completely stereoselective toward isomer 9(II).

Finally, the generation of target c[$\Delta^4$A6,11]-dicarba human insulin was achieved after regioselective thiolysis and iodolysis of 10(II) with a suitably protected B-chain 11. Again, iodine oxidation of the monocyclic A-B conjugate 12(II) under acidic conditions gave two isomeric peptides (A and B) from the single geometric isomer. The dicarba isomer 13(II) was isolated as a 1:1 A:B mixture in 7% yield and 98% purity after preparative RP-HPLC.

Scheme 12

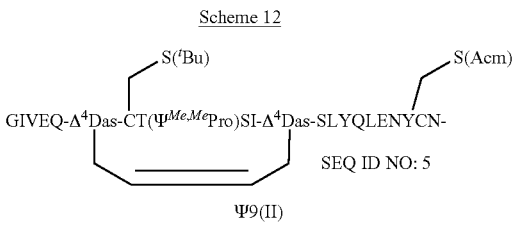

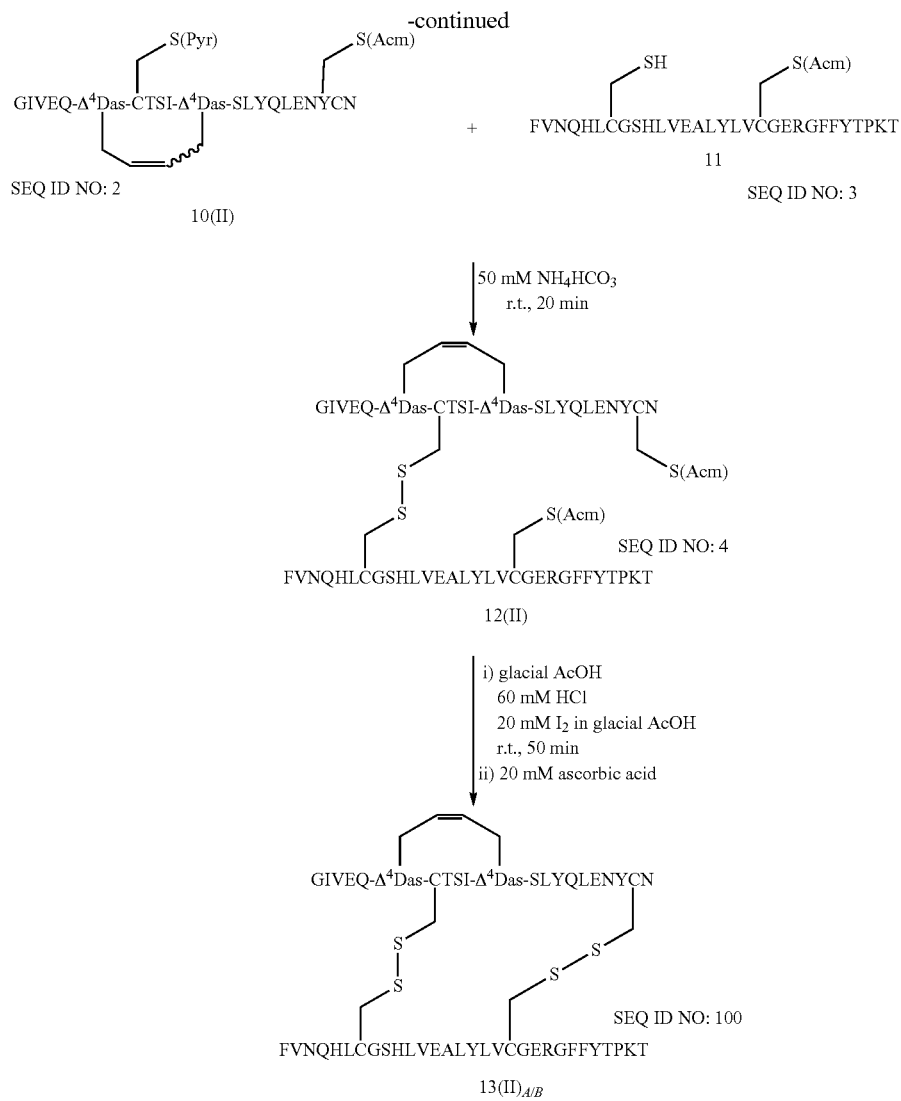

4. Alternating Spps-Catalysis Strategies c[Δ⁴A6,11]-Dicarba Human Insulin by SPPS-Catalysis-SPPS A new synthetic strategy to enable stereospecific formation of the A6-A11 dicarba bridge was examined. The new approach was designed to allow a controlled and predictable synthesis of both cis and trans geometric isomers from a common precursor. Towards this end, the combined utility of alkyne metathesis and semi-hydrogenation was considered. In this approach, initial ring closing alkyne metathesis (ROAM) generates a new alkyne bridge which can then undergo controlled semi-reduction to form the target C=C motif. This tandem catalytic approach towards unsaturated dicarba insulin analogues, however, is dependent on catalyst access to the alkyne bridge following ring closure.

The use of catalysis to produce large-membered saturated and unsaturated dicarba peptide analogues from highly hydrophobic sequences can often generate very low product yields as a result of peptide aggregation and an inability to suitably localise both reacting termini.

An alternating SPPS-Catalysis-SPPS approach was used, with truncated peptide sequences containing one or more metathesisable residues were constructed on resin via standard solid phase peptide synthesis (SPPS). Following subsequent catalysis cycles, e.g. RCM, ROAM, CM, H, the peptide could then be chain extended to introduce the strategically omitted residues via a second round of SPPS. Significantly, this approach is highly generic and enables the synthesis and catalysis (e.g. metathesis or hydrogenation, H) of 'difficult sequences' like the human insulin A chain.

To illustrate this approach, the above insulin A-chain sequence was reconstructed on resin and five of the N-terminal residues (i.e. GIVEQ) were omitted from the sequence. Hence, two linear peptides 14 and 15 (Note: Peptide 14 is a des1-5 analogue of 8) were constructed without the GIVEQ residues. The peptide 15 is specially designed to enable the regioselective installation of two dicarba bridges, the intramolecular A6-A11 bridge and the intermolecular A7-B7 bridge. Under analogous experimental conditions to those described above, these truncated sequences underwent near quantitative catalysis (i.e. RCM, CM, H) and the remaining five residues were then appended to the N-terminus following catalysis via continued SPPS synthesis. RP-HPLC analysis of the crude product mixture showed the two geometric isomers with an 86:14 bias toward isomer 17(I), the opposite isomer to that produced from the pseudoproline-inserted sequence ψ8.

The quantitative cyclisation yield of A-chain analogue 14 was extremely encouraging and suggested that enhanced reagent penetration could be achieved by omission of the five N-terminal hydrophobic residues. It was therefore postulated that this approach could also be used to achieve hydrogenation of newly installed C=C bridges. Excitingly, microwave-accelerated hydrogenation of the resin-bound desA1-5 unsaturated dicarba A-chain 17, using homogeneous Wilkinson's catalyst, produced an excellent yield of the desired saturated dicarba peptide 19 (98%). As before, continued microwave-accelerated SPPS was performed on the truncated A-chain 19, and the remaining five residues were appended to give saturated analogue 16.

Significantly, it is important to note that the full chain A chain analogue of 14 (i.e. 8) only underwent RCM to a maximum of 40% and completely resisted hydrogenation to yield peptide 16. This is in contrast to the metathesis and hydrogenation of the truncated sequence 14 (i.e. 8—GIVEQ) which gave a 100% and 95% conversion respectively (Schemes 13 and 14). This result highlights the benefit of the alternating SPPS-Catalysis-SPPS approach to insulin sequences.

TABLE 3

Ring closing metathesis

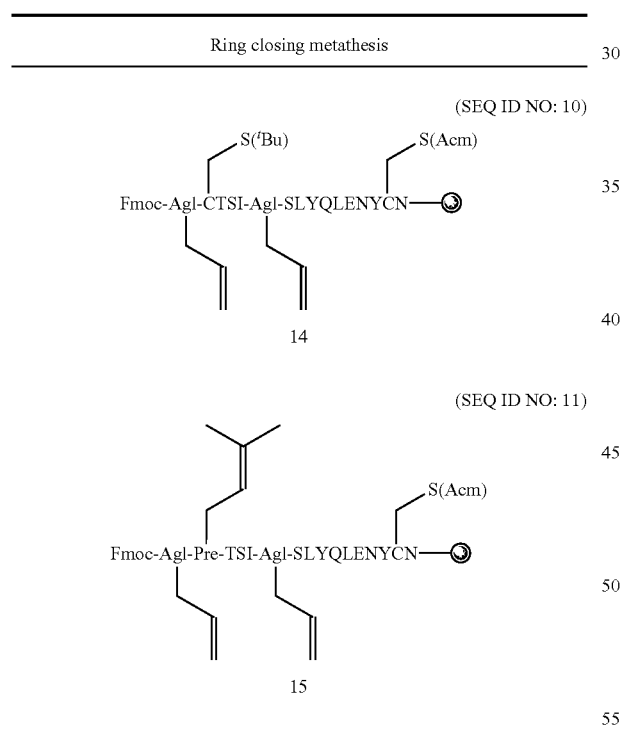

| RCM Substrate | Catalyst | Heat Source | Solvent | Temperature (° C.) | Duration (h) | Conversion (%) |
|---|---|---|---|---|---|---|
| 14 | 20 mol % $2^{nd}$ gen. Grubbs' catalyst | Microwave | CM | 100 | 2 | >95% to 17 |
| 15 | 20 mol % $2^{nd}$ gen. Grubbs' catalyst | Microwave | DCM | 100 | 2 | >95% to 18 |

Example

Scheme 13

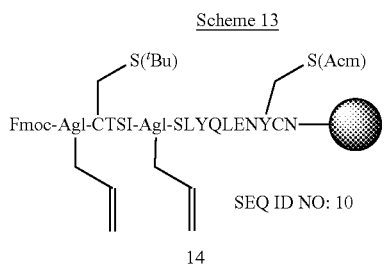

SEQ ID NO: 10

14 i) 20 mol % $2^{nd}$ gen. Grubb's catalyst
   DCM (5% 0.4M LiCl in DMF)
   100 W μwave, 100° C., 2 h
ii) 20% v/v piperidine in DMF
    r.t., 20 min
iii) TFA cleavage solution
     r.t., 2-4 h

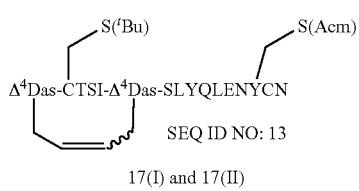

SEQ ID NO: 13

17(I) and 17(II)

TABLE 4

Hydrogenation

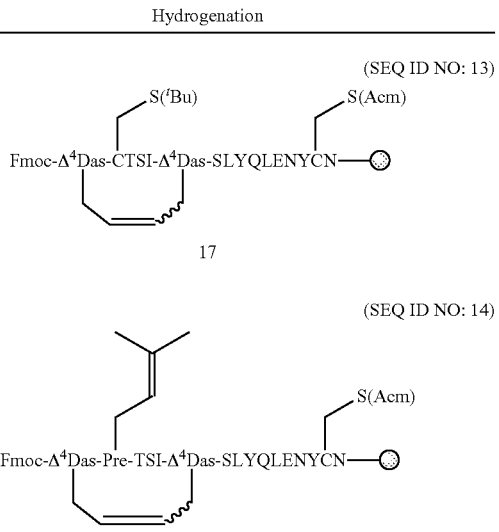

| $H_2$ Substrate | Heat Source | Solvent | Temperature (° C.) | Duration (h) | Pressure (psi) | Conversion (%) |
|---|---|---|---|---|---|---|
| 17 | Microwave | DCM:MeOH (9:1) | 70 | 2 | 90 | 91 to 19 |
| 18 | Microwave | DCM:MeOH (9:1) | 70 | 2 | 90 | 100 to 20 |

Example

Scheme 14

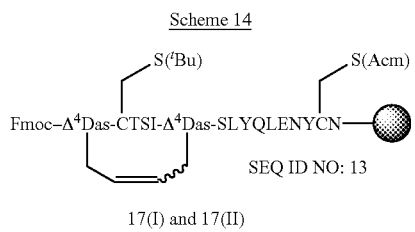

17(I) and 17(II)

i) Wilkinsons catalyst
       DCM:MeOH (9:1)
       100 W μwave, 70° C., 2 h
       90 psi $H_2$
    ii) 20% v/v piperidine in DMF
       r.t., 20 min
    iii) TFA cleavage solution
       r.t., 2-4 h

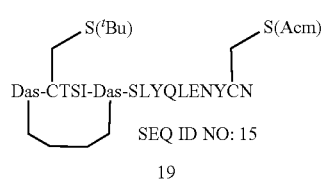

19

Once the required catalysis had been conducted on the resin-tethered sequence, the N-terminal protecting group was readily removed to facilitate SPPS construction of the full sequence (e.g. the addition of the remaining five N-terminal residues, GIVEQ (SEQ ID NO: 12), in the case above). Hence, additional residues were readily attached to the N-terminus of the carbocyclic peptide 19 to give the complete insulin A chain analogue 16 (Scheme 15).

Scheme 15

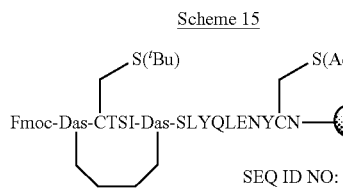

19 i) SPPS
    ii) 20% v/v piperidine in DMF
       r.t., 20 min
    iii) TFA cleavage solution
       r.t., 2-4 h

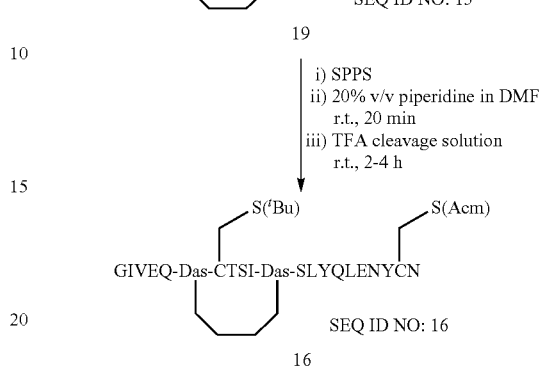

16

Following reduction of the metathesis installed dicarba bridge in 18, formed from resin-bound precursor 15, the prenyl group can be activated in 20 for further dicarba bridge formation via a cross metathesis reaction with cis-2-butene (Scheme 16). Notably, this reaction failed on the complete insulin A-chain (described above). With the five N-terminal residues deleted, however, the prenyl group was found to be accessible for the first time and underwent the required cross metathesis reaction to give resin-tethered peptide 21 with excellent conversion (Scheme 16). This is an example of an intermolecular cross metathesis reaction. Once activated, the generated crotylglycine substituent was reacted with N-acetyl allylglycine methyl ester to form a second dicarba bridge (i.e 22) analogous to that found between the A and B chains of insulin. Cross metathesis with the appropriately functionalised insulin B-chain then provides access to insulin analogues possessing multiple dicarba bridges.

Addition of the final five residues (i.e. GIVEQ (SEQ ID NO: 12)) to the N-terminus of 22 following the multiple catalysis transformations was straightforward (Scheme 16). This final transformation yielded the bis-dicarba peptide 23. This example (i.e. from 15→18→20→21→22→23) convincingly shows the benefit of the alternating SPPS-Catalysis-SPPS approach

Scheme 16

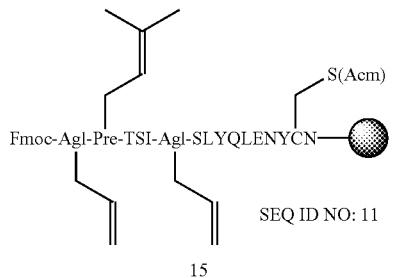

15

20 mol % $2^{nd}$ gen. Grubbs' catalyst
    DCM (5% 0.4M LiCl in DMF)
    100 W μwave, 100° C., 2 h

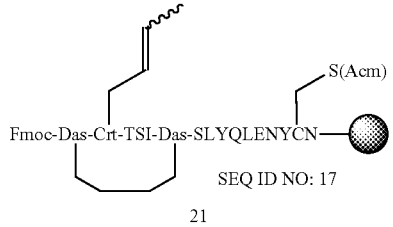

21

10 equiv. Ac-Agl-OMe
    20 mol % $2^{nd}$ gen. Hoveyda-Grubbs' catalyst
    DCM (5% 0.4M LiCl in DMF)
    100 W μwave, 100° C., 4 h

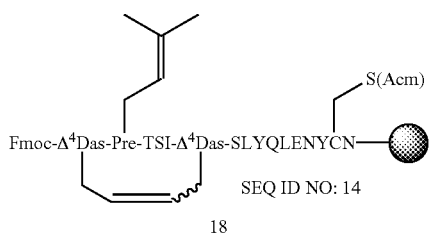

18 SEQ ID NO: 14

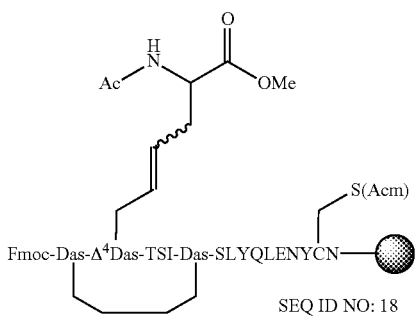

22 SEQ ID NO: 18

RhCl(PPh₃)₃
DCM:MeOH (9:1) (5% 0.4M LiCl in DMF)
80 psi H₂
100 W μwave, 70° C., 2 h i) SPPS
ii) 20% v/v piperidine in DMF
r.t., 20 min
iii) TFA cleavage solution
r.t., 2-4 h

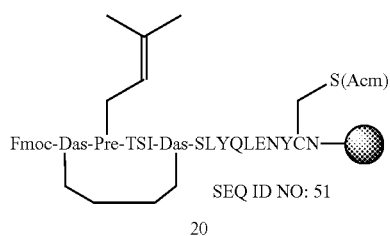

20 SEQ ID NO: 51

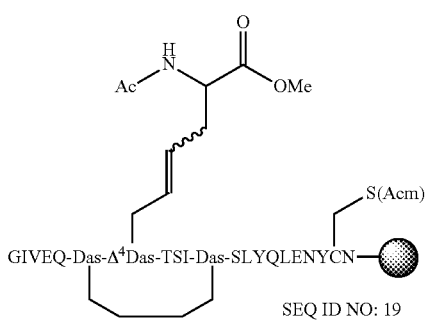

23 SEQ ID NO: 19

20 mol % 2^nd gen. Hoveyda-Grubbs' catalyst
DCM (5% 0.4M LiCl in DMF)
cis-2-butene (12 psi)
100 W μwave, 70° C., 4 h In addition, the alternating SPPS-Catalysis-SPPS method can also be applied to resin-bound peptide sequences prepared for ring closing alkyne metathesis. The tandem alkyne metathesis—-hydrogenation approach, however, requires i) access to non-proteinaceous, chiral alkynyl-containing amino acid residues, ii) the use of highly air and moisture sensitive catalysts, iii) the use of chemoselective and stereoselective hydrogenation catalysts, and iv) most importantly, catalyst access to the C≡C bridge following ring closure.

Sequence inclusion of two butynylglycine residues can be used to form an intramolecular alkyne bridge via alkyne metathesis. Microwave-accelerated solid phase peptide synthesis was used to construct octapeptide 24 (X=Thr) (Scheme 17). Exposure of the resin-bound peptide to Schrock's catalyst (microwave, 35 W, 70° C., 3 h) yielded the target cyclic peptide 25 in 45% yield. Significantly, substitution of the threonine residue with a turn-inducing proline residue (X=Pro, 26) gave a peptide which underwent excellent ring closing alkyne metathesis (ROAM) (80%) under analogous conditions to yield cyclic peptide 27 (Scheme 17). This example illustrates the importance of suitably localizing reactive termini for high ring closing yield. Pseudoproline residues, as used in alkene metathesis, are also invaluable for alkyne metathesis, and will be employed in all tungsten-catalysed ROAM reactions involving full-length dicarba A-chain sequences. Significantly, this reaction fails when the N-terminal GIVEQ (SEQ ID NO: 12) residues are attached prior to the catalysis. On the other hand, when these residues are initially deleted from the sequence exposed to the catalyst, the ROAM (and optional full or semi-hydrogenation) proceeds with high conversion. The initially deleted N-terminal residues are then added to the sequence following catalysis. Hence, addition of the remaining five residues yields peptide 28 in a straightforward manner (Scheme 17).

Scheme 17

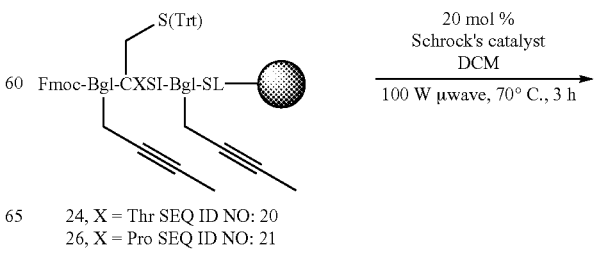

20 mol %
Schrock's catalyst
DCM
100 W μwave, 70° C., 3 h

24, X = Thr SEQ ID NO: 20
26, X = Pro SEQ ID NO: 21

-continued

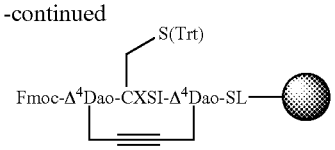

25, X = Thr SEQ ID NO: 22
27, X = Pro SEQ ID NO: 23 i) SPPS
ii) 20% v/v piperidine in DMF r.t., 20 min
iii) TFA cleavage solution r.t., 2-4 h

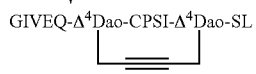

28 SEQ ID NO: 24

5. Interchain Dicarba Bridges: Synthesis of Olefinic Human Insulin A- and B-Chain Insulin Analogues The synthesis of interchain dicarba analogues of human insulin was expected to present a similar set of synthetic challenges to those experienced during the generation of intrachain C=C analogues. Several approaches were examined in this study, and involved: i) direct cross metathesis of full and truncated A- and B-chain peptides, ii) orthogonally protected $\Delta^4$-diaminosuberic acid (DAS) units for direct SPPS insertion into the primary sequence, and an RCM approach utilising a removable tether (Scheme 18).

Preformed Orthogonally-Protected Diaminosuberic Acid

One strategy for introducing an interchain dicarba bridge is by the introduction of a preformed dicarba bridge during peptide synthesis. As insulin, possesses two separate chains, an orthogonally protected DAS derivative would be required to facilitate controlled and sequential elongation of the A- and B-chains. In order to probe conformational preferences about insulin's A7-B7 interchain cystine bridge using dicarba analogues, we therefore required access to a library of both saturated and unsaturated (cis- and trans-) DAS derivatives. We have developed an efficient route to this unit via CM of readily accessible, protected allylglycine derivatives.

Although this process is non-selective, the use of a stoichiometric excess of one olefin would result in a statistical product mixture, and bias formation of the target $\Delta^4$DAS residue.

In order to avoid the complicated separation of excess reagents in solution, a resin-based preparation of orthogonally-protected $\Delta^4$DAS was also investigated. A model dipeptide Fmoc-L-Agl-L-Asn-NH$_2$ 136 was therefore constructed onto rink amide resin and subjected to CM with Ac-D,L-Agl-OMe in the presence of 20 mol % second generation Grubbs' catalyst (Scheme 19). Through the alteration of temperature and time, and the use of both conventional and microwave-based heating, 85% conversion to the required heterodimer 137 was obtained. Excess reagents and by-products were Scheme 18

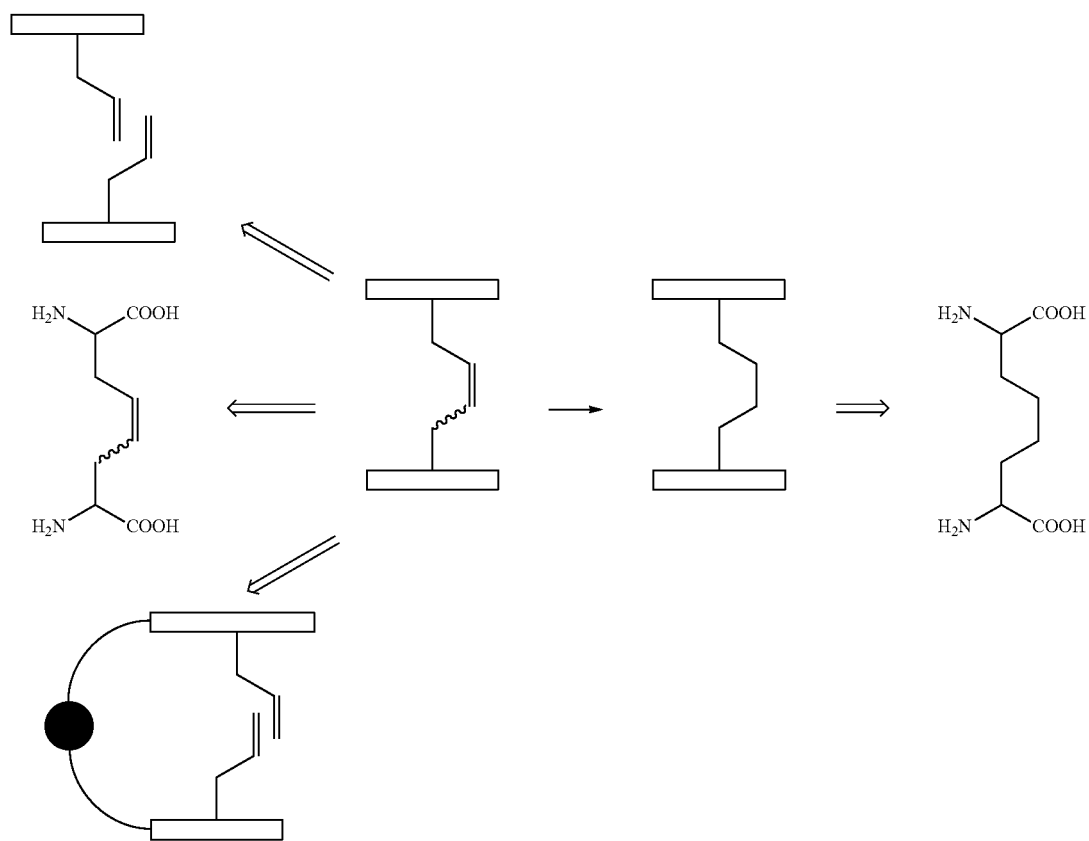

removed by simple filtration. The Δ⁴DAS can be directly incorporated into the primary sequence via SPPS to allow sequential and controlled N→C growth of the A- and B-chains. Convergent synthesis can then be used to attach the remaining C-terminal residues, and complete the insulin framework.

truncated at the $Gly_{B8}$ residue to minimise the size of the resulting cycle, and to provide a racemisation free C-terminal residue for future convergent SPPS. Microwave-accelerated RCM of the resin-tethered peptide in the presence of 20 mol % second generation Grubbs' catalyst gave 78% conversion to the target carbocycle 181 (Scheme 20).

Scheme 20

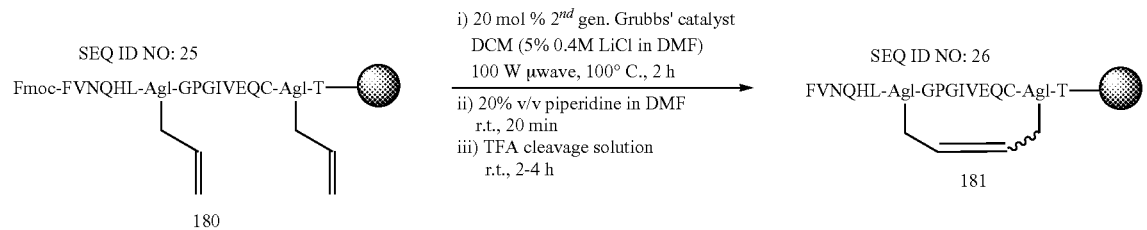

When RCM was performed on the peptide with its six N-terminal amino acids omitted (i.e. on 182), RCM proceeded with quantitative conversion. Following catalysis, the remaining residues were readily appended to the N-terminus via microwave-accelerated SPPS to give target peptide 181.

Scheme 19

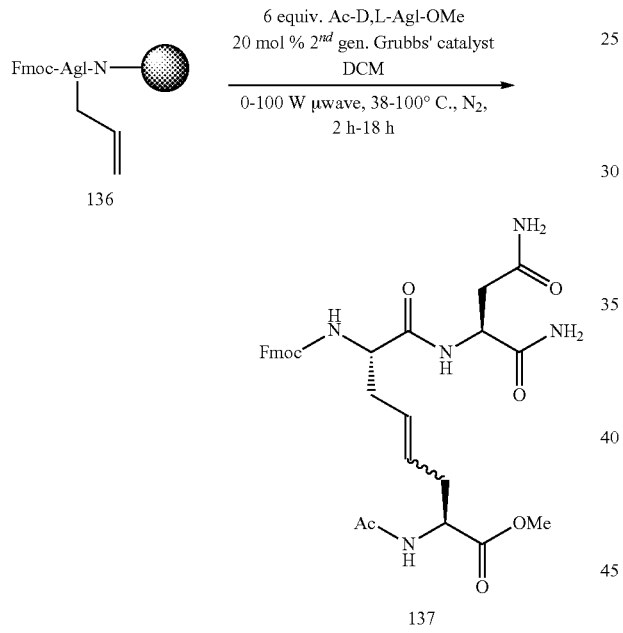

Scheme 21

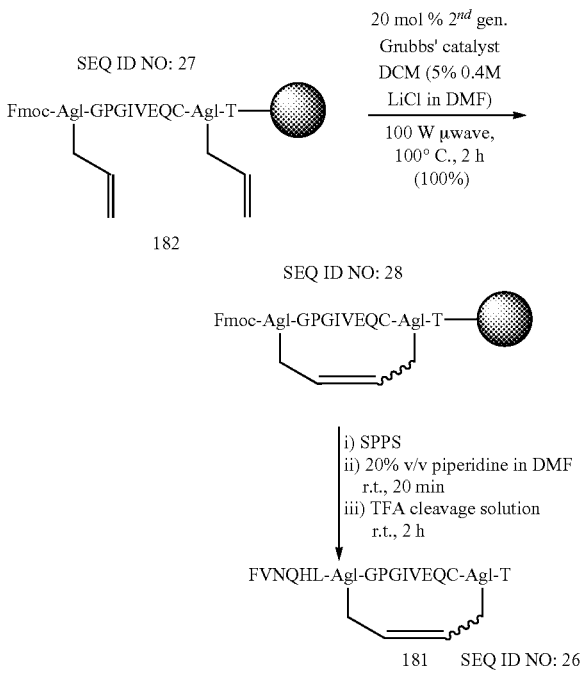

Removable Tethers: An RCM Approach

Figure 3:
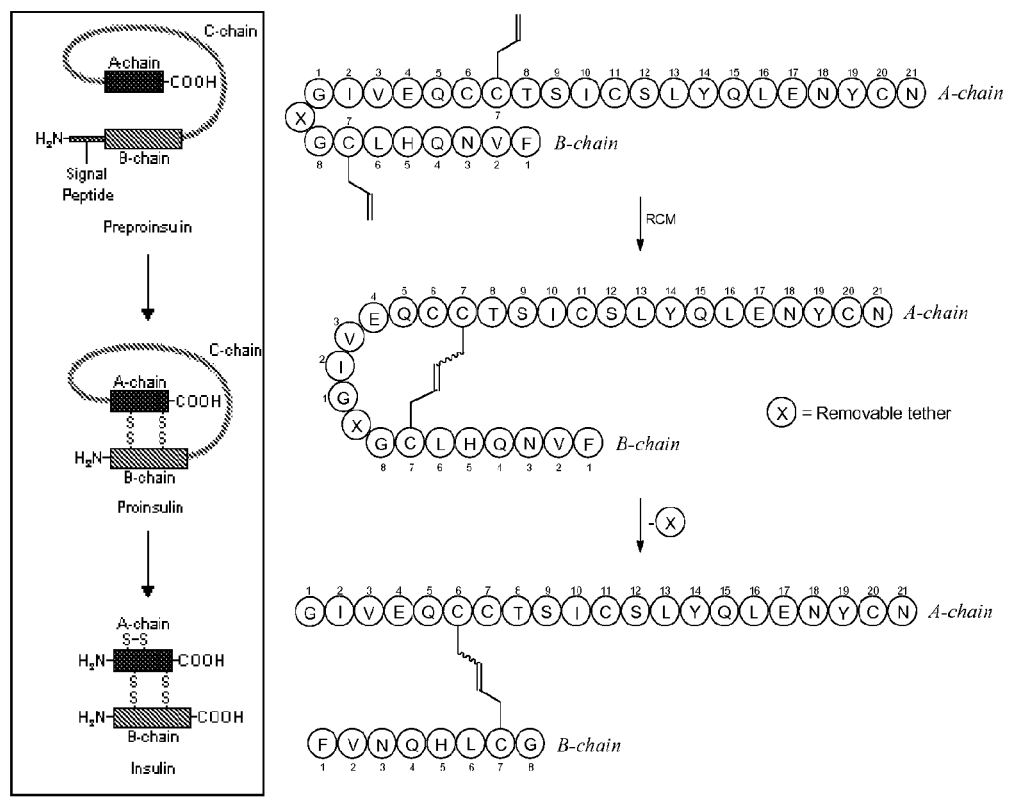
FIG. 3 is a schematic diagram showing an RCM approach using tethers to introduce interchain dicarba bridges (Preproinsulin (SEQ ID NO: 94), Proinsulin (SEQ ID NO: 95, Insulin (SEQ ID NO: 98)).

Native insulins are generated from a single-chain proinsulin precursor (A-C-B), where the inserted C-peptide sequence, varying in length from 26-38 residues, aids native disulfide folding (FIG. 3, left). Taking a lead from Nature, a removable, turn-inducing truncated sequence or residue (X) could be inserted between the A- and B-chains to promote formation of the target A7-B7 interchain dicarba bridge via RCM (FIG. 3, right). Following bridge formation, the X residue/s would then be removed, and ligation of the remaining B9-B21 segment via convergent SPPS would provide the complete 51 amino acid dicarba insulin target. This approach is shown schematically in FIG. 3.

This was initially investigated using a truncated A-chain sequence, and a readily available turn-inducing proline residue as the tether (X). The 17 residue sequence B1-8+Pro+ A1-8 180 was constructed using microwave-accelerated SPPS onto Fmoc-Thr(ᵗBu)-PEG-PS resin. The B-chain was The stable proline linker (X) was then replaced with a turn-promoting, removable tether to generate the target A7-B7 dicarba link and native N-terminal $Gly_{A1}$ residue. A hydroxy-6-nitrobenzaldehyde (HnB) residue, was selected for the role. This aldehyde is readily incorporated at the N-terminus of a peptide sequence via reductive amination, and promotes head-to-tail cyclisation reactions through the introduction of cisodial geometry in the peptide backbone. Furthermore, the auxiliary undergoes efficient and selective removal by mild photolysis.

The HnB residue could be used in a novel way via introduction between the allylglycine-containing insulin A- and B-chains to promote RCM. Following cross metathesis and additional sequence construction, cleavage of the HnB auxiliary via sequential hydrolysis and photolysis would then yield the A-B heterodimer with the target A7-B7 dicarba bridge (Scheme 22).
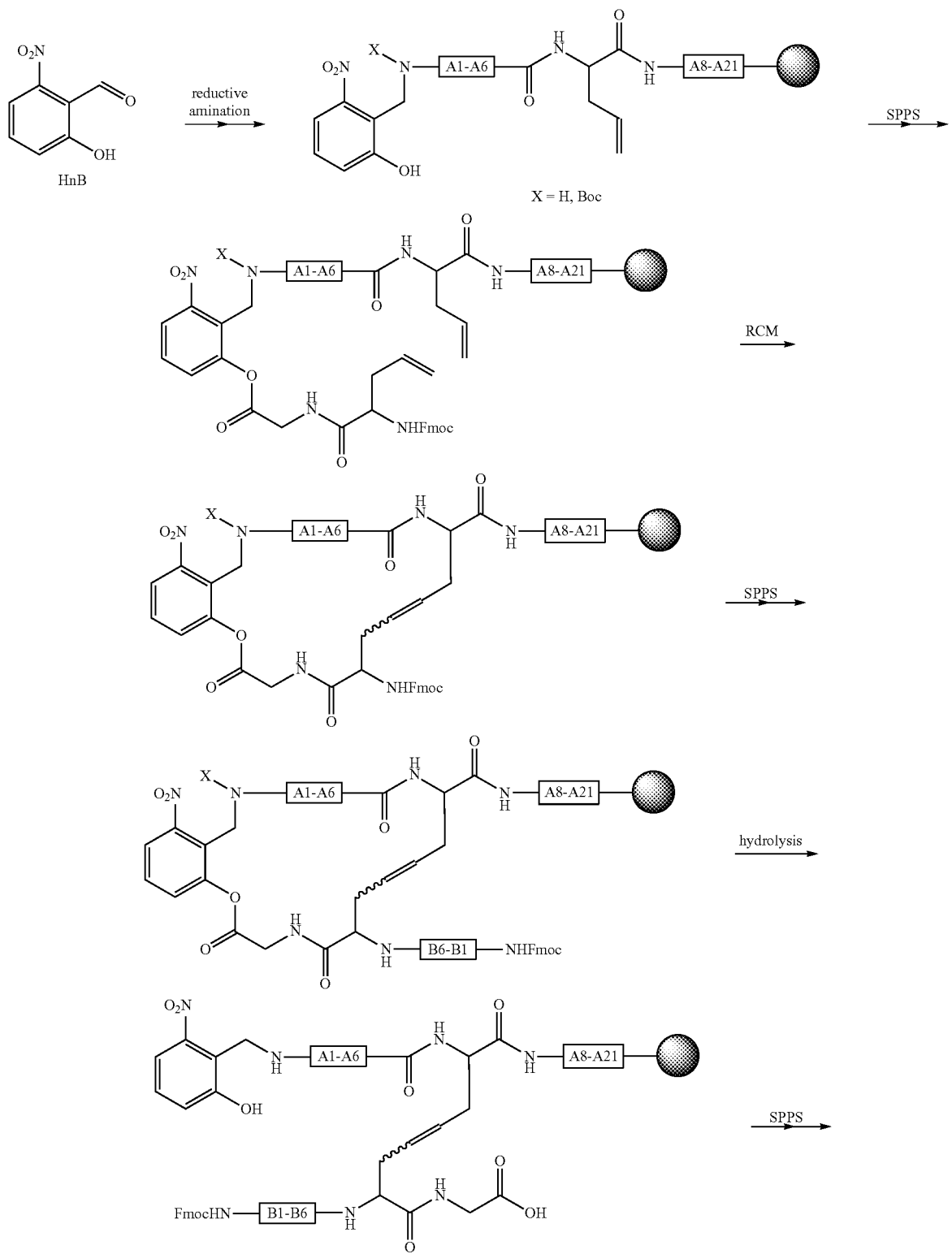
Scheme 22

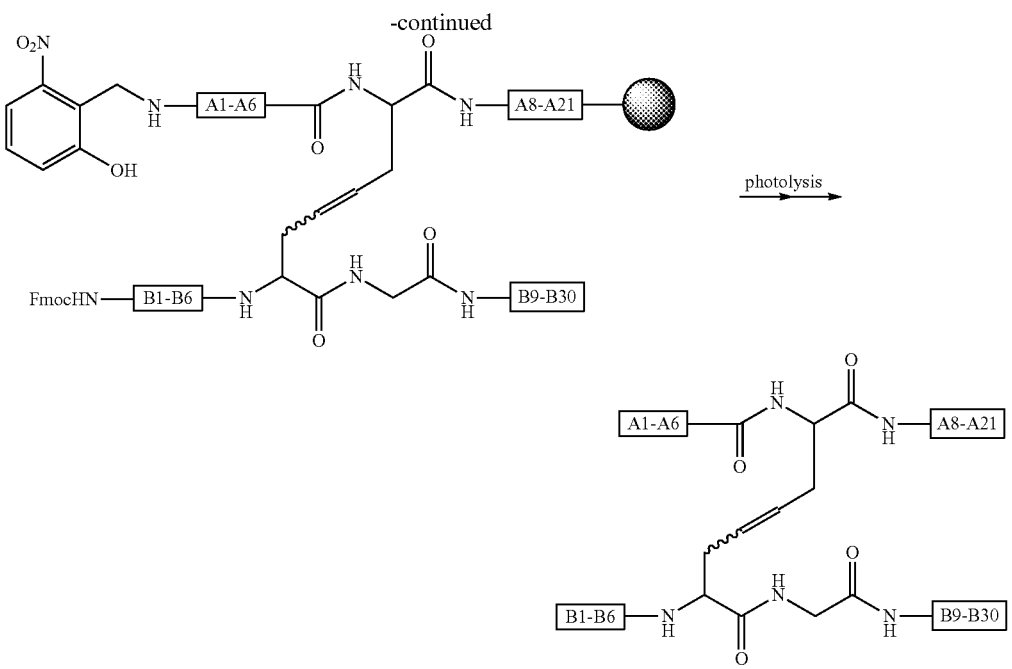

The photolabile HnB tether was synthesised from meta-nitrophenol in a three step reaction sequence (Scheme 23). This aldehyde was then successfully introduced into the truncated A-chain sequence (A1-A8) via reductive amination, to give a linear peptide in 90% yield (Scheme 23). The resultant secondary amine was then protected prior to esterification with an activated Fmoc-Gly-OH residue. Coupling of the second allylglycine residue and subsequent RCM with 20 mol % second generation Grubbs' catalyst was successful. The mass spectrum of a cleaved aliquot of resin showed, the target ring closed product with m/z 1431.5.

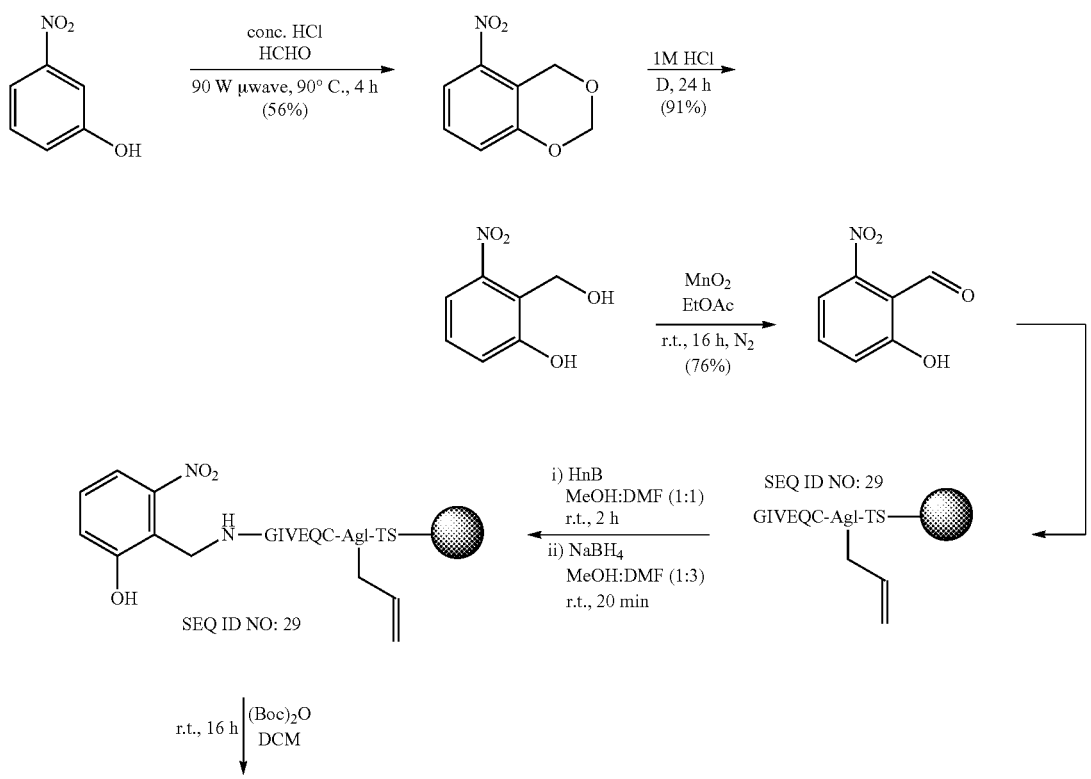

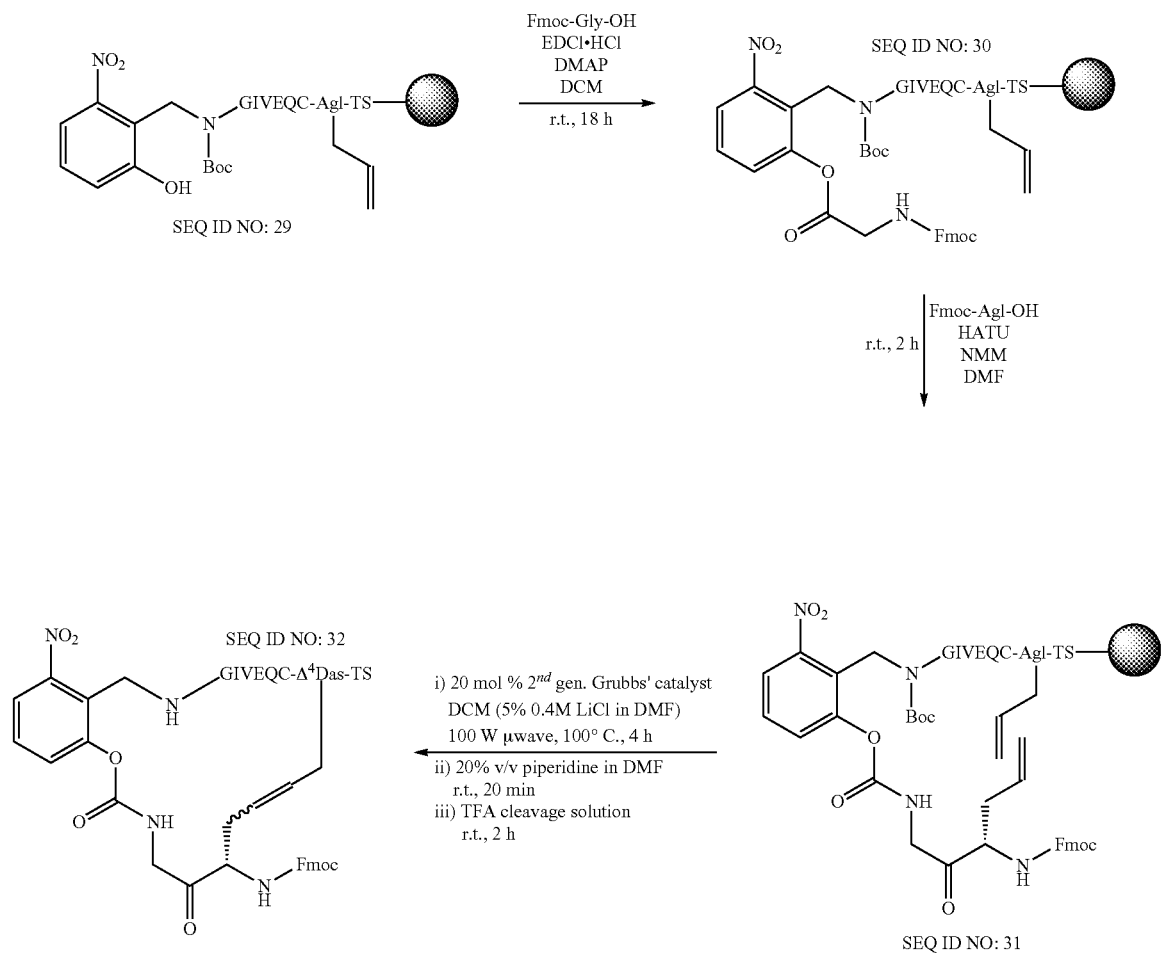

6. Fast and Slow Acting Dicarba Insulin Analogues c[Δ⁴A6,11]-Dicarba DKP Human Insulin The analysis of insulin surfaces involved in crystal packing interaction led to the identification of key amino acid residues responsible for dimer and hexamer formation. As a result, several analogues with altered self-association properties have been developed. DKP insulin is monomeric in solution, regardless of concentration. This molecule incorporates three amino acid substitutions within the B-chain to alter self-association. The first is a $His_{B10}\rightarrow Asp$ substitution which destabilises the hexamer interface. The second and third are a simple B28 and B29 residue 'swaps' (i.e. $Pro_{B28}\rightarrow Lys$, and $Lys_{B29}\rightarrow Pro$), which disrupt the dimer forming surface. Hence, to aid structural elucidation, DKP analogues of each dicarba insulin isomer were prepared.

Towards this end, we needed access to both dicarba isomers of human insulin. Unfortunately, the pseudoproline-inserted route previously described gives an excellent yield of only one geometric isomer. We were therefore forced to use the less productive method, where RCM is affected without the aid of a turn-inducing residue, to generate the two required A-chain isomers (I and II) for combination with a DKP-modified B-chain. Hence, synthesis of c[Δ⁴A6,11]-dicarba DKP human insulin via the previously described microwave-accelerated SPPS, RCM and thiol-activation process gave the expected isomeric A-chains 10(I) and 10(II) after cleavage and chromatographic purification.

With the required A-chains at hand, construction of the DKP human insulin B-chain 50 was performed via microwave-accelerated SPPS: Fmoc-L-Thr(ᵗBu)-PEG-PS resin, HBTU/HOBt-DIPEA activation and Fmoc-protected amino acids were employed. During chain elongation, orthogonally protected cysteine residues were incorporated into the primary sequence in positions B7 and B19, while aspartic acid, lysine and proline replaced the native residues at B10, B28 and B29 respectively. After synthesis completion the resin-tethered peptide was subjected to TFA-mediated cleavage, and the required insulin B-chain analogue 50 was then isolated in 13% yield and 90% purity after preparative RP-HPLC. Mass spectral analysis of the purified peptide gave molecular ion peaks at m/z 1160.3 $[M+3H]^{3+}$, 870.5 $[M+5H]^{4+}$ and 696.5 $[M+5H]^{5+}$ which were consistent with the DKP B-chain linear sequence 50. Following regioselective thiolysis and iodolysis of A- and B-chains 10(I)/(II) and 50 respectively (Scheme 24). The required dicarba-DKP insulin molecule was isolated as four isomers: $52(I)_{A/B}$, in 10% and 8% yield (90% purity), and $52(II)_{A/B}$, in 12% and 17% yield (90% purity).

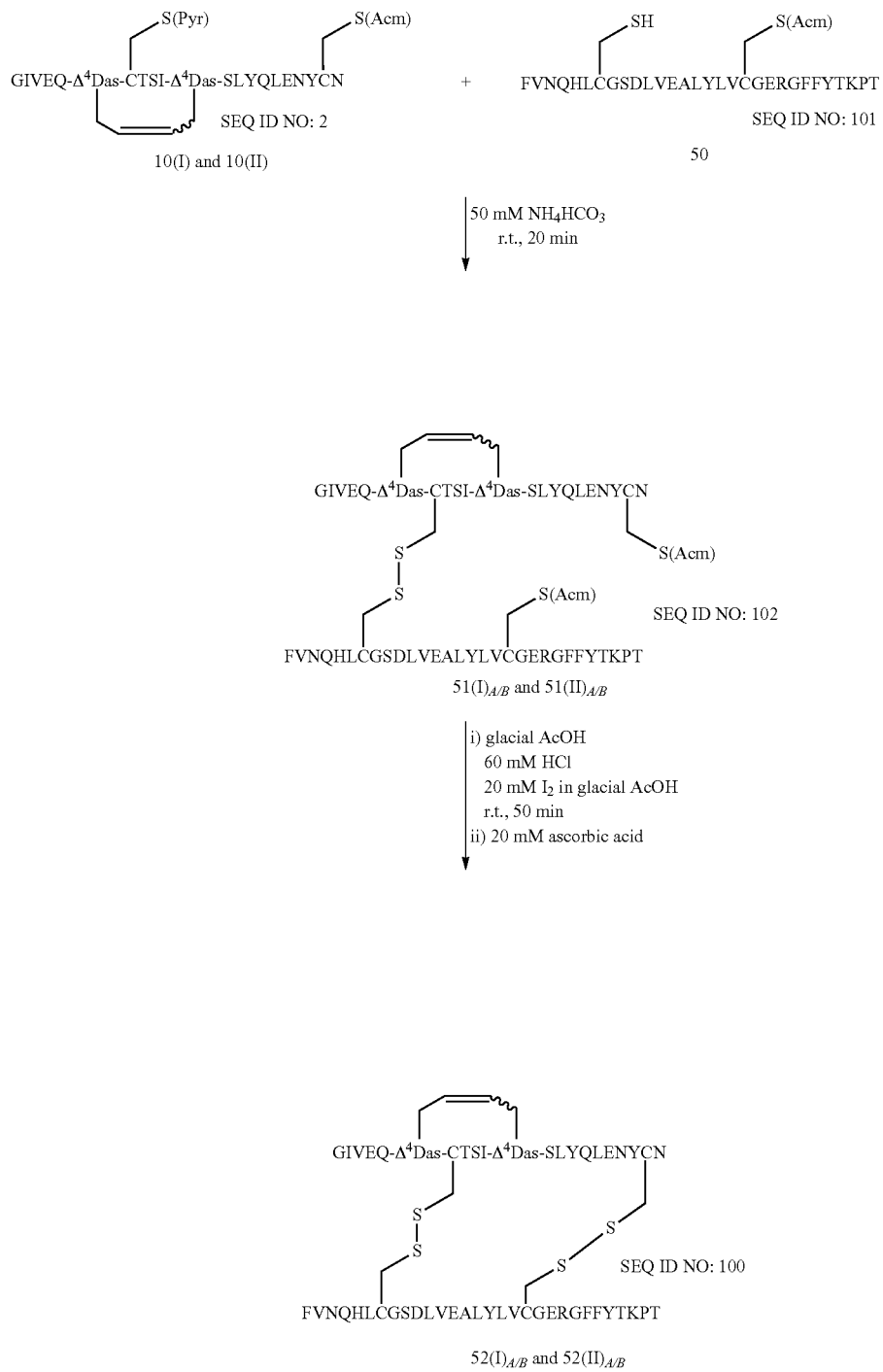

Scheme 24

Dicarba Human Insulin Glargine and Lispro Analogues

The alternating SPPS-catalysis strategy was used to construct several dicarba analogues of human insulin, notably the long and rapid acting insulin analogues glargine and lispro. Temporary deletion of the five N-terminal residues from the A chains of each of these insulins facilitated high yielding ring closing metathesis to the unsaturated carbocycles. The C═C bridge in these analogues could then be optionally reduced via hydrogenation to give the saturated dicarba A chains. The remaining GIVEQ (SEQ ID NO: 12) residues were then readily appended to the N-terminus to afford the complete A chains ready for ligation to their partner B chains. Previously described orthogonal protecting group strategies and activation protocols were then used to ligate the A and B chains to give the full dicarba insulin molecules (Scheme 25 and 26). These and other analogues were then subjected to biological testing.

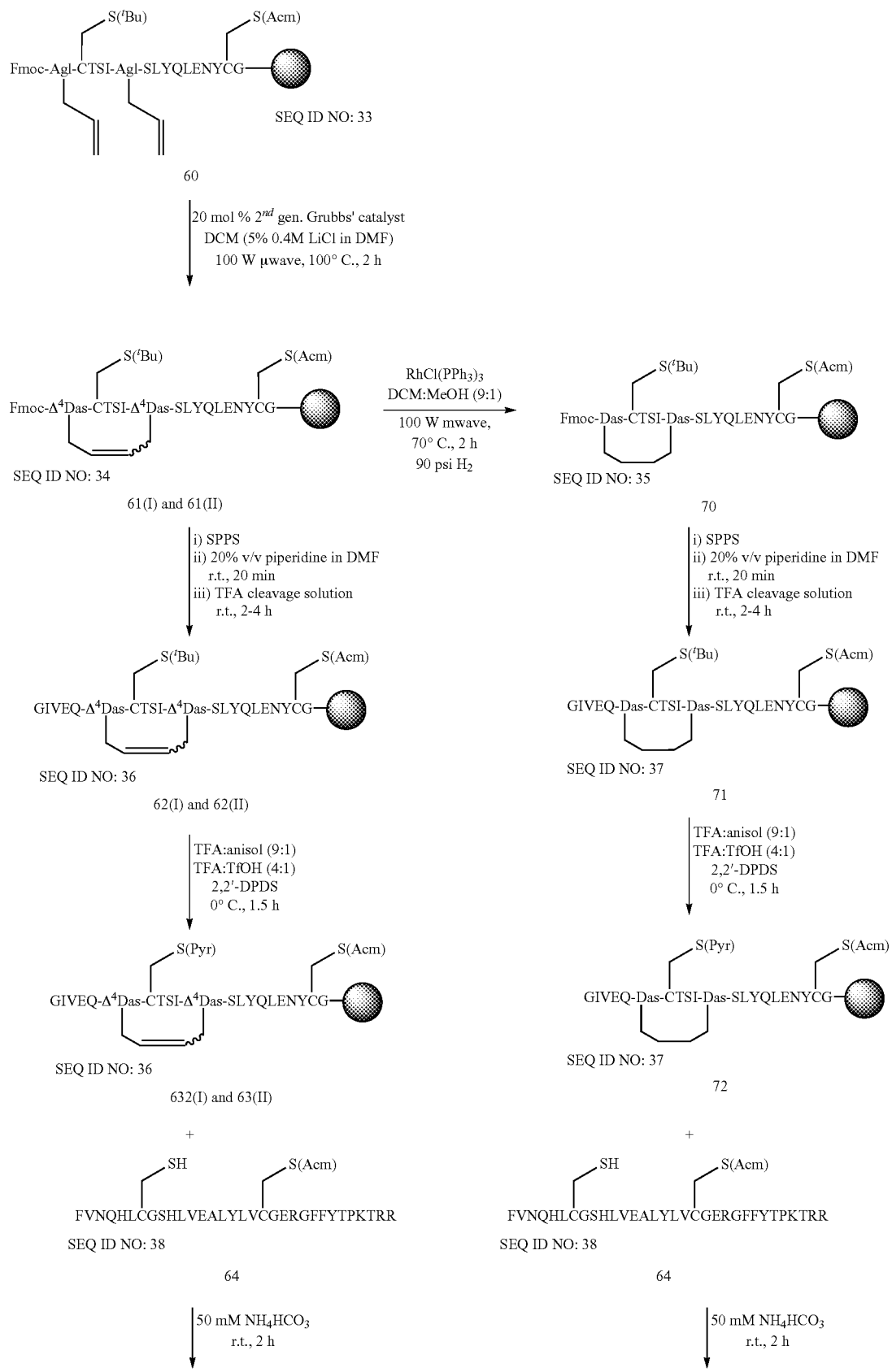

105
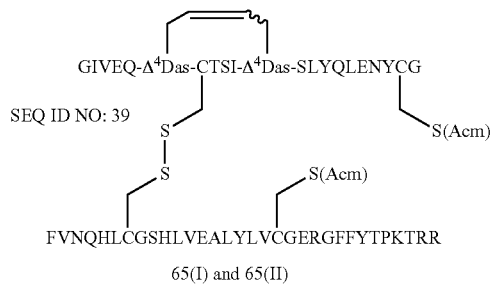
65(I) and 65(II)
106
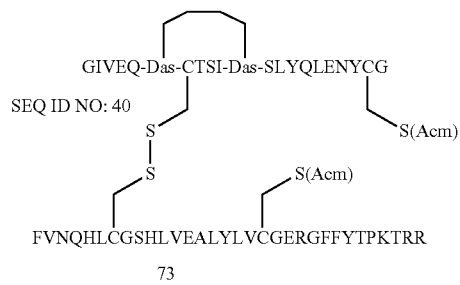
73
i) glacial AcOH
60 mM HCl
20 mM I$_2$ in glacial AcOH
r.t., 2.75 h
ii) 20 mM ascorbic acid
i) glacial AcOH
60 mM HCl
20 mM I$_2$ in glacial AcOH
r.t., 2.75 h
ii) 20 mM ascorbic acid
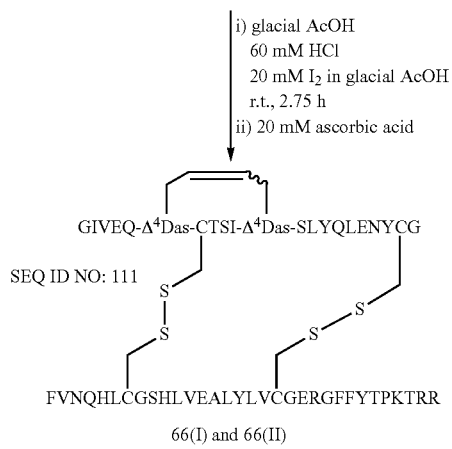
66(I) and 66(II)
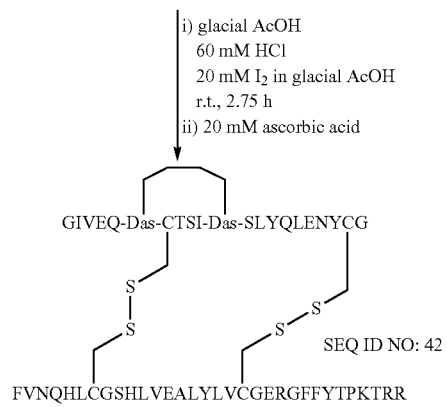
74
Scheme 26
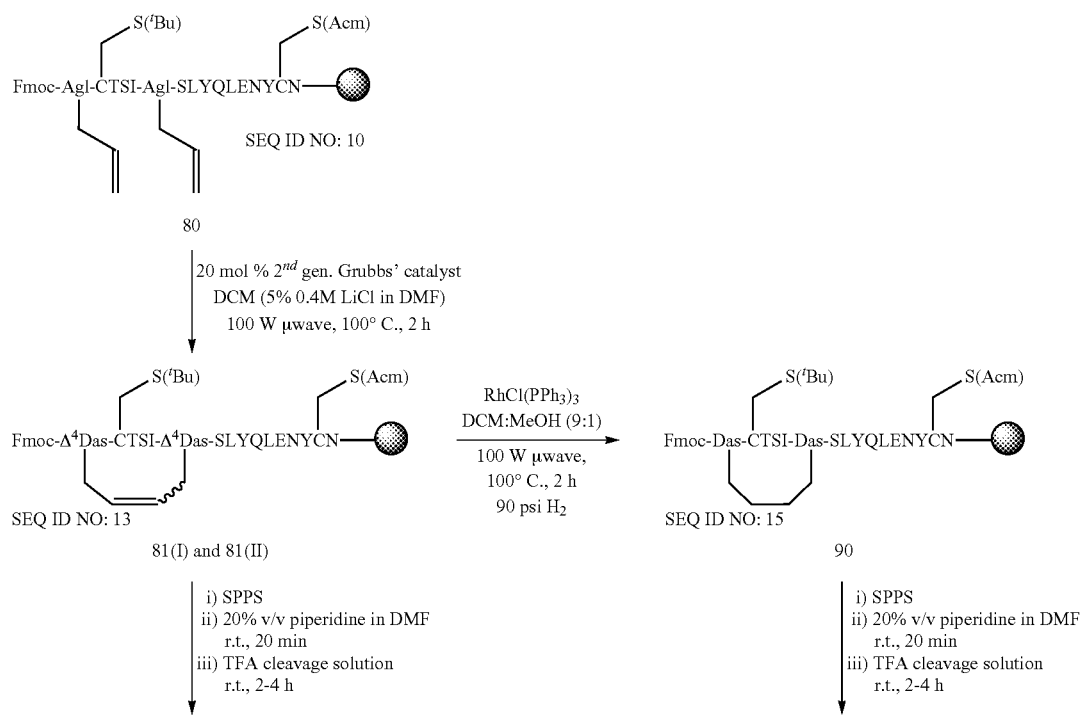

-continued
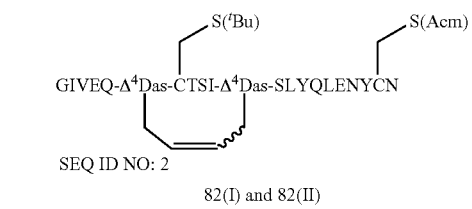
SEQ ID NO: 2
82(I) and 82(II)
| TFA:anisol (9:1)
| TFA:TfOH (4:1)
| 2,2'-DPDS
| 0° C., 1.5 h
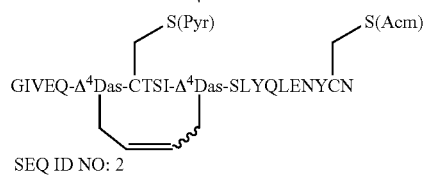
SEQ ID NO: 2
83(I) and 83(II)
+
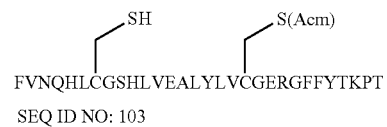
SEQ ID NO: 103
84
| 50 mM NH₄HCO₃
| r.t., 3 h
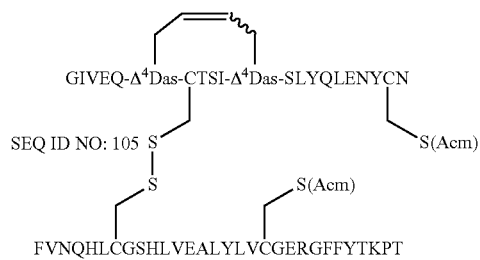
SEQ ID NO: 105
85(I) and 85(II)
| i) glacial AcOH
| 60 mM HCl
| 20 mM I₂ in glacial AcOH
| r.t., 2.75 h
| ii) 20 mM ascorbic acid
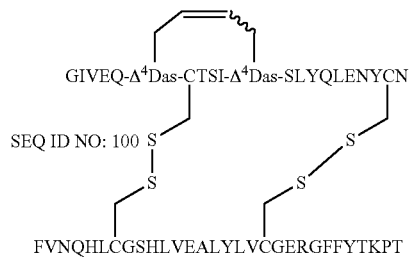
SEQ ID NO: 100
86(I)$_{A/B}$ and 86(II)$_{A/B}$
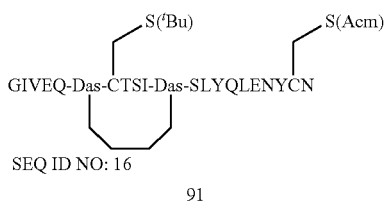
SEQ ID NO: 16
91
| TFA:anisol (9:1)
| TFA:TfOH (4:1)
| 2,2'-DPDS
| 0° C., 1.5 h
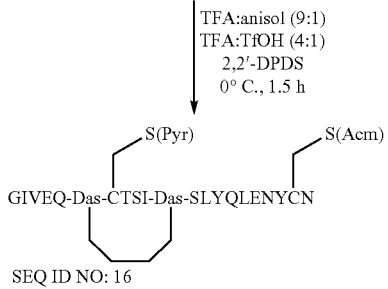
SEQ ID NO: 16
92
⇣ 2 steps
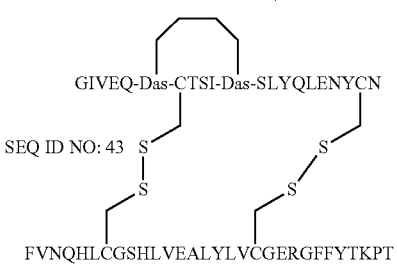
SEQ ID NO: 43

7. Biological Evaluation of Intrachain Dicarba Analogues of Insulin

With several A6-A11 dicarba analogues of insulin at hand, biological assessment was then undertaken to ascertain the role, structural or functional, played by the native intrachain cystine motif. Here, an absence in receptor binding affinity, and/or biological potency, would suggest that the A6-A11 S—S bond acts as a functional disulfide. From a biological perspective, insulin binds and activates specific cell surface tyrosine kinase receptors which elicit tyrosine phosphorylation on intracellular insulin receptor substrates (IRS). This, in turn, leads to translocation of vesicles containing the glucose transporter GLUT4 to the plasma membrane which ultimately promotes glucose uptake.

Metabolic Potency: Insulin Receptor Binding and Activation

The insulin receptor (IR) is a transmembrane glycoprotein that consists of two 735 residue α-subunits and two 620 residue β-subunits. The α-chains reside on the extracellular side of the plasma membrane and contain the cysteine-rich insulin binding domain. The IR exists as two isoforms, IR-A and -B, which differ from each other by the absence or presence of 12 amino acids (residues 717-728) on each α-subunit respectively. Although the two receptors display similar binding affinity towards insulin, they possess different levels of kinase activity. The metabolic action of insulin however, is primarily through IR-B. This isoform predominates in insulin responsive tissues and was therefore chosen for preliminary binding and activation studies.

Figure 4A:
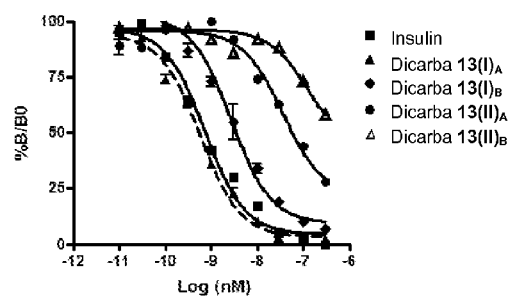
FIG. 4A is a graph showing competition binding curves for Eu-labelled insulin (ActRapid®) binding to the immunopurified human IR-B in the presence or absence of dicarba analogues 13(I) and 13(II).
Figure 4B:
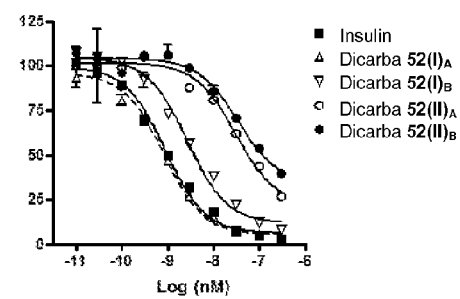
FIG. 4B is a graph showing competition binding curves for Eu-labelled insulin (ActRapid®) binding to the immunopurified human IR-B in the presence or absence of dicarba analogues 52(I) and 52(II).

Using immunocaptured IR-Bs and europium-labelled insulin, competitive binding assays were carried out in the presence and absence of increasing concentrations of each dicarba isomer. The analogue $13(I)_A$ possesses near identical nanomolar binding affinity ($IC_{50}$=0.57 nM) toward IR-B when compared to the native molecule ($IC_{50}$=0.72 nM). Additionally, the complementary geometric isomer $13(I)_B$ displayed only slightly diminished affinity for this same receptor ($IC_{50}$=2.65 nM). In contrast, however, affinity of the geometric isomers $13(II)_A$ and $13(II)_6$ for IR-B was 49- and 187-fold lower than that of native insulin respectively (FIG. 4A). As shown in FIG. 4B, a similar trend was also observed for the dicarba DKP insulin series. A summary of the 50% inhibitory concentration ($IC_{50}$) values for each analogue is presented in Table 5. This data suggests that the insulin receptor is highly sensitive to changes in geometry about the A6-A11 intrachain bridging motif.

TABLE 5

Inhibition of Eu-labelled insulin in binding to IR-B by dicarba analogues of insulin.

| Ligand | $IC_{50}$ (95% confidence interval) (nM) | $IC_{50}$ relative to insulin |
|---|---|---|
| Human insulin | 0.72 (0.54-0.72) | 1.00 |
| $13(I)_A$ | 0.57 (0.38-0.60) | 0.79 |
| $13(I)_B$ | 2.65 (2.85-6.14) | 3.70 |
| $13(II)_A$ | 35.3 (30.9-92.9) | 49.3 |
| $13(II)_B$ | 134 (30.1-255) | 187 |
| Human insulin | 0.88 (0.72-1.07) | 1.00 |
| $52(I)_A$ | 0.82 (0.78-1.43) | 0.94 |
| $52(I)_B$ | 2.67 (2.10-3.37) | 3.04 |
| $52(II)_A$ | 29.9 (19.8-45.3) | 34.2 |
| $52(II)_B$ | 33.6 (23.3-48.5) | 38.4 |

Figure 5A:
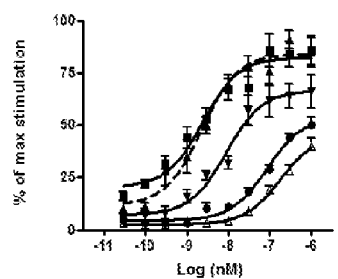
FIG. 5A is a graph showing activation of the immunopurified human IR isoforms by native insulin (ActRapid®) and intrachain dicarba analogues 13(I) and 13(II) to IR-B.
Figure 5B:
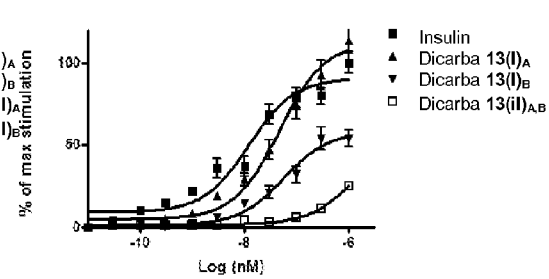
FIG. 5B is a graph showing activation of the immunopurified human IR isoforms by native insulin (ActRapid®) and intrachain dicarba analogues 13(I) and 13(II) to IR-A.

Similarly, preliminary receptor activation data is also highly encouraging. Consistent with the preceding binding results, $13(I)_A$ was able to induce IR-B phosphorylation comparable to that of native insulin, with ligand concentrations of approximately 4 nM required to achieve 50% phosphorylation in both cases (FIGS. 5A and 5B). The complementary isomer $13(I)_B$, however, was less effective (20%) at this same concentration. Additionally, isomers $13(II)_{A/B}$, which showed poor binding affinity, also displayed low phosphorylation potency. Here, activation of IR-B by these two ligands was only detected at 9-10 nM concentrations (FIGS. 5A and 5B). Again, this data suggests that the insulin receptor is highly sensitive to changes in the intrachain bridge geometry.

The eight dicarba insulin analogues retained their original binding and activation potency and were completely stable to storage for greater than three years. Existing insulin formulations are reportedly unstable when stored above 4° C. for approximately one month, and even less stable at temperatures in excess of 25° C. Notably, inactive oligomers and polymers are reported to constitute 90% of the total protein by mass after 6 months of storage at ambient temperature. Additionally, current preparations can precipitate and clog insulin pumps over a three day time period. This finding suggests that the A6-A11 intrachain disulfide bridge may play an important role in the degradation of native insulin, and that the generation of intrachain dicarba analogues could provide a simple solution to insulin's formulation instability.

Mitogenic Potency: IGF-I Receptor Binding and DNA Synthesis

Figure 6A:
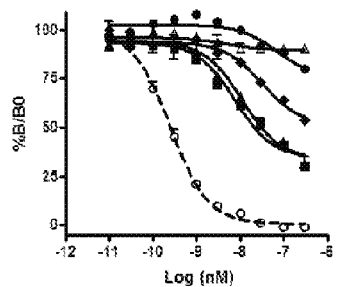
FIG. 6A is a graph showing competition binding curves of Eu-labelled IGF-I binding to the immunopurified human IGF-IR in the presence of each of $13(I)_A$, $13(I)_B$, $13(II)_A$ and $13(II)_B$ and native insulin (ActRapid®), with results expressed as the percentage of Eu-IGF-I bound in the absence of competing ligand ($B/B_o$).
Figure 6B:
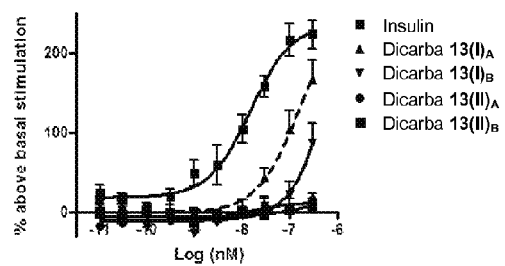
FIG. 6B is a graph showing stimulation of DNA synthesis in response to IGF-I, insulin and dicarba insulins $13(I)_A$, $13(I)_B$, $13(II)_A$ and $13(II)_B$ using L6 myoblast cells over expressing IR-B.

So far, biological data has revealed that the generated dicarba analogues possess both high ($13(I)_{A/B}$ and $52(I)_{A/B}$) and low ($13(II)_{A/B}$ and $52(II)_{A/B}$) metabolic activities. Altering the structure of insulin, however, also has the potential to significantly impact on mitogenicity. Major concerns have recently been raised in regard to the safety and tolerability of novel insulin analogues. It is widely believed that mitogenic stimulation is directly related to i) residence time on the receptor, dissociation rate from the receptor, receptor internalisation, and iv) the degree of phosphorylation in signalling proteins. More recently, however, insulin's interaction with the IGF-I receptor (IGF-IR) has been implicated in mitogenic activity. In addition to its role in mediating physiological growth and metabolic actions, the IGF-IR plays a well-established role in tumour development. Using immunocaptured IGF-IRs and europium-labelled IGF-I, competitive binding assays were carried out in the presence and absence of increasing concentrations of each dicarba insulin. The IGF-IR binding of the four analogues, $13(I)_{A/B}$ and $13(II)_{A/B}$, was found to mirror the measured IR-B relative binding affinities (FIGS. 6A and 6B) and Table 6. Significantly, however, DNA synthesis in the presence of the analogue, $13(I)_A$, was an order of magnitude lower than human insulin (FIGS. 6A and 6B): Replacement of the native A6-A11 cystine bridge with the unsaturated dicarba bridge has provided an insulin analogue with normal metabolic activity and significantly reduced mitogenic activity.

TABLE 6

Inhibition of Eu-labelled IGF-I for binding to IGF-IR by dicarba analogues of insulin.

| Ligand | $IC_{50}$ (95% confidence interval) (nM) | $IC_{50}$ relative to insulin |
|---|---|---|
| IGF-I | 0.25 (0.21-0.29) | 0.03 |
| Human insulin | 7.60 (5.34-10.8) | 1.00 |
| $13(I)_A$ | 11.3 (7.71-16.5) | 1.48 |
| $13(I)_B$ | 31.9 (15.8-64.5) | 4.20 |
| $13(II)_A$ | 72.5 (25.2-209) | 9.54 |
| $13(II)_B$ | 5.38 (0.37-78.8) | 0.71 |

Similarly, IGF-IR binding assays were also carried out in the presence of the four DKP dicarba analogues (preliminary data, where n=1, is not shown). Most notably, 52(I)$_A$ possessed comparable IGF-IR binding affinity when compared to native insulin. This was a surprising result considering insulin aspart B10, engineered as a rapid-acting mutant by exchanging His$_{B10}$ for aspartic acid, was removed from clinical trials due to its greatly enhanced IGF-IR binding and mitogenic potency (nine times each). Additionally, the remaining three DKP dicarba isomers each displayed a suppression in IGF-IR binding (data not shown).

Glucose Regulation: Glucose Uptake and Insulin Tolerance Tests

Figure 7:
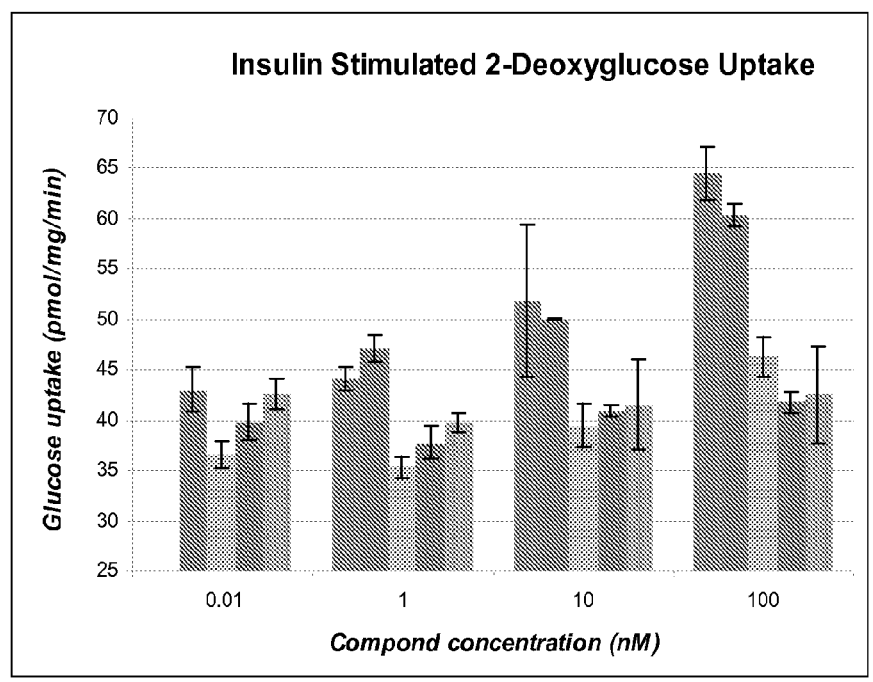
FIG. 7 is a graph showing a dose-response study of dicarba insulin (13(I) and 13(II)) stimulated 2-deoxy-D-glucose uptake in differentiated L6 GLUT4-myc cells.

Native insulin stimulates this process via translocation of the GLUT4 glucose transporter to plasma membranes. In the absence of stimuli such as insulin, GLUT4 resides in an inactive location where it is unable to promote uptake. The ability of our dicarba analogues to exhibit native insulin activity by inducing glucose uptake was investigated. Here, transport activity was measured using the non-metabolisable glucose analogue 2-deoxy-D-glucose (2DG), and differentiated L6 GLUT4-myc cells, in the presence of each dicarba insulin isomer. The results of these assays are summarised in FIG. 7. 13(I)$_A$, a lead dicarba insulin analogue, promoted 2DG uptake comparable to that of ActRapid® (native human insulin). Additionally, the remaining three isomers, although to a lesser extent, were also able to promote glucose uptake into GLUT4-expressed cells.

Figure 8:
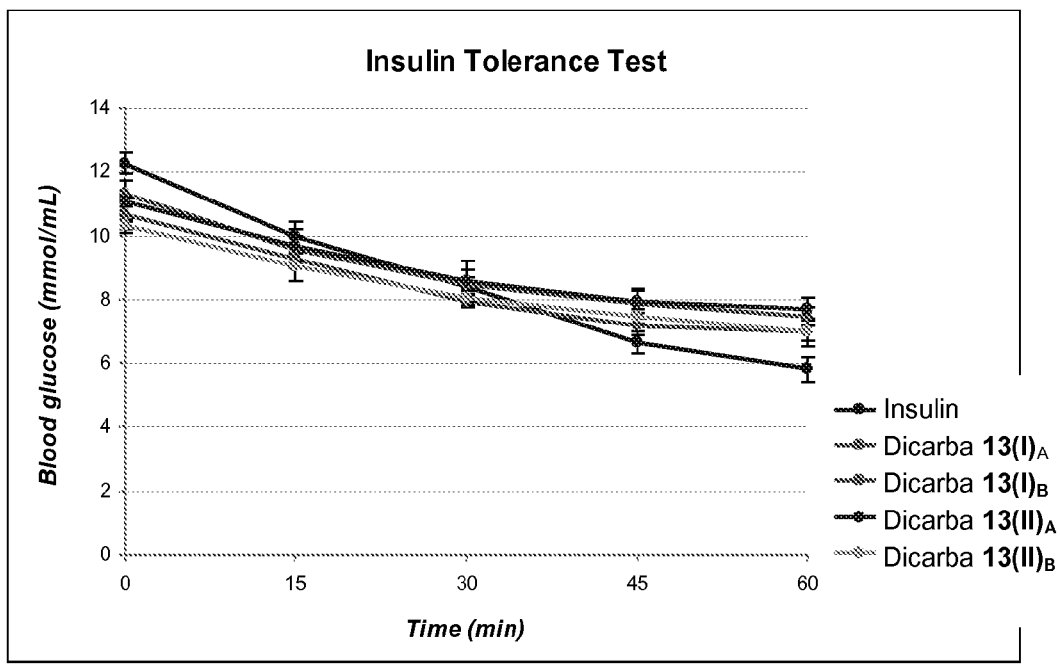
FIG. 8 is a graph showing the blood glucose content in anesthetised 7 week old male C57BL/6 mice following intraperitoneal bolus injection with dicarba analogues 13(I) and 13(II) or ActRapid®.

To complement these in vitro assays, the ability of each dicarba isomer to decrease blood glucose levels in whole plasma in vivo, was also investigated. Here, an intraperitoneal bolus of each dicarba insulin isomer (13(I)$_{A/B}$ and 13(II)$_{A/B}$) was injected into anesthetized 7 week old male C57BL/6 mice (1 I.U. kg$^{-1}$, where n=2). Blood samples were then obtained at t=0, 15, 30, 45 and 60 min by tail bleeding, and subsequently analysed for glucose content. Surprisingly, despite the large differences in vitro binding, phosphorylation and glucose uptake, an almost comparable decrease in blood glucose level was observed for all four dicarba isomers (FIG. 8). This initial study revealed that the dicarba insulin analogues were slightly less effective than commercially available ActRapid® (human insulin) in reducing blood glucose levels, but further studies on a larger subject range (where n is >2) needs to be performed to allow direct and accurate comparison.

The aforementioned study on A6-A11 dicarba insulins has revealed, for the first time, that the intrachain disulfide bridge serves a structural rather than functional role. Furthermore, the observed difference in activity between the cis and trans geometric isomers highlights the insulin receptor's exquisite structural sensitivity to conformational change in this region.

General Experimental Section

Instrumentation

Melting points (m.p.) were determined using a Reichert hot-stage melting point apparatus and are uncorrected.

Infrared spectra (IR) spectra were recorded on a Perkin-Elmer 1600 series Fourier Transform infrared spectrophotometer as potassium bromide discs of solids (KBr) or as thin films of liquid (neat) between sodium chloride plates. IR absorptions ($v_{max}$) are reported in wavenumbers (cm$^{-1}$) with the relative intensities expressed as s (strong), m (medium), w (weak) or prefixed b (broad).

Proton nuclear magnetic resonance ($^1$H NMR) spectra were recorded on Bruker AV200, DPX300 or DRX400 spectrometers operating at 200, 300 or 400 MHz respectively, as solutions in deuterated solvents as specified. Each resonance was assigned according to the following convention: Chemical shift (rotamers); multiplicity; number of protons; observed coupling constants (J=Hz) and proton assignment. Chemical shifts (δ), measured in parts per million (ppm), are reported relative to the internal reference tetramethylsilane (TMS) (δ 0.00) or according to the residual proton peak in the solvent used as specified. Multiplicities are denoted as singlet (s), doublet (d), triplet (t), quartet (q), pentet (p), multiplet (m) or prefixed broad (b), or a combination where necessary.

Carbon-13 nuclear magnetic resonance ($^{13}$C NMR) spectra were recorded on Bruker AV200, DPX300 or DRX400 spectrometers operating at 50, 75 or 100 MHz respectively, as solutions in deuterated solvents as specified. Chemical shifts (δ), measured in parts per million (ppm), are reported relative to the residual proton peak in the solvent used as specified. Assignments were determined from J-Modulated Spin Echo experiments showing quaternary and methylene signals in the opposite phase to those of methine and methyl resonances.

Correlation spectroscopy (COSY) was used to correlate chemical shifts of protons coupled to one another. Heteronuclear Multiple Quantum Correlation (HMQC) spectroscopy was used to correlate directly bonded $^{13}$C-$^1$H nuclei. Heteronuclear Multiple Bond Correlation (HMBC) spectroscopy was used to determine long range $^{13}$C-$^1$H connectivity. All two-dimensional (2D)-NMR experiments were recorded on Bruker DPX300 or DRX400 spectrometers.

Low resolution electrospray ionisation (ESI) mass spectra were recorded on a Micromass Platform Electrospray mass spectrometer (QMS-quadrupole mass electroscopy) as solutions in specified solvents. Spectra were recorded in the positive and/or negative mode (ESI$^+$/ESI$^-$). High resolution electrospray mass spectra (HRMS) were recorded on either a Bruker BioApex 47e Fourier Transform mass spectrometer (4.7 Tesla magnet) fitted with an analytical electrospray source, or an Agilent 6220 accurate mass LC-TOF equipped with an Agilent 1200 series LC system, as solutions in specified solvents. The mass spectrometers were calibrated with an internal standard solution of sodium iodide in MeOH.

Analytical thin layer chromatography (t.l.c.) was performed on plastic plates coated with 0.25 mm of silica gel (Polygram SIL G/UV$_{254}$). Column chromatography was carried out using Merck silica gel 60, 0.063-0.200 mm (70-230 mesh). The compounds were visualized under 254 nm ultraviolet irradiation or via the use of a chemical stain such as ninhydrin, vanillin or iodine, where necessary. Eluent mixtures are expressed as volume to volume ratios.

Reverse phase high performance liquid chromatography (RP-HPLC) was performed on Agilent 1200 instruments. For analytical runs, instruments were equipped with photodiode array (PDA) detection (controlled by ChemStation software) and an automated injector (100 µL loop volume). In preparative runs, instruments used multivariable wavelength (MVW) detection (controlled by ChemStation software) and an Agilent unit injector (2 mL loop volume). The solvent system used throughout this study (except where specified) was buffer A: 0.1% aqueous TFA; buffer B: 0.1% TFA in MeCN. Analytical experiments were carried out on Vydac C4 or C18 (4.6×250 mm, 5 im) analytical columns, at a flow rate of 1.5 mL min−1. Preparative RP-HPLC was carried out on Vydac C4 or C18 (22×250 mm, 10 µm) preparative columns, at a flow rate of 10 mL min−1. Linear gradients of 0.1% TFA in MeCN were employed as specified.

Microwave ring closing metathesis (RCM), cross metathesis (CM) and hydrogenation reactions were carried out on a OEM Discover™ system fitted with the Benchmate™ or Gas Addition™ option. The instrument produces a continuous focussed beam of microwave radiation at a maximum power delivery selected by the user, which reaches and maintains a selected temperature. Reactions were performed in 10 mL high pressure glass microwave vessels fitted with self-sealing Teflon septa as a pressure relief device. The vessels employ magnetic stirrer beads, and the temperature of each reaction was monitored continuously with a non-contact infrared sensor located below the microwave cavity floor or with a glass enclosed fibre optic temperature probe. Reaction times were measured from the time the microwave reached its maximum temperature until the reaction period had lapsed (cooling periods not inclusive).

Solvents and Reagents

Acetone, acetonitrile (MeCN), ammonium bicarbonate (NH4HCO3), concentrated hydrochloric acid (conc. HCl), 1,2-dichloroethane (DCE), dichloromethane (DCM), dimethyl sulfoxide (DMSO), ethanol (EtOH), ethyl acetate (EtOAc), diethyl ether (Et2O), glacial acetic acid (AcOH), hexanes (light petroleum), iso-propanol (i-PrOH), lithium chloride (LiCl), methanol (MeOH), pyridine, tetrahydrofuran (THF), triethylamine (Et3N), toluene, magnesium sulfate (MgSO4), sodium chloride (NaCl), sodium bicarbonate (NaHCO3), sodium carbonate (Na2CO3) and sodium hydroxide (NaOH) were used as supplied by Merck. Anhydrous THF and Et2O were stored over sodium (Na) wire and distilled from Na and benzophenone prior to use. DCM was dried over calcium chloride (CaCl2) and distilled from calcium hydride (CaH) prior to use. Toluene was stored over Na wire and distilled prior to use. Common reagents were used as supplied by Aldrich. Deuterated solvents were used as supplied by Cambridge Isotopes Laboratories.

Solid Phase Peptide Synthesis Procedures

Peptide Materials and Reagents

Automated microwave-accelerated solid-phase peptide synthesis (SPPS) was carried out using a CEM Liberty-Discover™ system. Manual SPPS was performed in polypropylene Terumo syringes (5 or 10 mL) fitted with a polyethylene porous (20 μm) filter. Resin wash and filtering steps were aided by the use of a Visprep™ SPE DL 24-port model vacuum manifold as supplied by Supelco. Coupling reactions and cleavage mixtures were shaken on a KS125 basic KA elliptical shaker supplied by Labortechnik at 400 revolutions per minute (rpm). Cleaved peptides were collected by centrifugation at a speed of 6,000 rpm, on a Hermle Z200A centrifuge supplied by Medos or at a speed of 6,000 rpm, on a TMC-1 mini centrifuge supplied by Thermoline.

4-Amino-2-pentenoic acid (allylglycine, Agl) was used as supplied by Peptech. Trifluoroacetic acid (TFA) and N,N-dimethylformamide (DMF) were supplied by Auspep and the latter was stored over 4 Å molecular sieves. Dichloromethane (DCM) and piperidine were supplied by Merck and stored over 4 Å molecular sieves. N,N'-Diisopropylcarbodiimide (DIC), diisopropylethylamine (DIPEA), 4-dimethylaminopyridine (DMAP), 2,2'-dipyridyl disulfide (2,2'-DPDS), N-methylmorpholine (NMM), N-methyl-2-pyrrolidone (NMP), thioanisole, trifluoromethanesulfonic acid (TfOH) and triisopropylsilane (TIPS) were used as supplied by Aldrich. N-Fluorenylmethoxycarbonylaminosuccinimide (Fmoc-OSu), O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU), N-hydroxybenzotriazol (HOBt) and Wang, Fmoc-Phe-Wang, Fmoc-Arg(Pbf)-Wang, Fmoc-Gly-Wang, rink amide, H-Thr(tBu)-2-chlorotrityl chloride and 2-chlorotrityl chloride resins were used as supplied by GL Biochem. Fmoc-amino acids were also used as supplied by GL Biochem and reactive sidechains were protected with the Acm, Boc, Pbf, tBu, and Trt protection groups. Fmoc-Asn(Trt)-PEG-PS and Fmoc-Thr(tBu)-PEG-PS resin was used as supplied by Applied Biosystems.

Manual Peptide Synthesis

Manual SPPS was carried out using fritted plastic syringes, allowing filtration of solution without the loss of resin. The tap fitted syringes were attached to a vacuum tank and all washings were removed in vacuo. This involved soaking the resin in the required solvent for a reported period of time followed by evacuation to allow the removal of excess reagents before subsequent coupling reactions.

Esterification of Wang Resin

In a fritted syringe, Wang resin was swollen with DCM (4 mL; 3×1 min, 1×60 min) and DMF (4 mL; 3×1 min, 1×30 min). Prior to coupling, the C-terminal amino acid was activated by addition of DIC (3 equiv.) to a solution of the protected amino acid residue, Fmoc-I-Xaa-OH (3 equiv.), in DMF (3 mL). This activated amino acid solution was added to the swollen resin and shaken gently for 1 min. A solution of DMAP (0.3 equiv.) in DMF (1 mL) was then added to the resin, and the reaction mixture was shaken gently for a further 2-18 h. At the end of this reaction period, the mixture was filtered and the resin-tethered amino acid was washed with DMF (4 mL; 3×1 min). To prevent the formation of truncated sequences, any remaining active sites were capped with an acetic anhydride capping solution (4 mL; DMF:acetic anhydride:NMM; 94:5:1) before being filtered and washed with DMF (4 mL; 3×1 min). Additional amino acid coupling were then carried out via either manual or automated microwave-accelerated SPPS.

Coupling to Preloaded Wang Resins

In a fritted syringe, the resin was swollen with DCM (5 mL; 3×1 min, 1×60 min) and DMF (5 mL; 3×1 min, 1×30 min). Prior to the first coupling, the Fmoc-Xaa-resin was subjected to Fmoc-deprotection in the presence of 20% v/v piperidine in DMF (5 mL; 1×1 min, 2×10 min) and further washed with DMF (5 mL; 5×1 min) to ensure traces of excess reagents had been removed.

Amino acid pre-activation was achieved by addition of NMM (6 equiv.) to a solution of the desired protected amino acid, Fmoc-L-Xaa-OH (3 equiv.), and HATU (3 equiv.) in DMF (3 mL). The mixture was sonicated for ~1 min and the resulting solution then added to the resin-tethered amino acid and shaken gently for a reported period of time. At the end of this reaction duration, the peptidyl-resin was washed with DMF (7 mL; 3×1 min) to ensure excess reagents were removed. Kaiser tests were performed to monitor coupling success and any incomplete coupling reactions were repeated with extended reaction times (indicated in parenthesis). Once negative test results for the presence of free amines was achieved, the resin-tethered peptide was deprotected with 20% v/v piperidine in DMF (5 mL; 1×1 min, 2×10 min) and further washed with DMF (5 mL; 5×1 min) to remove traces of base prior to subsequent amino acid couplings. The above procedure was repeated until the desired sequence was constructed and the resin then washed with DMF (5 mL; 3×1 min), DCM (5 mL; 3×1 min), MeOH (5 mL; 3×1 min), DCM (5 mL; 3×1 min) and MeOH (5 mL; 3×1 min), then left to dry in vacuo for 1 h. After sequence completion, a small aliquot of resin-tethered peptide was subjected to TFA-mediated cleavage (General Section) for chromatographic and mass spectral analysis.

Coupling to 2-Chlorotrityl Chloride Resin

In a fritted syringe, 2-chlorotrityl chloride resin was swollen with DCM (4 mL; 3×1 min, 1×60 min). The first amino acid (1 equiv.) was dissolved in DCM, added to the resin and left to shake gently for 5 min. A solution of DIPEA (3 equiv.)

in DCM was added to the reaction mixture dropwise over a period of 5 min and the resultant mixture was shaken gently for 2 h. At the end of this time period, MeOH (2 mL) was added in order to cap any remaining active sites before subsequent amino acid couplings. The resin-suspension was then shaken gently for 30 min, filtered and washed with DCM (4 mL; 3×1 min), DMF (4 mL; 3×1 min), i-PrOH (4 mL; 2×1 min), DMF (4 mL; 2×1 min), i-PrOH (4 mL; 2×1 min), MeOH (4 mL; 2×1 min) and Et2O (4 mL; 2×1 min). After re-swelling the resin with DCM (4 mL; 3×1 min) and DMF (4 mL; 3×1 min), the resin-amino acid was subjected to Fmoc-deprotection with 20% v/v piperidine in DMF (4 mL; 1×1 min, 2×10 min) and further washed with DMF (4 mL; 5×1 min) to ensure traces of excess reagents had been removed.

Subsequent amino acids were coupled using the following procedure: Amino acid activation was achieved by the addition of NMM (6 equiv.) to a solution of the desired protected amino acid, Fmoc-L-Xaa-OH (3 equiv.), and HATU (3 equiv.) in DMF (3 mL) before being sonicated for ~1 min. The resulting solution was added to the resin-tethered amino acid and shaken gently for the reported period of time. At the end of this reaction duration, the peptidyl-resin was washed with DMF (4 mL; 3×1 min) to ensure excess reagents were removed. Kaiser tests were performed to monitor coupling success and any incomplete coupling reactions were conducted a second time with extended reaction times (indicated in parenthesis). Once this test provided negative results for the presence of free amines, the resin-peptide was deprotected with 20% v/v piperidine in DMF (4 mL; 1×1 min, 2×10 min) and again washed with DMF (4 mL; 5×1 min) to remove traces of base prior to coupling the next amino acid. The above procedure was repeated until the desired peptide sequence was constructed. The above procedure was repeated until the desired peptide sequence was constructed, and the resin was then washed with DMF (4 mL; 3×1 min), DCM (4 mL; 3×1 min), MeOH (4 mL; 3×1 min), DCM (4 mL; 3×1 min) and MeOH (4 mL; 3×1 min), then left to dry in vacuo for 1 h. After sequence completion, a small aliquot of resin-tethered peptide was exposed to a mild TFA cleavage solution (General Section) for chromatographic and mass spectral analysis.

Automated Microwave Peptide Synthesis

Automated microwave-accelerated SPPS was carried out using a CEM Liberty-Discover™ synthesiser. This involved the flow of dissolved reagents from external nitrogen pressurised bottles to a resin-containing microwave reactor vessel fitted with a porous filter. Coupling and deprotection reactions were carried out within this vessel and were aided by microwave energy. Each reagent delivery, wash and evacuation step was carried out according to automated protocols of the instrument controlled by PepDriver software.

In a 50 mL centrifuge tube, the resin was swollen with DMF:DCM (10 mL; 1:1; 1×60 min) and connected to the Liberty™ resin manifold. The Fmoc-amino acids (0.2 M in DMF), activators (0.5 M HBTU/HOBt or HATU in DMF), activator base (2 M DIPEA in NMP) and deprotection agent (20% v/v piperidine in DMF) were measured out and solubilised in an appropriate volume of specified solvent as calculated by the PepDriver software program. The default microwave conditions used in the synthesis of each linear peptide included: Initial deprotection (36 W, 37° C., 2 min), deprotection (45 W, 75° C., 10 min), preactivation (0 W, 25° C., 2 min) and coupling (25 W, 75° C., 10 min). Each arginine residue underwent a double coupling involving the filtration and delivery of fresh reagents and a second preactivation (0 W, 25° C., 2 min) and coupling (25 W, 75° C., 10 min) step. Cystine and histidine residues were subjected to modified and lower temperature microwave conditions including: Initial deprotection (50 W, 37° C., 120 min), deprotection (50 W, 75° C., 600 min), preactivation (0 W, 25° C., 120 min) and coupling (25 W, 50° C., 600 min). On synthesis completion, the resin-bound peptides were automatically returned to the Liberty™ resin manifold as a suspension in DMF:DCM (1:1) and filtered through fritted plastic syringes (10 mL) prior to acid-mediated cleavage (General Section).

Kaiser Test

The Kaiser test is performed in order to monitor coupling success by detecting the presence of resin-bound free amines. Two drops each of 5% ninhydrin in EtOH, 80% phenol in EtOH and 2% v/v 0.001M potassium cyanide in pyridine were added to pre-washed (EtOH) resin beads in a tube and the mixture subsequently heated at 120° C. for 3-5 min. Blue colouration of the beads indicate the presence of free amines and provided evidence that an amino acid coupling had not been successful. This test cannot be performed on N-terminal asparagine, aspartic acid, serine and proline residues.

Resin Cleavage Procedures

TFA Cleavage

A small aliquot of resin-bound peptide (approx. 5 mg) was suspended in a cleavage solution (1 mL; TFA:TIPS:water:thioanisol; 95:2:2:1) and shaken gently for 2 h. The mixture was filtered through a fritted syringe and the beads rinsed with TFA (1×0.2 mL). The filtrate was concentrated under a constant stream of air and the resultant oil was induced to precipitate in ice-cold Et2O (1 mL). Cleaved peptides were collected by centrifugation (3×5 min) and dried for analysis by analytical RP-HPLC and mass spectrometry. For full scale resin cleavages, 10 mL of cleavage solution was used and after 4 h, the resin was rinsed with TFA (3×2 mL). The filtrate was concentrated under a constant stream of air and the resultant oil was induced to precipitate in ice-cold Et2O (35 mL). Collection by centrifugation was carried out over 5×6 min spin times.

Mild TFA Cleavage

A small aliquot of the resin-tethered peptide (~5 mg) was suspended in a cleavage solution (1 mL; 0.5% TFA in DCM) and shaken gently for 5 min. The mixture was filtered through a fritted syringe and the beads rinsed with DCM (1×0.2 mL). The filtrate was concentrated under a constant stream of air and the resultant oil was induced to precipitate in ice-cold diethyl ether (1 mL). Cleaved peptides were collected by centrifugation (3×5 min) and dried for analysis by analytical RP-HPLC and mass spectrometry. For full scale resin cleavages, 10 mL of cleavage solution was used and after 5 min, the resin beads were rinsed with DCM (3×10 mL). The filtrate was concentrated under a constant stream of air and the resultant oil was induced to precipitated in ice-cold Et2O (35 mL). Collection by centrifugation proceeded over 5×6 min spin times. In cases where precipitation in Et2O did not occur, the reaction mixture was concentrated under reduced pressure and peptide was then isolated from the oil by lyophilisation.

Acetic Acid Cleavage

A small aliquot of the resin-tethered peptide (~5 mg) was suspended in a cleavage solution (1 mL; 0.5% TFA in DCM) and shaken gently for 5 min. The mixture was filtered through a fritted syringe and the beads rinsed with DCM (1×0.2 mL). The filtrate was concentrated under a constant stream of air and the resultant oil was induced to precipitate in ice-cold Et2O (1 mL). Cleaved peptides were collected by centrifugation (3×5 min) and dried for analysis by analytical RP-HPLC and mass spectrometry. For full scale resin cleavages, 10 mL of cleavage solution was used and after 5 min, the resin beads were rinsed with DCM (3×10 mL). The filtrate was concentrated under a constant stream of air and the resultant oil was induced to precipitated in ice-cold Et2O (35 mL). Collection by centrifugation was carried out over 5×6 min spin times. In cases where precipitation in Et2O did not occur, the reaction mixture was concentrated under reduced pressure and peptide was then isolated from the oil by lyophilisation.

Metathesis Procedures

Catalysts and Materials

Catalysts: Tricyclohexylphosphine[1,3-bis(2,4,6-trimethylphenyl)-4,5-dihydro-imidazol-2-ylidene](benzylidene)ruthenium(II) dichloride (2nd generation Grubbs' catalyst) and (1,3-Bis-(2,4,6-trimethylphenyl)-2-imidazolidinylidene)dichloro(o-isopropoxyphenyl-methylene)ruthe-nium(II) (2nd generation Hoveyda-Grubbs' catalyst) were used as supplied by Aldrich. Tris(tert-butoxy)(2,2-dimethylpropylidyne) tungsten(VI) (Schrock's catalyst) was used as supplied by Strem Chemicals Inc. and stored under nitrogen in a sealed ampoule at −10° C. (protected from light).

Volatile olefins: 2-Methyl-2-butene and cis-2-butene were used as supplied by Aldrich.

Solvents: DCM, DCE, DCB and a 0.4 M solution of LiCl in DMF used in all metal-catalysed metathesis reactions were degassed with high purity argon in addition to the general freeze-pump-thaw procedure (General Section) prior to use.

Reaction vessels: Schlenk tubes or CEM Benchmate™ microwave reactor vessels were employed for ring closing and cross metathesis reactions involving the use of solid or liquid (non-volatile) reactants. Shield aerosol pressure reactors (Fischer-Porter tubes) (100 mL) fitted with pressure gauge heads or CEM Gas Addition™ microwave reactor vessels were used for CM reactions involving gaseous (cis-2-butene and) or volatile (2-methyl-2-butene) reactants. All vessels were equipped with stirrer beads.

Conventional Ring Closing and Cross Metathesis Procedures (Non-Volatile Reactant)

A Schlenk tube was loaded with substrate, deoxygenated solvent, deoxygenated solvent additive and catalyst in an inert (argon or nitrogen) environment. The reaction mixture was stirred at reflux (Δ) for a specified period of time and then cooled to room temperature. In solution-phase experiments, volatile species were removed under reduced pressure and the crude product was purified by column chromatography, where necessary, to give the required product. Metathesis reactions on the solid-phase were filtered through a fritted syringe, washed with DCM (3-7 mL; 3×1 min) and MeOH (3-7 mL; 3×1 min), then dried in vacuo for 1 h. The resin was subjected to acid-mediated cleavage (General Section) and the resultant isolated solid was then analysed by RP-HPLC and mass spectrometry.

Conventional Cross Metathesis Procedure (Volatile Reactant)

A Fischer-Porter tube was loaded with substrate, deoxygenated solvent, deoxygenated solvent additive, catalyst and reacting volatile olefin in an inert (nitrogen or argon) environment. The system was sealed and the reaction mixture then stirred at reflux (Δ) for a specified period of time and then cooled to room temperature. In solution-phase experiments, volatile species were removed under reduced pressure and the crude product was purified by column chromatography, where necessary, to give the required product. Metathesis reactions on the solid-phase were filtered through a fritted syringe, washed with DCM (3-7 mL; 3×1 min) and MeOH (3-7 mL; 3×1 min), then dried in vacuo for 1 h. The resin was subjected to acid-mediated cleavage (General Section) and the resultant isolated solid was then analysed by RP-HPLC and mass spectrometry.

Conventional Cross Metathesis Procedure (Gaseous Reactant)

A Fischer-Porter tube was loaded with substrate, deoxygenated solvent, deoxygenated solvent additive and catalyst under an inert (argon or nitrogen) environment. The system was sealed and the pressure vessel then connected to a vacuum manifold and purged three times using vacuum and argon flushing cycles. After charging the vessel with a gaseous olefinic reactant to the reported pressure, the reaction mixture was stirred at reflux (Δ) for a specified period of time. Once cooled to room temperature, solution-based reaction mixtures were concentrated under reduced pressure and purified by column chromatography, where necessary, to give the required product. Resin-based experiments were filtered through a fritted syringe, washed with DCM (3-7 mL; 3×1 min) and MeOH (3-7 mL; 3×1 min), then dried in vacuo for 1 h. The resin was subjected to acid-mediated cleavage (General Section) and the resultant isolated solid was then analysed by RP-HPLC and mass spectrometry.

Microwave-Accelerated Ring Closing and Cross Metathesis Procedure

A microwave reactor vessel was loaded with substrate, deoxygenated solvent, deoxygenated solvent additive, catalyst and reacting olefin in an inert (nitrogen or argon) environment. The system was sealed and the reaction mixture then irradiated with microwave energy whilst being stirred at specified temperature for a specified period of time. After cooling to room temperature, solution-based reaction mixtures were concentrated under reduced pressure and purified by column chromatography, where necessary, to give the required product. Resin-based experiments were filtered through a fritted syringe, washed with DCM (3-7 mL; 3×1 min) and MeOH (3-7 mL; 3×1 min), then dried in vacuo for 1 h. The resin was subjected to acid-mediated cleavage (General Section) and the resultant isolated solid was then analysed by RP-HPLC and mass spectrometry.

Microwave-Accelerated Cross Metathesis Procedure (Gaseous Reactant)

Microwave-accelerated cross metathesis involving volatile reactants was carried out on a CEM Discover™ system fitted with the Gas Addition™ option as described in the General Section. A microwave reactor vessel was loaded with substrate, deoxygenated solvent, deoxygenated solvent additive and catalyst in an inert (argon or nitrogen) environment. The system was sealed and the pressure vessel then connected to a vacuum manifold and purged three times using vacuum and argon flushing cycles. After charging the vessel with a gaseous olefinic reactant to the reported pressure, the reaction mixture was irradiated with microwave energy whilst being stirred at the specified temperature for a specified period of time. After cooling the reaction mixture to room temperature, the gas was vented from the system. In solution-phase experiments, volatile species were removed under reduced pressure and the crude product was purified by column chromatography, where necessary, to give the required product. Metathesis reactions on the solid-phase were filtered through a fritted syringe, washed with DCM (3-7 mL; 3×1 min) and MeOH (3-7 mL; 3×1 min), then dried in vacuo for 1 h. The resin was subjected to acid-mediated cleavage (General Section) and the resultant isolated solid was then analysed by RP-HPLC and mass spectrometry.

Metathesis experiments are described using the following format: substrate (mg), solvent (mL), additive, catalyst (mg), reacting olefin (in the case of cross metathesis), microwave power (W), reaction temperature (° C.), reaction time (h), percent conversion (%). Chromatographic purification conditions (isolated yield, %) are also listed where applicable.

Hydrogenation Procedures
Catalysts and Materials
Catalysts: Palladium on charcoal (Pd/C) with 10% Pd concentration was used as supplied by Aldrich and stored in a desiccator. Tris(triphenylphosphine)rhodium(I) chloride (Wilkinson's catalyst, Rh(PPh3)3Cl) was used as supplied by Aldrich and stored in an argon or nitrogen filled dry box.
Gases: High purity (<10 ppm oxygen) argon and hydrogen were supplied by BOC gases. Additional purification was achieved by passage of the gases through water, oxygen and hydrocarbon traps.
Solvents: MeOH and DCM used in metal-catalysed hydrogenation reactions were degassed with high purity argon in addition to the general freeze-pump-thaw procedure (General Section) prior to use.
Reaction vessels: Fischer-Porter shielded aerosol pressure reactors (100 mL) fitted with pressure gauge heads and stirrer beads were employed.

Freeze-Pump-Thaw Procedure
Within a sealed vessel, a solvent or liquid reagent was immersed in liquid nitrogen and the contents frozen. The vessel was then evacuated to remove a majority of the gas, and resealed. Once back at ambient temperature, the solvent was refrozen and the vessel evacuated a second time. This procedure was repeated until gas evolution was no longer observed during the thaw cycle.

Conventional Hydrogenation
A Fischer-Porter tube was loaded with substrate, deoxygenated solvent, deoxygenated solvent additive and catalyst under an inert (argon or nitrogen) environment. The system was sealed and the pressure vessel then connected to a vacuum manifold and purged three times using vacuum and argon flushing cycles. After charging the vessel with hydrogen gas to the reported pressure, the reaction mixture was stirred at room temperature for a specified period of time and the reaction then terminated by venting the hydrogen gas. In the case of resin-bound substrates, reaction mixtures were filtered through a fritted syringe, washed with DCM (3-7 mL; 3×1 min), DMF (3-7 mL; 3×1 min) and MeOH (3-7 mL; 3×1 min), then dried in vacuo for 1 h prior to resin cleavage (General Section). For solution-based experiments, the catalyst was removed by filtration through a celite plug and the solvent evaporated under reduced pressure. Peptides were analysed by analytical RP-HPLC and mass spectrometry.

Microwave-Accelerated Hydrogenation
Microwave hydrogenation reactions were carried out on a CEM Discover™ system fitted with the Gas Addition™ option as described in the General Section. A microwave reactor vessel was loaded with substrate, deoxygenated solvent, deoxygenated solvent additive and catalyst in an inert (argon or nitrogen) environment. The system was sealed and the pressure vessel then connected to a vacuum manifold and purged three times using vacuum and argon flushing cycles. After charging the vessel with hydrogen gas to a reported pressure, the reaction mixture was irradiated with microwave energy whilst being stirred at the specified temperature for a specified period of time. Once cooled to room temperature, the hydrogen gas was vented from the system and catalyst deactivation was achieved by exposure to oxygen. In the case of resin-bound substrates, reaction mixtures were filtered through a fritted syringe, washed with DCM (3-7 mL; 3×1 min), DMF (3-7 mL; 3×1 min) and MeOH (3-7 mL; 3×1 min), then dried in vacuo for 1 h prior to resin cleavage (General Section). For solution-based experiments, the catalyst was removed by filtration through a celite plug and the solvent evaporated under reduced pressure. Peptides were analysed by RP-HPLC and mass spectrometry.

Hydrogenation experiments are described by the following format: Substrate (mmol), solvent (mL), additive (mL), catalyst (mol %), hydrogen pressure (psi), microwave power (W), reaction temperature (° C.) and reaction time (h).

1. Preparation of Fmoc-Protected Non-Proteinaceous Chiral Amino Acids 1.1 Fmoc-L-Agl-OH 1

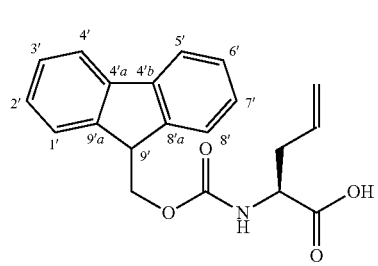

Fmoc-OSu 4 (14.7 g, 43.6 mmol) was added to stirred solution of L-allylglycine 3 (5.00 g, 43.5 mmol) and NaHCO$_3$ (18.3 g, 218 mmol) in water (50 mL) and acetone (50 mL). The resultant white suspension was stirred at room temperature and reaction progress was monitored by TLC (SiO$_2$; light petroleum:EtOAc; 1:1). After 24 h, the reaction mixture was acidified to pH 2 with concentrated HCl and the acetone removed under reduced pressure. The resultant suspension was extracted into DCM (3×50 mL) and the combined organic phase was then washed with 1M HCl (2×30 mL) and water (2×30 mL), dried (MgSO$_4$), filtered and concentrated in vacuo to afford the titled Fmoc-amino acid 1 as an off-white solid (14.1 g, 96%), m.p. 137.5-138.5° C. (lit. 134-136° C.). $v_{max}$ (KBr): 3484s, 3198bs, 3085m, 2967m, 2923m, 1723s, 1644m, 1525s, 1478w, 1449s, 1396m, 1340m, 1233s, 1189s, 1099m, 1048s, 998w, 966w, 943m, 924w, 850m, 781m, 761s, 740m, 648w, 623m, 582m, 560w, 540m, 424w cm$^{-1}$. $^1$H NMR (400 MHz, CDCl$_3$): δ 2.52-2.70 (2.34-2.49) (m, 2H, CHCH$_2$), 4.23 (t, J=6.9 Hz, 1H, H9'), 4.42 (2.30) (d, J=6.9 Hz, 2H, CH$_2$O), 4.52 (m, 1H, CHCH$_2$), 5.13-5.23 (m, 2H, CH=CH$_2$), 5.31 (5.87) (bd, J=7.8 Hz, 1H, NH), 5.75 (m, 1H, CH=CH$_2$), 6.63 (bs, 1H, OH), 7.31 (td, J=7.4, 0.8 Hz, 2H, H2', 7'), 7.38 (t, J=7.4 Hz, 2H, H3', 6'), 7.52-7.63 (m, 2H, 8'), 7.76 (d, J=7.5 Hz, 2H, H4', 5'). $^{13}$C NMR (100 MHz, CDCl$_3$): δ 36.7 (CHCH$_2$), 47.5 (C9'), 53.4 (CHCH$_2$), 68.1 (CH$_2$O), 122.0 (CH=CH$_2$), 120.1 (C2', 7'), 125.4 (C3', 6'), 127.9 (C1', 8'), 128.0 (C4', 5'), 131.1 (CH=CH$_2$), 141.7 (C8'a, 9' a), 144.0 (C4'a, 4' b), 156.3 (OCONH), 176.4 (COOH). Mass Spectrum (ESI$^+$, MeOH): m/z 338.4 [M+H]$^+$, C$_{20}$H$_{20}$NO$_4$ requires 338.1; 360.3 [M+Na]$^+$, C$_{20}$H$_{19}$NNaO$_4$ requires 360.1. Spectral data were consistent with those reported in the literature.

1.2 Fmoc-L-Pre-OH 2

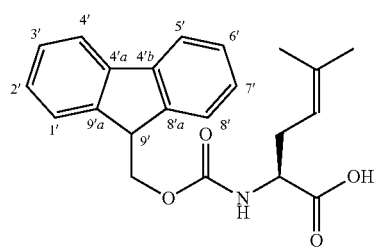

Fmoc-L-Agl-OH 1 was subjected to the general CM procedure described above: Fmoc-L-Agl-OH 1 (0.15 g, 0.44 mmol), DCM (10 mL), $2^{nd}$ generation Grubbs' catalyst (19 mg, 22 µmol), 2-methyl-2-butene (1 mL), Δ, 24 h, 95% conversion into 2. The reaction mixture was evaporated under reduced pressure to give the desired prenylglycine derivative 2 as a dark brown oil and recrystallised from light petroleum-EtOAc to give a colourless solid (0.15 mg, 92%), m.p. 109-111° C. $v_{max}$ (film): 3552m, 3416s, 3098w, 2930w, 1703s, 1655w, 1639w, 1619w, 1544m, 1477w, 1449w, 1380w, 1267w, 1236w, 1085w, 1054w, 935w, 739m, 621w, 475w, 426w cm$^{-1}$. $^1$H NMR (300 MHz, CDCl$_3$): δ 1.62 (s, 3H, CH$_3$), 1.73 (s, 3H, CH$_3$), 2.44-2.70 (m, 2H, CHCH$_2$), 4.23 (t, J=6.9 Hz, 1H, H9'), 4.42 (d, J=7.0 Hz, 2H, CH$_2$O), 5.08 (m, 1H, CH=), 5.25 (bd, J=7.8 Hz, 1H, NH), 7.31 (td, J=7.4, 1.0 Hz, 2H, H2', 7'), 7.40 (t, J=7.4 Hz, 2H, H3', 6'), 7.55-7.62 (m, 2H, H1', 8'), 7.76 (d, J=7.5 Hz, 2H, H4', 5'). $^{13}$C NMR (75 MHz, CDCl$_3$): δ 18.3 (CH$_3$), 26.2 (CH$_3$), 31.0 (CHCH$_2$), 47.5 (C9'), 53.9 (CHCH$_2$), 67.5 (CH$_2$O), 117.5 (CH=), 120.3 (C2', 7'), 125.4 (C3', 6'), 127.4 (C1', 8'), 128.1 (C4', 5'), 137.4 (CH=C), 141.7 (C8'a, 9' a), 144.1 (C4'a, 4' b), 156.3 (OCONH), 176.3 (COON). Mass spectrum (ESI$^+$, MeOH): m/z 366.1 [M+H]$^+$, C$_{22}$H$_{24}$NO$_4$ requires 366.2; 388.1 [M+Na]$^+$, C$_{22}$H$_{23}$NNaO$_4$ requires 388.2. Spectral data were consistent with those reported in the literature.

1.3 Fmoc-L-Bgl-OH 7

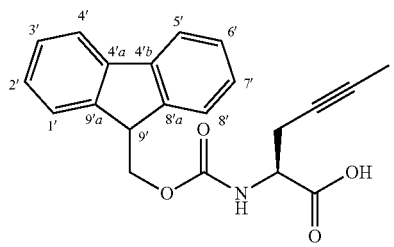

7

Fmoc-OSu 4 (1.75 g, 5.2 µmol) was added to stirred solution of crude (2S)-2-(but-2-ynyl)-glycine 6 and NaHCO$_3$ (0.50 g, 6.0 µmol) in H$_2$O (50 mL) and acetone (50 mL). The resultant pale yellow suspension was stirred at room temperature and reaction progress was monitored by TLC (SiO$_2$; light petroleum:EtOAc; 1:1). After 24 h, the reaction mixture was acidified to pH 2 with concentrated HCl and the was acetone removed under reduced pressure. The resultant suspension was extracted into EtOAc (3×15 mL) and the combined organic phase was then washed with 1M HCl (2×15 mL) and water (2×15 mL), dried (MgSO$_4$), filtered and concentrated in vacuo to give a pale yellow solid. The crude product was purified by column chromatography (SiO$_2$; 2→10% MeOH in DCM) to afford the titled Fmoc-amino acid 7 as a colourless crystalline solid (0.90 g, 62% over 2 steps). $^1$H n.m.r. (200 MHz, CDCl$_3$): δ 1.79 (t, J=2.5, 3H, CH$_3$), 2.72 (m, 2H, CH$_2$C≡), 4.25 (m, 1H, H9'), 4.43 (m, 2H, CH$_2$O), 4.54 (td, J=7.8, 5.7 Hz, 1H, CHCH$_2$CE), 6.57 (bd, J=8.4 Hz, 1H, NH), 7.36 (m, 4H, H2', 3', 6' 7'), 7.61 (m, 2H, 8'), 7.76 (m, 2H, H4', 5'), OH not observed. $^{13}$C n.m.r. (50 MHz, CDCl$_3$): δ3.7 (CH$_3$), 22.9 (CH$_2$C≡), 47.3 (C9'), 52.5 (CHCH$_2$C≡), 67.6 (CH$_2$O), 73.0 (C≡CCH$_3$), 78.6 (≡CCH$_3$), 120.1 (C2', 7'), 124.0 (C3', 6'), 127.2 (C1', 8'), 127.9 (C4', 5'), 141.5 (C8'a, 9' a), 143.5 (C4'a, 4' b), 156.7 (CONH), 172.3 (COOH). HPLC (Agilent: CHIRAL; MeOH:acetic acid:ammonium acetate; 98:2:0.5; 1.0 mL min$^{-1}$): $t_R$=12.0 min, >99% ee.

2. Preparation of Human Dicarba Insulin Analogues 2.1 c[Δ$^4$A6,11]-Dicarba Human Insulin Transformations 2.1.1 [A6,11]-Agl-[A7]-Cys($^t$Bu)-[A20]-Cys(Acm) Insulin A-Chain 8

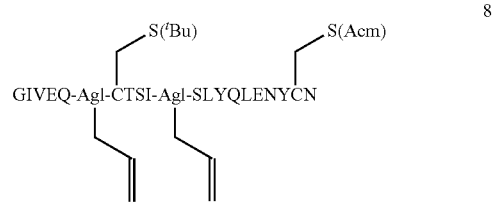

8

The automated, microwave-accelerated procedure outlined in the General Section was used for the synthesis of peptide 8 on Fmoc-Asn(Trt)-PEG-PS resin (526 mg, 100 µmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 8.

| Reagent | Total volume (mL) | Mass (g) or Volume (mL) | Reaction Time (min) |
| --- | --- | --- | --- |
| 0.5M HATU in DMF | 21 | 4.00 g | — |
| 2M DIPEA in NMP | 12 | 4.2 mL | — |
| Fmoc-L-Asn(Trt)-OH | 3.0 | 0.358 g | 12 |
| Fmoc-L-Agl-OH | 6.0 | 0.405 g | 12 |
| Fmoc-L-Cys(Acm)-OH | 3.0 | 0.249 g | 12 |
| Fmoc-L-Cys($^t$Bu)-OH | 3.0 | 0.240 g | 12 |
| Fmoc-L-Gln(Trt)-OH | 6.0 | 0.733 g | 12 |
| Fmoc-L-Glu(O$^t$Bu)-OH | 6.0 | 0.511 g | 12 |
| Fmoc-L-Gly-OH | 3.0 | 0.178 g | 12 |
| Fmoc-L-Ile-OH | 6.0 | 0.424 g | 12 |
| Fmoc-L-Leu-OH | 6.0 | 0.424 g | 12 |
| Fmoc-L-Ser($^t$Bu)-OH | 6.0 | 0.460 g | 12 |
| Fmoc-L-Thr($^t$Bu)-OH | 3.0 | 0.238 g | 12 |
| Fmoc-L-Tyr($^t$Bu)-OH | 6.0 | 0.551 g | 12 |
| Fmoc-L-Val-OH | 3.0 | 0.204 g | 12 |

After sequence completion, the resin-bound peptide was transferred into a fritted syringe and treated with an acetic anhydride solution (7 mL; DMF:acetic anhydride:NMM; 94:5:1) for 2 h. The resin was then washed with DMF (7 mL; 3×1 min), DCM (7 mL; 3×1 min) and MeOH (7 mL; 3×1 min), then left to dry in vacuo for 1 h. Prior to treatment with MeOH, a small aliquot of the resin-bound peptide was removed and subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The dried aliquot of Fmoc-deprotected resin-tethered peptide was subjected to TFA-mediated cleavage (General Section) for RP-HPLC and mass spectral analysis. This supported formation of the desired peptide 8 in 90% purity. Mass spectrum (ESI$^+$, MeCN:H$_2$O: HCOOH): m/z 833.5 [M+3H]$^{3+}$, ⅓(C$_{110}$H$_{175}$N$_{26}$O$_{36}$S$_2$) requires 833.4; 1249.5 [M+2H]$^{2+}$, ½(C$_{110}$H$_{174}$N$_{26}$O$_{36}$S$_2$) requires 1249.6. RP-HPLC (Agilent: Vydac C18 analytical column, 0→30% buffer B over 5 min then 30→60% buffer B over 30 min): $t_R$=18.6 min.

2.1.2 c[Δ⁴A6,11]-Dicarba-[A7]-Cys(ᵗBu)-[A20]-Cys(Acm) Insulin A-Chain 9

SEQ ID NO: 2

9(I) and 9(II)

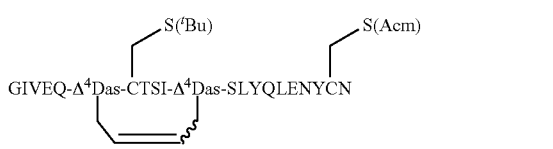

GIVEQ-Δ⁴Das-CTSI-Δ⁴Das-SLYQLENYCN

Resin-bound Fmoc-protected peptide 8 was subjected to the general microwave-accelerated RCM procedure outlined in the General Section under the following conditions: Resin-tethered 8 (768 mg, 100 µmol), DCM (6 mL), 2$^{nd}$ generation Grubbs' catalyst (17 mg, 20 µmol), 0.4 M LiCl in DMF (0.2 mL), 100° C., 2 h, 40% conversion into 9. Post metathesis, a small aliquot of resin-bound peptide was subjected to Fmoc-deprotection in the presence of 20% v/v piperidine in DMF (7 mL; 1×1 min, 2×10 min), then washed with DMF (7 mL; 5×1 min), DCM (7 mL; 3×1 min) and MeOH (7 mL; 3×1 min). The dried aliquot of Fmoc-deprotected resin-tethered peptide was subjected to TFA-mediated cleavage (General Section) for RP-HPLC and mass spectral analysis. This supported formation of the desired peptide as two isomers (9(I) and 9(II)) in a 3:2 ratio. 9(I): Mass spectrum (ESI⁺, MeCN:H₂O:HCOOH): m/z 1235.9 [M+2H]$^{2+}$, ½($C_{108}H_{170}N_{26}O_{36}S_2$) requires 1235.6; 824.2 [M+3H]$^{3+}$, ⅓($C_{108}H_{171}N_{26}O_{36}S_2$) requires 824.1. RP-HPLC (Agilent: Vydac C18 analytical column, 0→30% buffer B over 5 min then 30→60% buffer B over 30 min): $t_R$=9.2 min. 9(II): Mass spectrum (ESI⁺, MeCN:H₂O:HCOOH): m/z 1235.7 [M+2H]$^{2+}$, ½($C_{108}H_{170}H_{26}O_{36}S_2$) requires 1235.6, 824.5 [M+3H]$^{3+}$, ⅓($C_{108}H_{171}N_{26}O_{36}S_2$) requires 824.1. RP-HPLC (Agilent: Vydac C18 analytical column, 0→30% buffer B over 5 min then 30→60% buffer B over 30 min): $t_R$=9.6 min. The remaining resin-bound peptide 74 (1.12 g) was treated with a solution of DMSO:DMF (7 mL; 1:1) for 72 h and subjected to Fmoc-deprotected in the presence of 20% v/v piperidine in DMF (1×1 min, 2×20 min). After filtration, the resin was washed with DMF (5×1 min), DCM (3×1 min) and MeOH (3×1 min), then dried in vacuo for 1 h. Following TFA-mediated cleavage of the resin-bound peptide 9 (0.77 g), the grey solid was suspended in MeCN:H₂O (1:1) and lyophilised to give two isomers (9(I) and 9(II)) of the desired peptide 9, as a pale brown solid (125 mg) in 35% purity. Spectral data were in accordance with those reported previously.

2.1.4 c[Δ⁴6,11]-Dicarba-[7]-Cys(Pyr)[20]-Cys(Acm) Insulin A-Chain 10

SEQ ID NO: 2

10(I) and 10(II)

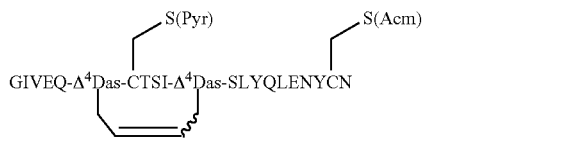

GIVEQ-Δ⁴Das-CTSI-Δ⁴Das-SLYQLENYCN

A solution of ice-cold TFA:TfOH (1 mL; 4:1) was added to a stirred solution of the cyclic peptide 9 (5.0 mg, 2.0 µmol) and 2,2'-DPDS (4.4 mg, 20 µmol) in TFA:anisol (1 mL; 9:1) at 0° C. After 1.5 h, the reaction mixture was reduced under a constant stream of air and ice-cold Et₂O (14 mL) was added to induce peptide precipitation. The resultant solid was then collected by centrifugation (3×6 min) and analysed by RP-HPLC and mass spectrometry. This supported formation of the S-activated peptide 10 as two isomers, 10(I) and 10(II), in a 3:2 ratio.

In several batches, the remaining cyclic peptide 9 (240 mg, 97 µmol) in TFA:anisol (8 mL; 9:1) was subjected to identical reaction conditions with 2,2'-DPDS (214 mg, 0.97 mmol) and ice-cold TFA:TfOH (8 mL; 4:1). The batches were combined, lyophilised and purified by RP-HPLC (Agilent: Vydac C18 preparative column, 15→45% buffer B over 30 min, $t_R$=19.7 and 20.5 min). Selected fractions were combined and lyophilised to give two isomers, 10(I) and 10(II), of the desired peptide as colourless solids (isomer I: 9.0 mg, 4% and isomer II: 6.7 mg, 3%) in >99%. 10(I): Mass spectrum (ESI⁺, MeCN:H₂O:HCOOH): m/z 1261.9 [M+2H]$^{2+}$, ½($C_{109}H_{165}N_{27}O_{36}S_3$) requires 1262.1. RP-HPLC (Agilent: Vydac C18 analytical column, 15→45% buffer B over 30 min): $t_R$=16.6 min. 10(II): Mass spectrum (ESI⁺, MeCN:H₂O:HCOOH): m/z 1262.1 [M+2H]$^{2+}$, ½($C_{109}H_{165}N_{27}O_{36}S_3$) requires 1262.1. RP-HPLC (Agilent: Vydac C18 analytical column, 15→45% buffer B over 30 min): $t_R$=18.1 min.

2.1.5 [19]-Cys(Acm) Insulin B-Chain 11

SEQ ID NO: 3

11

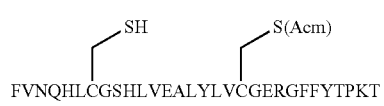

FVNQHLCGSHLVEALYLVCGERGFFYTPKT

The automated, microwave-accelerated procedure outlined in the General Section was used for the synthesis of peptide 11 on Fmoc-Thr('Bu)-PEG-PS resin (667 mg, 100 µmol). Quantities of HBTU, HOBt, DIPEA, piperidine and each Fmoc-amino acid were used as described by the automated protocols of the instrument and remained constant throughout this synthesis. The total amount of each coupling reagent and successive amino acid required, along with their reaction duration is summarised in the Table below:—

TABLE

Quantities of reagents and amino acids used in the synthesis of peptide 11.

| Reagent | Total volume (mL) | Mass (g) or Volume (mL) | Reaction Time (min) |
|---|---|---|---|
| 0.5M HBTU:HOBt in DMF | 31 | 5.879 g:2.094 g | — |
| 2M DIPEA in NMP | 16 | 5.6 mL | — |
| Fmoc-L-Ala-OH | 3 | 0.187 g | 12 |
| Fmoc-L-Arg(Pbf)-OH | 3 | 0.389 g | 12 |
| Fmoc-L-Asn(Trt)-OH | 3 | 0.358 g | 12 |
| Fmoc-L-Cys(Acm)-OH | 3 | 0.249 g | 12 |
| Fmoc-L-Cys(Trt)-OH | 3 | 0.351 g | 12 |
| Fmoc-L-Gln(Trt)-OH | 3 | 0.366 g | 12 |
| Fmoc-L-Glu(OᵗBu)-OH | 6 | 0.511 g | 12 |
| Fmoc-L-Gly-OH | 8 | 0.476 g | 12 |
| Fmoc-L-His(Boc)-OH | 6 | 0.744 g | 12 |
| Fmoc-L-Leu-OH | 11 | 0.778 g | 12 |
| Fmoc-L-Lys(Boc)-OH | 3 | 0.281 g | 12 |
| Fmoc-L-Phe-OH | 8 | 0.620 g | 12 |
| Fmoc-L-Pro-OH | 3 | 0.202 g | 12 |
| Fmoc-L-Ser(ᵗBu)-OH | 3 | 0.230 g | 12 |

TABLE-continued

Quantities of reagents and amino acids used in the synthesis of peptide 11.

| Reagent | Total volume (mL) | Mass (g) or Volume (mL) | Reaction Time (min) |
|---|---|---|---|
| Fmoc-L-Thr($^t$Bu)-OH | 3 | 0.238 g | 12 |
| Fmoc-L-Tyr($^t$Bu)-OH | 6 | 0.551 g | 12 |
| Fmoc-L-Val-OH | 8 | 0.543 g | 12 |

After sequence completion, the resin was transferred into a fritted syringe, washed with DMF (7 mL; 3×1 min), DCM (7 mL; 3×1 min) and MeOH (7 mL; 3×1 min), then left to dry in vacuo for 1 h. A small aliquot of resin-bound peptide was subjected to the cleavage procedure for RP-HPLC and mass spectral analysis. This supported formation of the desired peptide 11. Following global Fmoc-deprotection and TFA-mediated cleavage of the remaining peptide 11 from the resin (1.11 g), the resultant pale yellow solid was purified by RP-HPLC (Agilent: Vydac C18 preparative column, 25→45% buffer B over 30 min, $t_R$=16.0 min). Selected fractions were combined and lyophilised to give the desired peptide 11 as a colourless solid (106 mg, 30%) in 90% purity. Mass spectrum (ESI$^+$, MeCN:H$_2$O): m/z 700.9 [M+5H]$^{5+}$, $\frac{1}{5}$(C$_{161}$H$_{242}$N$_{41}$O$_{43}$S$_2$) requires 700.8; 876.0 [M+4H]$^{4+}$, C$_{161}$H$_{243}$N$_{41}$O$_{43}$S$_2$ requires 875.7; 1167.7 [M+3H]$^{3+}$, $\frac{1}{3}$(C$_{161}$H$_{242}$N$_{41}$O$_{43}$S$_2$) requires 1167.2; 1750.6 [M+2H]$^{2+}$, $\frac{1}{2}$(C$_{161}$H$_{241}$N$_{41}$O$_{43}$S$_2$) requires 1750.4. RP-HPLC (Agilent: Vydac C18 analytical column, 25→45% buffer B over 30 min): $t_R$=15.0 min.

2.1.6 Formation of the Monocyclic Dicarba A-B Heterodimer of Human Insulin 12

SEQ ID NO: 4

12(I) and 12(II)

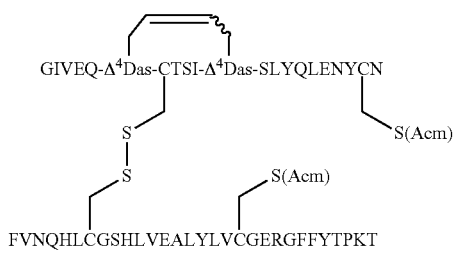

Isomer I:

The modified insulin A-chain 10(I) (1.10 mg, 0.44 µmol) in 50 mM NH$_4$HCO$_3$ (600 µL) was added dropwise to a stirred solution of the modified insulin B-chain 11 (1.53 mg, 0.44 µmol) in H$_2$O:MeCN (1.00 mL; 9:1). Reaction progress was monitored by RP-HPLC and mass spectrometry and after 8 h, the oxidation was terminated by addition of AcOH. 12(I): Mass spectrum (ESI$^+$, MeCN:H$_2$O:HCOOH): m/z 1183.4 [M+5H]$^{5+}$, $\frac{1}{5}$(C$_{265}$H$_{402}$N$_{67}$O$_{79}$S$_4$) requires 1183.0; 1479.0 [M+4H]$^{4+}$, $\frac{1}{4}$(C$_{265}$H$_{401}$N$_{67}$O$_{79}$S$_4$) requires 1478.5. RP-HPLC (Agilent: Vydac C18 analytical column, 0→4 25% buffer B over 5 min then 25→50% buffer B over 30 min): $t_R$=21.2 min.

The remaining modified A-chain 10(I) (7.91 mg, 3.13 µmol) in 50 mM NH$_4$HCO$_3$ (4 mL) was subjected to identical reaction conditions in the presence of the modified insulin B-chain 11 (11.0 mg, 3.13 µmol) in H$_2$O:MeCN (6 mL; 9:1), and the two batches were combined and lyophilised to give a pale yellow solid (21.5 mg). Spectral data were in accordance with those reported previously.

Isomer II:

The modified insulin A-chain 10(II) (1.05 mg, 0.42 µmol) in 50 mM NH$_4$HCO$_3$ (500 µL) was added dropwise to a stirred solution of the modified insulin B-chain 11 (1.46 mg, 0.42 µmol) in H$_2$O:MeCN (1.50 mL; 9:1). Reaction progress was monitored by RP-HPLC and mass spectrometry and after 8 h, the oxidation was terminated by addition of AcOH. 12(II): Mass spectrum (ESI$^+$, MeCN:H$_2$O:HCOOH): m/z 1183.5 [M+5H]$^{5+}$, $\frac{1}{5}$(C$_{265}$H$_{402}$N$_{67}$O$_{79}$S$_4$) requires 1183.0; 1479.2 [M+4H]$^{4+}$, $\frac{1}{4}$(C$_{265}$H$_{401}$N$_{67}$O$_{79}$S$_4$) requires 1478.5; 1971.8 [M+3H]$^{3+}$, $\frac{1}{3}$(C$_{265}$H$_{400}$N$_{67}$O$_{79}$S$_4$) requires 1970.9. RP-HPLC (Vydac C18 analytical column, 0→25% buffer B over 5 min then 25→50% buffer B over 30 min): $t_R$=20.8 min.

The remaining modified A-chain 10(II) (5.62 mg, 2.27 µmol) in 50 mM NH$_4$HCO$_3$ (3 mL) was subjected to identical reaction conditions in the presence of the modified insulin B-chain 11 (7.96 mg, 2.27 µmol) in H$_2$O:MeCN (4 mL; 9:1), and the two batches were combined and lyophilised to give a pale yellow solid (16.1 mg). Spectral data were in accordance with those reported previously.

2.1.7 c[Δ$^4$6,11]-Dicarba Insulin 13

SEQ ID NO: 5

13(I)$_{A/B}$ and 13(II)$_{A/B}$

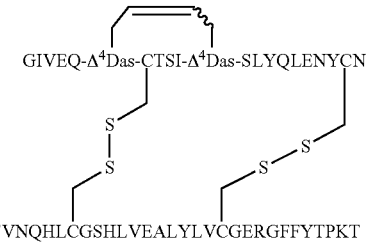

Isomer IA and IB:

A 20 mM solution of iodine in glacial acetic acid (1.3 mL) was added to a stirred solution of the monocyclic peptide 12(I) (2.63 mg, 0.45 µmol) in glacial acetic acid (3.2 mL) and 60 mM HCl (244 µL). Reaction progress was monitored by RP-HPLC and after 2.75 h, ice-cold Et$_2$O (35 mL) was added to induce peptide precipitation. The resultant yellow solid was collected by centrifugation (1×10 min) and 20 mM ascorbic acid (1 mL) was then added to quench any excess iodine before analysis via RP-HPLC and mass spectrometry.

The remaining A-B conjugate 12(I) (18.9 mg, 3.2 µmol) in glacial acetic acid (9.4 mL) and 60 mM HCl (1.8 mL) was subjected to identical reaction conditions in the presence of a 20 mM solution of iodine in glacial acetic acid (23 mL), and the combined batches were then purified by RP-HPLC$^†$ (Agilent: Vydac C4 preparative column, 0→30% buffer B over 5 min then 30→40% buffer B over 30 min: $t_R$=20.9 and 21.7 min). Selected fractions were combined and lyophilised to give two isomers, 13(I)$_A$ and 13(I)$_B$, of the desired c[Δ$^4$A6, 11]-dicarba human insulin analogue as colourless oils in 95% purity. Repurification of isomer 13(I)$_A$ (Agilent: Vydac C4 analytical column, 0→30% buffer B over 5 min then 30→40% buffer B over 30 min: $t_R$=16.2 min) gave insulin analogue 13(I)$_A$ as a colourless solid (0.70 mg, 3%) in >99% purity. 13(I)$_A$: Mass spectrum (ESI$^+$, MeCN:H$_2$O:HCOOH): m/z 961.9 [M+6H]$^{6+}$, ⅙(C$_{259}$H$_{391}$N$_{65}$O$_{77}$S$_4$) requires 962.0; 1154.5 [M+5H]$^{5+}$, ⅕(C$_{259}$H$_{390}$N$_{65}$O$_{77}$S$_4$) requires 1154.1; 1442.7 [M+4H]$^{4+}$, ¼(C$_{259}$H$_{389}$N$_{65}$O$_{77}$S$_4$) requires 1442.4. RP-HPLC (Agilent: Vydac C4 analytical column, 0→30% buffer B over 5 min then 30→40% buffer B over 30 min): $t_R$=15.8 min. Repurification of isomer 13(I)$_B$ (Agilent: Vydac C4 analytical column, 0→30% buffer B over 5 min then 30→40% buffer B over 30 min: $t_R$=17.2 min) gave insulin analogue 13(I)$_B$ as a colourless solid (0.46 mg, 2%) in >99% purity. 13(I)$_B$: Mass spectrum (ESI$^+$, MeCN:H$_2$O:HCOOH): m/z 1154.5 [M+5H]$^{5+}$, ⅕(C$_{259}$H$_{390}$N$_{65}$O$_{77}$S$_4$) requires 1154.1; 1443.0 [M+4H]$^{4+}$, ¼(C$_{259}$H$_{389}$N$_{65}$O$_{77}$S$_4$) requires 1442.4; 1923.9 [M+3H]$^{3+}$, ⅓(C$_{259}$H$_{388}$N$_{65}$O$_{77}$S$_4$) requires 1922.9. RP-HPLC (Agilent: Vydac C4 analytical column, 0→30% buffer B over 5 min then 30→40% buffer B over 30 min): $t_R$=16.1 min.

†Buffer A: 20 mM Aqueous triethylammonium acetate Buffer B: Buffer A:MeCN (1:9)

Isomer IIA and IIB:

A 20 mM solution of iodine in glacial acetic acid (1.3 mL) was added to a stirred solution of the monocyclic peptide 12(II) (2.51 mg, 0.43 μmol) in glacial acetic acid (3.1 mL) and 60 mM HCl (226 μL). Reaction progress was monitored by RP-HPLC and after 2.75 h, ice-cold Et2O (35 mL) was added to induce peptide precipitation. The resultant solid was collected by centrifugation (1×10 min) and 20 mM ascorbic acid (1 mL) was then added to quench any excess iodine before analysis via RP-HPLC and mass spectrometry.

The remaining A-B conjugate 12(II) (13.4 mg, 2.27 μmol) in glacial acetic acid (16 mL) and 60 mM HCl (1.3 mL) was subjected to identical reaction conditions in the presence of a 20 mM solution of iodine in glacial acetic acid (6.7 mL), and the combined batches were then purified by RP-HPLC† (Agilent: Vydac C18 preparative column, 0→30% buffer B over 5 min then 30→40% buffer B over 30 min: $t_R$=17.3 and 18.3 min). Selected fractions were combined and lyophilised to give two isomers (13(II)A and 13(II)B) of the desired c[Δ4A6,11]-dicarba human insulin analogue as colourless oils in 74% and 77% purity respectively. Repurification of isomer 13(II)A (Agilent: Vydac C4 analytical column, 0→30% buffer B over 5 min then 30→40% buffer B over 30 min: $t_R$=13.9 min) gave insulin analogue 13(II)A as a colourless solid (0.44 mg, 3%) in 92% purity. 13(II)A: Mass spectrum (ESI+, MeCN:H2O:HCOOH): m/z 1154.5 [M+5H]5+, ⅕(C259H390N65O77S4) requires 1154.1; 1443.1 [M+4H]4+, ¼(C259H389N65O77S4) requires 1442.4. RP-HPLC (Agilent: Vydac C4 analytical column, 0→30% buffer B over 5 min then 30→40% buffer B over 30 min): $t_R$=15.5 min. Repurification of isomer 13(II)B (Agilent: Vydac C4 analytical column, 0→30% buffer B over 5 min then 30→40% buffer B over 30 min: tR=15.4 min) gave insulin analogue 13(II)B as a colourless solid (0.52 mg, 3%) in 92% purity. 13(II)B: Mass spectrum (ESI+, MeCN:H2O:HCOOH): m/z 1154.8 [M+5H]5+, ⅕(C259H390N65O77S4) requires 1154.1; 1443.0 [M+4H]4+, ¼(C259H389N65O77S4) requires 1442.4. RP-HPLC (Agilent: Vydac C4 analytical column, 0→30% buffer B over 5 min then 30→40% buffer B over 30 min: tR=15.8 min.

3. Use of Pseudoproline Residues in Human Dicarba Insulin Analogues 3.1 Preparation of Pseudoproline Dipeptide Residues 3.1.1 Fmoc-L-Cys($^t$Bu)-F

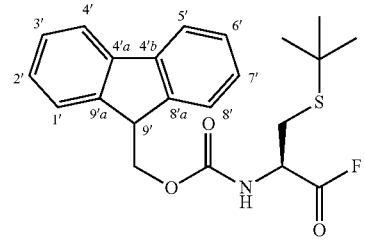

Cyanuric fluoride (0.13 g, 1.5 mmol) and pyridine (0.06 g, 0.75 mmol) were added to a stirred solution of Fmoc-L-Cys($^t$Bu)-OH (0.30 g, 0.75 mmol) in dry DCM (10 mL). The colourless solution was stirred at room temperature for 16 h, resulting in the formation of a white precipitate. The reaction mixture was diluted with water (10 mL) and the phases were separated. The organic phase was dried (MgSO$_4$), filtered and concentrated under reduced pressure to afford the titled compound as a colourless solid (0.30 g, 99%), m.p. 55-58° C. ν$_{max}$ (KBr): 3417s, 3067m, 2964m, 2901w, 2866w, 185s, 1699s, 1514s, 1450m, 1367m, 1338m, 1263m, 1160m, 1105m, 1081w, 1047m, 760m, 740m, 704w, 536m cm$^{-1}$. $^1$H NMR (400 MHz, CDCl$_3$): δ 1.35 (s, 9H, C(CH$_3$)$_3$), 3.05 (d, J=4.9 Hz, 2H, CH$_2$S), 4.25 (t, J=6.9 Hz, 1H, H9'), 4.39-4.51 (m, 2H, CH$_2$O), 4.84 (m, 1H, CHCH$_2$), 5.69 (d, J=7.8 Hz, 1H, NH), 7.33 (td, J=7.4, 1.0 Hz, 2H, H2', 7'), 7.42 (t, J=7.4 Hz, 2H, H3', 6'), 7.60 (bd, J=6.9 Hz, 2H, H1', 8'), 7.77 (d, J=7.6 Hz, 2H, H4', 5'). $^{13}$C NMR (100 MHz, CDCl$_3$): δ 29.5 (C(CH$_3$)$_3$), 30.8 (C(CH$_3$)$_3$), 43.3 (CH$_2$S), 47.1 (C9'), 53.0 (d, $^2$J$_{CF}$=61 Hz, CHCH$_2$), 67.7 (CH$_2$O), 120.1 (C2', 7'), 125.1 (C3', 6'), 127.2 (C1', 8'), 127.8 (C4', 5'), 141.4 (C8'a, 9' a), 143.8 (C4'a, 4' b), 155.7 (OCONH), 161.0 (d, $^1$J$_{CF}$=370 Hz, COF). Mass spectrum (ESI$^+$, MeOH): The final acid fluoride readily converted into its corresponding methyl ester during analysis: m/z 414.1 [M+H]$^+$, C$_{23}$H$_{28}$NO$_4$S requires 414.2; 436.1 [M+Na]$^+$, C$_{23}$H$_{27}$NNaO$_4$S requires 436.2.

3.1.5 Fmoc-L-Cys($^t$Bu)-L-Thr-OH

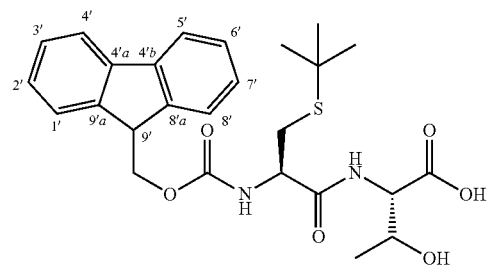 [SMILES: CC(O)[C@H](NC(=O)[C@H](CSC(C)(C)C)NC(=O)OCC1c2ccccc2-c2ccccc21)C(=O)O]

A solution of L-threonine (0.27 g, 2.2 mmol) in 10% w/v aq. Na$_2$CO$_3$ (3 mL) was added to a stirred solution of Fmoc-L-Cys($^t$Bu)-F (0.30 g, 0.75 mmol) in acetone (20 mL). The resultant white suspension was stirred at room temperature and monitored by TLC (SiO$_2$; light petroleum:EtOAc:MeOH:AcOH; 1:1:0.1:0.05). After 18 h the acetone was evaporated in vacuo and water (10 mL) was added. The resultant aqueous phase was diluted with EtOAc (15 mL), cooled in an ice bath and acidified to pH 2 with 1M HCl. The phases were separated and the aqueous layer further extracted with EtOAc (2×15 mL). The combined organic extract was washed with brine (1×30 mL), dried (MgSO$_4$), filtered and concentrated under reduced pressure to afford a pale yellow solid (0.39 g). Purification via column chromatography (SiO$_2$; light petroleum:EtOAc:MeOH:AcOH; 1:1:0.1:0.05) gave the titled compound as a colourless solid (0.37 g, 99%), m.p. 100-104° C. $v_{max}$ (KBr): 3428bs, 3058m, 2964m, 1722s, 1511m, 1461w, 1451m, 1367m, 1249m, 1161w, 1049m, 908s, 738s, 650s cm$^{-1}$. $^1$H NMR (400 MHz, CDCl$_3$): δ 1.32 (s, 9H, C(CH$_3$)$_3$), 1.28 (d, J=5.7 Hz, 3H, CHCH$_3$), 3.06 (d, J=4.6 Hz, 2H, CH$_2$S), 4.23 (t, J=6.9 Hz, 1H, H9'), 4.36-4.61 (m, 3H, CH$_2$O, CHCH$_2$), 4.68 (m, 1H, CHCHCH$_3$), 5.73 (d, J=7.8 Hz, 1H, NH), 7.30 (t, J=7.4 Hz, 2H, H2', 7'), 7.39 (t, J=7.5 Hz, 2H, H3', 6'), 7.56-7.64 (m, 2H, H1', 8'), 7.77 (d, J=7.5 Hz, 2H, H4', 5'). $^{13}$C NMR (100 MHz, CDCl$_3$): δ 21.1 (CHCH$_3$), 30.2 (C(CH$_3$)$_3$), 30.9 (C(CH$_3$)$_3$), 42.9 (CH$_2$S), 47.2 (C9'), 53.6 (CHCH$_2$), 57.6 (CHCHCH$_3$), 60.6 (CHCH$_3$), 67.5 (CH$_2$O), 120.1 (C2', 7'), 125.3 (C3', 6'), 127.2 (C1', 8'), 127.8 (C4', 5'), 141.4 (C8'a, 9' a), 143.8 (C4'a, 4' b), 156.1 (OCONH), 171.6 (CONH), 174.4 (COOH). Mass spectrum (ESI$^+$, MeOH): m/z 501.2061 [M+H]$^+$, C$_{26}$H$_{33}$N$_2$O$_6$S requires 501.2059.

3.1.6 Fmoc-L-Cys($^t$Bu)-L-Thr(ψ$^{Me,Me}$Pro)-OH

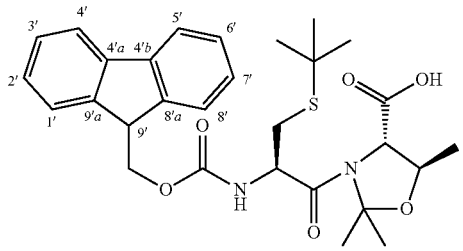 [SMILES: C[C@H]1OC(C)(C)N(C(=O)[C@H](CSC(C)(C)C)NC(=O)OCC2c3ccccc3-c3ccccc32)[C@@H]1C(=O)O]

(+)-10-Camphor sulfonic acid (111 mg, 479 μmol) was added to a stirred solution of Fmoc-L-Cys($^t$Bu)-Thr-OH (2.40 g, 4.79 mmol) and 2-methoxypropene (6.91 g, 95.9 mmol) in dry DCM (10 mL) at 0° C. The resultant dark red solution was stirred at room temperature in the presence of 4 Å molecular sieves and reaction progress was monitored by TLC(SiO$_2$; light petroleum:EtOAc:MeOH:AcOH; 1:1:0.1:0.05). After 19 h, the molecular sieves were filtered from the reaction mixture and rinsed with DCM (3×10 mL). The combined organic exact was evaporated in vacuo to yield a dark green oil (3.2 g). Purification via column chromatography (SiO$_2$; light petroleum:EtOAc:MeOH:AcOH; 1:1:0.1:0.05) yielded the titled compound as a pale yellow-orange solid (0.77 g, 30%), m.p. 80-84° C. The dipeptide existed as a 7:3 ratio of cis and trans isomers. $v_{max}$ (KBr): 3407bs, 3054m, 2974m, 2901w, 1718s, 1675s, 1518s, 1478w, 1450m, 1417m, 1366m, 1319w, 1265m, 1156w, 1105w, 1083w, 1048m, 939m, 895w, 876w, 759m, 737s, 703m, 621w cm$^{-1}$. $^1$H NMR (400 MHz, CDCl$_3$): δ 1.29 (d, J=5.8 Hz, 9H, C(CH$_3$)$_3$), 1.46 (d, J=6.0 Hz, 3H, CHCH$_3$), 1.58 (s, 3H, CCH$_3$), 1.70 (s, 3H, CCH$_3$), 2.72-2.83 (m, 2H, 2H, CH$_2$S), 4.10 (t, J=7.3 Hz, 1H, H9'), 4.25 (bd, J=7.3 Hz, 2H, CH$_2$O), 4.29-4.41 (m, 2H, CHCH$_3$, CHCH$_2$S), 4.45 (bd, J=6.4 Hz, 1H, CHCHCH$_3$), 5.98 (d, J=8.7 Hz, 1H, NH), 6.65 (bs, 1H, OH), 7.19-7.30 (m, 2H, H2', 7'), 7.30-7.39 (m, 2H, H3', 6'), 7.51 (dd, J=13.1, 7.5 Hz, 2H, H1', 8'), 7.70 (d, J=7.5 Hz, 2H, H4', 5'). $^{13}$C NMR (100 MHz, CDCl$_3$): δ 19.9 (CHCH$_3$), 24.0 (CCH$_3$), 26.3 (CCH$_3$), 30.9 (SCCH$_3$), 32.4 (CH$_2$S), 43.1 (CCH$_3$), 47.0 (C9'), 53.7 (CHCH$_2$S), 66.6 (CHCHCH$_3$), 67.6 (CH$_2$O), 75.2 (CHCH$_3$), 120.0 (C2', 7'), 125.3 (C3', 6'), 127.2 (C1', 8'), 127.8 (C4', 5'), 141.4 (C8'a, 9' a), 143.6 (C4'a, 4' b), 156.1 (OCONH), 169.0 (CONH), 176.3 (COOH). Mass spectrum (ESI$^+$, MeOH): m/z 563.2190 [M+Na]$^+$, C$_{29}$H$_{36}$N$_2$NaO$_6$S requires 563.2192.

3.1.7 Fmoc-L-Agl-Cl

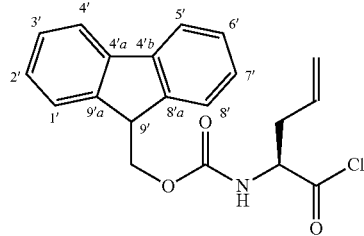 [SMILES: C=CC[C@H](NC(=O)OCC1c2ccccc2-c2ccccc21)C(=O)Cl]

Thionyl chloride (4.87 g, 40.9 mmol) was added to suspension of Fmoc-L-Agl-OH 1 (1.00 g, 2.97 mmol) in dry DCM (20 mL) and the mixture was sonicated at room temperature under a nitrogen atmosphere for 90 min. The resultant yellow-orange solution was concentrated under reduced pressure to afford the titled Fmoc-amino acid chloride as a pale yellow solid (1.06 g, 100%), m.p. 106-107° C. $v_{max}$ (KBr): 3310s, 3066w, 2960w, 1798s, 1700s, 1541s, 1449w, 1316m, 1269s, 1138w, 1104w, 1083w, 1056w, 1030w, 991w, 961w, 919w, 780m, 759m, 739s, 671w, 556w, 478w, 426w cm$^{-1}$. $^1$H NMR (400 MHz, CDCl$_3$): δ 2.69 (t, J=6.1 Hz, 2H, CHCH$_2$), 4.23 (t, J=6.6 Hz, 1H, H9'), 4.44-4.54 (m, 2H, CH$_2$O), 4.68 (m, 1H, CHCH$_2$), 5.24 (m, 2H, =CH$_2$), 5.27 (bs, 1H, NH), 5.71 (m, 1H, CH=), 7.32 (t, J=7.4 Hz, 2H, H2', 7'), 7.41 (t, J=7.5 Hz, 2H, H3', 6'), 7.58 (bd, J=6.1 Hz, 2H, H1', 8'), 7.77 (d, J=7.5 Hz, 2H, H4', 5'). $^{13}$C NMR (100 MHz, CDCl$_3$): δ 35.4 (CHCH$_2$), 47.2 (C9'), 62.1 (CHCH$_2$), 67.5 (CH$_2$O), 120.6 (=CH$_2$), 120.2 (C2', 7'), 125.1 (C3', 6'), 127.2 (C1', 8'), 128.0 (C4', 5'), 130.6 (CH=), 143.6 (C8'a, 9' a), 142.6 (C4'a, 4' b), 150.3 (OCONH), 177.2 (COOH). Mass spectrum (ESI$^+$, MeOH): The acid chloride readily converted into its corresponding methyl ester during analysis: m/z 352.3 [M+H]$^+$, C$_{21}$H$_{22}$NO$_4$ requires 352.4; 374.1 [M+Na]$^+$, O$_{21}$H$_{21}$NNaO$_4$ requires 374.4.

3.1.8 Fmoc-L-Agl-OPfp

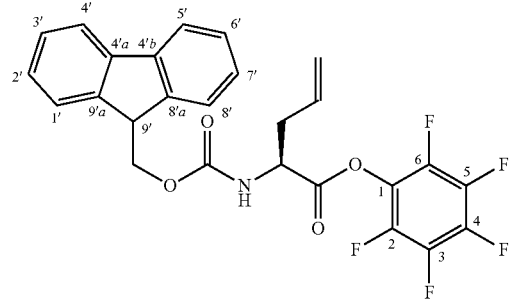 [SMILES: C=CC[C@H](NC(=O)OCC1c2ccccc2-c2ccccc21)C(=O)Oc1c(F)c(F)c(F)c(F)c1F]

PfpOH (0.65 g, 3.56 mmol) and 3% NaHCO$_3$ (15 mL) were added to a stirred solution of Fmoc-L-Agl-Cl (1.05 g, 2.96 mmol) in DCM (15 mL). The reaction mixture was stirred at room temperature under a nitrogen atmosphere and reaction progress was monitored by TLC (SiO$_2$; light petroleum:EtOAc; 1:1). After 25 h, the milky-white solution was diluted with DCM (15 mL) and brine (15 mL) and the phases were separated. The aqueous layer was further extracted with DCM (2×20 mL) and the combined organic extract then washed with a saturated Na$_2$CO$_3$ solution (2×30 mL) and brine (2×30 mL), dried (MgSO$_4$), filtered and concentrated under reduced pressure to afford the pentafluorophenyl ester as a colourless solid (1.41 g, 94%), m.p. 102-104° C. v$_{max}$ (KBr): 3320m, 3068w, 2945w, 2668w, 2462w, 1789m, 1698s, 1523s, 1448w, 1346w, 1282m, 1157w, 1110m, 998s, 921w, 758w, 732m, 622w, 551w, 425w cm$^{-1}$. $^1$H NMR (400 MHz, CDCl$_3$): δ 2.74 (bt, J=5.7 Hz, 2H, CHCH$_2$), 4.25 (t, J=6.9 Hz, 1H, H9'), 4.46 (bd, J=6.8 Hz, 2H, CH$_2$O), 4.83 (m, 1H, CHCH$_2$), 5.27 (m, 2H, =CH$_2$), 5.79 (m, 1H, CH=), 7.31 (td, J=7.4, 1.2 Hz, 2H, H2', 7'), 7.41 (t, J=7.0 Hz, 2H, H3', 6'), 7.59 (d, J=7.4 Hz, 2H, H1', 8'), 7.78 (d, J=6.7 Hz, 2H, H4', 5'). $^{13}$C NMR (75 MHz, CDCl$_3$): δ 36.6 (CHCH$_2$), 47.3 (C9'), 53.3 (CHCH$_2$), 67.5 (CH$_2$O), 120.2 (C2', 7'), 120.9 (=CH$_2$), 125.2 (C3', 6'), 127.2 (C1', 8'), 127.9 (C4', 5'), 130.4 (CH=), 141.5 (C8'a, 9' a), 143.6 (C4'a, 4' b), 158.0 (OCONH). (COOH, C1, C2, C3, C4, C5, C6 not observed). $^{19}$F NMR (300 MHz, CDCl$_3$): δ -161.1 (t, J=21.6 Hz, 1F, F4), −156.4 (t, J=21.5 Hz, 2F, F3, 5), −151.3 (d, J=17.9 Hz, 2F, F2, 6). Mass spectrum (ESI$^+$, MeOH): m/z 504.3 [M+H]$^+$, C$_{26}$H$_{19}$F$_5$NO$_4$ requires 504.1; 526.0 [M+Na]$^+$, C$_{26}$H$_{18}$F$_5$NNaO$_4$ requires 526.1.

3.1.9 Fmoc-L-Agl-L-Thr-OH

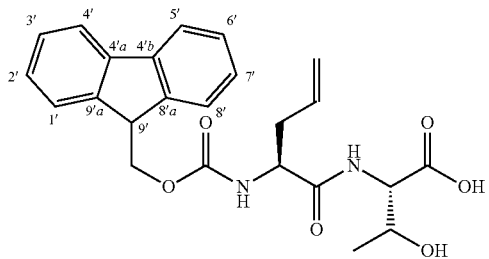 [SMILES: C=CC[C@H](NC(=O)OCC1c2ccccc2-c2ccccc21)C(=O)N[C@H](C(=O)O)C(C)O]

A solution of L-threonine (1.00 g, 8.37 mmol) in 10% w/v aq. Na$_2$CO$_3$ (8 mL) was added to a stirred solution of Fmoc-L-Agl-OPfp (1.41 g, 2.79 mmol) in acetone (30 mL). The resultant white suspension was stirred at room temperature and monitored by TLC (SiO$_2$; light petroleum:EtOAc: MeOH; 1:1:0.5). After 24 h, the acetone was removed under reduced pressure and the reaction mixture diluted with EtOAc (15 mL) and water (15 mL). The reaction mixture was then cooled in an ice bath and acidified to pH 2 with 1M HCl. The phases were separated and the aqueous layer further extracted with EtOAc (3×20 mL). The combined organic extract was washed with brine (1×30 mL), dried (MgSO$_4$), filtered and concentrated under reduced pressure to yield the desired dipeptide as a colourless solid (1.21 g, 99%), m.p. 141-146° C. v$_{max}$ (KBr): 3415m, 3366m, 3308s, 3098w, 2949w, 1689s, 1649s, 1536s, 1448w, 1379w, 1289m, 1260m, 1108w, 1081w, 1037w, 1015w, 995w, 919w, 758w, 738m, 673w, 482w, 427w cm$^{-1}$. $^1$H NMR (400 MHz, MeOD): δ 1.18 (d, J=6.4 Hz, 3H, CH$_3$), 2.43 (m, 1H, CHCHa), 2.61 (m, 1H, CHCHb), 4.21-4.36 (m, 3H, H9', CHCHOH, CHOH), 4.37 (d, J=6.9 Hz, 2H, CH$_2$O), 4.43 (m, 1H, CHCH$_2$), 5.09 (d, J=10.2 Hz, 1H, =CHa) 5.15 (d, J=17.1 Hz, 1H, =CHb), 5.82 (m, 1H, CH=), 7.31 (td, J=7.4, 1.3 Hz, 2H, H2', 7'), 7.39 (t, J=7.5 Hz, 2H, H3', 6'), 7.66 (bt, J=6.7 Hz, 2H, H1', 8'), 7.79 (d, J=7.6 Hz, 2H, H4', 5'). $^{13}$C NMR (75 MHz, CDCl$_3$): δ 18.0 (CH$_3$), 35.1 (CHCH$_2$), 47.4 (C9'), 53.8 (CHCH$_2$), 56.6 (CHCHOH), 65.6 (CH$_2$O), 66.0 (CHOH), 116.2 (=CH$_2$), 118.5 (C2', 7'), 123.8 (C3', 6'), 125.7 (C1', 8'), 126.3 (C4', 5'), 132.4 (CH=), 140.4 (C8'a, 9' a), 142.5 (C4'a, 4' b), 151.0 (OCONH), 171.5 (CONH), 172.1 (COOH). Mass spectrum (ESI$^+$, MeOH): m/z 461.4 [M+Na]$^+$, C$_{24}$H$_{26}$N$_2$NaO$_6$ requires 461.2.

3.1.10 Fmoc-L-Agl-L-Thr(ψ$^{Me, Me}$Pro)-OH

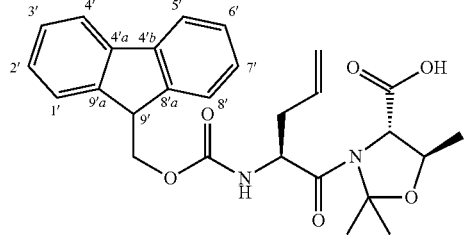 [SMILES: C=CC[C@H](NC(=O)OCC1c2ccccc2-c2ccccc21)C(=O)N1[C@H](C(=O)O)[C@@H](C)OC1(C)C]

Dimethoxypropane (2.86 g, 2.75 mmol) and pTsOH.H$_2$O (79 mg, 0.41 mmol) were added to a stirred solution of Fmoc-L-Agl-L-Thr-OH (1.21 g, 2.76 mmol) in hot DCE (40 mL). The resultant solution was stirred at reflux in the presence of 4 Å molecular sieves and the reaction was monitored by TLC (SiO$_2$; light petroleum:EtOAc:MeOH; 1:1:0.2). After 21 h, the molecular sieves were filtered from the reaction mixture and rinsed with DCE (3×10 mL). The combined organic extract was washed with brine (1×30 mL), dried (MgSO$_4$), filtered and concentrated in vacuo to afford the titled compound as a pale brown solid (1.24 g). Purification via column chromatography (SiO$_2$; light petroleum:EtOAc:MeOH: AcOH; 1:1:0.1:0.05) gave the titled compound as a pale brown solid (1.00 g, 76%), m.p. 102-105° C. v$_{max}$ (KBr): 3419m, 3307m, 3068m, 2081m, 1715s, 1660s, 1537s, 1519s, 1450s, 1379m, 1324m, 1251s, 1165m, 1104m, 1050m, 1016w, 993m, 912m, 854w, 750m, 741s, 648w, 620w. $^1$H NMR (400 MHz, CDCl$_3$): δ 1.48 (d, J=6.0 Hz, 3H, CHCH$_3$), 1.60 (s, 3H, CH$_3$), 1.68 (s, 3H, CH$_3$), 2.41 (m, 1H, CHCHa), 2.50 (m, 1H, CHCHb), 4.09-4.47 (m, 6H, H9', CH$_2$O, CHCH$_2$, CHCHCH$_3$, CHCH$_3$), 5.05-5.21 (m, 2H, =CH$_2$), 5.76 (m, 1H, CH=), 6.12 (d, J=8.6 Hz, 1H, NH), 7.22-7.32 (m, 2H, H2', 7'), 7.32-7.42 (m, 2H, H3', 6'), 7.46-7.62 (m, 2H, H1', 8'), 7.69-7.79 (m, 2H, H4', 5'). $^{13}$C NMR (75 MHz, CDCl$_3$): δ 20.0 (CHCH$_3$), 23.7 (CH$_3$), 26.4 (CH$_3$), 38.5 (CHCH$_2$), 47.0 (C9'), 53.3 (CHCH$_2$), 65.6 (CHCHCH$_3$), 67.7 (CH$_2$O), 75.0 (CHCH$_3$), 97.5 (C(CH$_3$)$_2$), 119.7 (=CH$_2$), 120.4 (C2', 7'), 124.8 (C3', 6'), 127.6 (C1', 8'), 128.0 (C4', 5'), 131.8 (CH=), 141.3 (C8'a, 9' a), 143.9 (C4'a, 4' b), 156.1 (OCONH), 169.5 (CONH), 171.8 (COOH). Mass spectrum (ESI$^+$, MeOH): m/z 479.3 [M+H]$^+$, C$_{27}$H$_{31}$N$_2$O$_6$ requires 479.3; 501.2 [M+Na]$^+$, C$_{27}$H$_{30}$N$_2$NaO$_6$ requires 501.2.

3.1.11 Fmoc-L-Pre-L-Thr(ψ$^{Me,Me}$Pro)-OH

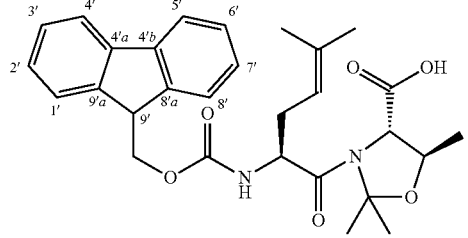 [SMILES: CC(C)=CC[C@H](NC(=O)OCC1c2ccccc2-c2ccccc21)C(=O)N1[C@H](C(=O)O)[C@@H](C)OC1(C)C]

Fmoc-L-Agl-L-Thr(ψ$^{Me,Me}$Pro)-OH was subjected to the conventional CM procedure outlined in the General Section under the following conditions: Fmoc-L-Agl-L-Thr(ψ$^{Me,Me}$Pro)-OH (0.30 g, 0.62 mmol), DCM (5 mL), 2$^{nd}$ generation Grubbs' catalyst (26 mg, 31 μmol), 2-methyl-2-butene (1 mL), Δ, 48 h, 100% conversion into the titled pseudoproline dipeptide. The reaction mixture was cooled to room temperature and concentrated under reduced pressure to afford a dark brown oil (0.40 g). Purification via column chromatography (SiO$_2$; light petroleum:EtOAc:MeOH:AcOH; 1:1:0.1:0.05) gave the titled compound as a pale brown solid (0.28 g, 87%), m.p. 81-84° C. $v_{max}$ (KBr): 3419bs, 3055w, 2986w, 1706m, 1652s, 1518m, 1450m, 1379w, 1266s, 1105w, 896w, 740s, 704m cm$^{-1}$. $^1$H NMR (400 MHz, CDCl$_3$): δ 1.45 (d, J=6.0 Hz, 3H, CHCH$_3$), 1.58, 1.66 (s, 2×3H, C(CH$_3$)$_2$), 1.62 (s, 3H, =C(CH$_3$)$_2$), 1.69 (s 3H, =C(CH$_3$)$_2$), 2.27-2.58 (m, 2H, CH$_2$CH=), 4.02-4.50 (m, 6H, H9', CH$_2$O, CHCH$_2$, H2'', H3''), 5.10 (t, J=6.9 Hz, 1H, CH=), 6.01 (d, J=8.6 Hz, 1H, NH), 7.13-7.46 (m, 4H, H2', 7', 3', 6'), 7.46-7.65 (m, 2H, H1', 8'), 7.67-7.81 (m, 2H, H4', 5'). $^{13}$C NMR (50 MHz, CDCl$_3$): δ 17.9 (=CCH$_3$), 20.2 (CHCH$_3$), 23.7 (CCH$_3$), 26.4 (CCH$_3$), 26.0 (=CCH$_3$), 33.1 (CH$_2$CH=), 47.0 (C9'), 53.6 (CHCH$_2$), 65.7 (CHCHCH$_3$), 68.0 (CH$_2$O), 74.9 (CHCH$_3$), 97.3 (C(CH$_3$)$_2$), 117.5 (=C(CH$_3$)$_2$), 120.0 (C2', 7'), 122.2 (C3', 6'), 126.9 (C1', 8'), 127.6 (C4', 5'), 136.6 (CH=), 141.3 (C8'a, 9' a), 144.4 (C4'a, 4' b), 156.0 (OCONH), 169.7 (CONH), 171.9 (COOH). Mass spectrum (ESI$^+$, DCM:MeOH): m/z 529.2312 [M+Na]$^+$, C$_{29}$H$_{34}$N$_2$NaO$_6$ requires 529.2315.

3.2 Pseudoproline Insertion: Synthesis of c[Δ$^4$A6,11]-Dicarba Human Insulin 3.2.1 [A6,11]-Agl-[A7]-Cys($^t$Bu)-[A20]-Cys(Acm) Insulin A-Chain ψ8

SEQ ID NO: 1

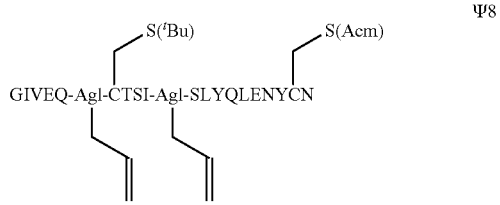

The automated, microwave-accelerated procedure outlined in the General Section was used for the synthesis of peptide ψ8 on Fmoc-Asn(Trt)-PEG-PS resin (588 mg, 100 μmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide Ψ8

| Reagent | Total volume (mL) | Mass (g) or Volume (mL) | Reaction Time (min) |
|---|---|---|---|
| 0.5M HATU in DMF | 21 | 4.00 g | — |
| 2M DIPEA in NMP | 12 | 4.2 mL | — |
| Fmoc-L-Agl-OH | 6.0 | 0.405 g | 12 |
| Fmoc-L-Asn(Trt)-OH | 3.0 | 0.358 g | 12 |
| Fmoc-L-Cys(Acm)-OH | 3.0 | 0.249 g | 12 |
| Fmoc-L-Cys($^t$Bu)-L-Thr(Ψ$^{Me,Me}$Pro)-OH | 3.0 | 0.240 g | 12 |
| Fmoc-L-Gln(Trt)-OH | 6.0 | 0.733 g | 12 |
| Fmoc-L-Glu(O$^t$Bu)-OH | 6.0 | 0.511 g | 12 |
| Fmoc-L-Gly-OH | 3.0 | 0.178 g | 12 |
| Fmoc-L-Ile-OH | 6.0 | 0.424 g | 12 |
| Fmoc-L-Leu-OH | 6.0 | 0.424 g | 12 |

TABLE-continued

Quantities of reagents and amino acids used in the synthesis of peptide Ψ8

| Reagent | Total volume (mL) | Mass (g) or Volume (mL) | Reaction Time (min) |
|---|---|---|---|
| Fmoc-L-Ser($^t$Bu)-OH | 6.0 | 0.460 g | 12 |
| Fmoc-L-Tyr($^t$Bu)-OH | 6.0 | 0.551 g | 12 |
| Fmoc-L-Val-OH | 3.0 | 0.204 g | 12 |
| Fmoc-L-Asn(Trt)-OH | 3.0 | 0.358 g | 12 |

After sequence completion, the resin-bound peptide was transferred into a fritted syringe and treated with an acetic anhydride solution (7 mL; DMF:acetic anhydride:NMM; 94:5:1) for 2 h. The resin was then washed with DMF (7 mL; 3×1 min), DCM (7 mL; 3×1 min) and MeOH (7 mL; 3×1 min), then left to dry in vacuo for 1 h. Prior to treatment with MeOH, a small aliquot of the resin-bound peptide was removed and subjected to Fmoc-deprotection in the presence of 20% v/v piperidine in DMF (1 mL; 1×1 min, 2×10 min), and washed with DMF (1 mL; 5×1 min), DCM (1 mL; 3×1 min) and MeOH (1 mL; 3×1 min). The dried aliquot of Fmoc-deprotected resin-tethered peptide was then exposed to a TFA cleavage solution (General Section) for RP-HPLC and mass spectral analysis. This supported formation of the desired peptide ψ8 in 85% purity. Mass spectrum (ESI$^+$, MeCN:H$_2$O: HCOOH): m/z 833.1 [M+3H]$^{3+}$, ⅓(C$_{110}$H$_{175}$N$_{26}$O$_{36}$S$_2$) requires 833.4; 1249.7 [M+2H]$^{2+}$, ½(C$_{110}$H$_{174}$N$_{26}$O$_{36}$S$_2$) requires 1249.6. RP-HPLC (Agilent: Vydac C18 analytical column, 0→30% buffer B over 5 min then 30→60% buffer B over 30 min): $t_R$=18.8 min.

3.2.2 c[Δ$^4$A6,11]-Dicarba-[A7]-Cys($^t$Bu)-[A20]-Cys(Acm) Insulin A-Chain ψ9

SEQ ID NO: 9

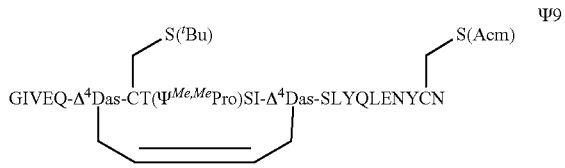

Resin-bound peptide ψ8 was subjected to the general microwave-accelerated RCM procedure outlined in the General Section under the following conditions: Resin-bound ψ8 (778 mg, 100 μmol), DCM (6 mL), 0.4 M LiCl in DMF (0.2 mL), 2$^{nd}$ generation Grubbs' catalyst (17 mg, 20 μmol), 100 W μwave, 100° C., 2 h, 98% conversion into ψ9. Post metathesis, a small aliquot of resin-bound peptide was subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The aliquot of Fmoc-deprotected resin-tethered peptide was subjected to TFA-mediated cleavage (General Section) for RP-HPLC and mass spectral analysis. This supported formation of the desired peptide ψ9 as one isomer in 80% purity. Mass spectrum (ESI$^+$, MeCN:H$_2$O:HCOOH): m/z 1255.8 [M+2H]$^{2+}$, ½(C$_{111}$H$_{174}$N$_{26}$O$_{36}$S$_2$) requires 1255.6. RP-HPLC (Agilent: Vydac C18 analytical column, 0→30% buffer B over 5 min then 30→60% buffer B over 30 min): $t_R$=13.5 min. The remaining resin-bound peptide ψ9 (1.12 g) was treated with a solution of DMSO:DMF (7 mL; 1:1) for 72 h and subjected to Fmoc-deprotected in the presence of 20% v/v piperidine in DMF (1×1 min, 2×20 min). After filtration, the resin was washed with DMF (5×1 min), DCM (3×1 min) and MeOH (3×1 min), then dried in vacuo for 1 h. Following global Fmoc-deprotection and TFA-mediated cleavage of the remaining resin-bound peptide (0.68 g), the grey solid was suspended in MeCN:H$_2$O (1:1) and lyophilised to give the desired peptide 4'9 as a pale brown solid (120 mg) in 80% purity. Spectral data were in accordance with those reported previously.

3.2.3 c[Δ$^4$A6,11]-Dicarba-[A7]-Cys(Pyr)-[A20]-Cys(Acm) Insulin A-Chain 10

SEQ ID NO: 2

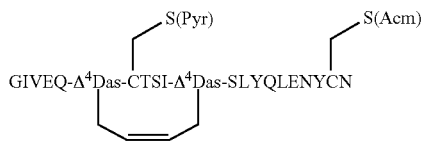

A solution of ice-cold TFA:TfOH (5 mL; 4:1) was added to a stirred solution of the cyclic peptide ψ9(II) (100 mg, 39.8 μmol) and 2,2'-DPDS (87.7 mg, 398 μmol) in TFA:anisol (5 mL; 9:1) at 0° C. After 1.5 h, the reaction mixture was reduced under a constant stream of air and ice-cold Et$_2$O (35 mL) was added to induce peptide precipitation. The resultant solid was then collected by centrifugation (4×5 min) and analysed by RP-HPLC and mass spectrometry. This supported formation of the S-activated peptide 10(II). The crude product was dissolved in H$_2$O:MeCN (1:1), lyophilised and then purified by RP-HPLC (Agilent: Vydac C18 preparative column, 15→45% buffer B over 30 min, $t_R$=22.0 min). Selected fractions were combined and lyophilised to give the desired peptide 10(II) as a colourless solid (34.3 mg, 34%) in >99%. Mass spectrum (ESI$^+$, MeCN:H$_2$O:HCOOH): m/z 841.7 [M+3H]$^{3+}$, ⅓(C$_{109}$H$_{166}$N$_{27}$O$_{36}$S$_3$) requires 841.7; 1262.4 [M+2H]$^{2+}$, ½(C$_{109}$H$_{165}$N$_{27}$O$_{36}$S$_3$) requires 1262.1. RP-HPLC (Agilent: Vydac C18 analytical column, 15→45% buffer B over 30 min): $t_R$=18.0 min.

3.2.4 The monocyclic A-B heterodimer of c[Δ$^4$A6,11]-Dicarba Human Insulin

SEQ ID NO: 4

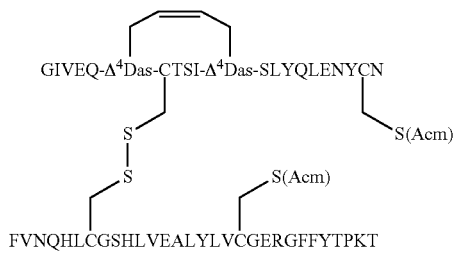

The modified insulin A-chain 10(II) (14.6 mg, 5.77 μmol) in 50 mM NH$_4$HCO$_3$ (7 mL) was added dropwise to a stirred solution of the modified insulin B-chain 11 (20.2 mg, 5.77 μmol) in H$_2$O:MeCN (20 mL; 9:1). Reaction progress was monitored by RP-HPLC and mass spectrometry, and after 3.25 h the oxidation was terminated by addition of AcOH. 12(II): Mass spectrum (ESI$^+$, MeCN:H$_2$O:HCOOH): m/z 1183.3 [M+5H]$^{5+}$, ⅕(C265H$_{402}$N67O79S4) requires 1183.0; 1478.8 [M+4H]$^{4+}$, ¼(C$_{265}$H$_{400}$N$_{67}$O$_{79}$S$_4$) requires 1478.5; 1971.6 [M+3H]$^{3+}$, ⅓(C$_{265}$H$_{400}$N$_{67}$O$_{79}$S$_4$) requires 1970.9. RP-HPLC (Agilent: Vydac C18 analytical column, 0→25% buffer B over 5 min then 25→50% buffer B over 30 min): $t_R$=20.8 min.

The remaining modified A-chain 10(II) (19.7 mg, 7.85 μmol) in 50 mM NH$_4$HCO$_3$ (10 mL) was subjected to identical reaction conditions in the presence of the modified insulin B-chain 11 (27.5 mg, 7.85 μmol) in H$_2$O:MeCN (30 mL; 9:1), and the two batches were combined and lyophilised to give a pale yellow solid (49.8 mg). Spectral data were in accordance with those reported previously.

3.2.5 c[A4A6,11]-Dicarba Human Insulin 13

SEQ ID NO: 5

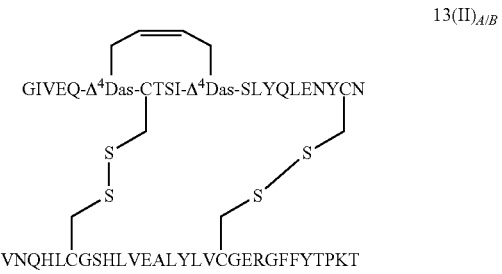

A 20 mM solution of iodine in glacial acetic acid (1.5 mL) was added to a stirred solution of the monocyclic peptide 12(II) (3.1 mg, 0.51 μmol) in glacial acetic acid (3.7 mL) and 60 mM HCl (280 μL). Reaction progress was monitored by RP-HPLC and after 2.75 h, ice-cold Et$_2$O (35 mL) was added to induce peptide precipitation. The resultant yellow solid was collected by centrifugation (1×10 min) and 20 mM ascorbic acid (1 mL) was then added to quench any excess iodine before analysis via RP-HPLC and mass spectrometry.

The remaining A-B conjugate 12(II) (75.5 mg, 12.8 μmol) in glacial acetic acid (93 mL) and 60 mM HCl (7 mL) was subjected to identical reaction conditions in the presence of a 20 mM solution of iodine in glacial acetic acid (38 mL), and the combined batches were then purified by RP-HPLC (Agilent: Vydac C18 preparative column, 15→45% buffer B over 30 min: $t_R$=17.6 min). Selected fractions were combined and lyophilised to give the desired c[Δ$^4$A6,11]-dicarba insulin analogue as a colourless solid in 70% purity. Repurification of peptide 13(II)$_{A/B}$ (Agilent: Vydac C18 analytical column, 0→30% buffer B over 5 min then 30→40% buffer B over 30 min: $t_R$=13.9 min) gave a 1:1 mixture of isomeric insulin analogues 13(II)$_A$ and 13(II)$_B$ as a colourless solid (5.1 mg, 7%) in 98% purity. 13(II)$_{A/B}$: Mass spectrum (ESI$^+$, MeCN:H$_2$O:HCOOH): m/z 961.9 [M+6H]$^{6+}$, ⅙(C$_{259}$H$_{391}$N$_{65}$O$_{77}$S$_4$) requires 962.0; 1154.4 [M+5H]$^{5+}$, ⅕(C$_{259}$H$_{390}$N$_{65}$O$_{77}$S$_4$) requires 1154.1; 1442.7 [M+4H]$^{4+}$, ¼(C$_{259}$H$_{389}$N$_{65}$O$_{77}$S$_4$) requires 1442.4; 1923.9 [M+3H]$^{3+}$, ⅓(C$_{259}$H$_{388}$N$_{65}$O$_{77}$S$_4$) requires 1922.9. RP-HPLC (Agilent: Vydac C4 analytical column, 0→30% buffer B over 5 min then 30→40% buffer B over 30 min): $t_R$=12.8 min.

4. Preparation of Fast and Slow Acting Dicarba Insulin Analogues

4.1 c[Δ⁴A6,11]-Dicarba 'DKP' Human Insulin Transformations

4.1.1 [B10]-Asp-[B19]-Cys(Acm)-[B28]-Lys-[B29]-Pro Insulin B-Chain

SEQ ID NO: 101

FVNQHLCGSHLVEALYLVCGERGFFYTPKT

The automated, microwave-accelerated procedure outlined in the General Section was used for the synthesis of peptide 50 on Fmoc-Thr($^t$Bu)-PEG-PS resin (667 mg, 100 µmol). Quantities of HBTU, HOBt, DIPEA, piperidine and each Fmoc-amino acid were used as described by the automated protocols of the instrument and remained constant throughout this synthesis. The total amount of each coupling reagent and successive amino acid required, along with their reaction duration is summarised in the Table below:—

TABLE

Quantities of reagents and amino acids used in the synthesis of peptide 50

| Reagent | Total volume (mL) | Mass (g) or Volume (mL) | Reaction Time (min) |
|---|---|---|---|
| 0.5M HBTU:HOBt in DMF | 31 | 5.88:2.09 g | — |
| 2M DIPEA in NMP | 16 | 5.6 mL | — |
| Fmoc-L-Ala-OH | 3 | 0.187 g | 12 |
| Fmoc-L-Arg(Pbf)-OH | 3 | 0.389 g | 12 |
| Fmoc-L-Asn(Trt)-OH | 3 | 0.358 g | 12 |
| Fmoc-L-Cys(Acm)-OH | 3 | 0.249 g | 12 |
| Fmoc-L-Cys(Trt)-OH | 3 | 0.351 g | 12 |
| Fmoc-L-Gln(Trt)-OH | 3 | 0.366 g | 12 |
| Fmoc-L-Glu(O$^t$Bu)-OH | 6 | 0.511 g | 12 |
| Fmoc-L-Gly-OH | 8 | 0.476 g | 12 |
| Fmoc-L-His(Boc)-OH | 6 | 0.744 g | 12 |
| Fmoc-L-Leu-OH | 11 | 0.778 g | 12 |
| Fmoc-L-Lys(Boc)-OH | 3 | 0.281 g | 12 |
| Fmoc-L-Phe-OH | 8 | 0.620 g | 12 |
| Fmoc-L-Pro-OH | 3 | 0.202 g | 12 |
| Fmoc-L-Ser($^t$Bu)-OH | 3 | 0.230 g | 12 |
| Fmoc-L-Thr($^t$Bu)-OH | 3 | 0.238 g | 12 |
| Fmoc-L-Tyr($^t$Bu)-OH | 6 | 0.551 g | 12 |
| Fmoc-L-Val-OH | 8 | 0.543 g | 12 |

After sequence completion, the resin was transferred into a fritted syringe, washed with DMF (7 mL; 3×1 min), DCM (7 mL; 3×1 min) and MeOH (7 mL; 3×1 min), then left to dry in vacuo for 1 h. The resin-bound peptide 50 (1.11 g) was subjected to TFA-mediated cleavage (General Section) and the resultant pale yellow solid then purified by RP-HPLC†(Agilent: Vydac C18 preparative column, 20→50% buffer B over 30 min, $t_R$=21.6 min). Selected fractions were combined and lyophilised to give the desired peptide 50 as a colourless solid (44 mg, 13%) in 90% purity. Mass spectrum (ESI⁺, MeCN:H₂O): m/z 1160.3 [M+3H]³⁺, ⅓(C₁₅₉H₂₄₀N₃₉O₄₅S₂) requires 1159.9; 870.5 [M+4H]⁴⁺, ¼(C₁₅₉H₂₄₁N₃₉O₄₅S₂) requires 870.2. RP-HPLC (Agilent: Vydac C18 analytical column, 20→50% buffer B over 30 min): $t_R$=18.1 min.

†Buffer A: 20 mM Aqueous triethylammonium acetate Buffer B: Buffer A:MeCN (1:9)

4.1.2 Formation of the Monocyclic Dicarba A-B Heterodimer of 'DKP' Human Insulin 51

SEQ ID NO: 102

51(I) and 51(II)

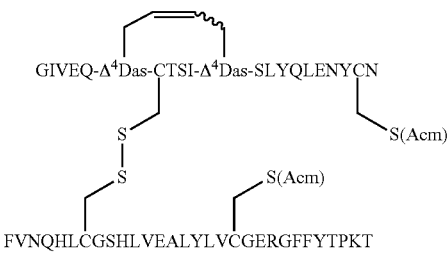

FVNQHLCGSHLVEALYLVCGERGFFYTPKT

Isomer I:

The modified insulin A-chain 10(I) (0.85 mg, 0.34 µmol) in 50 mM NH₄HCO₃ (500 µL) was added dropwise to a stirred solution of the modified insulin B-chain 50 (1.17 mg, 0.34 µmol) in H₂O:MeCN (1.00 mL; 9:1). Reaction progress was monitored by RP-HPLC and mass spectrometry and after 2 h, the oxidation was terminated by addition of AcOH. 51(I): Mass spectrum (ESI⁺, MeCN:H₂O:HCOOH): m/z 1178.7 [M+5H]⁵⁺, ⅕(C₂₆₃H₄₀₀N₆₅O₈₁S₄) requires 1178.6; 1473.4 [M+4H]⁴⁺, ¼(C₂₆₃H₃₉₉N₆₅O₈,S₄) requires 1472.9; 1964.5 [M+3H]³⁺, ⅓(C₂₆₃H₃₉₈N₆₅O₈₁S₄) requires 1963.6. RP-HPLC (Agilent: Vydac C4 analytical column, 0→25% buffer B over 5 min then 25→45% buffer B over 30 min): $t_R$=24.0 min.

The remaining modified A-chain 10(I) (3.39 mg, 1.34 µmol) in 50 mM NH₄HCO₃ (2 mL) was subjected to identical reaction conditions in the presence of the modified insulin B-chain 50 (4.67 mg, 1.34 µmol) in H₂O:MeCN (3 mL; 9:1), and the two batches were combined and lyophilised to give a pale yellow solid (10.1 mg). Spectral data were in accordance with those reported previously.

Isomer II:

The modified insulin A-chain 10(II) (0.61 mg, 0.24 µmol) in 50 mM NH₄HCO₃ (300 µL) was added dropwise to a stirred solution of the modified insulin B-chain 50 (0.84 mg, 0.24 µmol) in H₂O:MeCN (0.5 mL; 9:1). Reaction progress was monitored by RP-HPLC and mass spectrometry and after 2 h, the oxidation was terminated by addition of AcOH. 51(II): Mass spectrum (ESI⁺, MeCN:H₂O:HCOOH): m/z 1178.7 [M+5H]⁵⁺, ⅕(C₂₆₃H₄₀₀N₆₅O₈₁S₄) requires 1178.6; 1473.1 [M+4H]⁴⁺, ¼(C₂₆₃H₃₉₉N₆₅O₈₁S₄) requires 1472.9; 1954.5 [M+3H]³⁺, ⅓(C₂₆₃H₃₉₈N₆₅O₈₁S₄) requires 1963.6. RP-HPLC (Vydac C4 analytical column, 0→25% buffer B over 5 min then 25→45% buffer B over 30 min): $t_R$=23.5 min.

The remaining modified A-chain 10(II) (0.82 mg, 0.32 µmol) in 50 mM NH₄HCO₃ (400 µL) was subjected to identical reaction conditions in the presence of the modified insulin B-chain 50 (1.13 mg, 0.32 µmol) in H₂O:MeCN (0.5 mL; 9:1) and the two batches were combined and lyophilised to give a pale yellow solid (3.4 mg). Spectral data were in accordance with those reported previously.

4.1.3 c[Δ⁴A6,11]-Dicarba 'DKP' Insulin 52

SEQ ID NO: 100

52(I)$_{A/B}$ and 52(II)$_{A/B}$

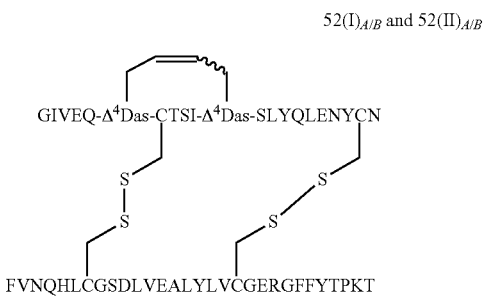

GIVEQ-Δ⁴Das-CTSI-Δ⁴Das-SLYQLENYCN

FVNQHLCGSDLVEALYLVCGERGFFYTPKT

Isomer IA and IB:

A 20 mM solution of iodine in glacial acetic acid (0.86 mL) was added to a stirred solution of the monocyclic peptide 51(I) (1.99 mg, 0.33 μmol) in glacial acetic acid (2.26 mL) and 60 mM HCl (167 μL). Reaction progress was monitored by RP-HPLC and after 2.75 h, ice-cold Et₂O (35 mL) was added to induce peptide precipitation. The resultant yellow solid was collected by centrifugation (1×10 min) and 20 mM ascorbic acid (1 mL) was then added to quench excess iodine before analysis via RP-HPLC and mass spectrometry.

The remaining A-B conjugate 51(I) (8.07 mg, 1.37 μmol) in glacial acetic acid (9.16 mL) and 60 mM HCl (0.68 mL) was subjected to identical reaction conditions in the presence of a 20 mM solution of iodine in glacial acetic acid (3.49 mL), and the combined batches were then purified by RP-HPLC† (Agilent: Vydac C4 preparative column, 0→30% buffer B over 5 min then 30→40% buffer B over 30 min: $t_R$=29.2 and 30.9 min). Selected fractions were combined and lyophilised to give two isomers, 52(I)$_A$ and 52(I)$_B$, of the desired c[Δ⁴A6,11]-dicarba DKP human insulin analogue as colourless oils in 75% and 80% purity respectively. Repurification of isomer 52(I)$_A$ (Agilent: Vydac C4 analytical column, 0→30% buffer B over 5 min then 30→40% buffer B over 60 min: $t_R$=28.3 min) gave insulin analogue 52(I)$_A$ as a colourless solid (1.0 mg, 10%) in 90% purity. 52(I)$_A$: Mass spectrum (ESI⁺, MeCN:H₂O:HCOOH): m/z 1149.9 [M+5H]⁵⁺, ⅕(C₂₅₇H₃₈₈N₆₃O₇₉S₄) requires 1149.7; 1437.3 [M+4H]⁴⁺, ¼(C₂₅₇H₃₈₇N₆₃O₇₉S₄) requires 1436.9. RP-HPLC (Agilent: Vydac C4 analytical column, 0→30% buffer B over 5 min then 30→40% buffer B over 30 min): $t_R$=22.6 min. Repurification of isomer 52(I)$_B$ (Agilent: Vydac C4 analytical column, 0→30% buffer B over 5 min then 30→40% buffer B over 60 min: $t_R$=28.9 min) gave insulin analogue 52(I)$_B$ as a colourless solid (0.78 mg, 8%) in 90% purity. 52(I)$_B$: Mass spectrum (ESI⁺, MeCN:H₂O:HCOOH): m/z 1150.2 [M+5H]⁵⁺, ⅕(C₂₅₇H₃₈₈N₆₃O₇₉S₄) requires 1149.7; 1437.5 [M+4H]⁴⁺, ¼(C₂₅₇H₃₈₇N₆₃O₇₉S₄) requires 1436.9. RP-HPLC (Agilent: Vydac C4 analytical column, 0→30% buffer B over 5 min then 30→40% buffer B over 30 min): $t_R$=22.4 min.

†Buffer A: 20 mM Aqueous triethylammonium acetate Buffer B: Buffer A:MeCN (1:9)

Isomer IIA and IIB:

A 20 mM solution of iodine in glacial acetic acid (0.63 mL) was added to a stirred solution of the monocyclic peptide 51(II) (1.45 mg, 0.25 μmol) in glacial acetic acid (1.65 mL) and 60 mM HCl (122 μL). Reaction progress was monitored by RP-HPLC and after 2.75 h, ice-cold Et₂O (35 mL) was added to induce peptide precipitation. The resultant solid was collected by centrifugation (1×10 min) and 20 mM ascorbic acid (1 mL) was then added to quench any excess iodine before analysis via RP-HPLC and mass spectrometry.

The remaining A-B conjugate 51(II) (1.95 mg, 0.33 μmol) in glacial acetic acid (2.21 mL) and 60 mM HCl (164 mL) was subjected to identical reaction conditions in the presence of a 20 mM solution of iodine in glacial acetic acid (0.84 mL) and the combined batches then purified by RP-HPLC† (Agilent: Vydac C18 preparative column, 0→30% buffer B over 5 min then 30→40% buffer B over 60 min: $t_R$=22.1 and 22.3 min). Selected fractions were combined and lyophilised to give two isomers, 52(II)$_A$ and 52(II)$_B$, of the desired c[Δ⁴A6,11]-dicarba DKP human insulin analogue as colourless solids (52(II)$_A$: 0.38 mg, 12% and 52(II)$_B$: 0.55 mg, 17%) in 90% purity. 52(II)$_A$: Mass spectrum (ESI⁺, MeCN:H₂O:HCOOH): m/z 1150.3 [M+5H]⁵⁺, ⅕(C₂₅₇H₃₈₈N₆₃O₇₉S₄) requires 1149.7; 1436.8 [M+4H]⁴⁺, ¼(C₂₅₇H₃₈₇N₆₃O₇₉S₄) requires 1436.9. RP-HPLC (Agilent: Vydac C4 analytical column, 0→30% buffer B over 5 min then 30→40% buffer B over 30 min): $t_R$=18.4 min. 52(II)$_B$: Mass spectrum (ESI⁺, MeCN:H₂O:HCOOH): m/z 1150.0 [M+5H]⁵⁺, ⅕(C₂₅₇H₃₈₈N₆₃O₇₉S₄) requires 1149.7; 1437.5 [M+4H]⁴⁺, ¼(C₂₅₇H₃₈₇N₆₃O₇₉S₄) requires 1436.9. RP-HPLC (Agilent: Vydac C4 analytical column, 0→30% buffer B over 5 min then 30→40% buffer B over 30 min): $t_R$=18.9 min.

†Buffer A: 20 mM Aqueous triethylammonium acetate Buffer B: Buffer A:MeCN (1:9)

4.2 c[Δ⁴A6,11]-Dicarba Human Insulin Glargine Transformations

4.2.1 des$_{A1-5}$-[A6,11]-Agl-[A7]-Cys(ᵗBu)-[A20]-Cys(Acm) Human Insulin Glargine A-Chain 60

SEQ ID NO: 33

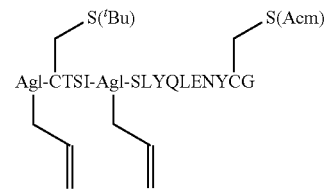

Agl-CTSI-Agl-SLYQLENYCG

The automated, microwave-accelerated procedure outlined in the General Section was used for the synthesis of peptide 60 on Fmoc-Gly-PEG-PS resin (1.10 g, 200 μmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 60

| Reagent | Total volume (mL) | Mass (g) or Volume (mL) | Reaction Time (min) |
| --- | --- | --- | --- |
| 0.5M HATU in DMF | 17.0 | 3.24 g | — |
| 2M DIPEA in NMP | 9.0 | 3.1 mL | — |
| Fmoc-L-Asn(Trt)-OH | 3.0 | 0.358 g | 12 |
| Fmoc-L-Agl-OH | 6.0 | 0.405 g | 12 |
| Fmoc-L-Cys(Acm)-OH | 3.0 | 0.249 g | 12 |
| Fmoc-L-Cys(ᵗBu)-OH | 3.0 | 0.240 g | 12 |
| Fmoc-L-Gln(Trt)-OH | 3.0 | 0.367 g | 12 |
| Fmoc-L-Glu(OᵗBu)-OH | 3.0 | 0.256 g | 12 |
| Fmoc-L-Ile-OH | 3.0 | 0.212 g | 12 |
| Fmoc-L-Leu-OH | 6.0 | 0.424 g | 12 |

TABLE-continued

Quantities of reagents and amino acids used in the synthesis of peptide 60

| Reagent | Total volume (mL) | Mass (g) or Volume (mL) | Reaction Time (min) |
|---|---|---|---|
| Fmoc-L-Ser($^t$Bu)-OH | 6.0 | 0.460 g | 12 |
| Fmoc-L-Thr($^t$Bu)-OH | 3.0 | 0.238 g | 12 |
| Fmoc-L-Tyr($^t$Bu)-OH | 6.0 | 0.551 g | 12 |

After sequence completion, the resin-bound peptide was transferred into a fritted syringe and treated with an acetic anhydride solution (7 mL; DMF:acetic anhydride:NMM; 94:5:1) for 2 h. The resin was then washed with DMF (7 mL; 3×1 min), DCM (7 mL; 3×1 min) and MeOH (7 mL; 3×1 min), then left to dry in vacuo for 1 h. Prior to treatment with MeOH, a small aliquot of the resin-bound peptide was removed and subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The aliquot of Fmoc-deprotected resin-tethered peptide was subjected to TFA-mediated cleavage (General Section) for RP-HPLC and mass spectral analysis. This supported formation of the desired peptide 60 in 70% purity. Mass spectrum (ESI$^+$, MeCN:H$_2$O: HCOOH): m/z 958.3 [M+2H]$^{2+}$, ½(C$_{85}$H$_{133}$N$_{19}$O$_{27}$S$_2$) requires 958.0. RP-HPLC (Agilent: Vydac C18 analytical column, 15→45% buffer B over 30 min): t$_R$=18.9 min.

4.2.2 des$_{41-5}$-c[Δ$^4$A6,11]-Dicarba-[A7]-Cys($^t$Bu)-[A20]-Cys(Acm) Human Insulin Glargine A-Chain 61

SEQ ID NO: 34

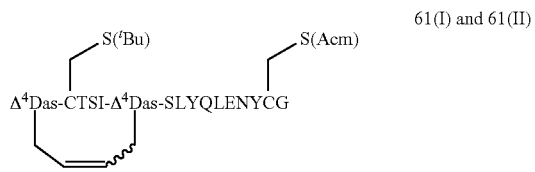

Resin-bound peptide 60 was subjected to the microwave-accelerated RCM procedure outlined in the General Section under the following conditions: Resin-bound 60 (1.35 g, 0.20 mmol), DCM (13 mL), 0.4 M LiCl in DMF (0.5 mL), 2$^{nd}$ generation Grubbs' catalyst (34 mg, 40 µmol), 100 W µwave, 100° C., 4 h, 100% conversion into 61. Post metathesis, a small aliquot of resin-bound peptide was subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The aliquot of Fmoc-deprotected resin-tethered peptide was subjected to TFA-mediated cleavage (General Section) for RP-HPLC and mass spectral analysis. This supported formation of the desired peptide as two isomers, 61(I) and 61(II), in a 7:3 ratio. 61(I): Mass spectrum (ESI$^+$, MeCN:H$_2$O: HCOOH): m/z 944.0 [M+2H]$^{2+}$, ½(C$_{83}$H$_{129}$N$_{19}$O$_{27}$S$_2$) requires 943.9. RP-HPLC (Agilent: Vydac C18 analytical column, 15→45% buffer B over 30 min): t$_R$=17.8 min. 61(II): Mass spectrum (ESI$^+$, MeCN:H$_2$O:HCOOH): m/z 944.2 [M+2H]$^{2+}$, ½(C$_{83}$H$_{129}$N$_{19}$O$_{27}$S$_2$) requires 943.9. RP-HPLC (Agilent: Vydac C18 analytical column, 15→45% buffer B over 30 min): t$_R$=17.9 min.

4.2.3 c[Δ$^4$A6,11]-Dicarba-[A7]-Cys($^t$Bu)-[A20]-Cys(Acm) Human Insulin Glargine A-Chain 62

SEQ ID NO: 36

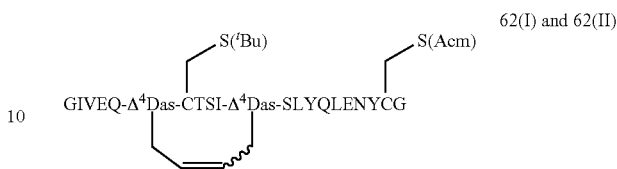

The automated, microwave-accelerated procedure outlined in the General Section was used to attach the remaining 5 residues on resin-bound peptide 61 (1.16 g, 0.20 mmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 61

| Reagent | Total volume (mL) | Mass (g) or Volume (mL) | Reaction Time (min) |
|---|---|---|---|
| 0.5M HATU in DMF | 11.0 | 2.10 g | — |
| 2M DIPEA in NMP | 6.0 | 2.1 mL | — |
| Fmoc-L-Gly-OH | 6.0 | 0.357 g | 12 |
| Fmoc-L-Gln(Trt)-OH | 6.0 | 0.733 g | 12 |
| Fmoc-L-Glu(O$^t$Bu)-OH | 6.0 | 0.511 g | 12 |
| Fmoc-L-Ile-OH | 6.0 | 0.424 g | 12 |
| Fmoc-L-Val-OH | 6.0 | 0.407 g | 12 |

After sequence completion, the resin-bound peptide was transferred into a fritted syringe and subjected to Fmoc-deprotection in the presence of 20% v/v piperidine in DMF (7 mL; 1×1 min, 2×10 min). The resin was washed with DMF (7 mL; 5×1 min), DCM (7 mL; 3×1 min) and MeOH (7 mL; 3×1 min), then left to dry in vacuo for 1 h. The resin-bound peptide (0.98 g) was subjected to TFA-mediated cleavage (General Section), and RP-HPLC and mass spectral analysis of the resultant pale brown solid (300 mg) supported formation of the desired peptide as two isomers, 62(I) and 62(II), in a 7:3 ratio. 62(I): Mass spectrum (ESI$^+$, MeCN:H$_2$O:HCOOH): m/z 1207.2 [M+2H]$^{2+}$, ½(C$_{106}$H$_{167}$N$_{25}$O$_{35}$S$_2$) requires 1207.1. RP-HPLC (Agilent: Vydac C18 analytical column, 15→45% buffer B over 30 min): t$_R$=18.6 min. 62(II): Mass spectrum (ESI$^+$, MeCN:H$_2$O:HCOOH): m/z 1207.2 [M+2H]$^{2+}$, ½(C$_{106}$H$_{167}$N$_{25}$O$_{35}$S$_2$) requires 1207.1. RP-HPLC (Agilent: Vydac C18 analytical column, 15→45% buffer B over 30 min): t$_R$=19.5 min.

4.2.4 c[Δ$^4$A6,11]-Dicarba-[A7]-Cys(Pyr)-[A20]-Cys(Acm) Human Insulin Glargine A-Chain 63

SEQ ID NO: 36

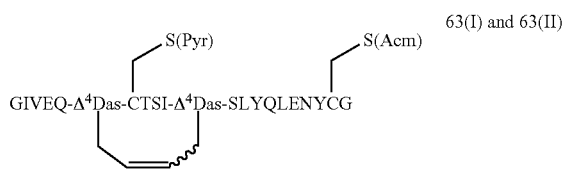

A solution of ice-cold TFA:TfOH (8 mL; 4:1) was added to a stirred solution of the cyclic peptide 62 (300 mg, 114 µmol) and 2,2'-DPDS (0.251 g, 1.14 mmol) in TFA:anisol (8 mL; 9:1) at 0° C. After 1.5 h, the reaction mixture was reduced under a constant stream of air and ice-cold $Et_2O$ (40 mL) was added to induce peptide precipitation. The resultant solid was collected by centrifugation (3×10 min), lyophilised and analysed by RP-HPLC and mass spectrometry. This supported formation of the S-activated peptide 63 as two isomers, 63(I) and 63(II), in a 7:3 ratio. Following purification by RP-HPLC (Agilent: Vydac C18 preparative column, 15→45% buffer B over 30 min, $t_R$=22.9 and 21.9 min), selected fractions were combined and lyophilised to give two isomers (63(I) and 63(II)) of the desired peptide as colourless solids in 64% and 51% purity respectively. Repurification of isomer 63(I) (Agilent: Vydac C18 analytical column, 15→45% buffer B over 30 min: $t_R$=17.5 min) then gave insulin analogue 63(I) as a colourless solid (2.96 mg, 1%) in 90% purity. 63(I): Mass spectrum ($ESI^+$, $MeCN:H_2O$: HCOOH): m/z 822.7 $[M+H]^+$, $C_{107}H_{163}N_{26}O_{35}S_3$ requires 822.7; 1233.8 $[M+2H]^{2+}$, $½(C_{107}H_{162}N_{26}O_{35}S_3)$ requires 1233.5. RP-HPLC (Agilent: Vydac C18 analytical column 15→45% buffer B over 30 min): $t_R$=17.8 min. Repurification of isomer 63(II) (Agilent: Vydac C18 analytical column, 15→45% buffer B over 30 min: $t_R$=19.5 min) then gave insulin analogue 63(II) as a colourless solid (1.95 mg, 0.8%) in 94% purity. 63(II): Mass spectrum ($ESI^+$, $MeCN:H_2O$: HCOOH): m/z 822.7 $[M+H]^+$, $C_{107}H_{163}N_{26}O_{35}S_3$ requires 822.7; 1233.5 $[M+2H]^{2+}$, $½(C_{107}H_{162}N_{26}O_{35}S_3)$ requires 1233.5. RP-HPLC (Agilent: Vydac C18 analytical column, 15→45% buffer B over 30 min): $t_R$=18.7 min.

4.2.5 [B19]-Cys(Acm) Human Insulin Glargine B-Chain 64

SEQ ID NO: 38

FVNQHLCGSHLVEALYLVCGERGFFYTPKTRR

The automated, microwave-accelerated procedure outlined in the General Section was used for the synthesis of peptide 64 on Fmoc-Thr($^t$Bu)-PEG-PS resin (0.95 g, 0.20 mmol). Quantities of HBTU, HOBt, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 64

| Reagent | Total volume (mL) | Mass (g) or Volume (mL) | Reaction Time (min) |
|---|---|---|---|
| 0.5M HBTU:HOBt in DMF | 73 | 13.8 g:4.93 g | — |
| 2M DIPEA in NMP | 37 | 12.9 mL | — |
| Fmoc-L-Ala-OH | 6 | 0.37 g | 12 |
| Fmoc-L-Arg(Pbf)-OH | 21 | 2.72 g | 12 |
| Fmoc-L-Asn(Trt)-OH | 6 | 0.72 g | 12 |
| Fmoc-L-Cys(Acm)-OH | 6 | 0.50 g | 12 |
| Fmoc-L-Cys(Trt)-OH | 6 | 0.73 g | 12 |
| Fmoc-L-Gln(Trt)-OH | 6 | 0.73 g | 12 |

TABLE-continued

Quantities of reagents and amino acids used in the synthesis of peptide 64

| Reagent | Total volume (mL) | Mass (g) or Volume (mL) | Reaction Time (min) |
|---|---|---|---|
| Fmoc-L-Glu(O$^t$Bu)-OH | 11 | 0.94 g | 12 |
| Fmoc-L-Gly-OH | 16 | 0.95 g | 12 |
| Fmoc-L-His(Boc)-OH | 11 | 1.36 g | 12 |
| Fmoc-L-Leu-OH | 21 | 1.48 g | 12 |
| Fmoc-L-Lys(Boc)-OH | 6 | 0.56 g | 12 |
| Fmoc-L-Phe-OH | 16 | 1.24 g | 12 |
| Fmoc-L-Pro-OH | 6 | 0.40 g | 12 |
| Fmoc-L-Ser($^t$Bu)-OH | 6 | 0.46 g | 12 |
| Fmoc-L-Thr($^t$Bu)-OH | 11 | 0.87 g | 12 |
| Fmoc-L-Tyr($^t$Bu)-OH | 11 | 1.01 g | 12 |
| Fmoc-L-Val-OH | 16 | 1.09 g | 12 |

After sequence completion, the resin was transferred into a fritted syringe, washed with DMF (7 mL; 3×1 min), DCM (7 mL; 3×1 min) and MeOH (7 mL; 3×1 min), then left to dry in vacuo for 1 h. A small aliquot of resin-bound peptide was subjected to the cleavage procedure outlined in the General Section for RP-HPLC and mass spectral analysis. This supported formation of the desired peptide 64 in 48% purity. Following global Fmoc-deprotection and TFA-mediated cleavage of the remaining peptide from the resin (1.59 g), the resultant colourless solid (520 mg) was purified by RP-HPLC (Agilent: Vydac C18 preparative column, 0→25% buffer B over 5 min then 25→45% buffer B over 30 min, $t_R$=18.9 min). Selected fractions were combined and lyophilised to give the desired peptide 64 as a colourless solid (48 mg, 6%) in 96% purity. Mass spectrum ($ESI^+$, $MeCN:H_2O:HCOOH$): m/z 636.5 $[M+6H]^{6+}$, $⅙(C_{173}H_{269}N_{49}O_{45}S_2)$ requires 636.2; 763.6 $[M+5H]^{5+}$, $⅕(C_{173}H_{268}N_{49}O_{45}S_2)$ requires 763.2; 954.2 $[M+4H]^{4+}$, $¼(C_{173}H_{267}N_{49}O_{45}S_2)$ requires 953.7; 1271.9 $[M+3H]^{3+}$, $⅓(C_{173}H_{266}N_{49}O_{45}S_2)$ requires 1271.3. RP-HPLC (Agilent: Vydac C18 analytical column, 0→25% buffer B over 5 min then 25→45% buffer B over 30 min): $t_R$=17.6 min.

4.2.6 The Monocyclic A-B Heterodimer of c[$Δ^4$A6,11]-Dicarba Human Insulin Glargine 65

SEQ ID NO: 39

65(I) and 65(II)

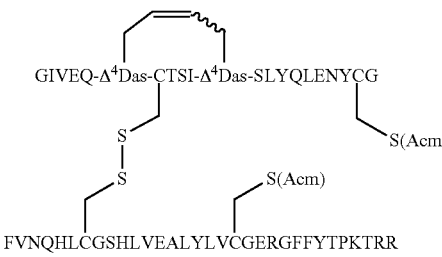

GIVEQ-$Δ^4$Das-CTSI-$Δ^4$Das-SLYQLENYCG

FVNQHLCGSHLVEALYLVCGERGFFYTPKTRR

Isomer I:

The modified insulin A-chain 63(I) (1.96 mg, 0.79 µmol) in 50 mM $NH_4HCO_3$ (1.0 mL) was added dropwise to a stirred solution of the modified insulin B-chain 64 (3.03 mg, 0.79 µmol) in $H_2O:MeCN$ (3.0 mL; 9:1). Reaction progress was monitored by RP-HPLC and mass spectrometry, and after 2 h the oxidation was terminated by addition of AcOH. Mass spectrum ($ESI^+$, $MeCN:H_2O:HCOOH$): m/z 1029.1 $[M+6H]^{6+}$, $⅙(C_{275}H_{424}N_{74}O_{80}S_4)$ requires 1028.5; 1234.3

[M+5H]$^{5+}$, ⅕($C_{275}H_{423}N_{74}O_{80}S_4$) requires 1234.0; 1543.0 [M+4H]$^{4+}$, ¼($C_{275}H_{422}N_{74}O_{80}S_4$) requires 1542.3. RP-HPLC (Agilent: Vydac C18 analytical column, 0→25% buffer B over 5 min then 25→45% buffer B over 30 min): $t_R$=20.2 min.

Isomer II:

The modified insulin A-chain 63(II) (1.95 mg, 0.79 μmol) in 50 mM $NH_4HCO_3$ (1.0 mL) was added dropwise to a stirred solution of the modified insulin B-chain 64 (3.01 mg, 0.79 μmol) in $H_2O$:MeCN (3.0 mL; 9:1). Reaction progress was monitored by RP-HPLC and mass spectrometry, and after 2 h the oxidation was terminated by addition of AcOH. Mass spectrum (ESI$^+$, MeCN:$H_2O$:HCOOH): m/z 1028.8 [M+6H]$^{6+}$, ⅙($C_{275}H_{424}N_{74}O_{80}S_4$) requires 1028.5; 1234.5 [M+5H]$^{5+}$, ⅕($C_{275}H_{423}N_{74}O_{80}S_4$) requires 1234.0; 1543.1 [M+4H]$^{4+}$, ¼($C_{275}H_{422}N_{74}O_{80}S_4$) requires 1542.3. RP-HPLC (Agilent: Vydac C18 analytical column, 0→25% buffer B over 5 min then 25→45% buffer B over 30 min): $t_R$=20.7 min.

4.2.7 c[Δ$^4$A6,11]-Dicarba Human Insulin Glargine 66

SEQ ID NO: 106

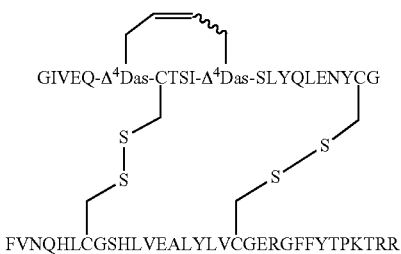

66(I) and 66(II)

Isomer I:

A 20 mM solution of iodine in glacial acetic acid (2.2 mL) was added to a stirred solution of the mono-cyclic peptide 65(I) (5.0 mg, 0.81 μmol) in glacial acetic acid (5.6 mL) and 60 mM HCl (420 μL). Reaction progress was monitored by RP-HPLC and after 2.75 h, ice-cold $Et_2O$ (35 mL) was added to induce peptide precipitation. The resultant yellow solid was collected by centrifugation (1×10 min) and 20 mM ascorbic acid (1 mL) was then added to quench any excess iodine before analysis via RP-HPLC and mass spectrometry. Following purification by RP-HPLC (Agilent: Vydac C18 analytical column, 0→30% buffer B over 5 min then 30→40% buffer B over 60 min, $t_R$=21.5 min), selected fractions were combined and lyophilised to give the desired c[Δ$^4$A6,11]-dicarba human insulin glargine analogue 66(I) as a colourless solid (635 μg, 13%) in >99% purity. Mass spectrum (ESI$^+$, MeCN:$H_2O$:HCOOH): m/z 1004.9 [M+6H]$^{6+}$, ⅙($C_{269}H_{412}N_{72}O_{78}S_4$) requires 1004.5; 1205.4 [M+5H]$^{5+}$, ⅕($C_{269}H_{411}N_{72}O_{78}S_4$) requires 1205.2; 1506.4 [M+4H]$^{4+}$, ¼($C_{269}H_{410}N_{72}O_{78}S_4$) requires 1506.2. RP-HPLC (Agilent: Vydac C18 analytical column, 0→30% buffer B over 5 min then 30→40% buffer B over 30 min): $t_R$=18.7 min.

Isomer II:

A 20 mM solution of iodine in glacial acetic acid (2.2 mL) was added to a stirred solution of the mono-cyclic peptide 65(II) (5.0 mg, 0.81 μmol) in glacial acetic acid (5.6 mL) and 60 mM HCl (420 μL). Reaction progress was monitored by RP-HPLC and after 2.75 h, ice-cold $Et_2O$ (35 mL) was added to induce peptide precipitation. The resultant solid was collected by centrifugation (1×10 min) and 20 mM ascorbic acid (1 mL) was then added to quench any excess iodine before analysis via RP-HPLC and mass spectrometry. Following purification by RP-HPLC (Agilent: Vydac C18 analytical column, 0→25% buffer B over 5 min then 25→40% buffer B over 60 min, $t_R$=32.6 min), selected fractions were combined and lyophilised to give the desired c[Δ$_4$6,11]-dicarba human insulin glargine analogue 66(II) as a colourless solid (620 μg, 13%) in >99% purity. Mass spectrum (ESI$^+$, MeCN:$H_2O$:HCOOH): m/z 1004.8 [M+6H]$^{6+}$, ⅙($C_{269}H_{412}N_{72}O_{78}S_4$) requires 1004.5; 1205.8 [M+5H]$^{5+}$, ⅕($C_{269}H_{411}N_{72}O_{78}S_4$) requires 1205.2; 1506.9 [M+4H]$^{4+}$, ¼($C_{269}H_{410}N_{72}O_{78}S_4$) requires 1506.2. RP-HPLC (Agilent: Vydac C18 analytical column, 0→30% buffer B over 5 min then 30→40% buffer B over 30 min): $t_R$=14.6 min.

4.3 c[A6,11]-Dicarba Human Insulin Glargine Transformations 4.3.1 des$_{A1-5}$-c[A6,11]-Dicarba-[A7]-Cys($^t$Bu)-[A20]-Cys(Acm) Human Insulin

SEQ ID NO: 35

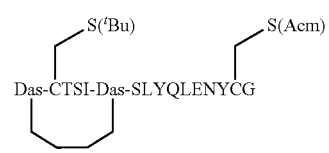

70

Resin-bound peptide 61 was subjected to the microwave-accelerated hydrogenation procedure outlined in the General Section under the following conditions: Resin-bound 61 (0.52 g, 0.20 mmol), DCM (4.5 mL), MeOH (0.5 mL), Wilkinsons catalyst, $H_2$ (80 psi), 80 W μwave, 80° C., 4 h, 100% conversion into 70. Post metathesis, a small aliquot of resin-bound peptide was subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The dried aliquot of Fmoc-deprotected resin-tethered peptide was subjected to TFA-mediated cleavage (General Section) for RP-HPLC and mass spectral analysis. This supported formation of the saturated carbocycle 70. Mass spectrum (ESI$^+$, MeCN:$H_2O$:HCOOH): m/z 945.0 [M+2H]$^{2+}$, ½($C_{83}H_{131}N_{19}O_{27}S_2$) requires 944.9. RP-HPLC (Agilent: Vydac C18 analytical column, 15→45% buffer B over 30 min): $t_R$=18.7 min.

4.3.2 c[A6,11]-Dicarba-[A7]-Cys($^t$Bu)-[A20]-Cys(Acm) Human Insulin Glargine A-Chain 71

SEQ ID NO: 37

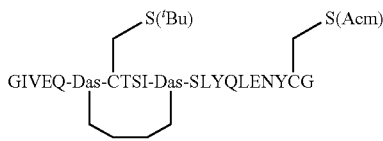

71

The automated, microwave-accelerated procedure outlined in the General Section was used to attach the remaining 5 residues on resin-bound peptide 70 (0.55 g, 0.10 mmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 71

| Reagent | Total volume (mL) | Mass (g) or Volume (mL) | Reaction Time (min) |
|---|---|---|---|
| 0.5M HATU in DMF | 6.0 | 1.14 g | — |
| 2M DIPEA in NMP | 3.0 | 1.0 mL | — |
| Fmoc-L-Gly-OH | 3.0 | 0.178 g | 12 |
| Fmoc-L-Gln(Trt)-OH | 3.0 | 0.367 g | 12 |
| Fmoc-L-Glu(O$^t$Bu)-OH | 3.0 | 0.256 g | 12 |
| Fmoc-L-Ile-OH | 3.0 | 0.212 g | 12 |
| Fmoc-L-Val-OH | 3.0 | 0.204 g | 12 |

After sequence completion, the resin-bound peptide was transferred into a fritted syringe and subjected to Fmoc-deprotection in the presence of 20% v/v piperidine in DMF (7 mL; 1×1 min, 2×10 min). The resin was washed with DMF (7 mL; 5×1 min), DCM (7 mL; 3×1 min) and MeOH (7 mL; 3×1 min), then left to dry in vacuo for 1 h. The resin-bound peptide (0.49 g) was subjected to TFA-mediated cleavage (General Section), and RP-HPLC and mass spectral analysis of the resultant solid (100 mg) supported formation of the desired peptide 71 in 45% purity. Mass spectrum (ESI$^+$, MeCN:H$_2$O: HCOOH): m/z 805.6 [M+H]$^+$, $C_{106}H_{170}N_{25}O_{35}S_2$ requires 805.7; 1208.4 [M+2H]$^{2+}$, ½($C_{106}H_{169}N_{25}O_{35}S_2$) requires 1208.1. RP-HPLC (Agilent: Vydac C18 analytical column, 15→45% buffer B over 30 min): $t_R$=19.2 min.

4.3.3 c[A6,11]-Dicarba-[A7]-Cys(Pyr)-[A20]-Cys(Acm) Human Insulin Glargine A-Chain 72

SEQ ID NO: 37

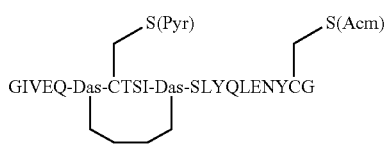

72

A solution of ice-cold TFA:TfOH (3 mL; 4:1) was added to a stirred solution of the cyclic peptide 71 (100 mg, 37.9 μmol) and 2,2'-DPDS (83.5 mg, 0.38 mmol) in TFA:anisol (3 mL; 9:1) at 0° C. After 1.5 h, the reaction mixture was reduced under a constant stream of air and ice-cold Et$_2$O (40 mL) was added to induce peptide precipitation. The resultant solid was collected by centrifugation (3×10 min), lyophilised and analysed by RP-HPLC and mass spectrometry, which supported formation of S-activated peptide 72. Following purification by RP-HPLC (Agilent: Vydac C18 preparative column, 15→45% buffer B over 30 min, $t_R$=21.6 min), selected fractions were combined and lyophilised to give the desired peptide as a colourless solid in 56% purity. Repurification of the isolated solid (Agilent: Vydac C18 analytical column, 15→45% buffer B over 30 min: $t_R$=18.1 min) then gave the saturated insulin analogue 72 as a colourless solid (1.0 mg, 1%) in >99% purity. Mass spectrum (ESI$^+$, MeCN:H$_2$O: HCOOH): m/z 823.6 [M+H]$^+$, $C_{107}H_{165}N_{26}O_{35}S_3$ requires 823.4; 1234.3 [M+2H]$^{2+}$, ½($C_{107}H_{164}N_{26}O_{35}S_3$) requires 1234.6. RP-HPLC (Agilent: Vydac C18 analytical column 15→45% buffer B over 30 min): $t_R$=17.8 min.

4.3.4 The monocyclic A-B Heterodimer of c[A6,11]-Dicarba Human Insulin

SEQ ID NO: 40

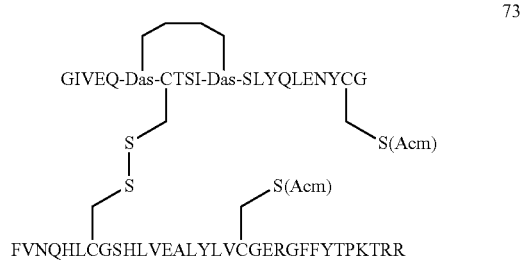

73

The modified insulin A-chain 72 (1.00 mg, 0.41 μmol) in 50 mM NH$_4$HCO$_3$ (500 μL) was added dropwise to a stirred solution of the modified insulin B-chain 64 (1.55 mg, 0.41 μmol) in H$_2$O:MeCN (1.5 mL; 9:1). Reaction progress was monitored by RP-HPLC and mass spectrometry, and after 1.5 h the oxidation was terminated by addition of AcOH. Mass spectrum (ESI$^+$, MeCN:H$_2$O:HCOOH): m/z 1028.9 [M+6H]$^{6+}$, ⅙($C_{275}H_{426}N_{74}O_{80}S_4$) requires 1028.8; 1235.5 [M+5H]$^{5+}$, ⅕($C_{275}H_{426}N_{74}O_{80}S_4$) requires 1234.4; 1542.8 [M+4H]$^{4+}$, ¼($C_{275}H_{426}N_{74}O_{80}S_4$) requires 1542.8. RP-HPLC (Agilent: Vydac C18 analytical column, 0→25% buffer B over 5 min then 25→45% buffer B over 30 min): $t_R$=20.1 min.

4.3.5 c[A6,11]-Dicarba Human Insulin Glargine 74

SEQ ID NO: 42

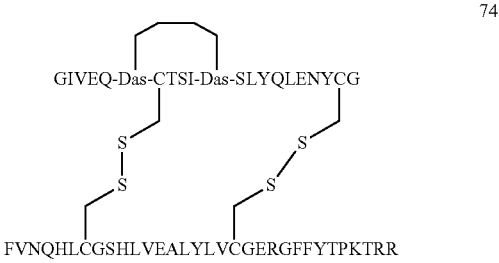

74

A 20 mM solution of iodine in glacial acetic acid (1.0 mL) was added to a stirred solution of the mono-cyclic peptide 73 (2.4 mg, 0.41 μmol) in glacial acetic acid (2.7 mL) and 60 mM HCl (200 μL). Reaction progress was monitored by RP-HPLC and after 2.75 h, ice-cold Et$_2$O (35 mL) was added to induce peptide precipitation. The resultant yellow solid was collected by centrifugation (1×10 min) and 20 mM ascorbic acid (1 mL) was then added to quench any excess iodine before analysis via RP-HPLC and mass spectrometry. Following purification by RP-HPLC (Agilent: Vydac C18 analytical column, 0→25% buffer B over 5 min then 25→40% buffer B over 60 min, $t_R$=33.4 min), selected fractions were combined and lyophilised to give c[A6,11]-dicarba human insulin glargine 74 as a colourless solid (320 μg, 14%) in >99% purity. Mass spectrum (ESI$^+$, MeCN:H$_2$O:HCOOH): m/z 1005.0 [M+6H]$^{6+}$, ⅙($C_{269}H_{414}N_{72}O_{78}S_4$) requires 1004.8; 1206.3 [M+5H]$^{5+}$, ⅕($C_{269}H_{413}N_{72}O_{78}S_4$) requires 1205.6; 1507.1 [M+4H]$^{4+}$, ¼($C_{269}H_{414}N_{72}O_{78}S_4$) requires 1506.7. RP-HPLC (Agilent: Vydac C18 analytical column, 0→30% buffer B over 5 min then 30→40% buffer B over 30 min): $t_R$=14.7 min.

4.4 c[Δ⁴A6,11]-Dicarba Human Insulin Lispro Transformations

4.4.1 des$_{A1-5}$-[A6,11]-Agl-[A7]-Cys($^t$Bu)-[A20]-Cys(Acm) Human Insulin A-Chain 80

SEQ ID NO: 10

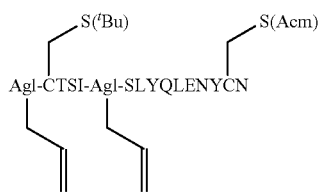

The automated, microwave-accelerated procedure outlined in the General Section was used for the synthesis of peptide 80 on Fmoc-Asn(Trt)-PEG-PS resin (1.18 g, 0.20 mmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 80

| Reagent | Total volume (mL) | Mass (g) or Volume (mL) | Reaction Time (min) |
|---|---|---|---|
| 0.5M HATU in DMF | 34 | 6.46 g | — |
| 2M DIPEA in NMP | 17 | 5.9 mL | — |
| Fmoc-L-Asn(Trt)-OH | 6 | 0.72 g | 12 |
| Fmoc-L-Agl-OH | 11 | 0.74 g | 12 |
| Fmoc-L-Cys(Acm)-OH | 6 | 0.50 g | 12 |
| Fmoc-L-Cys($^t$Bu)-OH | 6 | 0.48 g | 12 |
| Fmoc-L-Gln(Trt)-OH | 6 | 0.73 g | 12 |
| Fmoc-L-Glu(O$^t$Bu)-OH | 6 | 0.51 g | 12 |
| Fmoc-L-Ile-OH | 6 | 0.42 g | 12 |
| Fmoc-L-Leu-OH | 11 | 0.78 g | 12 |
| Fmoc-L-Ser($^t$Bu)-OH | 11 | 0.84 g | 12 |
| Fmoc-L-Thr($^t$Bu)-OH | 6 | 0.48 g | 12 |
| Fmoc-L-Tyr($^t$Bu)-OH | 11 | 1.01 g | 12 |

After sequence completion, the resin-bound peptide was transferred into a fritted syringe and treated with an acetic anhydride solution (7 mL; DMF:acetic anhydride:NMM; 94:5:1) for 2 h. The resin was then washed with DMF (7 mL; 3×1 min), DCM (7 mL; 3×1 min) and MeOH (7 mL; 3×1 min), then left to dry in vacuo for 1 h. Prior to treatment with MeOH, a small aliquot of the resin-bound peptide was removed and subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The dried aliquot of Fmoc-deprotected resin-tethered peptide was subjected to TFA-mediated cleavage (General Section) for RP-HPLC and mass spectral analysis. This supported formation of the desired peptide 80 in 80% purity. Mass spectrum (ESI$^+$, MeCN:H$_2$O:HCOOH): m/z 986.5 [M+2H]$^{2+}$, ½(C$_{87}$H$_{136}$N$_{20}$O$_{28}$S$_2$) requires 986.5. RP-HPLC (Agilent: Vydac C18 analytical column, 15→45% buffer B over 30 min): t$_o$=18.5 min.

4.4.2 des$_{A1-5}$-c[Δ⁴A6,11]-Dicarba-[A7]-Cys($^t$Bu)-[A20]-Cys(Acm) Human Insulin A-Chain 81

SEQ ID NO: 13

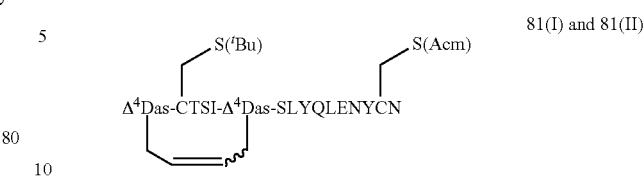

Resin-bound peptide 80 was subjected to the microwave-accelerated RCM procedure outlined in the General Section under the following conditions: Resin-bound 80 (1.82 g, 0.20 μmol), DCM (13 mL), 0.4 M LiCl in DMF (0.6 mL), 2$^{nd}$ generation Grubbs' catalyst (34 mg, 40 μmol), 100 W μwave, 100° C., 2 h, 100% conversion into 81. Post metathesis, a small aliquot of resin-bound peptide was subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The dried aliquot of Fmoc-deprotected resin-tethered peptide was subjected to TFA-mediated cleavage (General Section) for RP-HPLC and mass spectral analysis. This supported formation of the desired peptide as two isomers, 81(I) and 81(II), in a 75:25 ratio. 81(I): Mass spectrum (ESI$^+$, MeCN:H$_2$O:HCOOH): m/z 972.6 [M+2H]$^{2+}$, ½(C$_{85}$H$_{132}$N$_{20}$O$_{28}$S$_2$) requires 972.4. RP-HPLC (Agilent: Vydac C18 analytical column, 15→45% buffer B over 30 min): t$_R$=17.3 min. 81(II): Mass spectrum (ESI$^+$, MeCN:H$_2$O:HCOOH): m/z 972.6 [M+2H]$^{2+}$, ½(C$_{85}$H$_{132}$N$_{20}$O$_{28}$S$_2$) requires 972.4. RP-HPLC (Agilent: Vydac C18 analytical column, 15→45% buffer B over 30 min): t$_R$=17.5 min.

4.4.3 c[Δ⁴A6,11]-Dicarba-[A7]-Cys($^t$Bu)-[A20]-Cys(Acm) Human Insulin A-Chain 82

SEQ ID NO: 2

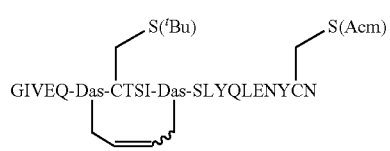

The automated, microwave-accelerated procedure outlined in the General Section was used to attach the remaining 5 residues on resin-bound peptide 81 (1.66 g, 0.20 μmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 82

| Reagent | Total volume (mL) | Mass (g) or Volume (mL) | Reaction Time (min) |
|---|---|---|---|
| 0.5M HATU in DMF | 11.0 | 2.10 g | — |
| 2M DIPEA in NMP | 6.0 | 2.1 mL | — |
| Fmoc-L-Gly-OH | 6.0 | 0.36 g | 12 |
| Fmoc-L-Gln(Trt)-OH | 6.0 | 0.73 g | 12 |
| Fmoc-L-Glu(O$^t$Bu)-OH | 6.0 | 0.51 g | 12 |

TABLE-continued

Quantities of reagents and amino acids used in the synthesis of peptide 82

| Reagent | Total volume (mL) | Mass (g) or Volume (mL) | Reaction Time (min) |
|---|---|---|---|
| Fmoc-L-Ile-OH | 6.0 | 0.42 g | 12 |
| Fmoc-L-Val-OH | 6.0 | 0.41 g | 12 |

After sequence completion, the resin-bound peptide was transferred into a fritted syringe and subjected to Fmoc-deprotection in the presence of 20% v/v piperidine in DMF (7 mL; 1×1 min, 2×10 min). The resin was washed with DMF (7 mL; 5×1 min), DCM (7 mL; 3×1 min) and MeOH (7 mL; 3×1 min), then left to dry in vacuo for 1 h. The resin-bound peptide (1.50 g) was subjected to TFA-mediated cleavage (General Section) and RP-HPLC and mass spectral analysis of the resultant pale brown solid (241 mg) supported formation of the desired peptide as two isomers, 82(I) and 82(II), in a 75:25 ratio. 82(I): Mass spectrum (ESI$^+$, MeCN:H$_2$O:HCOOH): m/z 824.2 [M+3H]$^{3+}$, ⅓(C$_{108}$H$_{171}$N$_{26}$O$_{36}$S$_2$) requires 824.1; 1235.6 [M+2H]$^{2+}$, ½(C$_{108}$H$_{170}$N$_{26}$O$_{36}$S$_2$) requires 1235.6. RP-HPLC (Agilent: Vydac C18 analytical column, 15→45% buffer B over 30 min): $t_R$=18.2 min. 82(II): Mass spectrum (ESI$^+$, MeCN:H$_2$O:HCOOH): m/z 824.3 [M+3H]$^{3+}$, ⅓(C$_{108}$H$_{171}$N$_{26}$O$_{36}$S$_2$) requires 824.1; 1235.6 [M+2H]$^{2+}$, ½(C$_{108}$H$_{170}$N$_{26}$O$_{36}$S$_2$) requires 1235.6. RP-HPLC (Agilent: Vydac C18 analytical column, 15→45% buffer B over 30 min): $t_R$=19.2 min.

4.4.4 c[$\Delta^4$A6,11]-Dicarba-[A7]-Cys(Pyr)-[A20]-Cys(Acm) Human Insulin A-Chain 83

SEQ ID NO: 2

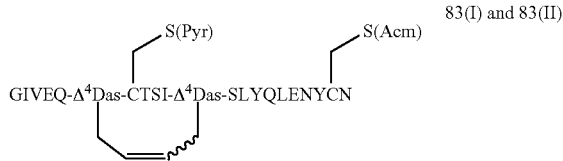

83(I) and 83(II)

A solution of ice-cold TFA:TfOH (7 mL; 4:1) was added to a stirred solution of the cyclic peptide 82 (241 mg, 97.5 μmol) and 2,2'-DPDS (225 mg, 975 μmol) in TFA:anisol (7 mL; 9:1) at 0° C. After 1.5 h, the reaction mixture was reduced under a constant stream of air and ice-cold Et$_2$O (35 mL) was added to induce peptide precipitation. The resultant solid was then collected by centrifugation (3×6 min) and analysed by RP-HPLC and mass spectrometry. This supported formation of the S-activated peptide 83 as two isomers, 83(I) and 83(II), in a 75:25 ratio. Following purification by RP-HPLC (Agilent: Vydac C18 preparative column, 15→45% buffer B over 30 min, $t_R$=22.5 and 23.7 min), selected fractions were combined and lyophilised to give two isomers, 83(I) and 83(II), of the desired peptide as colourless solids (83(I): 26 mg, 11% and 83(II): 9.8 mg, 4%) in 92% and 46% purity respectively. 83(I): Mass spectrum (ESI$^+$, MeCN:H$_2$O:HCOOH): m/z 1261.9 [M+2H]$^{2+}$, ½(C$_{109}$H$_{165}$N$_{27}$O$_{36}$S$_3$) requires 1262.1. RP-HPLC (Agilent: Vydac C18 analytical column, 15→45% buffer B over 30 min): $t_R$=16.7 min. 83(II): Mass spectrum (ESI$^+$, MeCN:H$_2$O:HCOOH): m/z 1262.1 [M+2H]$^{2+}$, ½(C$_{109}$H$_{165}$N$_{27}$O$_{36}$S$_3$) requires 1262.1. RP-HPLC (Agilent: Vydac C18 analytical column, 15→45% buffer B over 30 min): $t_R$=18.2 min. Repurification of peptide 83(II) (Agilent: Vydac C18 preparative column, 15→45% buffer B over 30 min: $t_R$=21.7 min, and then Agilent: Vydac C18 analytical column, 15→45% buffer B over 30 min: $t_R$=18.1 min) then gave the required A-chain isomer 83(II) as a colourless solid (1.5 mg, 0.6%) in >99% purity. Spectral data were consistent with those reported previously.

4.4.5 [B19]-Cys(Acm) Human Insulin Lispro B-Chain 84

SEQ ID NO: 103

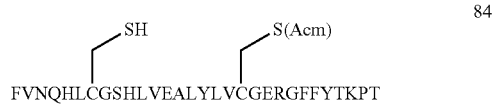

84

FVNQHLCGSHLVEALYLVCGERGFFYTKPT

The automated, microwave-accelerated procedure outlined in the General Section was used for the synthesis of peptide 84 on Fmoc-Thr($^t$Bu)-PEG-PS resin (1.11 g, 0.20 mmol). Quantities of HBTU, HOBt, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 84

| Reagent | Total volume (mL) | Mass (g) or Volume (mL) | Reaction Time (min) |
|---|---|---|---|
| 0.5M HBTU:HOBt in DMF | 67 | 12.71:4.53 g | — |
| 2M DIPEA in NMP | 34 | 11.8 mL | — |
| Fmoc-L-Ala-OH | 6 | 0.37 g | 12 |
| Fmoc-L-Arg(Pbf)-OH | 11 | 1.43 g | 12 |
| Fmoc-L-Asn(Trt)-OH | 6 | 0.72 g | 12 |
| Fmoc-L-Cys(Acm)-OH | 6 | 0.50 g | 12 |
| Fmoc-L-Cys(Trt)-OH | 6 | 0.73 g | 12 |
| Fmoc-L-Gln(Trt)-OH | 6 | 0.73 g | 12 |
| Fmoc-L-Glu(O$^t$Bu)-OH | 11 | 0.94 g | 12 |
| Fmoc-L-Gly-OH | 16 | 0.95 g | 12 |
| Fmoc-L-His(Boc)-OH | 11 | 1.36 g | 12 |
| Fmoc-L-Leu-OH | 21 | 1.48 g | 12 |
| Fmoc-L-Lys(Boc)-OH | 6 | 0.56 g | 12 |
| Fmoc-L-Phe-OH | 16 | 1.24 g | 12 |
| Fmoc-L-Pro-OH | 6 | 0.40 g | 12 |
| Fmoc-L-Ser($^t$Bu)-OH | 6 | 0.46 g | 12 |
| Fmoc-L-Thr($^t$Bu)-OH | 6 | 0.48 g | 12 |
| Fmoc-L-Tyr($^t$Bu)-OH | 11 | 1.01 g | 12 |
| Fmoc-L-Val-OH | 16 | 1.09 g | 12 |

After sequence completion, the resin was transferred into a fritted syringe, washed with DMF (7 mL; 3×1 min), DCM (7 mL; 3×1 min) and MeOH (7 mL; 3×1 min), then left to dry in vacuo for 1 h. A small aliquot of resin-bound peptide was subjected to the cleavage procedure outlined in the General Experimental Section for RP-HPLC and mass spectral analysis. This supported formation of the desired peptide 84 in 75% purity. Following global Fmoc-deprotection and TFA-mediated cleavage of the remaining peptide 84 from the resin (2.17 g), the resultant pale yellow solid (630 mg) was purified by RP-HPLC (Agilent: Vydac C18 preparative column, 25→45% buffer B over 30 min, $t_R$=19.8 min). Selected fractions were combined and lyophilised to give the desired peptide 84 as a colourless solid (82 mg, 12%) in 94% purity. Mass spectrum (ESI$^+$, MeCN:H$_2$O): m/z 701.4 [M+5H]$^{5+}$, $\frac{1}{5}$(C$_{161}$H$_{244}$N$_{41}$O$_{43}$S$_2$) requires 700.8; 876.0 [M+4H]$^{4+}$, C$_{161}$H$_{243}$N$_{41}$O$_{43}$S$_2$ requires 875.7; 1167.7 [M+3H]$^{3+}$, $\frac{1}{3}$(C$_{161}$H$_{242}$N$_{41}$O$_{43}$S$_2$) requires 1167.2. RP-HPLC (Agilent: Vydac C18 analytical column, 20→50% buffer B over 30 min): $t_R$=15.7 min.

4.4.6 The Monocyclic A-B Heterodimer of c[Δ$^4$A6,11]-Dicarba Human Insulin Lispro 85

SEQ ID NO: 105

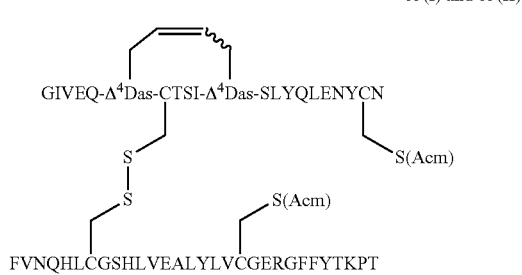

85(I) and 85(II)

Isomer I:

The modified insulin A-chain 83(I) (26 mg, 10.3 µmol) in 50 mM NH$_4$HCO$_3$ (13 mL) was added dropwise to a stirred solution of the modified insulin B-chain 84 (36 mg, 10.3 µmol) in H$_2$O:MeCN (36 mL; 9:1). Reaction progress was monitored by RP-HPLC and mass spectrometry and after 3 h, the oxidation was terminated by addition of AcOH. The reaction mixture was then lyophilised to give a pale yellow solid (62 mg). Mass spectrum (ESI$^+$, MeCN:H$_2$O:HCOOH): m/z 1183.6 [M+5H]$^{5+}$, $\frac{1}{5}$(C$_{265}$H$_{402}$N$_{67}$O$_{79}$S$_4$) requires 1183.0; 1478.7 [M+4H]$^{4+}$, $\frac{1}{4}$(C$_{265}$H$_{401}$N$_{67}$O$_{79}$S$_4$) requires 1478.5. RP-HPLC (Agilent: Vydac C18 analytical column, 0→25% buffer B over 5 min then 25→45% buffer B over 30 min): $t_R$=20.3 min.

Isomer II:

The modified insulin A-chain 83(II) (1.5 mg, 0.59 µmol) in 50 mM NH$_4$HCO$_3$ (750 µL) was added dropwise to a stirred solution of the modified insulin B-chain 84 (2.08 mg, 0.59 µmol) in H$_2$O:MeCN (2.1 mL; 9:1). Reaction progress was monitored by RP-HPLC and mass spectrometry and after 3 h, the oxidation was terminated by addition of AcOH. The reaction mixture was then lyophilised to give a pale yellow solid (5 mg). Mass spectrum (ESI$^+$, MeCN:H$_2$O:HCOOH): m/z 1183.5 [M+5H]$^{5+}$, $\frac{1}{5}$(C$_{265}$H$_{402}$N$_{67}$O$_{79}$S$_4$) requires 1183.0; 1479.1 [M+4H]$^{4+}$, $\frac{1}{4}$(C$_{265}$H$_{401}$N$_{67}$O$_{79}$S$_4$) requires 1478.5; 1971.3 [M+3H]$^{3+}$, $\frac{1}{3}$(C$_{265}$H$_{400}$N$_{67}$O$_{79}$S$_4$) requires 1970.9. RP-HPLC (Vydac C18 analytical column, 0→25% buffer B over 5 min then 25→50% buffer B over 30 min): $t_R$=20.7 min.

4.4.7 c[Δ$^4$A6,11]-Dicarba Human Insulin Lispro 86

SEQ ID NO: 107

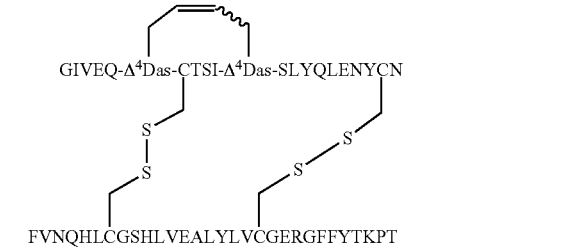

86(I)$_{A/B}$ and 86(II)$_{A/B}$

Isomer IA and IB:

A 20 mM solution of iodine in glacial acetic acid (13.8 mL) was added to a stirred solution of the monocyclic peptide 85(I) (31 mg, 5.24 µmol) in glacial acetic acid (34.8 mL) and 60 mM HCl (2.7 mL). Reaction progress was monitored by RP-HPLC and after 2.75 h, ice-cold Et$_2$O (5×35 mL) was added to induce peptide precipitation. The resultant yellow solid was collected by centrifugation (1×10 min) and 20 mM ascorbic acid (1 mL) was then added to quench any excess iodine before analysis via RP-HPLC and mass spectrometry.

The remaining A-B conjugate 85(I) (31 mg, 5.24 µmol) in glacial acetic acid (34.8 mL) and 60 mM HCl (2.7 mL) was subjected to identical reaction conditions in the presence of a 20 mM solution of iodine in glacial acetic acid (138 mL), and the combined batches were then purified by RP-HPLC (Agilent: Vydac C18 analytical column, 0→25% buffer B over 5 min then 25→40% buffer B over 60 min: $t_R$=34.6 and 35.5 min). Selected fractions were combined and lyophilised to give two isomers, 86(I)$_A$ and 86(I)$_B$, of the desired c[Δ$^4$A6,11]-dicarba human insulin lispro analogue as colourless solids (86(I)$_A$: 2.87 mg, 5% and 86(I)$_B$: 3.65 mg, 6%) in >99% purity. 86(I)$_A$: Mass spectrum (ESI$^+$, MeCN:H$_2$O:HCOOH): m/z 1154.6 [M+5H]$^{5+}$, $\frac{1}{5}$(C$_{259}$H$_{390}$N$_{65}$O$_{77}$S$_4$) requires 1154.1; 1442.9 [M+4H]$^{4+}$, $\frac{1}{4}$(C$_{259}$H$_{389}$N$_{65}$O$_{77}$S$_4$) requires 1442.4; 1923.7 [M+3H]$^{3+}$, $\frac{1}{3}$(C$_{259}$H$_{388}$N$_{65}$O$_{77}$S$_4$) requires 1922.9. RP-HPLC (Agilent: Vydac C18 analytical column, 0→30% buffer B over 5 min then 30→40% buffer B over 30 min): $t_R$=18.4 min. 86(I)$_B$: Mass spectrum (ESI$^+$, MeCN:H$_2$O:HCOOH): m/z 1154.7 [M+5H]$^{5+}$, $\frac{1}{5}$(C$_{259}$H$_{390}$N$_{65}$O$_{77}$S$_4$) requires 1154.1; 1443.0 [M+4H]$^{4+}$, $\frac{1}{4}$(C$_{259}$H$_{389}$N$_{65}$O$_{77}$S$_4$) requires 1442.4; 1923.7 [M+3H]$^{3+}$, $\frac{1}{3}$(C$_{259}$H$_{388}$N$_{65}$O$_{77}$S$_4$) requires 1922.9. RP-HPLC (Agilent: Vydac C18 analytical column, 0→30% buffer B over 5 min then 30→40% buffer B over 30 min): $t_R$=19.1 min.

Isomer IIA and IIB:

The iodine-catalysed disulfide oxidation was carried out according to a procedure described by Lin et al.[324] A 20 mM solution of iodine in glacial acetic acid (2.2 mL) was added to a stirred solution of the mono-cyclic peptide 85(II) (5.0 mg, 0.85 µmol) in glacial acetic acid (5.7 mL) and 60 mM HCl (420 µL). Reaction progress was monitored by RP-HPLC and after 2.75 h, ice-cold Et$_2$O (35 mL) was added to induce peptide precipitation. The resultant solid was collected by centrifugation (1×10 min) and 20 mM ascorbic acid (1 mL) was then added to quench any excess iodine before analysis via RP-HPLC and mass spectrometry. Following purification by RP-HPLC (Agilent: Vydac C18 analytical column, 0→25% buffer B over 5 min then 25→45% buffer B over 60 min, $t_R$=32.9 and 33.5 min), selected fractions were combined and lyophilised to give two isomers (86(II)$_A$ and 86(II)$_B$) of the desired c[Δ$^4$A6,11]-dicarba human insulin lispro analogue as colourless solids (86(II)$_A$: 0.15 mg, 3% and 86(II)$_B$: 0.22 mg, 5%) in 95% and >99% purity respectively.

86(II)$_A$: Mass spectrum (ESI$^+$, MeCN:H$_2$O:HCOOH): m/z 1154.7 [M+5H]$^{5+}$, $\frac{1}{5}$(C$_{259}$H$_{390}$N$_{65}$O$_{77}$S$_4$) requires 1154.1; 1443.1 [M+4H]$^{4+}$, $\frac{1}{4}$(C$_{259}$H$_{389}$N$_{65}$O$_{77}$S$_4$) requires 1442.4. RP-HPLC (Agilent: Vydac C18 analytical column, 0→30% buffer B over 5 min then 30→40% buffer B over 30 min): t$_R$=14.7 min. 86(II)$_B$: Mass spectrum (ESI$^+$, MeCN:H$_2$O: HCOOH): m/z 1154.8 [M+5H]$^{5+}$, $\frac{1}{5}$(C$_{259}$H$_{390}$N$_{65}$O$_{77}$S$_4$) requires 1154.1; 1442.9 [M+4H]$^{4+}$, $\frac{1}{4}$(C$_{259}$H$_{389}$N$_{65}$O$_{77}$S$_4$) requires 1442.4; 1923.8 [M+3H]$^{3+}$, $\frac{1}{3}$(C$_{259}$H$_3$O$_{65}$O$_{77}$S$_4$) requires 1922.9. RP-HPLC (Agilent: Vydac C18 analytical column, 0→30% buffer B over 5 min then 30→40% buffer B over 30 min): t$_R$=15.1 min.

4.5 c[A6,11]-Dicarba Human Insulin Lispro Transformations 4.5.1 des$_{A1-5}$-c[A6,11]-Dicarba-[A7]-Cys($^t$Bu)-[A20]-Cys(Acm) Human Insulin A-Chain 90

SEQ ID NO: 15

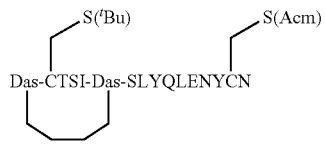

90

Resin-bound peptide 81 was subjected to the microwave-accelerated hydrogenation procedure outlined in the General Section under the following conditions: Resin-bound 81 (792 mg, 100 µmol), DCM (4.5 mL), MeOH (0.5 mL), Wilkinsons catalyst, H$_2$ (90 psi), 100 W µwave, 100° C., 2 h, 95% conversion into 90. Post metathesis, a small aliquot of resin-bound peptide was subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The dried aliquot of Fmoc-deprotected resin-tethered peptide was subjected to TFA-mediated cleavage (General Section) for RP-HPLC and mass spectral analysis. This supported formation of the saturated carbocycle 90. Mass spectrum (ESI$^+$, MeCN:H$_2$O: HCOOH): m/z 973.6 [M+2H]$^{2+}$, $\frac{1}{2}$(C$_{85}$H$_{134}$N$_{20}$O$_{28}$S$_2$) requires 973.5. RP-HPLC (Agilent: Vydac C18 analytical column, 15→45% buffer B over 30 min): t$_R$=18.2 min.

4.5.2 c[A6,11]-Dicarba-[A7]-Cys($^t$Bu)-[A20]-Cys(Acm) Human Insulin A-Chain

SEQ ID NO: 16

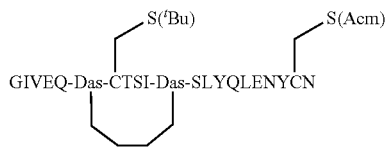

91

The automated, microwave-accelerated procedure outlined in the General Section was used to attach the remaining 5 residues on resin-bound peptide 90 (1.69 g, 200 µmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 91

| Reagent | Total volume (mL) | Mass (g) or Volume (mL) | Reaction Time (min) |
| --- | --- | --- | --- |
| 0.5M HATU in DMF | 11.0 | 2.10 g | — |
| 2M DIPEA in NMP | 6.0 | 2.1 mL | — |
| Fmoc-L-Gly-OH | 6.0 | 0.36 g | 12 |
| Fmoc-L-Gln(Trt)-OH | 6.0 | 0.73 g | 12 |
| Fmoc-L-Glu(O$^t$Bu)-OH | 6.0 | 0.51 g | 12 |
| Fmoc-L-Ile-OH | 6.0 | 0.42 g | 12 |
| Fmoc-L-Val-OH | 6.0 | 0.41 g | 12 |

After sequence completion, the resin-bound peptide was transferred into a fritted syringe and subjected to Fmoc-deprotection in the presence of 20% v/v piperidine in DMF (7 mL; 1×1 min, 2×10 min). The resin was washed with DMF (7 mL; 5×1 min), DCM (7 mL; 3×1 min) and MeOH (7 mL; 3×1 min), then left to dry in vacuo for 1 h. The resin-bound peptide (1.51 g) was subjected to TFA-mediated cleavage (General Section) and RP-HPLC and mass spectral analysis of the isolated pale brown solid (220 mg) supported formation of the desired peptide 91 in 70% purity. Mass spectrum (ESI$^+$, MeCN:H$_2$O:HCOOH): m/z 824.7 [M+3H]$^{3+}$, $\frac{1}{3}$(C$_{108}$H$_{173}$N$_{26}$O$_{36}$S$_2$) requires 824.7; 1236.8 [M+2H]$^{2+}$, $\frac{1}{2}$(C$_{108}$H$_{172}$N$_{26}$O$_{36}$S$_2$) requires 1236.6. RP-HPLC (Agilent: Vydac C18 analytical column, 15→45% buffer B over 30 min): t$_R$=18.7 min.

4.5.3 c[A6,11]-Dicarba-[A7]-Cys(Pyr)-[A20]-Cys(Acm) Human Insulin A-Chain 92

SEQ ID NO: 16

92(I) and 92(II)

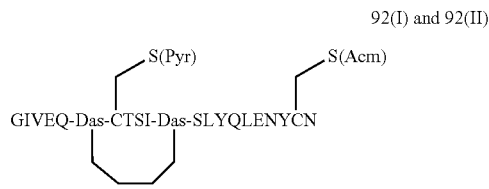

A solution of ice-cold TFA:TfOH (7 mL; 4:1) was added to a stirred solution of the cyclic peptide 91 (220 mg, 89.0 µmol) and 2,2'-DPDS (205 mg, 890 µmol) in TFA:anisol (7 mL; 9:1) at 0° C. After 1.5 h, the reaction mixture was reduced under a constant stream of air and ice-cold Et$_2$O (35 mL) was added to induce peptide precipitation. The resultant solid was then collected by centrifugation (3×6 min) and analysed by RP-HPLC and mass spectrometry. This supported formation of the saturated S-activated carbocycle 92. Mass spectrum (ESI$^+$, MeCN:H$_2$O:HCOOH): m/z 1263.1 [M+2H]$^{2+}$, $\frac{1}{2}$(C$_{109}$H$_{167}$N$_{27}$O$_{36}$S$_3$) requires 1263.1. RP-HPLC (Agilent: Vydac C18 analytical column, 15→45% buffer B over 30 min): t$_R$=17.5 min.

4.6 c[Δ⁴A6,11]-Dicarba-[A21]-Xaa Human Insulin Transformations

4.6.1 The Monocyclic A-B Heterodimer of c[Δ⁴A6,11]-dicarba-[A21]-Gly Human Insulin 100

SEQ ID NO: 44

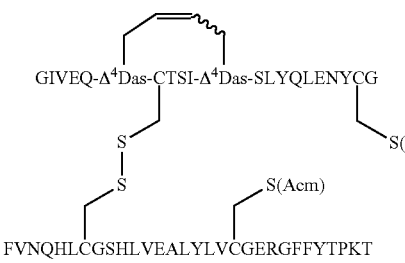

100(I)

Isomer I:

The modified insulin A-chain 63(I) (1.0 mg, 0.4 µmol) in 50 mM $NH_4HCO_3$ (500 µL) was added dropwise to a stirred solution of the modified insulin B-chain 11 (1.42 mg, 0.4 µmol) in $H_2O$:MeCN (1.5 mL; 9:1). Reaction progress was monitored by RP-HPLC and mass spectrometry, and after 2 h the oxidation was terminated by addition of AcOH. Mass spectrum (ESI⁺, MeCN:$H_2O$:HCOOH): m/z 1172.3 $[M+5H]^{5+}$, ⅕($C_{263}H_{399}N_{66}O_{78}S_4$) requires 1171.6; 1464.6 $[M+4H]^{4+}$, ¼($C_{263}H_{398}N_{66}O_{78}S_4$) requires 1464.2. RP-HPLC (Agilent: Vydac O18 analytical column, 0→25% buffer B over 5 min then 25→45% buffer B over 30 min): $t_R$=21.1 min.

4.6.2 c[Δ⁴A6,11]-Dicarba-[A21]-Gly Human Insulin 101

SEQ ID NO: 45

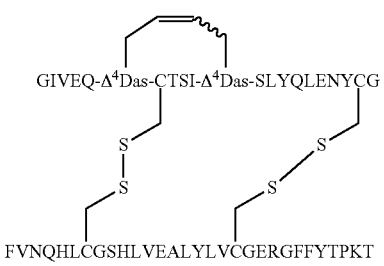

101(I)

Isomer I:

A 20 mM solution of iodine in glacial acetic acid (1.0 mL) was added to a stirred solution of the mono-cyclic peptide 100(I) (2.4 mg, 0.41 µmol) in glacial acetic acid (2.7 mL) and 60 mM HCl (200 µL). Reaction progress was monitored by RP-HPLC and after 2.75 h, ice-cold $Et_2O$ (35 mL) was added to induce peptide precipitation. The resultant yellow solid was collected by centrifugation (1×10 min) and 20 mM ascorbic acid (1 mL) was then added to quench any excess iodine before analysis via RP-HPLC and mass spectrometry. Following purification by RP-HPLC (Agilent: Vydac C18 analytical column, 0→25% buffer B over 5 min then 25→40% buffer B over 60 min, $t_R$=23.0 min), selected fractions were combined and lyophilised to give the desired c[Δ⁴A6,11]-[A21]-Gly dicarba human insulin analogue 101(I) as a colourless solid (290 µg, 9%) in >99% purity. Mass spectrum (ESI⁺, MeCN:$H_2O$:HCOOH): m/z 1143.2 $[M+5H]^{5+}$, ⅕($C_{257}H_{387}N_{64}O_{76}S_4$) requires 1142.7; 1428.5 $[M+4H]^{4+}$, ¼($C_{257}H_{386}N_{64}O_{76}S_4$) requires 1428.2; 1904.1 $[M+3H]^{3+}$, ⅓($C_{257}H_{385}N_{64}O_{76}S_4$) requires 1903.9. RP-HPLC (Agilent: Vydac C18 analytical column, 0→30% buffer B over 5 min then 30→40% buffer B over 30 min): $t_R$=20.5 min.

4.6.3 des$_{A1-5}$-[A6,11]-Agl-[A7]-Cys($^t$Bu)-[A20]-Cys(Acm)-[A21]-Asp Human Insulin A-Chain 102

SEQ ID NO: 46

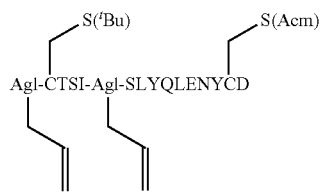

102

Esterification of Fmoc-L-Asp(O$^t$Bu)-OH (123 mg, 300 µmol) on Wang resin (91 mg, 100 µmol) was performed according to the procedure described in the General Section using DIC (47 µL, 300 µmol) and DMAP (3.7 mg, 30 µmol) for 16 h. The automated microwave-accelerated procedure was then used for the synthesis of peptide 102 on Fmoc-Asp (O$^t$Bu)-Wang resin (128 mg, 100 µmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 102

| Reagent | Total volume (mL) | Mass (g) or Volume (mL) | Reaction Time (min) |
|---|---|---|---|
| 0.5M HATU in DMF | 17.0 | 3.24 g | — |
| 2M DIPEA in NMP | 9.0 | 3.1 mL | — |
| Fmoc-L-Asn(Trt)-OH | 3.0 | 0.36 g | 12 |
| Fmoc-L-Agl-OH | 6.0 | 0.41 g | 12 |
| Fmoc-L-Cys(Acm)-OH | 3.0 | 0.25 g | 12 |
| Fmoc-L-Cys($^t$Bu)-OH | 3.0 | 0.24 g | 12 |
| Fmoc-L-Gln(Trt)-OH | 3.0 | 0.37 g | 12 |
| Fmoc-L-Glu(O$^t$Bu)-OH | 3.0 | 0.26 g | 12 |
| Fmoc-L-Ile-OH | 3.0 | 0.21 g | 12 |
| Fmoc-L-Leu-OH | 6.0 | 0.42 g | 12 |
| Fmoc-L-Ser($^t$Bu)-OH | 6.0 | 0.46 g | 12 |
| Fmoc-L-Thr($^t$Bu)-OH | 3.0 | 0.24 g | 12 |
| Fmoc-L-Tyr($^t$Bu)-OH | 6.0 | 0.55 g | 12 |

After sequence completion, the resin-bound peptide was transferred into a fritted syringe and treated with an acetic anhydride solution (4 mL; DMF:acetic anhydride:NMM; 94:5:1) for 2 h. The resin was washed with DMF (4 mL; 3×1 min), DCM (4 mL; 3×1 min) and MeOH (4 mL; 3×1 min), then left to dry in vacuo for 1 h. Prior to treatment with MeOH, a small aliquot of the resin-bound peptide was removed and subjected to Fmoc-deprotection in the presence of 20% v/v piperidine in DMF (1 mL; 1×1 min, 2×10 min), and washed with DMF (1 mL; 5×1 min), DCM (1 mL; 3×1 min) and MeOH (1 mL; 3×1 min). The dried aliquot of Fmoc-deprotected resin-tethered peptide was subjected to TFA-mediated cleavage (General Section) and RP-HPLC and mass spectral analysis of the resultant solid supported formation of the desired peptide 102 in 70% purity. Mass spectrum (ESI$^+$, MeCN:H$_2$O:HCOOH): m/z 987.1 [M+2H]$^{2+}$, ½(C$_{87}$H$_{135}$N$_{19}$O$_{29}$S$_2$) requires 987.0. RP-HPLC (Agilent: Vydac C18 analytical column, 15→45% buffer B over 30 min): t$_R$=19.1 min.

4.6.4 des$_{A1-5}$-c[Δ$^4$A6,11]-Dicarba-[A7]-Cys($^t$Bu)-[A20]-Cys(Acm)-[A21]-Asp Human Insulin A-Chain 103

SEQ ID NO: 47

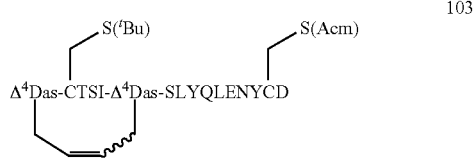

103

Resin-bound peptide 102 was subjected to the general microwave-accelerated RCM procedure outlined in the General Section under the following conditions: Resin-bound 102 (368 mg, 100 μmol), DCM (4.75 mL), 0.4 M LiCl in DMF (0.25 mL), 2$^{nd}$ generation Grubbs' catalyst (17 mg, 20 μmol), 100 W μwave, 100° C., 2 h, 100% conversion into 103. Post metathesis, a small aliquot of resin-bound peptide was subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The dried aliquot of Fmoc-deprotected resin-tethered peptide was subjected to TFA-mediated cleavage (General Section) for RP-HPLC and mass spectral analysis. This supported formation of the desired cyclic peptide 103. Mass spectrum (ESI$^+$, MeCN:H$_2$O:HCOOH): m/z 973.0 [M+2H]$^{2+}$, ½(C$_{85}$H$_{131}$N$_{19}$O$_{29}$S$_2$) requires 972.9. RP-HPLC (Agilent: Vydac C18 analytical column, 15→45% buffer B over 30 min): t$_R$=18.1 min.

4.6.5 c[Δ$^4$A6,11]-Dicarba-[A7]-Cys($^t$Bu)-[A20]-Cys(Acm)-[A21]-Asp Human Insulin A-Chain 104

SEQ ID NO: 48

104(I) and 104(II)

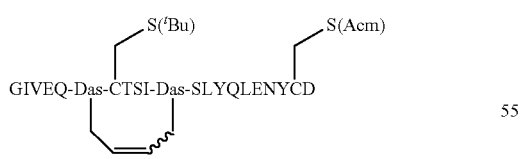

The automated, microwave-accelerated procedure outlined in the General Section was used to attach the remaining 5 residues on resin-bound peptide 103 (351 g, 100 μmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 104

| Reagent | Total volume (mL) | Mass (g) or Volume (mL) | Reaction Time (min) |
|---|---|---|---|
| 0.5M HATU in DMF | 6.0 | 1.14 g | — |
| 2M DIPEA in NMP | 3.0 | 1.0 mL | — |
| Fmoc-L-Gly-OH | 3.0 | 0.178 g | 12 |
| Fmoc-L-Gln(Trt)-OH | 3.0 | 0.367 g | 12 |
| Fmoc-L-Glu(O$^t$Bu)-OH | 3.0 | 0.256 g | 12 |
| Fmoc-L-Ile-OH | 3.0 | 0.212 g | 12 |
| Fmoc-L-Val-OH | 3.0 | 0.204 g | 12 |

After sequence completion, the resin-bound peptide was transferred into a fritted syringe and subjected to Fmoc-deprotection in the presence of 20% v/v piperidine in DMF (7 mL; 1×1 min, 2×10 min). The resin was washed with DMF (7 mL; 5×1 min), DCM (7 mL; 3×1 min) and MeOH (7 mL; 3×1 min), then left to dry in vacuo for 1 h. The resin-bound peptide (359 g) was subjected to TFA-mediated cleavage (General Section) and RP-HPLC and mass spectral analysis of the resultant pale brown solid (260 mg) supported formation of the desired peptide as two isomers, 104(I) and 104(II), in a 73:27 ratio. 104(I): Mass spectrum (ESI$^+$, MeCN:H$_2$O:HCOOH): m/z 824.8 [M+3H]$^{3+}$, ⅓(C$_{108}$H$_{170}$N$_{25}$O$_{37}$S$_2$) requires 824.4; 1236.8 [M+2H]$^{2+}$, ½(C$_{108}$H$_{169}$N$_{25}$O$_{37}$S$_2$) requires 1236.0. RP-HPLC (Agilent: Vydac C18 analytical column, 15→45% buffer B over 30 min): t$_R$=18.8 min. 104 (II): Mass spectrum (ESI$^+$, MeCN:H$_2$O:HCOOH): m/z 824.8 [M+3H]$^{3+}$, ⅓(C$_{108}$H$_{170}$N$_{25}$O$_{37}$S$_2$) requires 824.4; 1236.8 [M+2H]$^{2+}$, ½(C$_{108}$H$_{169}$N$_{25}$O$_{37}$S$_2$) requires 1236.0. RP-HPLC (Agilent: Vydac C18 analytical column, 15→45% buffer B over 30 min): t$_R$=19.6 min.

4.6.6 c[Δ$^4$A6,11]-Dicarba-[A7]-Cys(Pyr)-[A20]-Cys(Acm)-[A21]-Asp Human Insulin A-Chain 105

SEQ ID NO: 48

105(I) and 105(II)

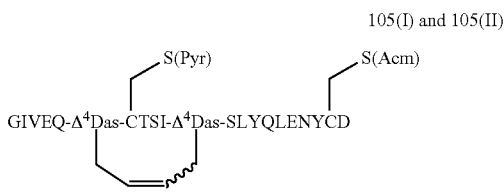

A solution of ice-cold TFA:TfOH (7 mL; 4:1) was added to a stirred solution of the cyclic peptide 104 (260 mg, 10.5 μmol) and 2,2'-DPDS (242 mg, 105 μmol) in TFA:anisol (7 mL; 9:1) at 0° C. After 1.5 h, the reaction mixture was reduced under a constant stream of air and ice-cold Et$_2$O (35 mL) was added to induce peptide precipitation. The resultant solid was then collected by centrifugation (3×6 min) and analysed by RP-HPLC and mass spectrometry. This supported formation of the S-activated peptide 105 as two isomers, 105(I) and 105(II), in a 7:3 ratio. Following purification by RP-HPLC (Agilent: Vydac C18 preparative column, 15→45% buffer B over 30 min, t$_R$=21.7 and 23.6 min), selected fractions were combined and lyophilised to give two isomers of the desired peptide as colourless solids (105(I): 8.0 mg, 3% and 105(II): 3.6 mg, 1%) in 95% and 85% purity respectively. 105(I): Mass spectrum (ESI$^+$, MeCN:H$_2$O:HCOOH): m/z 842.3 [M+3H]$^{3+}$, ⅓(C$_{109}$H$_{165}$N$_{26}$O$_{37}$S$_3$) requires 842.0; 1262.9 [M+2H]$^{2+}$, ½(C$_{109}$H$_{164}$N$_{26}$O$_{37}$S$_3$) requires 1262.5. RP-HPLC (Agilent: Vydac C18 analytical column, 15→45% buffer B over 30 min): t$_R$=17.5 min. 105(II): Mass spectrum (ESI$^+$, MeCN:H$_2$O:HCOOH): m/z 842.3 [M+3H]$^{3+}$, ⅓(C$_{109}$H$_{165}$N$_{26}$O$_{37}$S$_3$) requires 842.0; 1262.6 [M+2H]$^{2+}$, ½(C$_{109}$H$_{164}$N$_{26}$O$_{37}$S$_3$) requires 1262.5. RP-HPLC (Agilent: Vydac C18 analytical column, 15→45% buffer B over 30 min): t$_R$=18.3 min.

4.6.7 The Monocyclic A-B Heterodimer of c[Δ$^4$A6,11]-dicarba-[A21]-Asp Human Insulin 106

SEQ ID NO: 49

106(I) and 106(II)

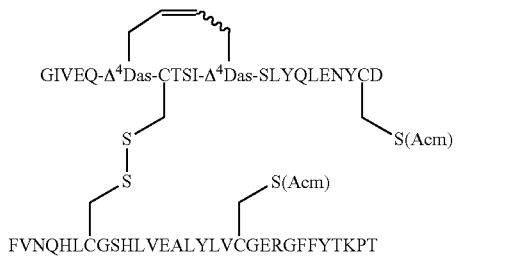

Isomer I:

The modified insulin A-chain 105(I) (8.0 mg, 3.2 µmol) in 50 mM NH$_4$HCO$_3$ (4 mL) was added dropwise to a stirred solution of the modified insulin B-chain 84 (11.0 mg, 3.17 µmol) in H$_2$O:MeCN (11 mL; 9:1). Reaction progress was monitored by RP-HPLC and mass spectrometry and after 2.5 h, the oxidation was terminated by addition of AcOH. The reaction mixture was then lyophilised to give a pale yellow solid (19 mg). Mass spectrum (ESI$^+$, MeCN:H$_2$O:HCOOH): m/z 1183.6 [M+5H]$^{5+}$, ⅕(C$_{265}$H$_{401}$N$_{66}$O$_{80}$S$_4$) requires 1183.2; 1479.5 [M+4H]$^{4+}$, ¼(C$_{265}$H$_{400}$N$_{66}$O$_{80}$S$_4$) requires 1478.7; 1972.3 [M+3H]$^{3+}$, ⅓(C$_{265}$H$_{499}$N$_{66}$O$_{80}$S$_4$) requires 1971.3. RP-HPLC (Agilent: Vydac C18 analytical column, 0→25% buffer B over 5 min then 25→45% buffer B over 30 min): t$_R$=21.4 min.

Isomer II:

The modified insulin A-chain 105(II) (3.6 mg, 1.4 µmol) in 50 mM NH$_4$HCO$_3$ (1.8 mL) was added dropwise to a stirred solution of the modified insulin B-chain 84 (5.0 mg, 1.4 µmol) in H$_2$O:MeCN (2.5 mL; 9:1). Reaction progress was monitored by RP-HPLC and mass spectrometry and after 3 h, the oxidation was terminated by addition of AcOH. The reaction mixture was then lyophilised to give a pale yellow solid (9 mg). Mass spectrum (ESI$^+$, MeCN:H$_2$O:HCOOH): m/z 1183.6 [M+5H]$^{5+}$, ⅕(C$_{265}$H$_{401}$N$_{66}$O$_{80}$S$_4$) requires 1183.2; 1479.5 [M+4H]$^{4+}$, ¼(C$_{265}$H$_{400}$N$_{66}$O$_{80}$S$_4$) requires 1478.7; 1972.3 [M+3H]$^{3+}$, ⅓(C$_{265}$H$_{499}$N$_{66}$O$_{80}$S$_4$) requires 1971.3. RP-HPLC (Agilent: Vydac C18 analytical column, 0→25% buffer B over 5 min then 25→45% buffer B over 30 min): t$_R$=20.8 min.

4.6.8 c[Δ$^4$A6,11]-Dicarba-[A21]-Asp Human Insulin 107

SEQ ID NO: 50

107(I)$_{A/B}$ and 107(II)$_{A/B}$

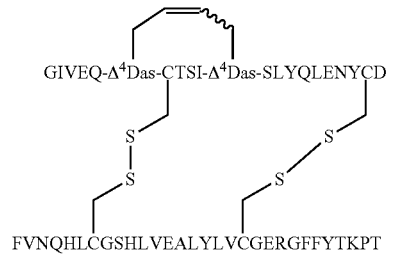

Isomer IA and IB:

A 20 mM solution of iodine in glacial acetic acid (8.2 mL) was added to a stirred solution of the monocyclic peptide 106(I) (19 mg, 3.2 µmol) in glacial acetic acid (21.4 mL) and 60 mM HCl (1.6 mL). Reaction progress was monitored by RP-HPLC and after 2.75 h, ice-cold Et$_2$O (5×35 mL) was added to induce peptide precipitation. The resultant yellow solid was collected by centrifugation (1×10 min) and 20 mM ascorbic acid (1 mL) was then added to quench any excess iodine before analysis via RP-HPLC and mass spectrometry. Following purification by RP-HPLC (Agilent: Vydac C18 analytical column, 0→30% buffer B over 5 min then 30→40% buffer B over 60 min, t$_R$=23.7 and 24.3 min), selected fractions were combined and lyophilised to give two isomers, 107(II)$_A$ and 107(II)$_B$, of the desired c[Δ$^4$A6,11]-dicarba-[A21]-Asp human insulin analogue as colourless solids (107(II)$_A$: 0.8 mg, 4% and 107(II)$_B$: 1.8 mg, 10%) in >99% and 97% purity respectively. 107(II)$_A$: Mass spectrum (ESI$^+$, MeCN:H$_2$O:HCOOH): m/z 962.5 [M+6H]$^{6+}$, ⅙(C$_{259}$H$_{390}$N$_{64}$O$_{78}$S$_4$) requires 962.1; 1155.1 [M+5H]$^{5+}$, ⅕(C$_{259}$H$_{389}$N$_{64}$O$_{78}$S$_4$) requires 1154.3; 1443.6 [M+4H]$^{4+}$, ¼(C$_{259}$H$_{388}$N$_{64}$O$_{78}$S$_4$) requires 1442.7. RP-HPLC (Agilent: Vydac C18 analytical column, 0→30% buffer B over 5 min then 30→40% buffer B over 30 min): t$_R$=19.5 min. 107(II)$_B$: Mass spectrum (ESI$^+$, MeCN:H$_2$O:HCOOH): m/z 962.8 [M+6H]$^{6+}$, ⅙(C$_{259}$H$_{390}$N$_{64}$O$_{78}$S$_4$) requires 962.1; 1155.3 [M+5H]$^{5+}$, ⅕(C$_{259}$H$_{389}$N$_{64}$O$_{78}$S$_4$) requires 1154.3; 1443.6 [M+4H]$^{4+}$, ¼(C$_{259}$H$_{388}$N$_{64}$O$_{78}$S$_4$) requires 1442.7. RP-HPLC (Agilent: Vydac C18 analytical column, 0→30% buffer B over 5 min then 30→40% buffer B over 30 min): t$_R$=20.4 min.

Isomer IIA and IIB:

A 20 mM solution of iodine in glacial acetic acid (3.7 mL) was added to a stirred solution of the mono-cyclic peptide 106(II) (8.6 mg, 1.5 µmol) in glacial acetic acid (9.7 mL) and 60 mM HCl (720 µL). Reaction progress was monitored by RP-HPLC and after 2.75 h, ice-cold Et$_2$O (3×35 mL) was added to induce peptide precipitation. The resultant solid was collected by centrifugation (1×10 min) and 20 mM ascorbic acid (1 mL) was then added to quench any excess iodine before analysis via RP-HPLC and mass spectrometry. Following purification by RP-HPLC (Agilent: Vydac C18 analytical column, 0→30% buffer B over 5 min then 30→40% buffer B over 60 min, t$_R$=18.2 min), selected fractions were combined and lyophilised to give a 4:6 mixture of isomeric insulin analogues 107(II)$_A$ and 107(II)$_B$ as a colourless solid (0.9 mg, 10%) in 97% purity. 107(II)$_{A/B}$: Mass spectrum (ESI$^+$, MeCN:H$_2$O:HCOOH): m/z 963.0 [M+6H]$^{6+}$, ⅙(C$_{259}$H$_{390}$N$_{64}$O$_{78}$S$_4$) requires 962.1; 1155.2 [M+5H]$^{5+}$, ⅕(C$_{259}$H$_{389}$N$_{64}$O$_{78}$S$_4$) requires 1154.3; 1444.0 [M+4H]$^{4+}$, ¼(C$_{259}$H$_{388}$N$_{64}$O$_{78}$S$_4$) requires 1442.7. RP-HPLC (Agilent: Vydac C18 analytical column, 0→30% buffer B over 5 min then 30→40% buffer B over 30 min): t$_R$=16.4 and 16.7 min.

4.6.9 des$_{A1-5}$-[A6,11]-Agl-[A7]-Cys($^t$Bu)-[A20]-Cys(Acm)-[A21]-β-Asn Human Insulin A-Chain 108

SEQ ID NO: 46

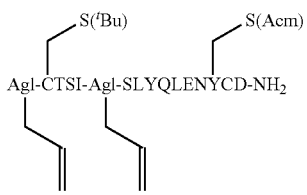

108

Attachment of Fmoc-L-Asp-O$^t$Bu (123 mg, 300 µmol) on Rink Amide resin (250 mg, 100 µmol) was performed according to the procedure described in the General Section using HATU (114 mg, 300 µmol) and NMM (66 µL, 0.60 µmol) for 18 h. The automated microwave-accelerated procedure was then used for the synthesis of peptide 108 on Fmoc-β-Asn (O$^t$Bu)-Rink Amide resin (289 mg, 100 µmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 108

| Reagent | Total volume (mL) | Mass (g) or Volume (mL) | Reaction Time (min) |
|---|---|---|---|
| 0.5M HATU in DMF | 17.0 | 3.24 g | — |
| 2M DIPEA in NMP | 9.0 | 3.1 mL | — |
| Fmoc-L-Asn(Trt)-OH | 3.0 | 0.36 g | 12 |
| Fmoc-L-Agl-OH | 6.0 | 0.41 g | 12 |
| Fmoc-L-Cys(Acm)-OH | 3.0 | 0.25 g | 12 |
| Fmoc-L-Cys($^t$Bu)-OH | 3.0 | 0.24 g | 12 |
| Fmoc-L-Gln(Trt)-OH | 3.0 | 0.37 g | 12 |
| Fmoc-L-Glu(O$^t$Bu)-OH | 3.0 | 0.26 g | 12 |
| Fmoc-L-Ile-OH | 3.0 | 0.21 g | 12 |
| Fmoc-L-Leu-OH | 6.0 | 0.42 g | 12 |
| Fmoc-L-Ser($^t$Bu)-OH | 6.0 | 0.46 g | 12 |
| Fmoc-L-Thr($^t$Bu)-OH | 3.0 | 0.24 g | 12 |
| Fmoc-L-Tyr($^t$Bu)-OH | 6.0 | 0.55 g | 12 |

After sequence completion, the resin-bound peptide was transferred into a fritted syringe and treated with an acetic anhydride solution (4 mL; DMF:acetic anhydride:NMM; 94:5:1) for 2 h. The resin was washed with DMF (4 mL; 3×1 min), DCM (4 mL; 3×1 min) and MeOH (4 mL; 3×1 min), then left to dry in vacuo for 1 h. Prior to treatment with MeOH, a small aliquot of the resin-bound peptide was removed and subjected to Fmoc-deprotection in the presence of 20% v/v piperidine in DMF (1 mL; 1×1 min, 2×10 min), and washed with DMF (1 mL; 5×1 min), DCM (1 mL; 3×1 min) and MeOH (1 mL; 3×1 min). The dried aliquot of Fmoc-deprotected resin-tethered peptide was subjected to TFA-mediated cleavage (General Section) and RP-HPLC and mass spectral analysis of the resultant solid supported formation of the desired peptide 108 in 85% purity. Mass spectrum (ESI$^+$, MeCN:H$_2$O:HCOOH): m/z 986.7 [M+2H]$^{2+}$, ½(C$_{87}$H$_{136}$N$_{20}$O$_{28}$S$_2$) requires 986.5. RP-HPLC (Agilent: Vydac C18 analytical column, 15→45% buffer B over 30 min): t$_R$=18.7 min.

4.6.10 des$_{A1-5}$-c[Δ$^4$A6,11]-Dicarba-[A7]-Cys($^t$Bu)-[A20]-Cys(Acm)-[A21]-β-Asn Human Insulin A-Chain 109

SEQ ID NO: 47

109(I) and 109(II)

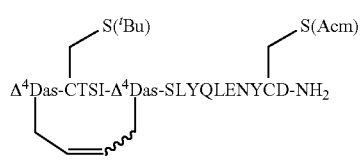

Resin-bound peptide 108 was subjected to the general microwave-accelerated RCM procedure outlined in the General Section under the following conditions: Resin-bound 108 (368 mg, 100 µmol), DCM (4.75 mL), 0.4 M LiCl in DMF (0.25 mL), 2$^{nd}$ generation Grubbs' catalyst (17 mg, 20 µmol), 100 W µwave, 100° C., 2 h, 100% conversion into 109. Post metathesis, a small aliquot of resin-bound peptide was subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The dried aliquot of Fmoc-deprotected resin-tethered peptide was subjected to TFA-mediated cleavage (General Section) for RP-HPLC and mass spectral analysis. This supported formation of the desired peptide as two isomers, 109(I) and 109(II), in a 75:25 ratio. 109(I): Mass spectrum (ESI$^+$, MeCN:H$_2$O:HCOOH): m/z 972.5 [M+2H]$^{2+}$, ½(C$_{85}$H$_{132}$N$_{20}$O$_{28}$S$_2$) requires 972.4. RP-HPLC (Agilent: Vydac 018 analytical column, 15→45% buffer B over 30 min): t$_R$=17.8 min. 109(II): Mass spectrum (ESI$^+$, MeCN:H$_2$O:HCOOH): m/z 972.5 [M+2H]$^{2+}$, ½(C$_{85}$H$_{132}$N$_{20}$O$_{28}$S$_2$) requires 972.4. RP-HPLC (Agilent: Vydac C18 analytical column, 15→45% buffer B over 30 min): t$_R$=18.0 min.

4.6.11 c[Δ$^4$A6,11]-Dicarba-[A7]-Cys($^t$Bu)-[A20]-Cys(Acm)-[A21]-β-Asn Human Insulin A-Chain 110

SEQ ID NO: 48

110(I) and 110(II)

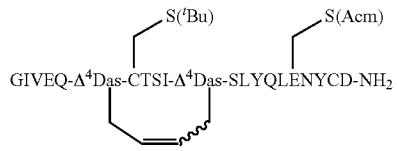

The automated, microwave-accelerated procedure outlined in the General Section was used to attach the remaining 5 residues on resin-bound peptide 109 (352 mg, 100 µmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 110

| Reagent | Total volume (mL) | Mass (g) or Volume (mL) | Reaction Time (min) |
|---|---|---|---|
| 0.5M HATU in DMF | 6.0 | 1.14 g | — |
| 2M DIPEA in NMP | 3.0 | 1.0 mL | — |
| Fmoc-L-Gly-OH | 3.0 | 0.178 g | 12 |
| Fmoc-L-Gln(Trt)-OH | 3.0 | 0.367 g | 12 |
| Fmoc-L-Glu(O$^t$Bu)-OH | 3.0 | 0.256 g | 12 |
| Fmoc-L-Ile-OH | 3.0 | 0.212 g | 12 |
| Fmoc-L-Val-OH | 3.0 | 0.204 g | 12 |

After sequence completion, the resin-bound peptide was transferred into a fritted syringe and subjected to Fmoc-deprotection in the presence of 20% v/v piperidine in DMF (7 mL; 1×1 min, 2×10 min). The resin was washed with DMF (7 mL; 5×1 min), DCM (7 mL; 3×1 min) and MeOH (7 mL; 3×1 min), then left to dry in vacuo for 1 h. The resin-bound peptide (397 mg) was subjected to TFA-mediated cleavage (General Section) and RP-HPLC and mass spectral analysis of the resultant pale brown solid (78 mg) supported formation of the desired peptide as two isomers, 110(I) and 110(II), in a 75:25 ratio. 110(I): Mass spectrum (ESI$^+$, MeCN:H$_2$O:HCOOH): m/z 824.4 [M+3H]$^{3+}$, ⅓($C_{108}H_{171}N_{26}O_{36}S_2$) requires 824.1; 1235.6 [M+2H]$^{2+}$, ½($C_{108}H_{170}N_{26}O_{36}S_2$) requires 1235.6. RP-HPLC (Agilent: Vydac C18 analytical column, 15→45% buffer B over 30 min): $t_R$=18.4 min. 110(II): Mass spectrum (ESI$^+$, MeCN:H$_2$O:HCOOH): m/z 824.3 [M+3H]$^{3+}$, ⅓($C_{108}H_{171}N_{26}O_{36}S_2$) requires 824.1; 1235.7 [M+2H]$^{2+}$, ½($C_{108}H_{170}N_{26}O_{36}S_2$) requires 1235.6. RP-HPLC (Agilent: Vydac 018 analytical column, 15→45% buffer B over 30 min): $t_R$=19.4 min.

4.6.12 c[Δ$^4$A6,11]-Dicarba-[A7]-Cys(Pyr)-[A20]-Cys(Acm)-[A21]-β-Asn Human Insulin A-Chain 111

SEQ ID NO: 48

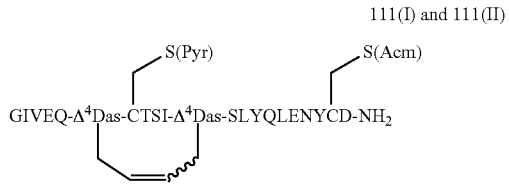

111(I) and 111(II)

A solution of ice-cold TFA:TfOH (3 mL; 4:1) was added to a stirred solution of the cyclic peptide 110 (78.0 mg, 31.5 μmol) and 2,2'-DPDS (72.5 mg, 315 μmol) in TFA:anisol (3 mL; 9:1) at 0° C. After 1.5 h, the reaction mixture was reduced under a constant stream of air and ice-cold Et$_2$O (35 mL) was added to induce peptide precipitation. The resultant solid was then collected by centrifugation (3×10 min) and analysed by RP-HPLC and mass spectrometry. This supported formation of the S-activated peptide 111 as two isomers, 111(I) and 111(II), in a 75:25 ratio. Following purification by RP-HPLC (Agilent: Vydac C18 preparative column, 15→45% buffer B over 30 min, $t_R$=20.3 and 21.3 min), selected fractions were combined and lyophilised to give two isomers of the desired peptide as colourless solids (111(I): 13.5 mg, 17% and 111(II): 6.0 mg, 8%) in 95% and 89% purity respectively. 111(I): Mass spectrum (ESI$^+$, MeCN:H$_2$O:HCOOH): m/z 841.9 [M+3H]$^{3+}$, ⅓($C_{109}H_{166}N_{27}O_{36}S_3$) requires 841.7; 1262.2 [M+2H]$^{2+}$, ½($C_{109}H_{165}N_{27}O_{36}S_3$) requires 1262.1. RP-HPLC (Agilent: Vydac C18 analytical column, 15→45% buffer B over 30 min): $t_R$=17.3 min. 111(II): Mass spectrum (ESI$^+$, MeCN:H$_2$O:HCOOH): m/z 842.0 [M+3H]$^{3+}$, ⅓($C_{109}H_{166}N_{27}O_{36}S_3$) requires 841.7; 1262.2 [M+2H]$^{2+}$, ½($C_{109}H_{165}N_{27}O_{36}S_3$) requires 1262.1. RP-HPLC (Agilent: Vydac C18 analytical column, 15→45% buffer B over 30 min): $t_R$=18.8 min.

4.6.13 The Monocyclic A-B Heterodimer of c[Δ$^4$A6,11]-dicarba-[A21]-β-Asn Human Insulin 112

SEQ ID NO: 108

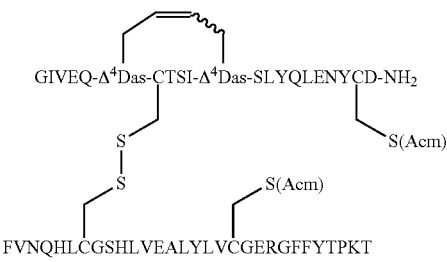

112(I) and 112(II)

Isomer I:

The modified insulin A-chain 111(I) (13.5 mg, 5.35 μmol) in 50 mM NH$_4$HCO$_3$ (7 mL) was added dropwise to a stirred solution of the modified insulin B-chain 84 (18.7 mg, 5.35 μmol) in H$_2$O:MeCN (19 mL; 9:1). Reaction progress was monitored by RP-HPLC and mass spectrometry and after 2 h, the oxidation was terminated by addition of AcOH. The reaction mixture was then lyophilised to give a pale yellow solid (32 mg). 112(I): Mass spectrum (ESI$^+$, MeCN:H$_2$O:HCOOH): m/z 1183.7 [M+5H]$^{5+}$, ⅕($C_{265}H_4O_2N_{67}O_{79}S_4$) requires 1183.0; 1479.2 [M+4H]$^{4+}$, ¼($C_{265}H_{400}N_{67}O_{79}S_4$) requires 1478.5; 1972.3 [M+3H]$^{3+}$, ¼($C_{265}H_{400}N_{67}O_{79}S_4$) requires 1471.0. RP-HPLC (Agilent: Vydac C18 analytical column, 0→25% buffer B over 5 min then 25→45% buffer B over 30 min): $t_R$=21.1 min.

Isomer II:

The modified insulin A-chain 111(II) (6.0 mg, 2.4 μmol) in 50 mM NH$_4$HCO$_3$ (3 mL) was added dropwise to a stirred solution of the modified insulin B-chain 84 (8.3 mg, 2.4 μmol) in H$_2$O:MeCN (8 mL; 9:1). Reaction progress was monitored by RP-HPLC and mass spectrometry and after 2 h, the oxidation was terminated by addition of AcOH. The reaction mixture was then lyophilised to give a pale yellow solid (14 mg). 112(II): Mass spectrum (ESI$^+$, MeCN:H$_2$O:HCOOH): m/z 1183.7 [M+5H]$^{5+}$, ⅕($C_{265}H_4O_2N_{67}O_{79}S_4$) requires 1183.0; 1479.2 [M+4H]$^{4+}$, ¼($C_{265}H_{400}N_{67}O_{79}S_4$) requires 1478.5; 1972.4 [M+3H]$^{3+}$, ¼($C_{265}H_{400}N_{67}O_{79}S_4$) requires 1471.0. RP-HPLC (Agilent: Vydac C18 analytical column, 0→25% buffer B over 5 min then 25→45% buffer B over 30 min): $t_R$=21.1 min.

4.6.14 c[Δ⁴A6,11]-Dicarba-[A21]-β-Asn Human Insulin 113

SEQ ID NO: 109

113(I) and 113(II)

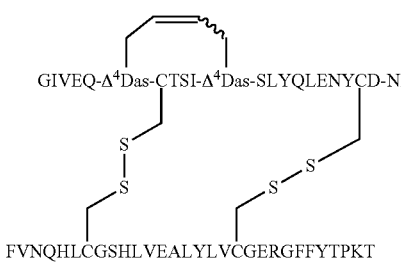

GIVEQ-Δ⁴Das-CTSI-Δ⁴Das-SLYQLENYCD-NH₂

FVNQHLCGSHLVEALYLVCGERGFFYTPKT

Isomer I:

A 20 mM solution of iodine in glacial acetic acid (14.7 mL) was added to a stirred solution of the monocyclic peptide 112(I) (33 mg, 5.6 μmol) in glacial acetic acid (37.1 mL) and 60 mM HCl (2.9 mL). Reaction progress was monitored by RP-HPLC and after 2.75 h, ice-cold Et₂O (6×35 mL) was added to induce peptide precipitation. The resultant yellow solid was collected by centrifugation (1×10 min) and 20 mM ascorbic acid (1 mL) was then added to quench any excess iodine before analysis via RP-HPLC and mass spectrometry. Following purification by RP-HPLC (Agilent: Vydac C18 analytical column, 0→25% buffer B over 5 min then 25→40% buffer B over 60 min, $t_R$=39.2 min), selected fractions were combined and lyophilised to give the desired c[Δ⁴A6,11]-dicarba human insulin analogue 113(I) as a colourless solid (3.2 mg, 10%) in 98% purity. Mass spectrum (ESI⁺, MeCN:H₂O:HCOOH): m/z 1154.9 [M+5H]⁵⁺, ⅕($C_{259}H_{390}N_{65}O_{77}S_4$) requires 1154.1; 1443.0 [M+41-]⁴⁺, ¼($C_{259}H_{389}N_{65}O_{77}S_4$) requires 1442.4; 1923.8 [M+3H]³⁺, ⅓($C_{259}H_{388}N_{65}O_{77}S_4$) requires 1922.9. RP-HPLC (Agilent: Vydac C18 analytical column, 0→30% buffer B over 5 min then 30→40% buffer B over 30 min): $t_R$=20.2 min.

Isomer II:

A 20 mM solution of iodine in glacial acetic acid (6.7 mL) was added to a stirred solution of the monocyclic peptide 112(II) (14 mg, 2.4 μmol) in glacial acetic acid (16.8 mL) and 60 mM HCl (1.3 mL). Reaction progress was monitored by RP-HPLC and after 2.75 h, ice-cold Et₂O (3×35 mL) was added to induce peptide precipitation. The resultant yellow solid was collected by centrifugation (1×10 min) and 20 mM ascorbic acid (1 mL) was then added to quench any excess iodine before analysis via RP-HPLC and mass spectrometry. Following purification by RP-HPLC (Agilent: Vydac C18 analytical column, 0→25% buffer B over 5 min then 25→40% buffer B over 60 min, $t_R$=34.2 min), selected fractions were combined and lyophilised to give the desired c[Δ⁴A6,11]-dicarba human insulin analogue 113(II) as a colourless solid (1.4 mg, 10%) in >99% purity. Mass spectrum (ESI⁺, MeCN:H₂O:HCOOH): m/z 1154.7 [M+5H]⁵⁺, ⅕($C_{259}H_{390}N_{65}O_{77}S_4$) requires 1154.1; 1442.9 [M+4H]⁴⁺, ¼($C_{259}H_{389}N_{65}O_{77}S_4$) requires 1442.4. RP-HPLC (Agilent: Vydac C18 analytical column, 0→30% buffer B over 5 min then 30→40% buffer B over 30 min): $t_R$=16.3 min.

5. Alternating SPPS-Catalysis Strategies

5.1 Ring Closing Alkene Metathesis (RCM) on Resin-Supported Peptides

5.1.1 Several Examples of this Method have Previously been Disclosed in Section 4: "Preparation of Fast and Slow Acting Dicarba Insulin Analogues" and are Therefore not Repeated Here.

5.1.2 Linear des₁₋₅-[6,11]-Agl-[7]-Pre-[20]-Cys(Acm) Insulin A-Chain 15

SEQ ID NO: 11

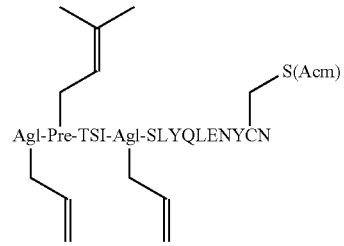

Agl-Pre-TSI-Agl-SLYQLENYCN

The automated, microwave-accelerated procedure outlined in the General Section was used for the synthesis of peptide 15 on Fmoc-Asn(Trt)-PEG-PS resin (667 mg, 100 μmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 15

| Reagent | Total volume (mL) | Mass (g) or Volume (mL) | Reaction Time (min) |
|---|---|---|---|
| 0.5M HATU in DMF | 17.0 | 3.24 g | — |
| 2M DIPEA in NMP | 9.0 | 3.1 mL | — |
| Fmoc-L-Asn(Trt)-OH | 3.0 | 0.358 g | 12 |
| Fmoc-L-Agl-OH | 6.0 | 0.405 g | 12 |
| Fmoc-L-Cys(Acm)-OH | 3.0 | 0.249 g | 12 |
| Fmoc-L-Gln(Trt)-OH | 3.0 | 0.367 g | 12 |
| Fmoc-L-Glu(OᵗBu)-OH | 3.0 | 0.256 g | 12 |
| Fmoc-L-Ile-OH | 3.0 | 0.212 g | 12 |
| Fmoc-L-Leu-OH | 6.0 | 0.424 g | 12 |
| Fmoc-L-Pre-OH | 3.0 | 0.219 g | 12 |
| Fmoc-L-Ser(ᵗBu)-OH | 6.0 | 0.460 g | 12 |
| Fmoc-L-Thr(ᵗBu)-OH | 3.0 | 0.238 g | 12 |
| Fmoc-L-Tyr(ᵗBu)-OH | 6.0 | 0.551 g | 12 |

After sequence completion, the resin-bound peptide was transferred into a fritted syringe and treated with an acetic anhydride solution (7 mL; DMF:acetic anhydride:NMM; 94:5:1) for 2 h. The resin was then washed with DMF (7 mL; 3×1 min), DCM (7 mL; 3×1 min) and MeOH (7 mL; 3×1 min), then left to dry in vacuo for 1 h. Prior to treatment with MeOH, a small aliquot of the resin-bound peptide was removed and subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The dried aliquot of Fmoc-deprotected resin-tethered peptide was subjected to TFA-mediated cleavage (General Section) for RP-HPLC and mass spectral analysis. This supported formation of the desired peptide 15 in 85% purity. Mass spectrum (ESI⁺, MeCN:H₂O: HCOOH): m/z 970.1 [M+2H]²⁺, ½($C_{87}H_{134}N_{20}O_{28}S$) requires 969.5; 978.7 [M+H₂O+2H]²⁺, ½($C_{87}H_{136}N_{20}O_{29}S$) requires 978.5; 1026.8 [M+TFA+2H]²⁺, ½($C_{89}H_{135}F_3N_{20}O_{30}S$) requires 1026.5. RP-HPLC (Agilent: Vydac C18 analytical column, 15→45% buffer B over 30 min): $t_R$=21.6 min.

5.1.3 des$_{1-5}$-c[Δ$^4$6,11]-Dicarba-[7]-Pre-[20]-Cys(Acm) Insulin A-Chain 18

SEQ ID NO: 14

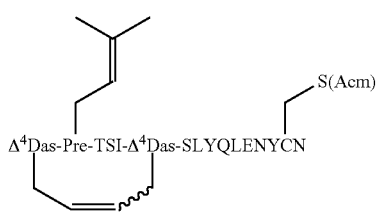

18(I) and 18(II)

Resin-bound peptide 15 was subjected to the microwave-accelerated RCM procedure outlined in the General Section under the following conditions: Resin-bound 15 (801 mg, 100 μmol), DCM (6 mL), 0.4 M LiCl in DMF (0.2 mL), 2$^{nd}$ generation Grubbs' catalyst (17 mg, 20 μmol), 100 W μwave, 100° C., 2 h, 95% conversion into 18. Post metathesis, a small aliquot of resin-bound peptide was subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The aliquot of Fmoc-deprotected resin-tethered peptide was subjected to TFA-mediated cleavage (General Section) for RP-HPLC and mass spectral analysis. This supported formation of the desired peptide as two isomers, 18(I) and 18(II), in a 3:7 ratio. 18(I): Mass spectrum (ESI$^+$, MeCN:H$_2$O:HCOOH): m/z 955.5 [M+2H]$^{2+}$, ½(C$_{85}$H$_{130}$N$_{20}$O$_{28}$S) requires 955.5; 964.3 [M+H$_2$O+2H]$^{2+}$, ½(C$_{85}$H$_{132}$N$_{20}$O$_{29}$S) requires 964.5; 1013.0 [M+TFA+2H]$^{2+}$, ½(C$_{87}$H$_{131}$F$_3$N$_{20}$O$_{30}$S) requires 1012.5. RP-HPLC (Agilent: Vydac C18 analytical column, 15→45% buffer B over 30 min): t$_R$=21.3 min. 18(II): Mass spectrum (ESI$^+$, MeCN:H$_2$O:HCOOH): m/z 955.5 [M+2H]$^{2+}$, ½(C$_{85}$H$_{130}$N$_{20}$O$_{28}$S) requires 955.5; 964.2 [M+H$_2$O+2H]$^{2+}$, ½(C$_{85}$H$_{132}$N$_{20}$O$_{29}$S) requires 964.5; 1012.6 [M+TFA+2H]$^{2+}$, ½(C$_{87}$H$_{131}$F$_3$N$_{20}$O$_{30}$S) requires 1012.5. RP-HPLC (Agilent: Vydac C18 analytical column, 15→45% buffer B over 30 min): t$_R$=21.7 min.

5.1.4 des$_{1-5}$-c[6,11]-Dicarba-[7]-Pre-[20]-Cys(Acm) Insulin A-Chain 20

SEQ ID NO: 51

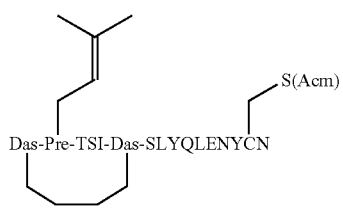

20

Resin-bound peptide 18 was subjected to the microwave-accelerated hydrogenation procedure outlined in the General Section under the following conditions: Resin-bound 18 (432 mg, 60 μmol), DCM (4.5 mL), MeOH (0.5 mL), Wilkinsons catalyst, H$_2$ (80 psi), 80 W μwave, 70° C., 2 h, 100% conversion into 20. Post metathesis, a small aliquot of resin-bound peptide was subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The aliquot of Fmoc-deprotected resin-tethered peptide was subjected to TFA-mediated cleavage (General Section) for RP-HPLC and mass spectral analysis. This supported formation of the saturated carbocycle 20 and 10% over reduction to cyclic peptide 29. Mass spectrum (ESI$^+$, MeCN:H$_2$O:HCOOH): m/z 957.5 [M$_{29}$+2H]$^{2+}$; 965.6 [M$_{20}$+H$_2$O+2H]$^{2+}$, ½(C$_{85}$H$_{134}$N$_{20}$O$_{29}$S) requires 965.5; 1013.5 [M$_{20}$+TFA+2H]$^{2+}$, ½(C$_{87}$H$_{133}$F$_3$N$_{20}$O$_{30}$S) requires 1013.5. RP-HPLC (Agilent: Vydac C18 analytical column, 15→45% buffer B over 30 min): t$_R$=21.6 min.

SEQ ID NO: 52

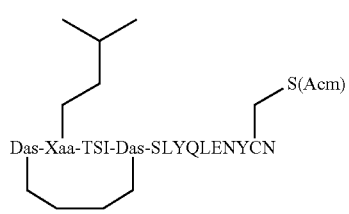

29

5.1.5 des$_{1-5}$-c[6,11]-Dicarba-[7]-Crt-[20]-Cys(Acm) Insulin A-Chain 21

SEQ ID NO: 17

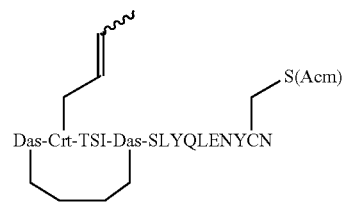

21

Resin-bound peptide 20 was subjected to the microwave-accelerated CM procedure outlined in the General Section under the following conditions: Resin-bound 20 (216 mg, 30 μmol), DCM (4 mL), 0.4 M LiCl in DMF (0.2 mL), 2$^{nd}$ generation Hoveyda-Grubbs' catalyst (3.8 mg, 6 μmol), cis-2-butene (12 psi), 80 W μwave, 70° C., 4 h, 95% conversion into 21. After the first 2 h, the reaction mixture was purge-charged with argon to remove any volatile by-products and re-filled with butene for the second 2 h reaction duration. Post metathesis, a small aliquot of resin-bound peptide was subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The aliquot of Fmoc-deprotected resin-tethered peptide was subjected to TFA-mediated cleavage (General Section) for RP-HPLC and mass spectral analysis. This supported formation of the desired peptide 21. Trace amounts of hydrated starting materials and over reduced peptide were also detected in the mass spectrum. Mass spectrum (ESI$^+$, MeCN:H$_2$O:HCOOH): m/z 949.7 [M$_{21}$+2H]$^{2+}$, ½(C$_{84}$H$_{130}$N$_{20}$O$_{28}$S) requires 949.5; 957.7 [M$_{29}$+2H]$^{2+}$; 965.7 [M$_{20}$+H$_2$O+2H]$^{2+}$; 1013.6 [M$_{20}$+TFA+2H]$^{2+}$. RP-HPLC (Agilent: Vydac C18 analytical column, 15→45% buffer B over 30 min): t$_{R(131)}$=16.2 min.

5.1.6 Cross Metathesis of the Activated A-Chain 21 and Ac-Agl-OMe 22

SEQ ID NO: 18

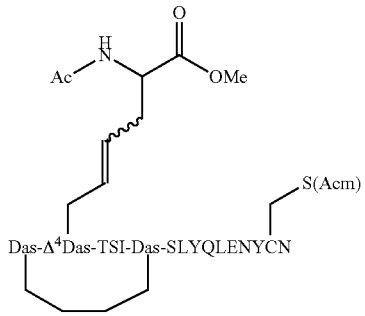

22

Resin-bound Fmoc-protected peptide 21 was subjected to the general microwave-accelerated cross metathesis procedure outlined in the General Section under the following conditions: Resin-bound 21 (207 mg, 30 μmol), DCM (4 mL), 0.4 M LiCl in DMF (0.2 mL), $2^{nd}$ generation Hoveyda Grubbs' catalyst (3.8 mg, 6 μmol), Ac-D,L-Agl-OMe (51 mg, 300 μmol) 100 W μwave, 100° C., 2 h, 90% conversion into 22. Post metathesis, a small aliquot of resin-bound peptide was subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The aliquot of Fmoc-deprotected resin-tethered peptide was subjected to TFA-mediated cleavage for RP-HPLC and mass spectral analysis. This supported formation of the desired peptide 22. Mass spectrum (ESI$^+$, MeCN:H$_2$O:HCOOH): m/z 1014.1 [M$_{22}$+2H]$^{2+}$, ½(C$_{99}$H$_{137}$N$_{21}$O$_{31}$S) requires 1014.0, 964.8 [M20+H$_2$O+2H]$^{2+}$, 957.4 [M$_{29}$+2H]$^{2+}$. RP-HPLC (Agilent: Vydac C18 analytical column, 15→45% buffer B over 30 min): $t_{R(22)}$=20.4 min.

5.1.7 Addition of GIVEQ (SEQ ID NO: 12) to Peptide 22→23

SEQ ID NO: 19

23

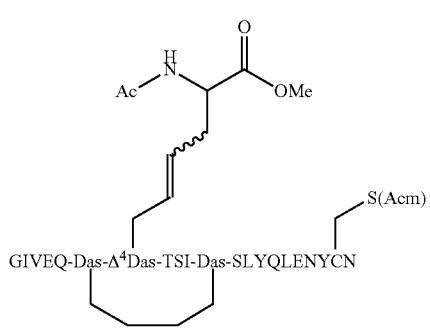

The automated, microwave-accelerated SPPS procedure outlined in the General Section was used to attach the remaining five residues (GIVEQ) on resin-bound peptide 22 (200 mg, 30 μmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in Table below:—

TABLE

Quantities of reagents and amino acids used in the synthesis of peptide 23

| Reagent | Total volume (mL) | Mass (g) or Volume (mL) | Reaction Time (min) |
|---|---|---|---|
| 0.5M HATU in DMF | 6.0 | 1.14 g | — |
| 2M DIPEA in NMP | 3.0 | 1.0 mL | — |
| Fmoc-L-Gly-OH | 3.0 | 0.178 g | 12 |
| Fmoc-L-Gln(Trt)-OH | 3.0 | 0.367 g | 12 |
| Fmoc-L-Glu(O$^t$Bu)-OH | 3.0 | 0.256 g | 12 |
| Fmoc-L-Ile-OH | 3.0 | 0.212 g | 12 |
| Fmoc-L-Val-OH | 3.0 | 0.204 g | 12 |

After sequence completion, the resin-bound peptide was transferred into a fritted syringe and subjected to Fmoc-deprotection in the presence of 20% v/v piperidine in DMF (4 mL; 1×1 min, 2×10 min). The resin was washed with DMF (4 mL; 5×1 min), DCM (4 mL; 3×1 min) and MeOH (4 mL; 3×1 min), left to dry in vacuo for 1 h, and subjected to TFA-mediated cleavage for RP-HPLC and mass spectral analysis. This supported formation of the desired peptide 23 and trace amounts of the over reduced peptide drawn below. Mass spectrum (ESI$^+$, MeCN:H$_2$O:HCOOH): m/z 1277.0 [M$_{23}$+2H]$^{2+}$, ½(C$_{112}$H$_{175}$N$_{27}$O$_{39}$S) requires 1277.1; 1220.9 [M$_{below}$+2H]$^{2+}$. RP-HPLC (Agilent: Vydac C18 analytical column, 15→45% buffer B over 30 min): $t_{R(23)}$=19.3 min.

SEQ ID NO: 52

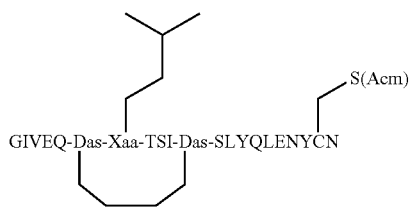

5.2 Ring Closing Alkyne Metathesis (RCAM) on Resin-Supported Peptides

5.2.1 Linear des$_{A1-5/14-21}$-[6,11]-Bgl Insulin A-Chain 24

SEQ ID NO: 20

24

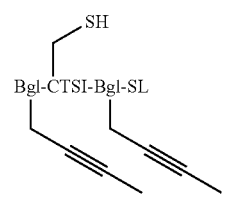

Esterification of Fmoc-L-Leu-OH (106 mg, 300 μmol) on Wang resin (91 mg, 100 μmol) was performed according to the general protocol described in the General Section using DIC (47 μL, 300 μmol) and DMAP (3.7 mg, 30 μmol) for 2 h. The automated microwave-accelerated procedure was then used for the synthesis of peptide 24 on Fmoc-L-Leu-Wang resin (92 mg, 100 μmol). Quantities of HBTU, HOBt, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 24

| Reagent | Total volume (mL) | Mass (g) or Volume (mL) | Reaction Time (min) |
|---|---|---|---|
| 0.5M HBTU:HOBt in DMF | 8 | 1.52 g:0.55 g | — |
| 2M DIPEA in NMP | 4 | 1.4 mL | — |
| Fmoc-L-Cys(Trt)-OH | 3 | 0.351 g | 12 |
| Fmoc-L-Bgl-OH | 6 | 0.419 g | 12 |
| Fmoc-L-Ile-OH | 3 | 0.212 g | 12 |
| Fmoc-L-Ser(tBu)-OH | 6 | 0.460 g | 12 |
| Fmoc-L-Thr(tBu)-OH | 3 | 0.238 g | 12 |

After sequence completion, the resin-bound peptide was transferred into a fritted syringe and treated with an acetic anhydride solution (4 mL; DMF:acetic anhydride:NMM; 94:5:1) for 2 h. The resin was washed with DMF (4 mL; 3×1 min), DCM (4 mL; 3×1 min) and MeOH (4 mL; 3×1 min), then left to dry in vacuo for 1 h. Prior to treatment with MeOH, a small aliquot of the resin-bound peptide was removed and subjected to Fmoc-deprotection in the presence of 20% v/v piperidine in DMF (1 mL; 1×1 min, 2×10 min), and washed with DMF (1 mL; 5×1 min), DCM (1 mL; 3×1 min) and MeOH (1 mL; 3×1 min). The aliquot of Fmoc-deprotected resin-tethered peptide was subjected to TFA-mediated cleavage (General Section) and RP-HPLC and mass spectral analysis supported formation of the desired peptide 24. Mass spectrum (ESI$^+$, MeCN:H$_2$O:HCOOH): m/z 841.3 [M+H]$^+$, C$_{37}$H$_{61}$N$_8$O$_{12}$S requires 841.4. RP-HPLC (Vydac C18 analytical column, 0→30% buffer B over 30 min): t$_R$=28.9 min.

5.2.2 des$_{A1-5/A14-21}$-c[Δ$^4$A6,11]-Dao Insulin A-Chain 25

SEQ ID NO: 22

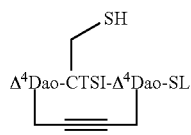

Resin-bound peptide 24 was dried via azeotropic distillation from THF and then subjected to the microwave-accelerated RCAM procedure outlined in the General Section under the following conditions: Resin-bound 24 (45 mg, 50 μmol), DCM (2 mL), Schrock's catalyst (4.7 mg, 10 μmol), 70° C., 3 h, 45% conversion into 25. Post metathesis, a small aliquot of resin-bound peptide was subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The aliquot of Fmoc-deprotected resin-tethered peptide was subjected to TFA-mediated cleavage (General Section) for RP-HPLC and mass spectral analysis. This indicated a mixture of both cyclic and linear peptides, 25 and 24 respectively. Mass spectrum (ESI$^+$, MeCN:H$_2$O:HCOOH): m/z 787.3 [M+H]$^+$, (C$_{33}$H$_{55}$N$_8$O$_{12}$S) requires 787.4; 841.4. RP-HPLC (Vydac C18 analytical column, 0→30% buffer B over 30 min): t$_{R(25)}$=21.0 min and t$_{R(24)}$=28.9 min.

5.2.3 Linear des$_{A1-5/A14-21}$-[A6,11]-Bgl-[A8]-Pro Insulin A-Chain 26

SEQ ID NO: 21

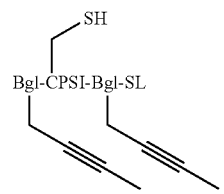

Esterification of Fmoc-L-Leu-OH (106 mg, 300 μmol) on Wang resin (91 mg, 100 μmol) was performed according to the general protocol described in the General Section using DIC (47 μL, 300 μmol) and DMAP (3.7 mg, 30 μmol) for 2 h. The automated microwave-accelerated procedure was then used for the synthesis of peptide 26 on Fmoc-L-Leu-Wang resin (92 mg, 100 μmol) for 2 h. Quantities of HBTU, HOBt, DIPEA, piperidine and each Fmoc-amino acid were used as described by the automated protocols of the instrument and remained constant throughout this synthesis. The total amount of each coupling reagent and successive amino acid required, along with their reaction duration is summarised in the Table below:—

TABLE

Quantities of reagents and amino acids used in the synthesis of peptide 26

| Reagent | Total volume (mL) | Mass (g) or Volume (mL) | Reaction Time (min) |
|---|---|---|---|
| 0.5M HBTU:HOBt in DMF | 8 | 1.52 g:0.56 g | — |
| 2M DIPEA in NMP | 4 | 1.4 mL | — |
| Fmoc-L-Cys(Trt)-OH | 5 | 0.58 g | 12 |
| Fmoc-L-Bgl-OH | 5 | 0.43 g | 12 |
| Fmoc-L-Ile-OH | 5 | 0.34 g | 12 |
| Fmoc-L-Pro-OH | 5 | 0.41 g | 12 |
| Fmoc-L-Ser(tBu)-OH | 6 | 0.48 g | 12 |

After sequence completion, the resin-bound peptide was transferred into a fritted syringe and treated with an acetic anhydride solution (4 mL; DMF:acetic anhydride:NMM; 94:5:1) for 2 h. The resin was washed with DMF (4 mL; 3×1 min), DCM (4 mL; 3×1 min) and MeOH (4 mL; 3×1 min), then left to dry in vacuo for 1 h. Prior to treatment with MeOH, a small aliquot of the resin-bound peptide was removed and subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The aliquot of Fmoc-deprotected resin-tethered peptide was subjected to TFA-mediated cleavage (General Section) and RP-HPLC and mass spectral analysis supported formation of the desired peptide 26. Mass spectrum (ESI$^+$, MeCN:H$_2$O:HCOOH): m/z 837.4 [M+H]$^+$, C$_{38}$H$_{61}$N$_8$O$_{11}$S requires 837.4. RP-HPLC (Vydac C18 analytical column, 0-, 30% buffer B over 30 min): t$_R$=29.5 min.

5.2.4 des$_{A1-5/A14-21}$-c[Δ$^4$A6,11]-Dao-[A8]-Pro Insulin A-Chain 27

SEQ ID NO: 23

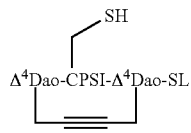

Resin-bound peptide 26 was dried via azeotropic distillation from THF and then subjected to the general microwave-accelerated RCAM procedure under the following conditions: Resin-bound 26 (45 mg, 50 µmol), DCM (2 mL), Schrock's catalyst (4.7 mg, 10 µmol), 70° C., 3 h, 80% conversion into 27. Post metathesis, a small aliquot of resin-bound peptide was subjected to Fmoc-deprotection in the presence of 20% v/v piperidine in DMF (1 mL; 1×1 min, 2×10 min), and washed with DMF (1 mL; 5×1 min), DCM (1 mL; 3×1 min) and MeOH (1 mL; 3×1 min). The aliquot of Fmoc-deprotected resin-tethered peptide was subjected to TFA-mediated cleavage for RP-HPLC and mass spectral analysis. This indicated a mixture of both cyclic and linear peptides, 27 and 26, respectively. Mass spectrum (ESI$^+$, MeCN:H$_2$O: HCOOH): m/z 783.5 [M+H]$^+$, C$_{34}$H$_{55}$N$_8$O$_{11}$S requires 783.4 837.4. RP-HPLC (Vydac C18 analytical column, 0→30% buffer B over 30 min): t$_{R(27)}$=23.2 min and t$_{R(26)}$=29.5 min.

6. Interchain Dicarba Bridges: Synthesis of Olefinic Human Insulin A- and B-Chain Peptide Analogues

6.1 Direct Cross Metathesis

6.1.1 des$_{A1-4/A12-21}$-[A6,11]-Cys(Acm)-[A7]-Agl-[A8,9]-Ser(Thr) Human Insulin A-Chain 154

SEQ ID NO: 55

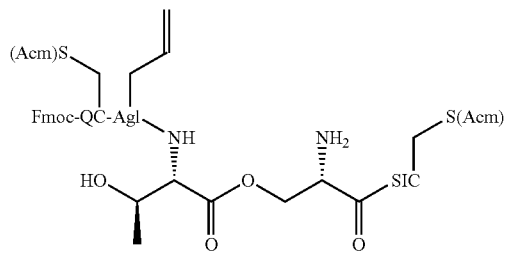

154

Esterification of Fmoc-L-Leu-OH (106 mg, 300 µmol) on Wang resin (110 mg, 100 µmol) was performed according to the general protocol described in the General Section using DIC (47 µL, 300 µmol) and DMAP (3.7 mg, 30 µmol) for 3 h. The automated microwave-accelerated procedure was then used for the synthesis of peptide 154 on Fmoc-L-Leu-Wang resin (129 mg, 100 µmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 154

| Reagent | Total volume (mL) | Mass (g) or Volume (mL) | Reaction Time (min) |
|---|---|---|---|
| 0.5M HATU in DMF | 13.0 | 2.47 g | — |
| 2M DIPEA in NMP | 7.0 | 2.4 mL | — |
| Fmoc-L-Agl-OH | 3.0 | 0.202 g | 12 |
| Fmoc-L-Cys(Acm)-OH | 6.0 | 0.700 g | 12 |
| Fmoc-L-Gln(Trt)-OH | 3.0 | 0.366 g | 12 |
| Fmoc-L-Glu(O$^t$Bu)-OH | 3.0 | 0.255 g | 12 |
| Fmoc-L-Gly-OH | 3.0 | 0.178 g | 12 |
| Fmoc-L-Ile-OH | 6.0 | 0.420 g | 12 |
| Boc-L-Ser(Fmoc-L-Thr($^t$Bu))-OH | 3.0 | 0.351 g | 12 |
| Fmoc-L-Val-OH | 3.0 | 0.204 g | 12 |

After sequence completion, the resin-bound peptide was transferred into a fritted syringe and treated with an acetic anhydride solution (7 mL; DMF:acetic anhydride:NMM; 94:5:1) for 2 h. The resin was washed with DMF (7 mL; 3×1 min), DCM (7 mL; 3×1 min) and MeOH (7 mL; 3×1 min), then left to dry in vacuo for 1 h. A small aliquot of the resin-tethered peptide was subjected to TFA-mediated cleavage (General Section) and mass spectral analysis supported formation of the desired peptide 154. Mass spectrum (ESI$^+$, MeOH): m/z 1115.2 [M+H]$^+$, C$_{50}$H$_{71}$N$_{10}$O$_{15}$S$_2$ requires 1115.4.

6.1.2 Butenolysis of the Resin-Bound A-Chain Analogue 154→700

SEQ ID NO: 57

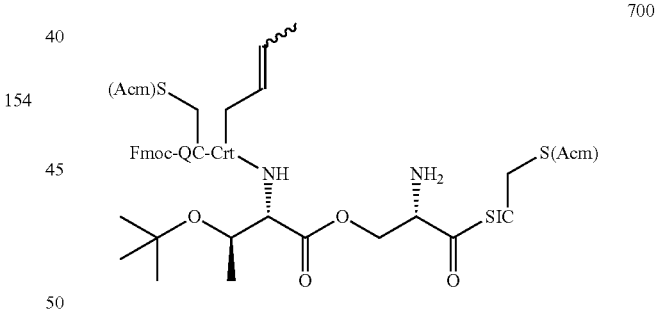

700

Resin-bound peptide 154 was subjected to the microwave-accelerated CM procedure outlined in the General Section under the following conditions: Resin-bound 154 (50 mg, 46 µmol), DCM (3 mL), 2$^{nd}$ generation Grubbs' catalyst (7.7 mg, 9.1 µmol), cis-2-butene (12 psi), 20 W µwave, 50° C., 1 h, 100% conversion into 700. Post metathesis, a small aliquot of the resin-bound peptide was subjected to the cleavage procedure outlined in General Section. Mass spectral analysis of the resultant pale brown showed 100% conversion to the required product 700. Mass spectrum (ESI$^+$, MeCN:H$_2$O: HCOOH): m/z 1129.3 [M+H]$^+$, C$_{51}$H$_{73}$N$_{10}$O$_{15}$S$_2$ requires 1129.5:

6.1.3 des$_{A1-4/A12-21}$-[A6,11]-Cys(tBu)-[A7]-Agl Human Insulin A-Chain 155

SEQ ID NO: 58

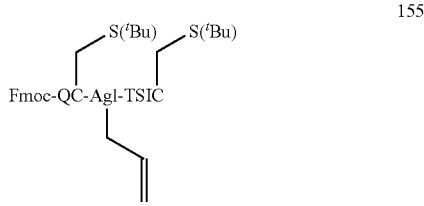

155

Esterification of Fmoc-L-Cys($^t$Bu)-OH (120 mg, 300 μmol) on Wang resin (110 mg, 100 μmol) was performed according to the general protocol described in the General Section using DIC (47 μL, 300 μmol) and DMAP (3.7 mg, 30 μmol) for 2 h. The automated microwave-accelerated procedure was then used for the synthesis of peptide 155 on Fmoc-L-Cys($^t$Bu)-Wang resin (131 mg, 100 μmol). Quantities of HBTU, HOBt, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 155

| Reagent | Total volume (mL) | Mass (g) or Volume (mL) | Reaction Time (min) |
|---|---|---|---|
| 0.5M HBTU:HOBt in DMF | 7.0 | 1.33 g:0.47 g | — |
| 2M DIPEA in NMP | 4.0 | 1.4 mL | — |
| Fmoc-L-Cys($^t$Bu)-OH | 3.0 | 0.240 | 12 |
| Fmoc-L-Gln(Trt)-OH | 3.0 | 0.366 | 12 |
| Fmoc-L-Agl-OH | 3.0 | 0.202 | 12 |
| Fmoc-L-Ile-OH | 3.0 | 0.212 | 12 |
| Fmoc-L-Ser($^t$Bu)-OH | 3.0 | 0.230 | 12 |
| Fmoc-L-Thr($^t$Bu)-OH | 3.0 | 0.238 | 12 |

After sequence completion, the resin-bound peptide was transferred into a fritted syringe and treated with an acetic anhydride solution (7 mL; DMF:acetic anhydride:NMM; 94:5:1) for 2 h. The resin was washed with DMF (7 mL; 3×1 min), DCM (7 mL; 3×1 min) and MeOH (7 mL; 3×1 min), then left to dry in vacuo for 0.5 h. A small aliquot of the resin-tethered peptide was subjected to TFA-mediated cleavage (General Section) and mass spectral analysis supported formation of the desired peptide 155. Mass spectrum (ESI$^+$, MeOH): m/z 1085.4 [M+H]$^+$, $C_{52}H_{77}N_8O_{13}S_2$ requires 1085.5; 1107.3 [M+Na]$^+$, $C_{52}H_{76}N_8NaO_{13}S_2$ requires 1107.5.

6.1.4 CM of Resin-Bound A-Chain Analogue 155 and Bz-D,L-Agl-OMe

SEQ ID NO: 59

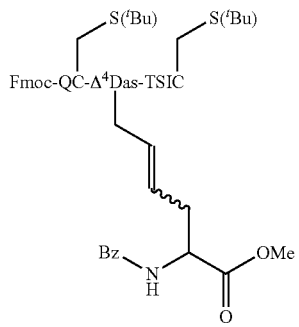

702

Resin-bound peptide 155 was subjected to the microwave-accelerated CM procedure outlined in the General Section under the following conditions: Resin-bound 155 (50 mg, 46 μmol), DCM (2 mL), 2$^{nd}$ generation Grubbs' catalyst (7.7 mg, 9.1 μmol), BZ-D,L-Agl-OMe (106 mg, 0.46 mmol), 100 W μwave, 100° C., 1 h. Post metathesis, a small aliquot of the resin-bound peptide was subjected to the cleavage procedure outlined in the General Section. Mass spectral analysis of the resultant pale brown solid showed the presence of both monomer 155 and heterodimer 702. Mass spectrum (ESI$^+$, MeCN: H$_2$O:HCOOH): m/z 1085.4, 1290.5 [M+H]$^+$, $C_{63}H_{88}N_9O_{16}S_2$ requires 1290.6.

6.1.5 des$_{A1-4/10-21}$-[A6]-Ala-[A7]-Agl Human Insulin A-Chain 156

SEQ ID NO: 60

156

Esterification of Fmoc-L-Ser($^t$Bu)-OH (115 mg, 300 μmol) on Wang resin (110 mg, 100 μmol) was performed according to the general protocol described in the General Section using DIC (47 μL, 300 μmol) and DMAP (3.7 mg, 30 μmol) for 3 h. The automated microwave-accelerated procedure was then used for the synthesis of peptide 156 on Fmoc-L-Ser($^t$Bu)-Wang resin (127 mg, 100 μmol). Quantities of HBTU, HOBt, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 156

| Reagent | Total volume (mL) | Mass (g) or Volume (mL) | Reaction Time (min) |
|---|---|---|---|
| 0.5M HBTU:HOBt in DMF | 5.0 | 0.95:0.34 g | — |
| 2M DIPEA in NMP | 3.0 | 1.0 mL | — |

TABLE-continued

Quantities of reagents and amino acids used in the synthesis of peptide 156

| Reagent | Total volume (mL) | Mass (g) or Volume (mL) | Reaction Time (min) |
|---|---|---|---|
| Fmoc-L-Agl-OH | 3.0 | 0.202 | 12 |
| Fmoc-L-Ala-OH | 3.0 | 0.187 | 12 |
| Fmoc-L-Gln(Trt)-OH | 3.0 | 0.366 | 12 |
| Fmoc-L-Thr($^t$Bu)-OH | 3.0 | 0.238 | 12 |

After sequence completion, the resin-bound peptide was transferred into a fritted syringe and treated with an acetic anhydride solution (7 mL; DMF:acetic anhydride:NMM; 94:5:1) for 2 h. The resin was washed with DMF (7 mL; 3×1 min), DCM (7 mL; 3×1 min) and MeOH (7 mL; 3×1 min), then left to dry in vacuo for 0.5 h. A small aliquot of the resin-tethered peptide was subjected to TFA-mediated cleavage and mass spectral analysis supported formation of the desired peptide 156. Mass spectrum (ESI$^+$, MeCN:H$_2$O:HCOOH): m/z 725.3 [M+H]$^+$, C$_{35}$H$_{45}$N$_6$O$_{11}$ requires 725.3. RP-HPLC (Agilent: Vydac C18 analytical column, 15→45% buffer B over 30 min): t$_R$=17.9 min.

6.1.6 CM of Resin-Bound A-Chain Analogue 156 and Bz-D,L-Agl-OMe

SEQ ID NO: 61

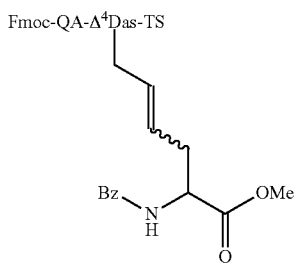

703

Resin-bound peptide 156 was subjected to the microwave-accelerated CM procedure outlined in the General Section under the following conditions: Resin-bound 156 (50 mg, 17 µmol), DCM (2 mL), 2$^{nd}$ generation Hoveyda-Grubbs' catalyst (2.1 mg, 3.4 µmol), Bz-D,L-Agl-OMe (39 mg, 0.17 µmol), 100 W µwave, 100° C., 4 h, 94% conversion into 703. Post metathesis, a small aliquot of the resin-bound peptide was subjected to the cleavage procedure outlined in the General Section. Chromatographic and mass spectral analysis showed a mixture of starting material 156 and heterodimer 703 in a 6:96 ratio. Mass spectrum (ESI$^+$, MeCN:H$_2$O:HCOOH): m/z 725.3, 930.2 [M+H]$^+$, C$_{46}$H$_{56}$N$_7$O$_{14}$ requires 930.4. RP-HPLC (Agilent: Vydac C18 analytical column, 15→45% buffer B over 30 min): t$_{R(156)}$=17.8 min and t$_{R(703)}$=22.5 min.

6.1.7 CM of Resin-Bound A-Chain Analogue 156 and Ac-D,L-Agl-OMe

SEQ ID NO: 61

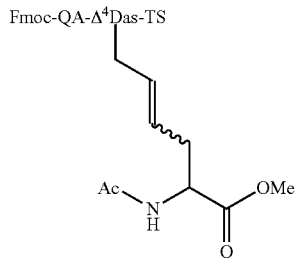

704

Resin-bound peptide 156 was subjected to the microwave-accelerated CM procedure outlined in the General Section under the following conditions: Resin-bound 156 (50 mg, 17 µmol), DCM (2 mL), 2$^{nd}$ generation Hoveyda-Grubbs' catalyst (2.1 mg, 3.4 µmol), Ac-D,L-Agl-OMe (29 mg, 0.17 µmol), 100 W µwave, 100° C., 4 h, 97% conversion into 704. Post metathesis, a small aliquot of the resin-bound peptide was subjected to the cleavage procedure outlined in the General Section. RP-HPLC and mass spectral analysis of the resultant pale brown solid showed mixture of starting material 156 and heterodimer 704 in a 3:97 ratio. Mass spectrum (ESI$^+$, MeCN:H$_2$O:HCOOH): m/z 725.1, 868.1 [M+H]$^+$, C$_{41}$H$_{54}$N$_7$O$_{14}$ requires 868.4. RP-HPLC (Agilent: Vydac C18 analytical column, 15→45% buffer B over 30 min): t$_{R(704)}$=16.9 and 17.0 min and t$_{R(156)}$=17.9 min.

6.1.8 Fmoc-L-Agl-L-Asn-NH$_2$ 136

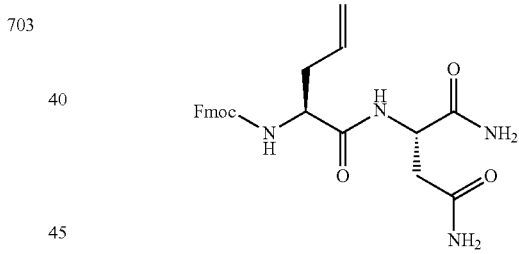

136

The manual SPPS procedure was used to prepared dipeptide 136 on Rink amide resin (192 mg, 100 µmol). Quantities of HATU and NMM remained constant throughout this synthesis. The total amount of each coupling reagent and successive amino acid required, along with their reaction duration is summarised in the table below:—

TABLE

Quantities of reagents and amino acids used in the synthesis of dipeptide 136

| Reagent | Mole (mmol) | Mass (mg) or Volume (µL) | Reaction Time (h) |
|---|---|---|---|
| HATU | 0.3 | 114 mg | — |
| NMM | 0.6 | 61 µL | — |
| Fmoc-L-Agl-OH | 0.3 | 101 mg | 2 |
| Fmoc-L-Asn-OH | 0.3 | 179 mg | 2 |

After sequence completion, the resin-bound peptide was transferred into a fritted syringe and treated with an acetic anhydride solution (4 mL; DMF:acetic anhydride:NMM; 94:5:1) for 2 h. The resin was washed with DMF (4 mL; 3×1 min), DCM (4 mL; 3×1 min) and MeOH (4 mL; 3×1 min), then left to dry in vacuo for 1 h. A small aliquot of the resin-tethered peptide was subjected to TFA-mediated cleavage and mass spectral analysis supported formation of the desired peptide 166. Mass spectrum (ESI$^+$, MeCN:H$_2$O: HCOOH): m/z 451.0 [M+H]$^+$, C$_{24}$H$_{26}$N$_5$O$_6$ requires 451.2. RP-HPLC (Agilent: Vydac C18 analytical column, 0→100% buffer B over 30 min): $t_R$=14.2 min.

6.1.9 Protected des$_{B1-3/B11-30}$-[B7]-Agl Human Insulin B-Chain 168

SEQ ID NO: 62

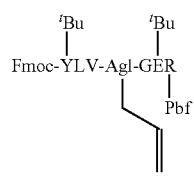

168

Esterification of Fmoc-L-Arg(Pbf)-OH (130 mg, 200 µmol) on 2-chlorotrityl chloride resin (334 mg, 200 µmol) was performed using DIPEA (105 µL, 600 µmol) for 2 h. The remaining 6 residues were then added to the resin-tethered amino acid. Quantities of HATU and NMM remained constant throughout this synthesis. The total amount of each coupling reagent and successive amino acid required, along with their reaction duration is summarised in the table below:—

TABLE

Quantities of reagents and amino acids used in the synthesis of dipeptide 168

| Reagent | Mole (mmol) | Mass (mg) or Volume (µL) | Reaction Time (h) |
|---|---|---|---|
| HATU | 0.3 | 114 mg | — |
| NMM | 0.6 | 61 µL | — |
| Fmoc-L-Agl-OH | 0.6 | 202 mg | 15 |
| Fmoc-L-Glu(O$^t$Bu)-OH | 0.6 | 358 mg | 3 |
| Fmoc-L-Gly-OH | 0.6 | 179 mg | 2 |
| Fmoc-L-Leu-OH | 0.6 | 214 mg | 3.5 |
| Fmoc-L-Tyr($^t$Bu)-OH | 0.6 | 278 mg | 2 |
| Fmoc-L-Val-OH | 0.6 | 179 mg | 2 |

After sequence completion, the resin-bound peptide was transferred to a fritted syringe and washed with DMF (4 mL; 3×1 min), DCM (4 mL; 3×1 min), PrOH (4 mL; 3×1 min) and MeOH (4 mL; 3×1 min), then left to dry in vacuo for 1 h. The resin-tethered peptide was subjected to TFA-mediated cleavage and lyophilised from MeCN:H$_2$O (1:1) to give a colourless solid (222 mg). Mass spectral analysis supported formation of the desired Fmoc- and sidechain-deprotected peptide 168. Mass spectrum (ESI$^+$, MeCN:H$_2$O:HCOOH): m/z 1419.6 [M+H]$^+$, C$_{74}$H$_{103}$N$_{10}$O$_{16}$S requires 1419.7.

6.1.10 CM of Resin-Bound Fmoc-L-Agl-L-Asn-NH$_2$ 136 and B-Chain Analogue 168

SEQ ID NO: 63

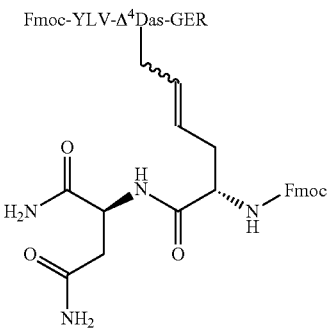

169

Resin-bound peptide 136 was subjected to the general microwave-accelerated CM procedure under the following conditions: Resin-bound 136 (67 mg, 25 µmol), DCM (4.75 mL), 0.4 M LiCl in DMF (0.25 mL), 2$^{nd}$ generation Grubbs' catalyst (4.4 mg, 5.2 µmol), 168 (0.22 g, 0.16 mmol), 100 W µwave, 100° C., 4 h. Post metathesis, a small aliquot of the resin-bound peptide was subjected to the cleavage procedure. RP-HPLC and mass spectral analysis of the resultant colourless solid showed a mixture of starting material 136 and product 169.

6.2 Preparation of a Preformed Diaminosuberic Acid Residue 6.2.1 Fmoc-L-Agl-L-Gly-OEt 160

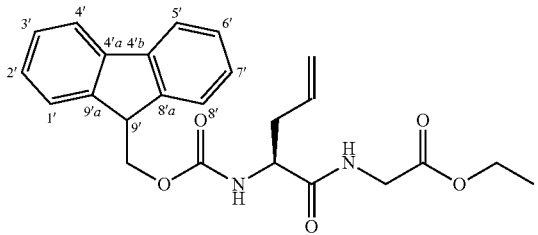

160

A solution of L-glycine ethyl ester (0.62 g, 4.45 mmol) in 10% w/v aq. Na$_2$CO$_3$ (5 mL) was added to a stirred solution of Fmoc-L-Agl-OPfp (0.75 g, 1.48 mmol) in acetone (50 mL). The resultant white suspension was stirred at room temperature and monitored by TLC (SiO$_2$; light petroleum:EtOAc: MeOH:AcOH; 1:1:0.1:0.05). After 18 h, the acetone was removed under reduced pressure and the reaction mixture diluted with DCM (15 mL) and water (10 mL). The phases were separated and the aqueous layer further extracted with DCM (2×10 mL). The combined organic extract was diluted with water (10 mL), cooled in an ice bath and acidified to pH 2 with 1M HCl. The phases were separated and the second aqueous layer further extracted with DCM (2×15 mL). The combined organic extract was washed with brine (1×20 mL) and water (1×20 mL), dried (MgSO$_4$), filtered and concentrated under reduced pressure to yield dipeptide 160 as a colourless solid (0.55 g, 88%), m.p. 143-145° C. $v_{max}$ (KBr): 3416s, 3308s, 3056m, 2985m, 1734s, 1675s, 1518s, 1478m, 1465m, 1450m, 1408m, 1377m, 1338m, 1265s, 1211s, 1105m, 1082w, 1033s, 996m, 925m, 896w, 860w, 737s, 704s, 621m cm$^{-1}$. $^1$H NMR (300 MHz, CDCl$_3$): δ 1.27 (t, J=7.1 Hz, 3H, CH$_2$CH$_3$), 2.53 (bs, 2H, H3), 3.95-4.05 (m, 2H, NHCH$_2$), 4.20 (q, J=7.2 Hz, 3H, CH$_2$CH$_3$, H9'), 4.29 (bs, 1H, CHCH$_2$), 4.35-4.50 (m, 2H, CH$_2$O), 5.16 (d, J=11.5 Hz, 2H, =CH$_2$), 5.34 (bs, 1H, NH), 5.76 (m, 1H, CH=), 6.57 (bs, 1H, NH), 7.30 (td, J=7.4, 1.2 Hz, 2H, H2', 7'), 7.39 (tt, J=7.4, 0.5 Hz, 2H, H3', 6'), 7.57 (d, J=7.4 Hz, 2H, H1', 8'), 7.75 (d, J=7.4 Hz, 2H, H4', 5'). $^{13}$C NMR (100 MHz, CDCl$_3$): δ 14.0 (CH$_2$CH$_3$), 36.9 (CH$_2$CH=), 41.4 (CH$_2$COO), 47.1 (H9'), 54.2 (CHCH$_2$), 61.6 (OCH$_2$CH$_3$), 67.3 (CH$_2$O), 119.2 (=CH$_2$), 120.0 (C2', 7'), 125.1 (C3', 6'), 127.1 (C1', 8'), 127.8 (C4', 5'), 132.8 (CH=), 141.3 (C8'a, 9' a), 143.8, 143.8 (C4'a, 4' b), 156.3 (OCONH), 169.7 (CONH), 171.9 (COOH). Mass spectrum (ESI$^+$, MeOH): m/z 423.2 [M+H]$^+$, C$_{24}$H$_{27}$N$_2$O$_5$ requires 423.2; 445.1 [M+Na], C$_{24}$H$_{26}$N$_2$NaO$_5$ requires 445.2.

6.2.2 Boc-L-Agl-OH 161

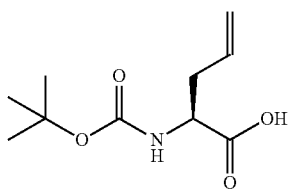

161

Di-tert-Butyldicarbonate (2.27 g, 10.4 mmol) was added to a stirred solution of L-allylglycine (1.00 g, 8.7 mmol) in 1M NaOH (20 mL) and dioxane (20 mL) at 0° C. The reaction mixture was warmed to room temperature and monitored by TLC (SiO$_2$; light petroleum:EtOAc:MeOH; 1:1:0.5). After 42 h, the dioxane was removed under reduced pressure and the resultant aqueous layer diluted with DCM (15 mL). The reaction mixture was cooled in an ice bath and carefully acidified to pH 2 with 1M H$_2$SO$_4$. The phases were separated and the aqueous layer further extracted with DCM (2×15 mL). The combined organic extract was washed with brine (1×30 mL), dried (MgSO$_4$), filtered and concentrated to afford the titled compound 161 as a colourless oil (1.76, 94%). $v_{max}$ (neat): 3432s, 3328bs, 3055m, 2983m, 2932w, 1713s, 1644m, 1505s, 1455w, 1439m, 1394m, 1368m, 1265s, 1162s, 1104w, 1055m, 1025m, 994w, 926m, 896w, 857w, 739s, 705s cm$^{-1}$. $^1$H NMR (400 MHz, CDCl$_3$): δ 1.45 (s, 9H, C(CH$_3$)$_3$), 2.36-2.73 (m, 2H, CHCH$_2$), 4.15 (4.42) (m, 1H, CHCH$_2$), 5.11-5.21 (m, 2H, =CH$_2$), 5.75 (m, 1H, CH=), 6.49 (5.26) (d, J=3.6 Hz, 1H, NH), 11.64 (bs, 1H, OH). $^{13}$C NMR (100 MHz, CDCl$_3$): δ 28.3 (C(CH$_3$)$_3$), 36.4 (CHCH$_2$), 52.8, 54.4 (CHCH$_2$), 80.2, 81.8, (C(CH$_3$)$_3$), 119.2 (=CH$_2$), 132.3 (CH=), 155.6, 156.9 (CONH), 176.1 (COOH). Mass spectrum (ESI$^+$, MeOH): m/z 216.1 [M+H]$^+$, C$_{10}$H$_{18}$NO$_4$ requires 216.1; 237.9 [M+Na], C$_{10}$H$_{17}$NNaO$_4$ requires 238.1.

6.2.3 Fmoc-L-Agl(Boc-L-Agl-OH)-L-Gly-OEt 162

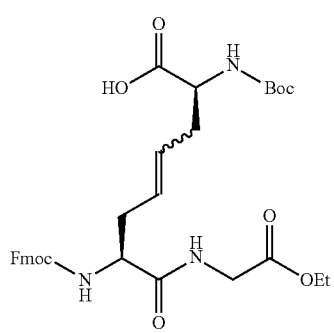

162

Fmoc-L-Agl-L-Gly-OEt 160 was subjected to microwave-accelerated CM procedure under the following conditions: Fmoc-L-Agl-L-Gly-OEt 160 (100 mg, 237 μmol), DCM (3 mL), 2$^{nd}$ generation Grubbs' catalyst (40 mg, 47 μmol), Boc-L-Agl-OH 161 (0.51 g, 2.37 mmol), i) 100° C., 1 h; ii) Δ, N$_2$, 5 d, 100% conversion into 162. The reaction mixture was cooled to room temperature and concentrated under reduced pressure to give a brown solid (0.67 g). Purification by column chromatography (SiO$_2$; light petroleum:EtOAc:MeOH: AcOH; 1:1:0.1:0.05) yielded the required heterodimer 162 contaminated with the Boc-L-Agl-OH homodimer. Mass spectrum (ESI$^+$, MeOH): m/z 238.1; 425.1; 632.0 [M+Na]$^+$, C$_{32}$H$_{39}$N$_3$NaO$_9$ requires 632.3.

6.2.4 Fmoc-L-Agl-L-Asn-OH 163

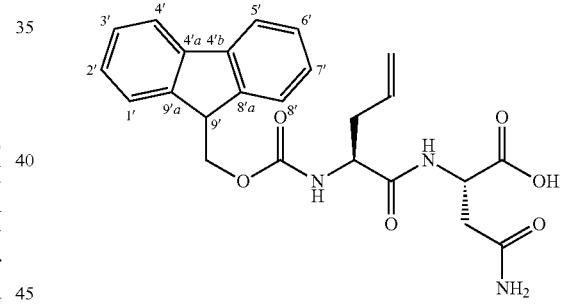

163

A solution of L-asparagine (1.17 g, 8.89 mmol) in 10% w/v aq. Na$_2$CO$_3$ (10 mL) was added to a stirred solution of Fmoc-L-Agl-OPfp (1.49 g, 2.96 mmol) in acetone (60 mL). The resultant white suspension was stirred at room temperature and monitored by TLC (SiO$_2$; light petroleum:EtOAc: MeOH; 1:1:0.1). After 22 h, the acetone was removed under reduced pressure and the reaction mixture diluted with EtOAc (15 mL) and water (15 mL). The reaction mixture was then cooled in an ice bath and acidified to pH 2 with 1M HCl. The resultant precipitate failed to extract into the organic layer so was filtered from the reaction mixture and dried over silica beads to give the desired dipeptide 163 as a colourless solid (1.33 g, 99%). $v_{max}$ (KBr): 3410m, 3298bs, 3068m, 2925m, 2854w, 1719s, 1689s, 1669s, 1618m, 1542m, 1492w, 1450m, 1438m, 1240m, 1399m, 1239m, 1104w, 1085w, 1043w, 995w, 919w, 757m, 739m, 690w cm$^{-1}$. $^1$H NMR (400 MHz, DMSO-d$_6$): δ 2.28 (m, 1H, CHaCH=), 2.45 (m, 1H, CHbCH=), 2.50-2.60 (m, 2H, CH$_2$CO), 4.11 (m, 1H, H9'), 4.16-4.32 (m, 3H, CHCOOH, CH$_2$O), 4.51 (m, 1H, CHCH$_2$CH=), 4.97-5.15 (m, 2H, =CH$_2$), 5.76 (m, 1H, CH=), 6.89 (bs, 2H, NH$_2$), 7.32 (tdd, J=7.4, 1.9, 1.3 Hz, 2H, H2', 7'), 7.41 (td, J=6.8, 0.7 Hz, 2H, H3', 6'), 7.48 (d, J=8.6 Hz, 1H, NH), 7.71 (t, J=6.9 Hz, 2H, H1', 8'), 7.88 (d, J=7.5 Hz, 2H, H4', 5'), 8.19 (d, J=7.9 Hz, 1H, NH), 12.55 (s, 1H, OH). $^{13}$C NMR (100 MHz, CDCl$_3$): δ 36.3 (CH$_2$C0), 36.6 (CH$_2$CH=), 46.6 (H9'), 48.7 (CHCOOH), 54.1 (CHCH$_2$CH=), 65.7 (CH$_2$O), 117.5 (=CH$_2$), 120.0 (C2', 7'), 125.3 (C3', 6'), 127.0 (C1', 8'), 127.6 (C4', 5'), 134.4 (CH=), 140.7 (C8'a, 9' a), 143.7, 143.9 (C4'a, 4' b), 155.8 (OCONH), 171.0 (CONH), 171.2 (CONH$_2$), 172.6 (COON). Mass spectrum (ESI$^+$, MeOH): m/z 452.0 [M+H]$^+$, C$_{24}$H$_{26}$N$_3$O$_6$ requires 452.2; 474.0 [M+Na]$^+$, C$_{24}$H$_{25}$N$_3$NaO$_6$ requires 474.2.

6.2.5 Fmoc-L-Agl-L-Asn(Xan)-OH 164

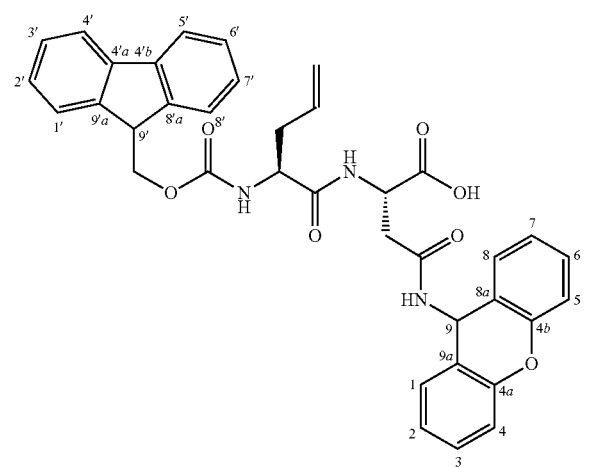

164

Trifluoromethanesulfonic acid (9.8 μL, 0.11 mmol) was added dropwise to a stirred solution of Fmoc-L-Agl-L-Asn-OH 163 (0.10 g, 0.22 mmol) and 9-hydroxyxanthene (57 mg, 0.29 mmol) in dry DMF (5 mL). After 3 d, the DMF was concentrated in vacuo and the resultant yellow liquid diluted with water (20 mL) to induce precipitation. The suspension was collected by filtration, washed with water (3×20 mL) and Et$_2$O (3×20 mL) and dried over silica beads to afford the desired xanthyl-protected dipeptide 164 as a colourless solid (107 mg, 76%), m.p. 264-266° C. ν$_{max}$ (KBr): 3298bs, 3042m, 2962m, 1740s, 1705s, 1689s, 1644s, 1604m, 1578s, 1540s, 1482m, 1454m, 1337m, 1306m, 1262m, 1215m, 1194m, 1151w, 1124w, 1102m, 1088m, 1050m, 1007m, 993w, 942w, 904m, 859w, 798w, 750s, 739s, 646m, 623m cm$^{-1}$. $^1$H NMR (400 MHz, CDCl$_3$): δ 2.31 (m, 1H, CHaCH=), 2.43 (m, 1H, CHbCH=), 2.58 (m, 1H, CHaCO), 2.70 (m, 1H, CHbCO), 4.13 (dt, J=9.0, 4.7 Hz, 1H, H9'), 4.20-4.35 (m, 3H, CHCOOH, CH$_2$O), 4.69 (q, J=6.36 Hz, 1H, CHCH$_2$CH=), 5.03 (d, J=10.1 Hz, 1H, =CHa), 5.07 (dd, J=17.2, 1.6 Hz, 1H, =CHb), 5.68-5.85 (m, 1H, CH=), 6.29 (d, J=8.7 Hz, 1H, H9), 7.06-7.16 (m, 4H, H2, 3, 7, 6), 7.29-7.44 (m, 8H, H1, 2, 4, 5, 2', 3', 6', 7'), 7.50 (d, J=8.6 Hz, 1H, OCONH), 7.72 (t, J=6.5 Hz, 2H, 8'), 7.88 (d, J=7.5 Hz, 2H, H4', 5'), 8.26 (d, J=8.3 Hz, 1H, CONH), 8.92 (d, J=8.9 Hz, 1H, CH$_2$CONH), 12.8 (s, 1H, COOH). $^{13}$C NMR (75 MHz, CDCl$_3$): δ 37.0 (CH$_2$CH=), 37.7 (CH$_2$CO), 43.0 (C9), 47.4 (C9'), 49.6 (CHCOOH), 54.9 (CHCH$_2$CH=), 66.4 (CH$_2$O), 116.7 (ArC), 118.2 (=CH$_2$), 120.8 (ArC), 122.3 (ArC), 122.4 (ArC), 124.1 (ArC), 124.2 (ArC), 126.7 (ArC), 127.8 (ArC), 128.3 (ArC), 129.6 (ArC), 129.8 (ArC), 129.9 (ArC), 135.1 (CH=), 141.4 (C8'a, 9' a), 144.4, 144.6 (C4'a, 4' b), 151.1 (C4a, 4b), 156.5 (OCONH), 169.6 (CONH), 171.8 (CH$_2$NHCO) 173.3 (COOH). Mass spectrum (ESI$^+$, MeOH): m/z 632.1 [M+H]$^+$, C$_{37}$H$_{34}$N$_3$O$_7$ requires 632.2; 654.1 [M+Na], C$_{37}$H$_{33}$N$_3$NaO$_7$ requires 654.2.

6.2.6 Fmoc-L-Agl-L-Asn(Xan)-OBn 165

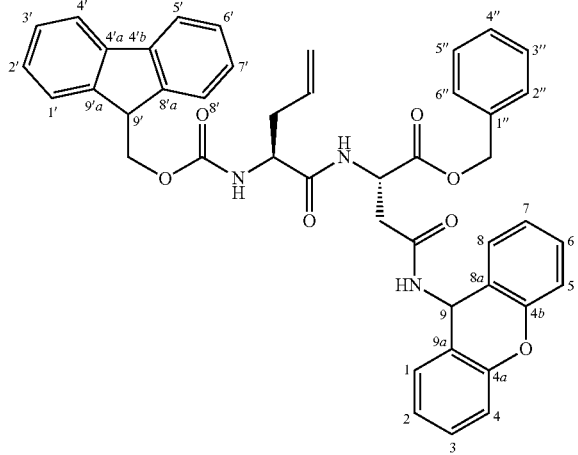

165

Benzyl bromide (0.37 g, 2.15 mmol) was added dropwise to a stirred solution of Fmoc-L-Agl-L-Asn(Xan)-OH 164 (0.68 g, 1.07 mmol) and triethylamine (0.22 g, 2.15 mmol) in dry acetone:THF:DMF (20 mL; 4:1:1). The reaction mixture was heated at reflux and monitored by TLC (SiO$_2$; light petroleum:EtOAc:MeOH; 1:1:0.2). After 16 h, the solvent mixture was removed in vacuo and the resultant yellow residue was diluted with water (50 mL) to induce precipitation. The suspension was collected by filtration, washed with water (3×20 mL) and Et$_2$O (3×20 mL) and dried over silica beads to give the fully protected asparagine derivative 165 as a colourless solid (0.65 g, 82%), m.p. 232-243° C. (dec.). ν$_{max}$ (KBr): 3285s, 3265s, 3067m, 2976m, 2957w, 1740s, 1687s, 1664s, 1647s, 1577m, 1546s, 1482m, 1452m, 1436m, 1399w, 1377m, 1332m, 1305m, 1292m, 1280m, 1260s, 1246m, 1222m, 1172m, 1124w, 1100w, 1085w, 1040m, 1011w, 998w, 923w, 901w, 759s, 742s, 691w cm$^{-1}$. $^1$H NMR (400 MHz, CDCl$_3$): δ 2.29 (m, 1H, CHaCH=), 2.40 (m, 1H, CHbCH=), 2.63 (m, 1H, CHaCO), 2.75 (m, 1H, CHbCO), 4.13 (dt, J=8.9, 4.8 Hz, 1H, H9'), 4.18-4.25 (m, 2H, CH$_2$O), 4.32 (m, 1H, CHCH$_2$CH=), 4.83 (q, J=6.4 Hz, 1H, CHCOOCH$_2$), 5.00 (d, 10.2 Hz, 1H, =CHa), 5.07 (dd, J=13.7, 1.5 Hz, 1H, =CHb), 5.13 (s, 2H, OCH$_2$Ph), 5.73 (m, 1H, CH=), 6.29 (d, J=8.7 Hz, 1H, H9), 7.03-7.16 (m, 4H, H2, 3, 7, 6), 7.23-7.45 (m, 13H, H1, 2, 4, 5, 2', 3', 6', 7', 2'', 3'', 4'', 5'', 6''), 7.53 (d, J=8.2 Hz, 1H, OCONH), 7.72 (dd, J=7.2, 3.6 Hz, 2H, H1', 8'), 7.88 (d, J=7.51 Hz, 2H, H4', 5'), 8.46 (d, J=8.0 Hz, 1H, CONH), 8.94 (d, J=8.8 Hz, 1H, CH$_2$CONH). $^{13}$C NMR (100 MHz, CDCl$_3$): δ 36.2 (CH$_2$CH=), 36.8 (CH$_2$CO), 42.4 (C9), 46.6 (C9'), 48.9 (CHCOOCH$_2$), 54.1 (CHCH$_2$CH=), 65.3 (OCH$_2$Ph), 65.7 (CH$_2$O), 116.0 (ArC), 117.5 (=CH$_2$), 120.1 (ArC), 121.5 (ArC), 121.6 (ArC), 123.4 (ArC), 125.3 (ArC), 127.0 (ArC), 127.6 (ArC), 127.6 (ArC), 127.9 (ArC), 128.3 (ArC), 128.9 (ArC), 129.0 (ArC), 129.1 (ArC), 134.3 (ArC), 135.8 (CH=), 140.7 (C8'a, 9' a), 143.7, 143.8 (C4'a, 4' b), 150.3, 150.4 (C4a, 4b), 155.8 (OCONH), 168.5 (CONH), 170.9 (CH$_2$NHCO), 171.3 (COCH$_2$Ph). Mass spectrum (ESI$^+$, MeOH): m/z 744.1 [M+Na], C$_{44}$H$_{39}$N$_3$NaO$_7$ requires 744.3.

6.2.7 Fmoc-L-Agl(Ac-L-Agl-OMe)-L-Asn-NH$_2$ 137

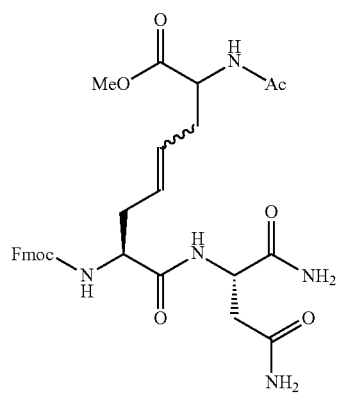

137

Resin-bound peptide 136 was subjected to microwave-accelerated CM procedure under the following conditions: Resin-bound 136 (67 mg, 25 µmol), DCM (3 mL), 2$^{nd}$ generation Grubbs' catalyst (4.2 mg, 5.0 µmol), Ac-D,L-Agl-OMe (25.7 g, 0.15 mmol), 100 W µwave, 100° C., 4 h, 85% conversion into 137. Post metathesis, a small aliquot of the resin-bound peptide was subjected to the cleavage procedure. RP-HPLC and mass spectral analysis of the resultant colourless solid showed a 15:85 mixture of starting material 136 and product 137. Mass spectrum (ESI$^+$, MeCN: H$_2$O:HCOOH): m/z 451.0, 594.1 [M+H]$^+$, C$_{30}$H$_{36}$N$_5$O$_8$ requires 594.2. RP-HPLC (Vydac C18 analytical column, 0→100% buffer B over 30 min): t$_{R(137)}$=13.3 min and t$_{R(136)}$=14.2 min.

6.3 Latent Interchain Dicarba Bridges: an RCM Approach

6.3.1 A Proline-Tethered A- and B-Chain Analogue of Human Insulin 180

SEQ ID NO: 64

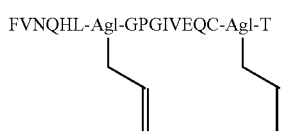

180

The automated, microwave-accelerated procedure was used for the synthesis of peptide 180 on Fmoc-Thr($^t$Bu)-PEG-PS resin (625 mg, 100 µmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 180

| Reagent | Total volume (mL) | Mass (g) or Volume (mL) | Reaction Time (min) |
|---|---|---|---|
| 0.5M HATU in DMF | 18 | 3.43 g | — |
| 2M DIPEA in NMP | 9 | 3.1 mL | — |
| Fmoc-L-Agl-OH | 6.0 | 0.402 g | 12 |
| Fmoc-L-Asn(Trt)-OH | 3.0 | 0.358 g | 12 |

TABLE-continued

Quantities of reagents and amino acids used in the synthesis of peptide 180

| Reagent | Total volume (mL) | Mass (g) or Volume (mL) | Reaction Time (min) |
|---|---|---|---|
| Fmoc-L-Cys(Trt)-OH | 3.0 | 0.351 g | 12 |
| Fmoc-L-Gln(Trt)-OH | 8.0 | 0.977 g | 12 |
| Fmoc-L-Glu(O$^t$Bu)-OH | 3.0 | 0.255 g | 12 |
| Fmoc-L-Gly-OH | 6.0 | 0.357 g | 12 |
| Fmoc-L-Ile-OH | 3.0 | 0.212 g | 12 |
| Fmoc-L-Leu-OH | 3.0 | 0.212 g | 12 |
| Fmoc-L-Phe-OH | 3.0 | 0.232 g | 12 |
| Fmoc-L-Pro-OH | 3.0 | 0.202 g | 12 |
| Fmoc-L-Val-OH | 3.0 | 0.204 g | 12 |

After sequence completion, the resin-bound peptide was transferred into a fritted syringe and treated with an acetic anhydride solution (7 mL; DMF:acetic anhydride:NMM; 94:5:1) for 2 h. The resin was washed with DMF (7 mL; 3×1 min), DCM (7 mL; 3×1 min) and MeOH (7 mL; 3×1 min), then left to dry in vacuo for 1 h. Prior to treatment with MeOH, a small aliquot of the resin-bound peptide was removed and subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The aliquot of Fmoc-deprotected resin-tethered peptide was subjected to TFA-mediated cleavage (General Section) and mass spectral analysis supported formation of the desired peptide 180. Mass spectrum (ESI$^+$, MeCN:H$_2$O:HCOOH): m/z 918.5 [M+2H]$^{2+}$, ½(C$_{82}$H$_{128}$N$_{22}$O$_{24}$S) requires 918.5. RP-HPLC (Agilent: Vydac C18 analytical column, 0→30% buffer B over 5 min then 30→60% buffer B over 30 min): t$_R$=12.2 min.

6.3.2 RCM of the Proline-Tethered A- and B-Chain Analogue 180→181

SEQ ID NO: 65

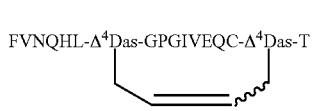

181(I) and 181(II)

Resin-bound peptide 180 was subjected to the microwave-accelerated RCM procedure outlined in the General Section under the following conditions: Resin-bound 180 (496 mg, 50 µmol), DCM (6 mL), 2$^{nd}$ generation Grubbs' catalyst (8.5 mg, 10 µmol), 0.4 M LiCl in DMF (0.2 mL), 100 W µwave, 100° C., 4 h, 78% conversion into 181. Post metathesis, a small aliquot of resin-bound peptide was subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The dried aliquot of Fmoc-deprotected resin-tethered peptide was subjected to TFA-mediated cleavage (General Section) for RP-HPLC and mass spectral analysis. This supported formation of the desired peptide as two isomers, 181(I) and 181(II), in a 1:1 ratio and a cyclic product 181 to linear starting material 180 ratio of 22:78. Mass spectrum (ESI$^+$, MeCN:H$_2$O:HCOOH): m/z 904.6 [M+2H]$^{2+}$, ½(C$_{80}$H$_{124}$N$_{22}$O$_{24}$S) requires 904.4; 918.7. RP-HPLC (Agilent: Vydac C18 analytical column, 0→30% buffer B over 5 min then 30→60% buffer B over 30 min): t$_{R(181)}$=9.3 and 10.0 min and t$_{R(180)}$=12.4 min.

6.3.3 A Truncated Proline-Tethered A- and B-Chain Analogue of Human Insulin 182

SEQ ID NO: 66

182

The automated, microwave-accelerated procedure was used for the synthesis of peptide 182 on Fmoc-Thr($^t$Bu)-PEG-PS resin (625 mg, 100 µmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 182

| Reagent | Total volume (mL) | Mass (g) or Volume (mL) | Reaction Time (min) |
| --- | --- | --- | --- |
| 0.5M HATU in DMF | 12.0 | 2.29 g | — |
| 2M DIPEA in NMP | 6.0 | 2.1 mL | — |
| Fmoc-L-Agl-OH | 6.0 | 0.405 g | 12 |
| Fmoc-L-Cys(Trt)-OH | 3.0 | 0.315 g | 12 |
| Fmoc-L-Gln(Trt)-OH | 3.0 | 0.366 g | 12 |
| Fmoc-L-Glu(O$^t$Bu)-OH | 3.0 | 0.255 g | 12 |
| Fmoc-L-Gly-OH | 6.0 | 0.357 g | 12 |
| Fmoc-L-Ile-OH | 3.0 | 0.212 g | 12 |
| Fmoc-L-Pro-OH | 3.0 | 0.202 g | 12 |
| Fmoc-L-Val-OH | 3.0 | 0.204 g | 12 |

After sequence completion, the resin-bound peptide was transferred into a fritted syringe and treated with an acetic anhydride solution (7 mL; DMF:acetic anhydride:NMM; 94:5:1) for 2 h. The resin was washed with DMF (7 mL; 3×1 min), DCM (7 mL; 3×1 min) and MeOH (7 mL; 3×1 min), then left to dry in vacuo for 1 h. A small aliquot of the resin-bound peptide was removed and subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The aliquot of Fmoc-deprotected resin-tethered peptide was exposed to a TFA cleavage solution (General Section) and mass spectral analysis of the resultant grey solid supported the formation of the required peptide 182. Mass spectrum (ESI$^+$, MeCN:H$_2$O:HCOOH): m/z 1097.3 [M+H]$^+$, C$_{47}$H$_{77}$N$_{12}$O$_{16}$S requires 1097.3.

6.3.4 RCM of the Truncated Proline-Tethered A- and B-Chain Analogue of Human Insulin 182→183

SEQ ID NO: 67

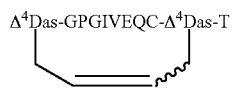

183

Resin-bound peptide 182 was subjected to the microwave-accelerated RCM procedure outlined in the General Section under the following conditions: Resin-bound 182 (416 mg, 50 µmol), DCM (6 mL), 2$^{nd}$ generation Grubbs' catalyst (8.5 mg, 10 µmol), 0.4 M LiCl in DMF (0.2 mL), 100 W µwave, 100° C., 4 h, 100% conversion into 183. Post metathesis, a small aliquot of resin-bound peptide was subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The dried aliquot of Fmoc-deprotected resin-tethered peptide was subjected to TFA-mediated cleavage (General Section) and mass spectral analysis supported formation of the desired peptide 183. Mass spectrum (ESI$^+$, MeCN:H$_2$O:HCOOH): m/z 1069.3 [M+H]$^+$, C$_{45}$H$_{73}$N$_{12}$O$_{16}$S requires 1069.5. RP-HPLC (Agilent: Vydac C18 analytical column, 0→30% buffer B over 5 min then 30→60% buffer B over 30 min): t$_R$=12.5 min.

6.3.5 Addition of FVNQHL to peptide 183→184

SEQ ID NO: 65

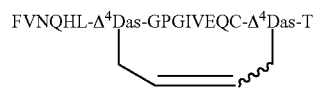

184

The automated, microwave-accelerated procedure was used to attach the remaining 6 residues on resin-bound peptide 183 (400 mg, 50 µmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 184

| Reagent | Total volume (mL) | Mass (g) or Volume (mL) | Reaction Time (min) |
| --- | --- | --- | --- |
| 0.5M HATU in DMF | 7.0 | 1.33 g | — |
| 2M DIPEA in NMP | 4.0 | 1.4 mL | — |
| Fmoc-L-Asn(Trt)-OH | 3.0 | 0.358 g | 12 |
| Fmoc-L-Gln(Trt)-OH | 3.0 | 0.366 g | 12 |
| Fmoc-L-His(Trt)-OH | 3.0 | 0.372 g | 12 |
| Fmoc-L-Leu-OH | 3.0 | 0.212 g | 12 |
| Fmoc-L-Phe-OH | 3.0 | 0.232 g | 12 |
| Fmoc-L-Val-OH | 3.0 | 0.204 g | 12 |

After sequence completion, the resin-bound peptide was transferred into a fritted syringe and washed with DMF (4 mL; 5×1 min), DCM (4 mL; 3×1 min) and MeOH (4 mL; 3×1 min), then left to dry in vacuo for 1 h. A small aliquot of resin was subjected to TFA-mediated cleavage and mass spectral analysis supported formation of the desired peptide 184. Mass spectrum (ESI$^+$, MeCN:H$_2$O:HCOOH): m/z 904.4 [M+2H]$^{2+}$, ½(C$_{80}$H$_{124}$N$_{22}$O$_{24}$S) requires 904.4. RP-HPLC (Agilent: Vydac C18 analytical column, 0→30% buffer B over 5 min then 30→60% buffer B over 30 min): t$_R$=9.3 and 9.9 min

6.3.6 5-Nitro-1,3-benzodioxane 185

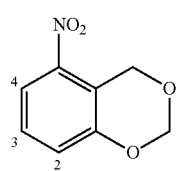

A microwave vessel was loaded with meta-nitrophenol (1.00 g, 7.19 mmol), formaldehyde solution (2 mL), and concentrated HCl (3 mL). The system was sealed and the reaction mixture then irradiated with microwaves (90 W) and stirred at 90° C. for 4 h. The resultant red solution was cooled to room temperature and diluted with water (15 mL) and EtOAc (15 mL). The phases were separated and the aqueous layer was further extracted with EtOAc (2×15 mL). The combined organic extract was washed with water (1×20 mL), dried (MgSO$_4$), filtered and concentrated under reduced pressure to afford a dark red oil (3.7 g). The crude product mixture was purified by column chromatography (SiO$_2$; light petroleum:EtOAc; 2:1) to afford the compound 185 as a colourless solid (0.73 g, 56%), m.p. 7677° C. $v_{max}$ (KBr): 3375 bs, 2968m, 2927m, 1611m, 1581w, 1530s, 1487w, 1457m, 1392w, 1349s, 1286m, 1212m, 1172w, 1151w, 1078w, 1037w, 998m, 943w, 904w, 837m, 809m, 791m, 767w, 740m, 732m cm$^{-1}$. $^1$H NMR (400 MHz, CDCl$_3$): δ 5.21 (s, 2H, CCH$_2$O), 5.27 (s, 2H, OCH$_2$O), 7.18 (dd, J=8.3, 1.0 Hz, 1H, H2), 7.32 (t, J=8.3 Hz, 1H, H3), 7.81 (dd, J=8.2, 1.1 Hz, 1H, H4). $^{13}$C NMR (100 MHz, CDCl$_3$): δ 65.9 (CH$_2$OH), 90.9 (OCH$_2$O), 118.1 (C4), 118.7 (CCH$_2$), 123.3 (C2), 128.3 (C3), 145.3 (CNO$_2$), 154.3 (COH).

6.3.7 2-Hydroxymethyl-3-nitrophenol 186

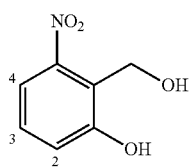

A microwave vessel was loaded with 185 (0.26 g, 1.43 mmol) and 1M HCl (6 mL). The vessel was sealed and the suspension was heated at reflux and monitored by TLC (SiO$_2$; light petroleum:EtOAc; 2:1). After 24 h, the product mixture was cooled to room temperature and diluted with EtOAc (15 mL). The phases were separated and the aqueous layer was further extracted with EtOAc (2×15 mL). The combined organic extract was washed with water (1×30 mL), dried (MgSO$_4$), filtered and concentrated under reduced pressure to afford a colourless solid (0.24 g). The crude product mixture was purified by column chromatography (SiO$_2$; light petroleum:EtOAc; 2:1) to give the desired product 186 as a colourless solid (0.22 g, 91%), m.p. 97-99° C. $v_{max}$ (KBr): 3437bs, 2968m, 2929m, 1643m, 1612m, 1531s, 1488w, 1456m, 1393w, 1349s, 1285s, 1212m, 1172w, 1151w, 1078w, 998m, 943w, 904w, 837m, 808m, 791m, 740m, 732m, 702w, 637m cm$^{-1}$. $^1$H NMR (400 MHz, MeOD): δ 4.81 (bs, 2H, CH$_2$OH), 7.07 (m, 1H, H2), 7.25-7.31 (m, 2H, H3, 4). $^{13}$C NMR (100 MHz, MeOD): δ 54.7 (CH$_2$O), 114.5 (C4), 119.4 (C2), 120.8 (CCH$_2$), 128.6 (C3), 150.8 (CNO$_2$), 157.0 (COH).

6.3.8 2-Hydroxy-6-nitrobenzaldehyde 187

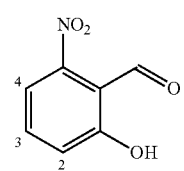

Manganese dioxide (1.13 g, 13.0 mmol) was added to a stirred solution of 186 (0.22 g, 1.30 mmol) in EtOAc (15 mL). The black suspension was stirred at room temperature and monitored by TLC (SiO$_2$; light petroleum:EtOAc; 2:1). After 16 h, the reaction mixture was filtered though a celite plug and concentrated in vacuo to give a brown solid. The crude product mixture was purified by column chromatography (SiO$_2$; light petroleum:EtOAc; 2:1) to give the compound 87 as a yellow solid (0.17 g, 76%), m.p. 52-53° C. (lit. 53-54° C.). $v_{max}$ (KBr): 3424bs, 3107m, 2928m, 1656s, 1560w, 1529s, 1450m, 1355s, 1283s, 1195m, 1176m, 1066w, 969m, 842m, 815m, 785s, 735s, 695m cm$^{-1}$. $^1$H NMR (400 MHz, CDCl$_3$): δ 7.26 (d, J=8.4 Hz, 1H, H2), 7.52 (dd, J=7.8, 0.9 Hz, 1H, H3), 7.61 (t, J=8.1 Hz, 1H, H4), 10.27 (s, 1H, CHO), 12.03 (s, 1H, OH). $^{13}$C NMR (100 MHz, MeOD): δ 112.4 (C4), 116.1 (CCHO), 124.2 (C2), 136.0 (C3), 151.3 (CNO$_2$), 163.3 (COH), 193.9 (CHO).

6.3.9 des$_{A10-21}$-[A7]-Agl Human Insulin A-Chain 188

SEQ ID NO: 68

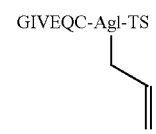

The automated, microwave-accelerated procedure was used for the synthesis of peptide 188 on rink amide resin (192 mg, 100 µmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide 188

| Reagent | Total volume (mL) | Mass (g) or Volume (mL) | Reaction Time (min) |
| --- | --- | --- | --- |
| 0.5M HATU in DMF | 10.0 | 1.91 g | — |
| 2M DIPEA in NMP | 5.0 | 1.7 mL | — |
| Fmoc-L-Agl-OH | 3.0 | 0.202 g | 12 |
| Fmoc-L-Cys(Trt)-OH | 3.0 | 0.315 g | 12 |
| Fmoc-L-Gln(Trt)-OH | 3.0 | 0.366 g | 12 |
| Fmoc-L-Glu(O$^t$Bu)-OH | 3.0 | 0.255 g | 12 |
| Fmoc-L-Gly-OH | 3.0 | 0.178 g | 12 |
| Fmoc-L-Ile-OH | 3.0 | 0.212 g | 12 |
| Fmoc-L-Ser($^t$Bu)-OH | 3.0 | 0.230 g | 12 |
| Fmoc-L-Thr($^t$Bu)-OH | 3.0 | 0.238 g | 12 |
| Fmoc-L-Val-OH | 3.0 | 0.204 g | 12 |

After sequence completion, the resin-bound peptide was transferred into a fritted syringe and washed with DMF (7 mL; 3×1 min), DCM (7 mL; 3×1 min) and MeOH (7 mL; 3×1 min), then left to dry in vacuo for 1 h. A small aliquot of Fmoc-deprotected resin-tethered peptide was subjected TFA-mediated cleavage (General Section) for RP-HPLC and mass spectral analysis. This supported formation of the desired peptide 188 in >95% purity. Mass spectrum (ESI+, MeCN:H$_2$O:HCOOH): m/z 932.2 [M+H]+, C$_{38}$H$_{66}$N$_{11}$O$_{14}$S requires 932.5. RP-HPLC (Agilent: Vydac C18 analytical column, 15→45% buffer B over 30 min): t$_R$=21.3 min.

6.3.10 Incorporation of HnB and Boc-protection of A-chain analogue 188→189

SEQ ID NO: 29

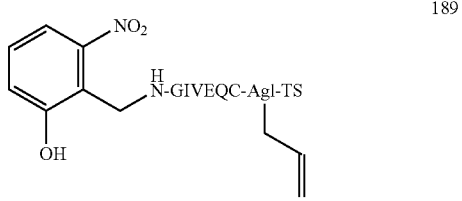

189

Resin-bound peptide 188 was swollen with DCM (4 mL; 3×1 min, 1×60 min) and DMF (4 mL; 3×1 min, 1×30 min), then subjected to the modified reductive amination. 2-Hydroxy-6-nitrobenzaldehyde 184 (33 mg, 200 µmol) in MeOH:DMF (2 mL, 1:1) was added to the resin-tethered peptide 188 (310 mg, 100 µmol) and allowed to shake gently for 30 min. The resin was filtered and a second portion of aldehyde 187 (33 mg, 200 µmol) in MeOH:DMF (2 mL, 1:1) was added. After 2 h, the resin was filtered, washed with MeOH:DMF (1:1; 4 mL, 3×1 min) and treated with a solution of sodium borohydride (39 mg, 1.0 mmol) in MeOH:DMF (5 mL, 1:3) for 30 min. After this reaction duration, the resin was filtered, washed with MeOH:DMF (1:3; 4 mL, 3×1 min), DMF (4 mL, 3×1 min) and MeOH:DCM (1:1; 4 mL, 3×1 min), then left to dry in vacuo for 1 h. A small aliquot of resin was subjected TFA-mediated cleavage (General Section) and RP-HPLC and mass spectral analysis confirmed 90% conversion to the required peptide 189. Mass spectrum (ESI+, MeCN:H$_2$O:HCOOH): m/z 933.0; 1083.2 [M+H]+, C$_{45}$H$_{71}$N$_{12}$O$_{17}$S requires 1083.5. RP-HPLC (Agilent: Vydac C18 analytical column, 15→45% buffer B over 30 min): t$_{R(189)}$=9.3 min and t$_{R(187)}$=21.4 min.

The resin-bound peptide 189 was re-swollen with DCM (4 mL; 3×1 min, 1×60 min) and DMF (4 mL; 3×1 min, 1×30 min) and the secondary amine then Boc-protected. Di-tert-butyldicarbonate (65.5 mg, 300 µmol) in dry DCM was added to the resin-tethered peptide and shaken gently at room temperature. After 16 h, a chloranil test was negative for the presence of secondary amines and hence the peptide was washed with DMF (7 mL; 3×1 min), DCM (7 mL; 3×1 min) and MeOH (7 mL; 3×1 min), then left to dry in vacuo for 1 h.

6.3.11 Esterification of A-chain analogue 189→190

SEQ ID NO: 29

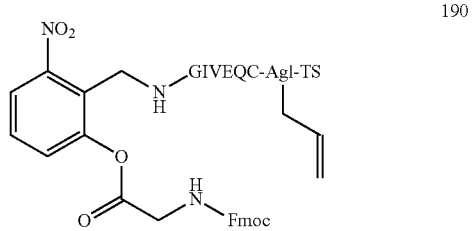

190

Fmoc-L-Gly-OH was esterified on the HnB-containing peptide 189 according to a procedure outline by Maarseveen et al. DMAP (1.2 mg, 10 µmol) in dry DCM (0.5 mL) was added dropwise to a stirred suspension of resin-bound peptide 189 (280 mg, 100 µmol), Fmoc-L-Gly-OH (89.2 mg, 300 µmol) and EDCI.HCl (57.4 mg, 300 µmol) in dry DCM:DMF (4 mL; 1:1). After 14 h, the resin was filtered and washed with DMF (7 mL; 3×1 min), DCM (7 mL; 3×1 min) and MeOH (7 mL; 3×1 min), then left to dry in vacuo for 1 h. A small aliquot of resin was subjected TFA-mediated cleavage (General Section) and mass spectral analysis supported formation of the required peptide 190. The ester linkage, however, was highly prone to acid-hydrolysis and rapidly decomposed into peptide 189. Mass spectrum (ESI+, MeCN:H$_2$O:HCOOH): m/z 681.6 [M+2H]$^{2+}$, ½(C$_{62}$H$_{85}$N$_{13}$O$_{20}$S) requires 681.8; 1083.3; 1212.4; 1362.3 [M+H]+, C$_{62}$H$_{84}$N$_{13}$O$_{20}$S requires 1362.6. RP-HPLC (Agilent: Vydac).

6.3.12 RCM of the HnB Tethered A- and B-Chain Analogue 191→192

SEQ ID NO: 32

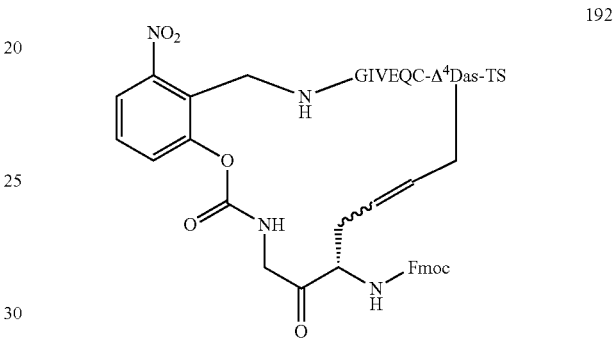

192

Resin-bound peptide 191 was subjected to the microwave-accelerated RCM procedure outlined in the General Section under the following conditions: Resin-bound 191 (280 mg, 100 µmol), DCM (3 mL), 0.4 M LiCl in DMF (0.1 mL), 2$^{nd}$ generation Grubbs' catalyst (17 mg, 20 µmol), 100 W µwave, 100° C., 4 h. Post metathesis, a small aliquot of resin-bound peptide was subjected to TFA-mediated cleavage (General Section) and mass spectral analysis supported formation of the desired peptide 192. Hydrolysed peptide 189 was also observed. Mass spectrum (ESI+, MeCN:H$_2$O:HCOOH): m/z 716.1 [M+2H]$^{2+}$, C$_{65}$H$_{88}$N$_{14}$O$_{21}$S requires 716.3; 1083.2; 1159.2; 1224.3, 1431.2 [M+H]+, C$_{65}$H$_{87}$N$_{14}$O$_{20}$S requires 1431.6. RP-HPLC (Agilent: Vydac C18 analytical column, 15→45% buffer B over 30 min): t$_{R(192)}$=22.2 min.

7. Multiple Dicarba Bridge Formation 7.1 bis-Dicarba Analogues of Human Insulin 7.1.1 Several Examples of this Method have Previously been Disclosed in Section 5: "Ring Closing Alkene Metathesis (RCM) on Resin-Supported Peptides" and Therefore have Not been Described Here.

7.1.2 [A6,11]-Agl-[A7]-Pre Human Insulin A-Chain ψ200

SEQ ID NO: 69

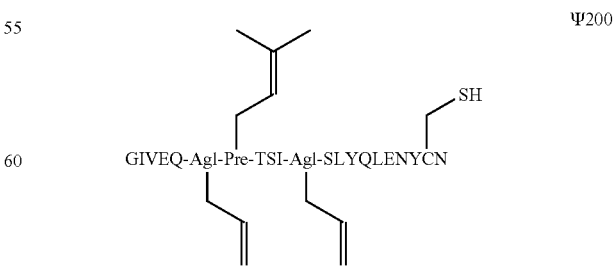

ψ200

The automated, microwave-accelerated procedure was used for the synthesis of peptide ψ200 on Fmoc-Asn(Trt)-

PEG-PS resin (526 mg, 100 μmol). Quantities of HATU, DIPEA, piperidine and each Fmoc-amino acid were used as described by the automated protocols of the instrument and remained constant throughout this synthesis. The total amount of each coupling reagent and successive amino acid required, along with their reaction duration is summarised in the table below:—

TABLE

Quantities of reagents and amino acids used in the synthesis of peptide ψ200

| Reagent | Total volume (mL) | Mass (g) or Volume (mL) | Reaction Time (min) |
|---|---|---|---|
| 0.5M HATU in DMF | 20 | 3.8 g | — |
| 2M DIPEA in NMP | 10 | 3.5 mL | — |
| Fmoc-L-Agl-OH | 6.0 | 0.405 g | 12 |
| Fmoc-L-Asn(Trt)-OH | 3.0 | 0.358 g | 12 |
| Fmoc-L-Cys(Trt)-OH | 3.0 | 0.240 g | 12 |
| Fmoc-L-Gln(Trt)-OH | 6.0 | 0.733 g | 12 |
| Fmoc-L-Glu(O$^t$Bu)-OH | 6.0 | 0.511 g | 12 |
| Fmoc-L-Gly-OH | 3.0 | 0.178 g | 12 |
| Fmoc-L-Ile-OH | 6.0 | 0.424 g | 12 |
| Fmoc-L-Leu-OH | 6.0 | 0.424 g | 12 |
| Fmoc-L-Pre-Thr(ψ$^{Me,Me}$Pro)-OH | 3.0 | 0.304 g | 12 |
| Fmoc-L-Ser($^t$Bu)-OH | 6.0 | 0.460 g | 12 |
| Fmoc-L-Tyr($^t$Bu)-OH | 6.0 | 0.551 g | 12 |
| Fmoc-L-Val-OH | 3.0 | 0.204 g | 12 |

After sequence completion, the resin-bound peptide was transferred into a fritted syringe and treated with an acetic anhydride solution (7 mL; DMF:acetic anhydride:NMM; 94:5:1) for 2 h. The resin was washed with DMF (7 mL; 3×1 min), DCM (7 mL; 3×1 min) and MeOH (7 mL; 3×1 min), then left to dry in vacuo for 1 h. Prior to treatment with MeOH, a small aliquot of the resin-bound peptide was removed and subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The aliquot of Fmoc-deprotected resin-tethered peptide was subjected to TFA-mediated cleavage and mass spectral analysis of the resultant grey solid supported formation of the desired peptide 4'200. Mass spectrum (ESI$^+$, MeOH): m/z 1197.2 [M+2H]$^{2+}$, ½($C_{107}H_{167}N_{25}O_{35}S$) requires 1197.1; 1206.1 [M+2H+$H_2O$]$^{2+}$, ½($C_{107}H_{169}N_{25}O_{36}S$) requires 1206.1; 798.5 [M+3H]$^{3+}$, ⅓($C_{107}H_{168}N_{25}O_{35}S$) requires 798.4; 804.4 [M+3H+$H_2O$]$^{3+}$, ⅓($C_{107}H_{170}N_{25}O_{36}S$) requires 804.4.

7.1.3  c[Δ$^4$A6,11]-Dicarba-[A7]-Pre-[A8]-Thr(ψ$^{Me,Me}$Pro) Human Insulin A-Chain ψ201

SEQ ID NO: 70

ψ201

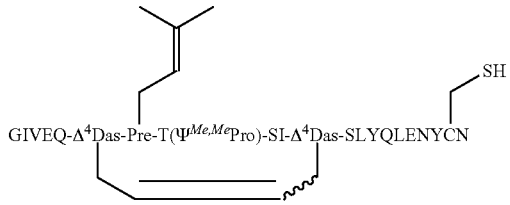

GIVEQ-Δ$^4$Das-Pre-T(Ψ$^{Me,Me}$Pro)-SI-Δ$^4$Das-SLYQLENYCN

Resin-bound peptide ψ200 was subjected to the microwave-accelerated RCM procedure outlined in the General Section under the following conditions: Resin-bound ψ200 (717 mg, 100 μmol), DCM (6 mL), 0.4 M LiCl in DMF (0.2 mL), 2nd generation Grubbs' catalyst (17 mg, 20 μmol), 100 W μwave, 100° C., 1 h, 100% conversion into ψ201. Post metathesis, a small aliquot of the resin-bound peptide was subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The aliquot of Fmoc-deprotected peptidyl-resin was subjected to TFA-mediated cleavage and mass spectral analysis supported formation of the desired peptide ψ201 with its pseudoproline ring intact. Mass spectrum (ESI+, MeOH): m/z 1203.3 [M+2H+ψPro]2+, ½($C_{108}H_{167}N_{25}O_{35}S$) requires 1203.1; 802.4 [M+3H+ψPro]3+, ⅓($C_{107}H_{169}N_{25}O_{35}S$) requires 802.4.

7.1.4  c[A6,11]-Dicarba-[A7]-Pre-[A8]-Thr(ψ$^{Me,Me}$Pro) Human Insulin A-Chain ψ202

SEQ ID NO: 71

Ψ202

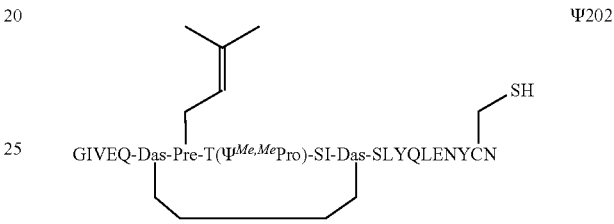

GIVEQ-Das-Pre-T(Ψ$^{Me,Me}$Pro)-SI-Das-SLYQLENYCN

TABLE

Optimisation of the hydrogenation yield in carbocyclic peptide ψ202

| Heat Source | Solvent* | Temperature (° C.) | Duration (h) | Pressure (psi) | Conversion (%) |
|---|---|---|---|---|---|
| μwave | DCM:MeOH (9:1) | 50 | 2 | 60 | 20 |
| μwave | DCM:MeOH (9:1) | 50 | 4 | 60 | 50 |

Method A:

Resin-bound peptide ψ201 was subjected to the microwave-accelerated hydrogenation under the following conditions: Resin-bound ψ201 (250 mg, 32 μmol), DCM (9 mL), MeOH (1 mL), Wilkinson's catalyst, H$_2$ (60 psi), 50 W μwave, 50° C., 2 h, 20% conversion into ψ202. Following hydrogenation, a small aliquot of the resin-bound peptide was subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The dried aliquot of Fmoc-deprotected peptidyl-resin was subjected to TFA-mediated cleavage and mass spectral analysis of the resultant brown solid showed the presence of saturated carbocycle ψ202. Mass spectrum (ESI$^+$, MeCN:H$_2$O:HCOOH): m/z 1203.5; 1204.4 [M+2H+ψPro]$^{2+}$, ½($C_{108}H_{169}N_{25}O_{35}S$) requires 1204.2.

Method B:

Resin-bound peptide ψ201 was subjected to the microwave-accelerated hydrogenation under the following conditions: Resin-bound ψ201 (235 mg, 32 μmol), DCM (9 mL), MeOH (1 mL), Wilkinson's catalyst, H$_2$ (60 psi), 50 W μwave, 50° C., 4 h, 50% conversion into ψ202. Following hydrogenation, a small aliquot of the resin-bound peptide was subjected to Fmoc-deprotection in the presence of 20% v/v piperidine in DMF (1 mL; 1×1 min, 2×10 min), then washed with DMF (1 mL; 5×1 min), DCM (1 mL; 3×1 min) and MeOH (1 mL; 3×1 min). The aliquot of Fmoc-deprotected peptidyl-resin was subjected to TFA-mediated cleavage and mass spectral analysis of the resultant brown solid indicated the presence of saturated carbocycle ψ202. Mass spectrum (ESI$^+$, MeCN:H$_2$O:HCOOH): m/z 1203.2; 1204.1 [M+2H+ψPro]$^{2+}$, ½($C_{108}H_{169}N_{25}O_{35}S$) requires 1204.2.

The invention claimed is:

1. A dicarba analogue of insulin comprising (1) an A-chain or a fragment, salt, solvate, derivative, isomer, or tautomer of the A-chain and (2) a B-chain or a fragment, salt, solvate, derivative, isomer, or tautomer of the B-chain and one or more intrachain dicarba bridges located on the A chain, the B chain or both, provided that the dicarba analogue is not [A7, B7-(2, 7-diaminosuberoyl]-des-(B26-B30)-insulin B25-amide.

2. The dicarba analogue according to claim 1, comprising one or more interchain dicarba bridges located between the A-chain and the B-chain.

3. The dicarba analogue according to claim 1, comprising one or more unsaturated dicarba bridges.

4. The dicarba analogue according to claim 1, wherein one or more of the disulfide bridge forming cysteine amino acid residue pairs of native insulin are replaced by a dicarba bridge.

5. The dicarba analogue according to claim 1, wherein the one or more intrachain dicarba bridges are located in the A-chain.

6. The dicarba analogue of insulin according to claim 1, comprising a dicarba bridge which includes at least one of the groups selected from —C—C—, —C=C— and —C≡C—.

7. The dicarba analogue according to claim 6, wherein the dicarba bridge is selected from the following:

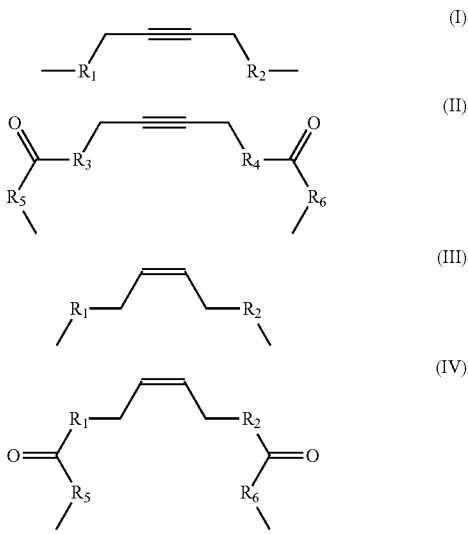

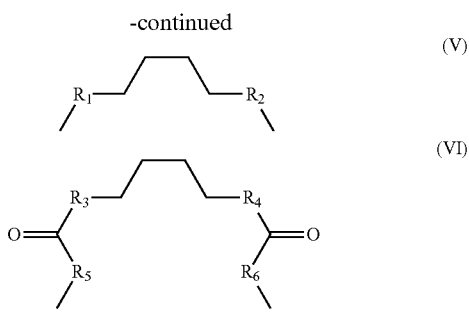

wherein $R_1$ to $R_6$ are each independently absent or selected from a divalent linking group.

8. The dicarba analogue according to claim 7, wherein the dicarba bridge has the formula (III) or (IV) and the —C=C— group is in a cis-conformation or a trans-conformation.

9. The dicarba analogue according to claim 1, wherein the dicarba bridge is formed via metathesis of two complementary metathesisable groups.

10. The dicarba analogue according to claim 9, wherein the metathesisable groups are each connected to an amino acid in insulin.

11. The dicarba analogue according to claim 10, wherein the metathesisable groups are located on the amino group or on the side chain of the amino acid.

12. The dicarba analogue according to claim 10 or 11, wherein the amino acid is selected from the group consisting of glycine or alanine.

13. The dicarba analogue according to claim 12, wherein the amino acid having the metathesisable group is selected from the group consisting of allylglycine, crotylglycine, prenylglycine and butynylglycine.

14. The dicarba analogue of insulin according to claim 1, wherein the dicarba analogue comprises one or more dicarba bridges which replace at least one of the disulfide bridges located between cysteine residue 6 and cysteine residue 11 of the A-chain of native human insulin, cysteine residue 7 of the A-chain and cysteine residue 7 of the B-chain of native human insulin, or cysteine residue 20 of the A-chain and cysteine residue 19 of the B-chain of native human insulin.

15. The dicarba analogue according to claim 1, having a stability after 6 hours of contact with human blood plasma greater than that of the corresponding insulin not containing at least one dicarba bridge.

16. The dicarba analogue according to claim 1, having a stability at room temperature that is greater than that of the corresponding insulin not containing at least one dicarba bridge.

17. A method for the synthesis of a dicarba analogue of insulin comprising an A-chain and a B-chain or fragments, salts, solvates, derivatives, isomers or tautomers of the A-chain, the B-chain or both, the method comprising:
(i) providing the A-chain having at least one pair of complementary metathesisable groups;
(ii) subjecting the A-chain to metathesis to form at least one dicarba bridge between the pair of complementary metathesisable groups; and
(iii) adding the B-chain.

18. The method of claim 17, which further comprises the step of hydrogenating the dicarba bridge(s) to form at least one alkane-containing dicarba bridge either before or after the B-chain is added.

19. The method of claim 17, which further comprises the step of semi-hydrogenating the dicarba bridge(s) to form at least one alkene-containing dicarba bridge either before or after the B-chain is added.

20. The method of claim 19 wherein the semi-hydrogenation step forms an alkene-containing dicarba bridge which is enriched in the cis- or trans-isomer.

21. The method of claim 17, wherein the A-chain comprises a turn inducing residue located between the at least two complementary metathesisable groups.

22. A method for the synthesis of a dicarba analogue of insulin comprising an A-chain and a B-chain or a fragments, salts, solvates, derivatives, isomers or tautomers thereof the A-chain, the B-chain or both, the method comprising:
(i) providing a part of the A-chain having at least two complementary metathesisable groups;
(ii) subjecting the A-chain to metathesis to form at least one dicarba bridge;
(iii) adding one or more further amino acids to one or both ends of the A-chain; and
(iv) adding the B-chain.

23. A method for the synthesis of a dicarba analogue of insulin comprising an A-chain and a B-chain or fragments, salts, solvates, derivatives, isomers or tautomers of the A-chain, the B-chain or both, the method comprising:
(i) providing a part of the A-chain and/or a part of the B-chain having at least two complementary metathesisable groups between them;
(ii) subjecting the A-chain and B-chain to metathesis to form at least one dicarba bridge; and
(iii) adding one or more further amino acids to one or both ends of the A-chain and/or B-chain,
wherein the A-chain comprises an intrachain dicarba bridge.

24. The method of claim 22 or 23, wherein the A-chain or B-chain or both comprise further complementary metathesisable groups, and the method includes a further metathesis step to form at least one further intrachain dicarba bridge, at least one interchain dicarba bridge or both between the complementary metathesisable groups.

25. A method for the synthesis of a dicarba analogue of insulin comprising an A-chain and a B-chain or fragments, salts, solvates, derivatives, isomers or tautomers of the A-chain, the B-chain or both, the method comprising:
(i) providing a reactable peptide comprising a removable tether between the A-chain and the B-chain, the A-chain and the B-chain each having at least one complementary metathesisable group; and
(ii) subjecting the reactable peptide to metathesis to form at least one dicarba bridge between the complementary metathesisable groups; and
(iii) removing the removeable tether to produce a dicarba bridge linking the A-chain and the B-chain of insulin.

26. The method of claim 25, wherein the peptide comprises further complementary metathesisable groups located on the A-chain or B-chain or both, and the reactable peptide is subjected to a second metathesis step either before or after the step of removing the removeable tether, to form at least one further intrachain dicarba bridge, at least one interchain dicarba bridge or both between the complementary metathesisable groups.

27. The method of claim 22, 23 or 25 which further comprises forming at least one disulfide bridge between the cysteine amino acid residues in the A-chain and/or B-chain.

28. The method of claim 22, 23 or 25 which further comprises the step of hydrogenating the dicarba bridge(s) to form at least one alkane-containing dicarba bridge either before or after the step of removing the removeable tether.

29. The method of claim 22, 23 or 25 which further comprises the step of semi-hydrogenating the dicarba bridge(s) to form at least one alkene-containing dicarba bridge either before or after the step of removing the removeable tether.

30. The method of claim 27, wherein the semi-hydrogenation step forms an alkene-containing dicarba bridge which is enriched in the cis- or trans-isomer.

31. The method of any one of claim 17, 22, 23 or 25 wherein the cross-metathesis of the complementary metathesisable groups is conducted under microwave radiation conditions.

32. The method of any one of claim 17, 22, 23 or 25 wherein the cross-metathesis is performed using a cross-metathesis catalyst in the presence of a solvent combination comprising a resin-swelling solvent and a co-ordinating solvent for the catalyst.

33. The method of claim 32, wherein the co-ordinating solvent is an alcohol.

34. A pharmaceutical composition comprising the dicarba analogue of insulin according to claim 1 and a pharmaceutically acceptable carrier.

35. A method for reducing hyperglycemia comprising, administering the dicarba analogue of insulin according to claim 1 to a subject in need thereof.

36. A method for the treatment of diabetes mellitus or metabolic syndrome comprising, administering the dicarba analogue of insulin according to claim 1 to a subject in need thereof.

37. The dicarba analogue of claim 1 having a structure selected from the group consisting of:

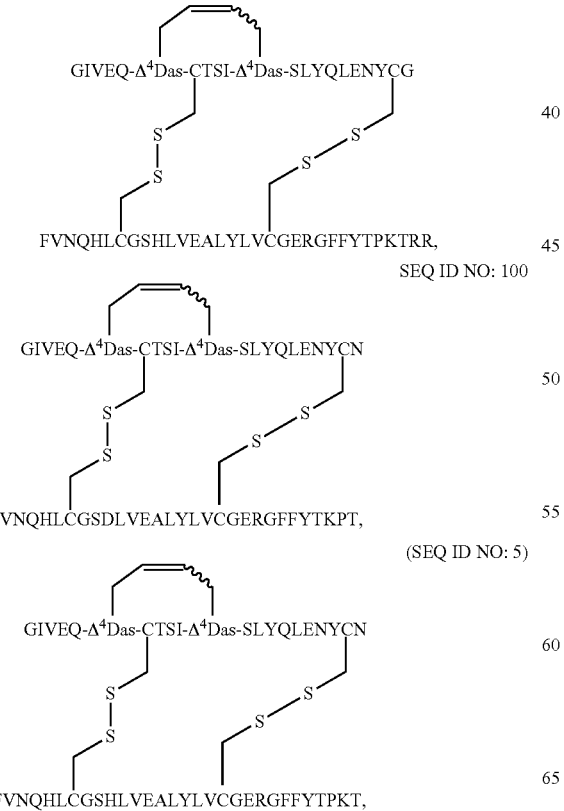

(SEQ ID NO: 106)

(SEQ ID NO: 100)

(SEQ ID NO: 5)

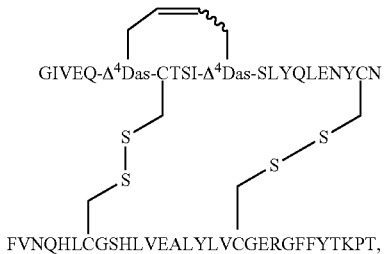

(SEQ ID NO: 107)

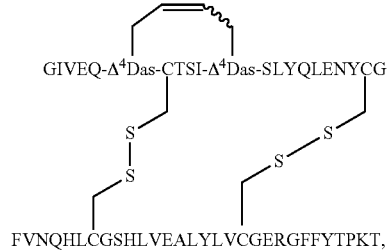

(SEQ ID NO: 45)

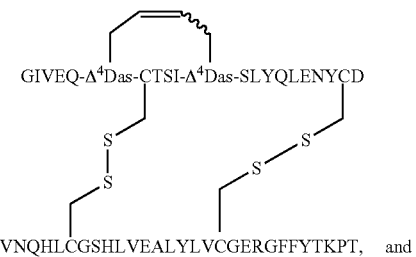

(SEQ ID NO: 50)

and

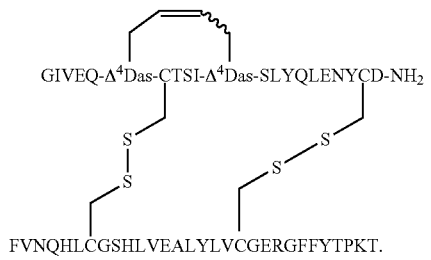

(SEQ ID NO: 109)

38. The dicarba analogue of claim 1 having a structure selected from the group consisting of:

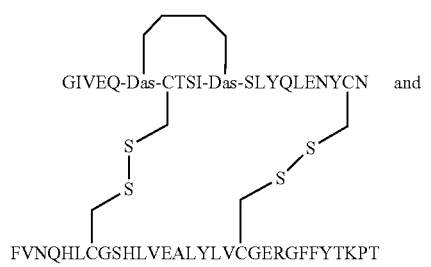

(SEQ ID NO: 43)

and (SEQ ID NO: 42)
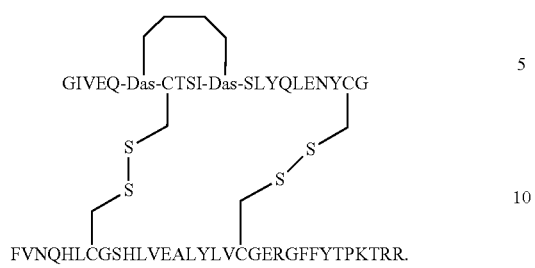
FVNQHLCGSHLVEALYLVCGERGFFYTPKTRR.
* * * * *

UNITED STATES PATENT AND TRADEMARK OFFICE
CERTIFICATE OF CORRECTION

PATENT NO. : 8,748,570 B2  
APPLICATION NO. : 13/502085  
DATED : June 10, 2014  
INVENTOR(S) : Robinson et al.

It is certified that error appears in the above-identified patent and that said Letters Patent is hereby corrected as shown below:

IN THE CLAIMS

At Column 272, lines 61-67, Structure (IV) " 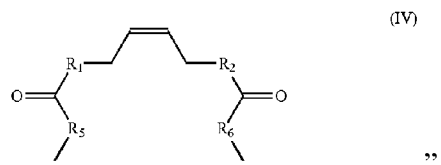 "

should be -- 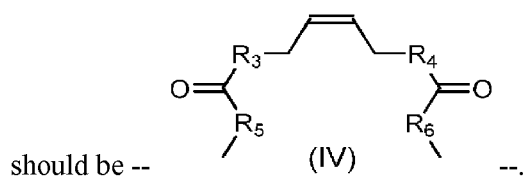 --.

Signed and Sealed this  
First Day of December, 2015

Michelle K. Lee  
*Director of the United States Patent and Trademark Office*